[19] United States Patent
Mauldin et al.

(10) Patent No.: US 11,672,664 B2
(45) Date of Patent: Jun. 13, 2023

(54) SYSTEMS, DEVICES, AND METHODS FOR JOINT FUSION

(71) Applicant: SI-Bone Inc., Santa Clara, CA (US)

(72) Inventors: Richard G. Mauldin, Erie, CO (US); Ralph F. Rashbaum, Plano, TX (US); Mark A. Reiley, Delray Beach, FL (US); Scott A. Yerby, Montara, CA (US); Paul M. Sand, Redwood City, CA (US); Bret W. Schneider, San Jose, CA (US); Jose Rodriguez, Houston, TX (US); Nicanor Domingo, Santa Clara, CA (US); Joanne Leung, Mountain View, CA (US)

(73) Assignee: SI-Bone Inc., Santa Clara, CA (US)

( * ) Notice: Subject to any disclaimer, the term of this patent is extended or adjusted under 35 U.S.C. 154(b) by 0 days.

(21) Appl. No.: 17/805,165

(22) Filed: Jun. 2, 2022

(65) Prior Publication Data
US 2022/0287846 A1  Sep. 15, 2022

Related U.S. Application Data

(60) Continuation of application No. 16/523,992, filed on Jul. 26, 2019, now Pat. No. 11,471,286, which is a (Continued)

(51) Int. Cl.
*A61F 2/30* (2006.01)
*A61F 2/46* (2006.01)
(Continued)

(52) U.S. Cl.
CPC ...... *A61F 2/30988* (2013.01); *A61B 17/0218* (2013.01); *A61B 17/1604* (2013.01); (Continued)

(58) Field of Classification Search
CPC ............ A61B 17/0218; A61B 17/1604; A61B 17/1659; A61B 17/1664; A61B 17/1671; (Continued)

(56) References Cited

U.S. PATENT DOCUMENTS

| 1,951,278 A | 3/1934 | Ericsson |
| 2,136,471 A | 11/1938 | Schneider |

(Continued)

FOREIGN PATENT DOCUMENTS

| CN | 1128944 A | 8/1996 |
| CN | 1190882 A | 8/1998 |

(Continued)

OTHER PUBLICATIONS

Acumed; Acutrak Headless Compressioin Screw (product information); 12 pgs; © 2005; retrieved Sep. 25, 2014 from http://www.rcsed.ac.uk/fellows/lvanrensburg/classification/surgtech/acumed/manuals/acutrak-brochure%200311.pdf.

(Continued)

*Primary Examiner* — Mohamed G Gabr
(74) *Attorney, Agent, or Firm* — Shay Glenn LLP

(57) ABSTRACT

The present invention relates generally to implants and tools for the fixation or fusion of joints or bone segments. These tools include tissue dilators and protectors. Other tools include broaches used to shape bores in bone. The tools can also include a system for removing an implant from bone. Implants can include assemblies of one or more implant structures that make possible the achievement of diverse interventions involving the fusion and/or stabilization of lumbar and sacral vertebra in a non-invasive manner, with minimal incision, and without the necessitating the removing the intervertebral disc. Implants for fusing both sacroiliac joints of a patient include a long implant that extends across both sacroiliac joints.

11 Claims, 101 Drawing Sheets

Related U.S. Application Data division of application No. 15/208,588, filed on Jul. 12, 2016, now Pat. No. 10,363,140, which is a continuation-in-part of application No. 14/216,938, filed on Mar. 17, 2014, now abandoned, and a continuation-in-part of application No. 14/217,089, filed on Mar. 17, 2014, now abandoned, and a continuation-in-part of application No. 14/216,790, filed on Mar. 17, 2014, now abandoned, and a continuation-in-part of application No. 14/217,008, filed on Mar. 17, 2014, now abandoned, said application No. 15/208,588 is a continuation-in-part of application No. 13/794,542, filed on Mar. 11, 2013, now abandoned.

(60) Provisional application No. 61/793,576, filed on Mar. 15, 2013, provisional application No. 61/793,357, filed on Mar. 15, 2013, provisional application No. 61/798,267, filed on Mar. 15, 2013, provisional application No. 61/800,966, filed on Mar. 15, 2013, provisional application No. 61/609,043, filed on Mar. 9, 2012.

(51) Int. Cl.
| | | |
|---|---|---|
| *A61F 2/44* | (2006.01) | |
| *A61B 17/16* | (2006.01) | |
| *A61B 17/02* | (2006.01) | |
| *A61B 17/34* | (2006.01) | |
| *A61B 17/84* | (2006.01) | |
| *A61B 17/88* | (2006.01) | |
| *A61B 17/70* | (2006.01) | |
| *A61B 17/92* | (2006.01) | |
| *A61B 17/68* | (2006.01) | |
| *A61B 17/00* | (2006.01) | |

(52) U.S. Cl.
CPC ...... *A61B 17/1659* (2013.01); *A61B 17/1664* (2013.01); *A61B 17/1671* (2013.01); *A61B 17/3439* (2013.01); *A61B 17/68* (2013.01); *A61B 17/7055* (2013.01); *A61B 17/7064* (2013.01); *A61B 17/7065* (2013.01); *A61B 17/7097* (2013.01); *A61B 17/84* (2013.01); *A61B 17/846* (2013.01); *A61B 17/88* (2013.01); *A61B 17/8872* (2013.01); *A61B 17/92* (2013.01); *A61F 2/4455* (2013.01); *A61F 2/4611* (2013.01); *A61B 2017/00526* (2013.01); *A61B 2017/3433* (2013.01); *A61F 2002/3092* (2013.01); *A61F 2002/3093* (2013.01); *A61F 2002/30156* (2013.01); *A61F 2002/30995* (2013.01)

(58) Field of Classification Search
CPC . A61B 17/3439; A61B 17/68; A61B 17/7055; A61B 17/7064; A61B 17/7065; A61B 17/7097; A61B 17/84; A61B 17/846; A61B 17/88; A61B 17/8872; A61B 17/92; A61B 2017/00526; A61B 2017/3433; A61F 2002/30156; A61F 2002/3092; A61F 2002/3093; A61F 2002/30995; A61F 2/30988; A61F 2/4455; A61F 2/4611
See application file for complete search history.

(56) References Cited

U.S. PATENT DOCUMENTS

| | | |
|---|---|---|
| 2,243,717 A | 5/1941 | Moreira |
| 2,414,882 A | 7/1947 | Longfellow |
| 2,562,419 A | 7/1951 | Ferris |
| 2,675,801 A | 4/1954 | Bambara et al. |
| 2,697,433 A | 12/1954 | Zehnder |
| 3,076,453 A * | 2/1963 | Tronzo ............... A61B 17/746 606/67 |
| 3,506,982 A | 4/1970 | Steffee |
| 3,694,821 A | 10/1972 | Moritz |
| 3,709,218 A | 1/1973 | Halloran |
| 3,744,488 A | 7/1973 | Cox |
| 4,059,115 A | 11/1977 | Jumashev et al. |
| 4,156,943 A | 6/1979 | Collier |
| 4,197,645 A | 4/1980 | Scheicher |
| 4,292,964 A | 10/1981 | Ulrich |
| 4,341,206 A | 7/1982 | Perrett |
| 4,344,190 A | 8/1982 | Lee et al. |
| 4,350,151 A | 9/1982 | Scott |
| 4,399,813 A | 8/1983 | Barber |
| 4,423,721 A | 1/1984 | Otte et al. |
| 4,475,545 A | 10/1984 | Ender |
| 4,501,269 A | 2/1985 | Bagby |
| 4,569,338 A | 2/1986 | Edwards |
| 4,612,918 A | 9/1986 | Slocum |
| 4,622,959 A | 11/1986 | Marcus |
| 4,630,601 A | 12/1986 | Harder et al. |
| 4,638,799 A | 1/1987 | Moore |
| 4,657,550 A | 4/1987 | Daher |
| 4,743,256 A | 5/1988 | Brantigan |
| 4,773,402 A | 9/1988 | Asher et al. |
| 4,787,378 A | 11/1988 | Sodhi |
| 4,790,303 A | 12/1988 | Steffee |
| 4,834,757 A | 5/1989 | Brantigan |
| 4,846,162 A | 7/1989 | Moehring |
| 4,877,019 A | 10/1989 | Vives |
| 4,878,915 A | 11/1989 | Brantigan |
| 4,898,186 A | 2/1990 | Ikada et al. |
| 4,904,261 A | 2/1990 | Dove et al. |
| 4,950,270 A | 8/1990 | Bowman et al. |
| 4,961,740 A | 10/1990 | Ray et al. |
| 4,969,888 A | 11/1990 | Scholten et al. |
| 4,981,481 A | 1/1991 | Kranz et al. |
| 5,034,011 A | 7/1991 | Howland |
| 5,034,013 A | 7/1991 | Kyle et al. |
| 5,035,697 A | 7/1991 | Frigg |
| 5,041,118 A | 8/1991 | Wasilewski |
| 5,053,035 A | 10/1991 | McLaren |
| 5,059,193 A | 10/1991 | Kuslich |
| 5,066,296 A | 11/1991 | Chapman et al. |
| 5,098,434 A | 3/1992 | Serbousek |
| 5,102,414 A | 4/1992 | Kirsch |
| 5,108,397 A | 4/1992 | White |
| 5,122,141 A | 6/1992 | Simpson et al. |
| 5,139,498 A | 8/1992 | Astudillo Ley |
| 5,139,500 A | 8/1992 | Schwartz |
| 5,147,367 A | 9/1992 | Ellis |
| 5,147,402 A | 9/1992 | Bohler et al. |
| 5,190,551 A | 3/1993 | Chin et al. |
| 5,197,961 A | 3/1993 | Castle |
| 5,242,444 A | 9/1993 | MacMillan |
| 5,298,254 A | 3/1994 | Prewett et al. |
| 5,334,205 A | 8/1994 | Cain |
| 5,380,325 A | 1/1995 | Lahille et al. |
| 5,390,683 A | 2/1995 | Pisharodi |
| 5,433,718 A | 7/1995 | Brinker |
| 5,443,466 A | 8/1995 | Shah |
| 5,458,638 A | 10/1995 | Kuslich et al. |
| 5,470,334 A | 11/1995 | Ross et al. |
| 5,480,402 A | 1/1996 | Kim |
| 5,569,249 A | 10/1996 | James et al. |
| 5,591,235 A | 1/1997 | Kuslich |
| 5,593,409 A | 1/1997 | Michelson |
| 5,607,424 A | 3/1997 | Tropiano |
| 5,609,635 A | 3/1997 | Michelson |
| 5,609,636 A | 3/1997 | Kohrs et al. |
| 5,626,616 A | 5/1997 | Speece |
| 5,643,264 A | 7/1997 | Sherman et al. |
| 5,645,599 A | 7/1997 | Samani |
| 5,658,337 A | 8/1997 | Kohrs et al. |
| 5,667,510 A | 9/1997 | Combs |
| 5,669,909 A | 9/1997 | Zdeblick et al. |

(56) References Cited

U.S. PATENT DOCUMENTS

| | | | |
|---|---|---|---|
| 5,672,178 | A | 9/1997 | Petersen |
| 5,683,391 | A | 11/1997 | Boyd |
| 5,709,683 | A | 1/1998 | Bagby |
| 5,713,904 | A | 2/1998 | Errico et al. |
| 5,716,358 | A | 2/1998 | Ochoa et al. |
| 5,725,581 | A | 3/1998 | Brånemark |
| 5,743,912 | A | 4/1998 | LaHille et al. |
| 5,759,035 | A | 6/1998 | Ricci |
| 5,766,174 | A | 6/1998 | Perry |
| 5,766,252 | A | 6/1998 | Henry et al. |
| 5,766,261 | A | 6/1998 | Neal et al. |
| 5,788,699 | A | 8/1998 | Bobst et al. |
| 5,800,440 | A | 9/1998 | Stead |
| 5,868,749 | A | 2/1999 | Reed |
| 5,897,556 | A | 4/1999 | Drewry et al. |
| 5,928,239 | A | 7/1999 | Mirza |
| 5,941,885 | A | 8/1999 | Jackson |
| 5,961,522 | A | 10/1999 | Mehdizadeh |
| 5,961,554 | A | 10/1999 | Janson et al. |
| 6,010,507 | A | 1/2000 | Rudloff |
| 6,015,409 | A | 1/2000 | Jackson |
| 6,030,162 | A | 2/2000 | Huebner et al. |
| 6,053,916 | A | 4/2000 | Moore |
| 6,056,749 | A | 5/2000 | Kuslich |
| 6,066,175 | A | 5/2000 | Henderson et al. |
| 6,086,589 | A | 7/2000 | Kuslich et al. |
| 6,096,080 | A | 8/2000 | Nicholson et al. |
| 6,120,292 | A | 9/2000 | Buser et al. |
| 6,120,504 | A | 9/2000 | Brumback et al. |
| 6,143,031 | A | 11/2000 | Knothe et al. |
| 6,197,062 | B1 | 3/2001 | Fenlin |
| 6,206,924 | B1 | 3/2001 | Timm |
| 6,210,442 | B1 | 4/2001 | Wing et al. |
| 6,214,049 | B1 | 4/2001 | Gayer et al. |
| 6,221,074 | B1 | 4/2001 | Cole et al. |
| 6,224,607 | B1 | 5/2001 | Michelson |
| 6,241,732 | B1 | 6/2001 | Overaker et al. |
| 6,264,657 | B1 | 7/2001 | Urbahns et al. |
| 6,270,528 | B1 | 8/2001 | McKay |
| 6,287,343 | B1 | 9/2001 | Kuslich et al. |
| 6,302,885 | B1 | 10/2001 | Essiger |
| 6,302,914 | B1 | 10/2001 | Michelson |
| 6,306,140 | B1 | 10/2001 | Siddiqui |
| 6,319,253 | B1 | 11/2001 | Ackeret et al. |
| 6,406,498 | B1 | 6/2002 | Tormala et al. |
| 6,409,768 | B1 | 6/2002 | Tepic et al. |
| 6,451,020 | B1 | 9/2002 | Zucherman et al. |
| 6,471,707 | B1 | 10/2002 | Miller et al. |
| 6,485,518 | B1 | 11/2002 | Cornwall et al. |
| 6,497,707 | B1 | 12/2002 | Bowman et al. |
| 6,517,541 | B1 | 2/2003 | Sesic |
| 6,520,969 | B2 | 2/2003 | Lambrecht et al. |
| 6,524,314 | B1 | 2/2003 | Dean et al. |
| 6,527,775 | B1 | 3/2003 | Warburton |
| 6,556,857 | B1 | 4/2003 | Estes et al. |
| 6,558,386 | B1 | 5/2003 | Cragg |
| 6,565,566 | B1 | 5/2003 | Wagner et al. |
| 6,575,899 | B1 | 6/2003 | Foley et al. |
| 6,575,991 | B1 | 6/2003 | Chesbrough et al. |
| 6,579,293 | B1 | 6/2003 | Chandran |
| 6,582,431 | B1 | 6/2003 | Ray |
| 6,582,467 | B1 | 6/2003 | Teitelbaum et al. |
| 6,595,998 | B2 | 7/2003 | Johnson et al. |
| 6,602,293 | B1 | 8/2003 | Biermann et al. |
| 6,605,090 | B1 | 8/2003 | Trieu et al. |
| 6,607,530 | B1 | 8/2003 | Carl et al. |
| 6,620,163 | B1 | 9/2003 | Michelson |
| 6,635,059 | B2 | 10/2003 | Randall et al. |
| 6,666,868 | B2 | 12/2003 | Fallin |
| 6,669,529 | B1 | 12/2003 | Scaries |
| 6,673,075 | B2 | 1/2004 | Santilli |
| 6,692,501 | B2 | 2/2004 | Michelson |
| 6,712,852 | B1 | 3/2004 | Chung et al. |
| 6,723,099 | B1 | 4/2004 | Goshert |
| 6,723,100 | B2 | 4/2004 | Biedermann et al. |
| 6,740,118 | B2 | 5/2004 | Eisermann et al. |
| 6,743,257 | B2 | 6/2004 | Castro |
| D493,533 | S | 7/2004 | Blain |
| 6,793,656 | B1 | 9/2004 | Mathews |
| 6,827,740 | B1 | 12/2004 | Michelson |
| 6,984,235 | B2 | 1/2006 | Huebner |
| 6,989,033 | B1 | 1/2006 | Schmidt |
| 6,991,461 | B2 | 1/2006 | Gittleman |
| 6,993,406 | B1 | 1/2006 | Cesarano et al. |
| 7,018,416 | B2 | 3/2006 | Hanson et al. |
| 7,118,579 | B2 | 10/2006 | Michelson |
| 7,147,666 | B1 | 12/2006 | Grisoni |
| 7,175,663 | B1 | 2/2007 | Stone |
| 7,211,085 | B2 | 5/2007 | Michelson |
| 7,223,269 | B2 | 5/2007 | Chappuis |
| 7,314,488 | B2 | 1/2008 | Reiley |
| 7,335,205 | B2 | 2/2008 | Aeschlimann et al. |
| 7,338,500 | B2 | 3/2008 | Chappuis |
| 7,396,365 | B2 | 7/2008 | Michelson |
| 7,452,359 | B1 | 11/2008 | Michelson |
| 7,452,369 | B2 | 11/2008 | Barry |
| 7,481,831 | B2 | 1/2009 | Bonutti |
| 7,527,649 | B1 | 5/2009 | Blain |
| 7,534,254 | B1 | 5/2009 | Michelson |
| 7,537,616 | B1 | 5/2009 | Branch et al. |
| 7,569,054 | B2 | 8/2009 | Michelson |
| 7,569,059 | B2 | 8/2009 | Cerundolo |
| 7,601,155 | B2 | 10/2009 | Petersen |
| 7,608,097 | B2 | 10/2009 | Kyle |
| 7,648,509 | B2 | 1/2010 | Stark |
| 7,686,805 | B2 | 3/2010 | Michelson |
| 7,699,852 | B2 | 4/2010 | Frankel et al. |
| 7,708,761 | B2 | 5/2010 | Petersen |
| 7,727,235 | B2 | 6/2010 | Contiliano et al. |
| 7,758,646 | B2 | 7/2010 | Khandkar et al. |
| 7,780,704 | B2 | 8/2010 | Markworth et al. |
| 7,846,162 | B2 | 12/2010 | Nelson et al. |
| 7,850,732 | B2 | 12/2010 | Heinz |
| 7,857,832 | B2 | 12/2010 | Cuibert et al. |
| 7,887,565 | B2 | 2/2011 | Michelson |
| 7,892,265 | B2 | 2/2011 | Perez-Cruet et al. |
| 7,901,439 | B2 | 3/2011 | Horton |
| 7,909,832 | B2 | 3/2011 | Michelson |
| 7,922,765 | B2 | 4/2011 | Reiley |
| 7,942,879 | B2 | 5/2011 | Christie et al. |
| 7,951,176 | B2 | 5/2011 | Grady et al. |
| 8,052,728 | B2 | 11/2011 | Hestad |
| 8,062,365 | B2 | 11/2011 | Schwab |
| 8,066,705 | B2 | 11/2011 | Michelson |
| 8,066,709 | B2 | 11/2011 | Michelson |
| 8,092,505 | B2 | 1/2012 | Sommers |
| 8,142,481 | B2 | 3/2012 | Warnick |
| 8,202,305 | B2 | 6/2012 | Reiley |
| 8,221,499 | B2 | 7/2012 | Lazzara et al. |
| 8,257,398 | B2 | 9/2012 | Jackson |
| 8,268,099 | B2 | 9/2012 | O'Neill et al. |
| 8,308,779 | B2 | 11/2012 | Reiley |
| 8,308,783 | B2 | 11/2012 | Morris et al. |
| 8,317,862 | B2 | 11/2012 | Troger et al. |
| 8,348,950 | B2 | 1/2013 | Assell et al. |
| 8,350,186 | B2 | 1/2013 | Jones et al. |
| 8,388,667 | B2 | 3/2013 | Reiley et al. |
| 8,394,129 | B2 | 3/2013 | Morgenstern Lopez |
| 8,398,635 | B2 | 3/2013 | Vaidya |
| 8,398,682 | B2 | 3/2013 | Jackson et al. |
| 8,414,648 | B2 | 4/2013 | Reiley |
| 8,425,570 | B2 | 4/2013 | Reiley |
| 8,430,930 | B2 | 4/2013 | Hunt |
| 8,449,585 | B2 | 5/2013 | Wallenstein et al. |
| 8,467,851 | B2 | 6/2013 | Mire et al. |
| 8,470,004 | B2 | 6/2013 | Reiley |
| 8,475,505 | B2 | 7/2013 | Nebosky et al. |
| 8,529,608 | B2 | 9/2013 | Terrill et al. |
| 8,597,299 | B2 | 12/2013 | Farr et al. |
| 8,608,802 | B2 | 12/2013 | Bagga |
| D697,209 | S | 1/2014 | Walthall et al. |
| 8,641,737 | B2 | 2/2014 | Matthis et al. |
| 8,663,332 | B1 | 3/2014 | To et al. |
| 8,672,986 | B2 | 3/2014 | Klaue et al. |

(56) References Cited

U.S. PATENT DOCUMENTS

| | | |
|---|---|---|
| 8,734,462 B2 | 5/2014 | Reiley et al. |
| 8,778,026 B2 | 7/2014 | Mauldin |
| 8,840,623 B2 | 9/2014 | Reiley |
| 8,840,651 B2 | 9/2014 | Reiley |
| 8,845,693 B2 | 9/2014 | Smith et al. |
| 8,858,601 B2 | 10/2014 | Reiley |
| 8,888,827 B2 | 11/2014 | Harper et al. |
| 8,894,685 B2 | 11/2014 | Mickiewicz et al. |
| 8,920,477 B2 | 12/2014 | Reiley |
| 8,926,670 B2 | 1/2015 | Jackson |
| 8,936,623 B2 | 1/2015 | Jackson |
| 8,945,190 B2 | 2/2015 | Cuibert et al. |
| 8,945,193 B2 | 2/2015 | Kirschman |
| 8,951,254 B2 | 2/2015 | Mayer et al. |
| 8,951,293 B2 | 2/2015 | Glazer et al. |
| 8,951,295 B2 | 2/2015 | Matityahu et al. |
| 8,961,571 B2 | 2/2015 | Lee et al. |
| 8,979,911 B2 | 3/2015 | Martineau et al. |
| 8,986,348 B2 | 3/2015 | Reiley |
| RE45,484 E | 4/2015 | Foley et al. |
| 9,039,743 B2 | 5/2015 | Reiley |
| 9,044,321 B2 | 6/2015 | Mauldin et al. |
| 9,060,876 B1 | 6/2015 | To et al. |
| 9,089,371 B1 | 7/2015 | Faulhaber |
| D738,498 S | 9/2015 | Frey et al. |
| 9,131,955 B2 | 9/2015 | Swofford |
| 9,149,286 B1 | 10/2015 | Greenhalgh et al. |
| 9,198,676 B2 | 12/2015 | Pilgeram et al. |
| 9,220,535 B2 | 12/2015 | Röbling et al. |
| 9,314,286 B2 | 4/2016 | Bottlang et al. |
| 9,314,348 B2 | 4/2016 | Emstad |
| 9,358,047 B2 | 6/2016 | Mishra et al. |
| 9,358,057 B1 | 6/2016 | Whipple et al. |
| 9,375,243 B1 | 6/2016 | Vestgaarden |
| 9,375,323 B2 | 6/2016 | Reiley |
| 9,445,852 B2 | 9/2016 | Sweeney |
| 9,451,999 B2 | 9/2016 | Simpson et al. |
| 9,452,065 B1 | 9/2016 | Lawson |
| 9,486,264 B2 | 11/2016 | Reiley et al. |
| 9,492,201 B2 | 11/2016 | Reiley |
| 9,498,264 B2 | 11/2016 | Harshman et al. |
| 9,510,872 B2 | 12/2016 | Donner et al. |
| 9,517,095 B2 | 12/2016 | Vaidya |
| 9,526,548 B2 | 12/2016 | Asfora |
| 9,554,909 B2 | 1/2017 | Donner |
| 9,561,063 B2 | 2/2017 | Reiley |
| 9,566,100 B2 | 2/2017 | Asfora |
| 9,603,613 B2 | 3/2017 | Schoenefeld et al. |
| 9,603,644 B2 | 3/2017 | Sweeney |
| D783,821 S | 4/2017 | Folsom et al. |
| 9,615,856 B2 | 4/2017 | Arnett et al. |
| 9,622,783 B2 | 4/2017 | Reiley et al. |
| 9,655,656 B2 | 5/2017 | Whipple |
| 9,662,124 B2 | 5/2017 | Assell et al. |
| 9,662,128 B2 | 5/2017 | Reiley |
| 9,662,157 B2 | 5/2017 | Schneider et al. |
| 9,662,158 B2 | 5/2017 | Reiley |
| 9,675,394 B2 | 6/2017 | Reiley |
| 9,743,969 B2 | 8/2017 | Reiley |
| 9,757,154 B2 | 9/2017 | Donner et al. |
| 9,763,695 B2 | 9/2017 | Mirda |
| 9,763,802 B2 | 9/2017 | Baynham |
| 9,775,648 B2 | 10/2017 | Greenberg et al. |
| 9,788,961 B2 | 10/2017 | Donner et al. |
| 9,808,298 B2 | 11/2017 | Stroncek et al. |
| 9,808,299 B2 | 11/2017 | Goel et al. |
| 9,808,337 B2 | 11/2017 | Housman et al. |
| 9,820,789 B2 | 11/2017 | Reiley |
| 9,833,321 B2 | 12/2017 | Rindal et al. |
| 9,839,448 B2 | 12/2017 | Reckling et al. |
| 9,848,889 B2 | 12/2017 | Taylor et al. |
| 9,848,892 B2 | 12/2017 | Biedermann et al. |
| 9,883,874 B1 | 2/2018 | Vestgaarden |
| 9,888,911 B2 | 2/2018 | Siegal |
| 9,936,983 B2 | 4/2018 | Mesiwala et al. |
| 9,949,776 B2 | 4/2018 | Mobasser et al. |
| 9,949,843 B2 | 4/2018 | Reiley et al. |
| 9,956,013 B2 | 5/2018 | Reiley et al. |
| 9,993,276 B2 | 6/2018 | Russell |
| 9,993,277 B2 | 6/2018 | Krinke et al. |
| 9,999,449 B2 | 6/2018 | Bonutti |
| 10,004,547 B2 | 6/2018 | Reiley |
| 10,034,676 B2 | 7/2018 | Donner |
| 10,058,430 B2 | 8/2018 | Donner et al. |
| 10,064,670 B2 | 9/2018 | Mootien et al. |
| 10,166,022 B2 | 1/2019 | Early et al. |
| 10,166,033 B2 | 1/2019 | Reiley et al. |
| 10,179,014 B1 | 1/2019 | Menmuir et al. |
| 10,188,403 B2 | 1/2019 | Mirochinik et al. |
| 10,194,951 B2 | 2/2019 | Jackson et al. |
| 10,194,962 B2 | 2/2019 | Schneider et al. |
| 10,201,427 B2 | 2/2019 | Mauldin et al. |
| 10,219,885 B2 | 3/2019 | Mamo et al. |
| D846,977 S | 4/2019 | Williams et al. |
| 10,245,044 B2 | 4/2019 | Petersen |
| 10,245,076 B2 | 4/2019 | Fitzpatrick |
| 10,245,087 B2 | 4/2019 | Donner et al. |
| 10,258,380 B2 | 4/2019 | Sinha |
| 10,258,393 B2 | 4/2019 | Caploon et al. |
| 10,258,394 B2 | 4/2019 | Harshman et al. |
| 10,271,882 B2 | 4/2019 | Biedermann et al. |
| 10,278,737 B2 | 5/2019 | Smith |
| 10,285,745 B2 | 5/2019 | Cummins et al. |
| 10,292,778 B2 | 5/2019 | Kostrzewski et al. |
| 10,314,631 B2 | 6/2019 | Gonzalez Blohm et al. |
| 10,321,937 B2 | 6/2019 | Cormier et al. |
| 10,321,945 B2 | 6/2019 | Schifano et al. |
| 10,335,202 B2 | 7/2019 | Ziolo et al. |
| 10,335,204 B2 | 7/2019 | Matthis et al. |
| 10,335,206 B2 | 7/2019 | Nichols et al. |
| 10,335,211 B2 | 7/2019 | Chan et al. |
| 10,335,212 B2 | 7/2019 | Paolino et al. |
| 10,335,216 B2 | 7/2019 | Mari et al. |
| 10,335,217 B2 | 7/2019 | Lindner |
| 10,342,586 B2 | 7/2019 | Schneider |
| 10,349,983 B2 | 7/2019 | Purcell et al. |
| 10,357,287 B2 | 7/2019 | Schlaepfer et al. |
| 10,363,070 B2 | 7/2019 | Jackson et al. |
| 10,363,140 B2 | 7/2019 | Mauldin et al. |
| 10,363,143 B2 | 7/2019 | Neubardt |
| 10,368,919 B2 | 8/2019 | Pham et al. |
| 10,413,332 B2 | 9/2019 | Schumacher et al. |
| 10,426,533 B2 | 10/2019 | Mauldin et al. |
| 10,426,539 B2 | 10/2019 | Schifano et al. |
| 10,433,880 B2 | 10/2019 | Donner et al. |
| 10,456,268 B2 | 10/2019 | Mercier et al. |
| 10,478,227 B2 | 11/2019 | Left et al. |
| 10,492,841 B2 | 12/2019 | Hartdegen et al. |
| 10,492,921 B2 | 12/2019 | McShane, III et al. |
| 10,517,734 B2 | 12/2019 | Donner |
| 10,531,898 B2 | 1/2020 | Boulot |
| 10,531,904 B2 | 1/2020 | Kolb |
| 10,537,340 B2 | 1/2020 | Mirochinik et al. |
| 10,555,758 B2 | 2/2020 | Magee et al. |
| 10,588,676 B2 | 3/2020 | Kang et al. |
| 10,588,677 B2 | 3/2020 | McDonnell |
| 10,596,003 B2 | 3/2020 | Donner et al. |
| 10,603,087 B2 | 3/2020 | Brenzel et al. |
| 10,610,275 B2 | 4/2020 | Brianza |
| 10,610,370 B2 | 4/2020 | Baynham |
| 10,617,453 B2 | 4/2020 | Beckett et al. |
| 10,653,454 B2 | 5/2020 | Frey et al. |
| 10,660,657 B2 | 5/2020 | Slobitker et al. |
| 10,660,679 B2 | 5/2020 | Kang et al. |
| 10,660,684 B2 | 5/2020 | Kang et al. |
| 10,682,131 B2 | 6/2020 | Fallin et al. |
| 10,682,150 B2 | 6/2020 | Stark |
| 10,682,437 B2 | 6/2020 | Roth |
| 10,711,334 B2 | 7/2020 | Patel et al. |
| 10,729,475 B2 | 8/2020 | Childs |
| 10,729,482 B2 | 8/2020 | Fantigrossi et al. |
| 10,743,995 B2 | 8/2020 | Fallin et al. |
| 10,758,283 B2 | 9/2020 | Frey et al. |
| 10,792,074 B2 | 10/2020 | Jackson |

(56) References Cited

U.S. PATENT DOCUMENTS

| | | |
|---|---|---|
| 10,799,277 B2 | 10/2020 | Kulper et al. |
| 10,799,367 B2 | 10/2020 | Vrionis et al. |
| 10,806,597 B2 | 10/2020 | Sournac et al. |
| 10,842,634 B2 | 11/2020 | Pasini et al. |
| D905,232 S | 12/2020 | Schifano et al. |
| 10,898,333 B2 | 1/2021 | Cordaro |
| 10,932,838 B2 | 3/2021 | Mehl et al. |
| 10,959,758 B2 | 3/2021 | Mesiwala et al. |
| 10,959,830 B2 | 3/2021 | Williams et al. |
| 10,993,757 B2 | 5/2021 | Schifano et al. |
| 11,006,985 B2 | 5/2021 | Caploon et al. |
| D922,568 S | 6/2021 | Schifano et al. |
| 11,033,309 B2 | 6/2021 | Zadeh |
| 11,071,573 B2 | 7/2021 | Schneider et al. |
| 11,116,519 B2 | 9/2021 | Sand et al. |
| 11,147,591 B2 | 10/2021 | Jackson |
| 11,147,597 B2 | 10/2021 | Jackson |
| 11,147,688 B2 | 10/2021 | Reckling et al. |
| 11,172,939 B2 | 11/2021 | Donner et al. |
| 11,224,467 B2 | 1/2022 | Peterson et al. |
| 11,234,830 B2 | 2/2022 | Mesiwala et al. |
| 11,266,767 B2 | 3/2022 | Roth et al. |
| 11,284,798 B2 | 3/2022 | Donner et al. |
| 11,284,887 B2 | 3/2022 | Hartdegen et al. |
| 11,291,485 B2 | 4/2022 | Mauldin et al. |
| D951,455 S | 5/2022 | Ginn |
| 11,337,821 B2 | 5/2022 | Mauldin et al. |
| 11,369,419 B2 | 6/2022 | Mesiwala et al. |
| 2001/0012942 A1 | 8/2001 | Estes et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0019637 A1 | 2/2002 | Frey et al. |
| 2002/0029043 A1 | 3/2002 | Ahrens et al. |
| 2002/0038123 A1 | 3/2002 | Visotsky et al. |
| 2002/0049497 A1 | 4/2002 | Mason |
| 2002/0077641 A1 | 6/2002 | Michelson |
| 2002/0082598 A1 | 6/2002 | Teitelbaum |
| 2002/0120275 A1 | 8/2002 | Schmieding et al. |
| 2002/0120335 A1 | 8/2002 | Angelucci et al. |
| 2002/0128652 A1 | 9/2002 | Ferree |
| 2002/0143334 A1 | 10/2002 | von Hoffmann et al. |
| 2002/0143335 A1 | 10/2002 | von Hoffmann et al. |
| 2002/0151903 A1 | 10/2002 | Takei et al. |
| 2002/0169507 A1 | 11/2002 | Malone |
| 2002/0183858 A1 | 12/2002 | Contiliano et al. |
| 2002/0198527 A1 | 12/2002 | Mückter |
| 2003/0018336 A1 | 1/2003 | Vandewalle |
| 2003/0032961 A1 | 2/2003 | Pelo et al. |
| 2003/0050642 A1 | 3/2003 | Schmieding et al. |
| 2003/0065332 A1 | 4/2003 | TenHuisen et al. |
| 2003/0074000 A1 | 4/2003 | Roth et al. |
| 2003/0078660 A1 | 4/2003 | Clifford et al. |
| 2003/0083668 A1 | 5/2003 | Rogers et al. |
| 2003/0083688 A1 | 5/2003 | Simonson |
| 2003/0088251 A1 | 5/2003 | Braun et al. |
| 2003/0097131 A1 | 5/2003 | Schon et al. |
| 2003/0139815 A1 | 7/2003 | Grooms et al. |
| 2003/0181979 A1 | 9/2003 | Ferree |
| 2003/0181982 A1 | 9/2003 | Kuslich |
| 2003/0199983 A1 | 10/2003 | Michelson |
| 2003/0229358 A1 | 12/2003 | Errico et al. |
| 2003/0233146 A1 | 12/2003 | Grinberg et al. |
| 2003/0233147 A1 | 12/2003 | Nicholson et al. |
| 2004/0010315 A1 | 1/2004 | Song |
| 2004/0024458 A1 | 2/2004 | Senegas et al. |
| 2004/0034422 A1 | 2/2004 | Errico et al. |
| 2004/0073216 A1 | 4/2004 | Lieberman |
| 2004/0073314 A1 | 4/2004 | White et al. |
| 2004/0082955 A1 | 4/2004 | Zirkle |
| 2004/0087948 A1 | 5/2004 | Suddaby |
| 2004/0097927 A1 | 5/2004 | Yeung et al. |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0138750 A1 | 7/2004 | Mitchell |
| 2004/0138753 A1 | 7/2004 | Ferree |
| 2004/0147929 A1 | 7/2004 | Biedermann et al. |
| 2004/0158324 A1 | 8/2004 | Lange |
| 2004/0176287 A1 | 9/2004 | Harrison et al. |
| 2004/0176853 A1 | 9/2004 | Sennett et al. |
| 2004/0181282 A1 | 9/2004 | Zucherman et al. |
| 2004/0186572 A1 | 9/2004 | Lange et al. |
| 2004/0210221 A1 | 10/2004 | Kozak et al. |
| 2004/0225360 A1 | 11/2004 | Malone |
| 2004/0230305 A1 | 11/2004 | Gorensek et al. |
| 2004/0260286 A1 | 12/2004 | Ferree |
| 2004/0267369 A1 | 12/2004 | Lyons et al. |
| 2005/0015059 A1 | 1/2005 | Sweeney |
| 2005/0015146 A1 | 1/2005 | Louis et al. |
| 2005/0033435 A1 | 2/2005 | Belliard et al. |
| 2005/0049590 A1 | 3/2005 | Alleyne et al. |
| 2005/0055023 A1 | 3/2005 | Sohngen et al. |
| 2005/0075641 A1 | 4/2005 | Singhatat et al. |
| 2005/0080415 A1 | 4/2005 | Keyer et al. |
| 2005/0107878 A1 | 5/2005 | Conchy |
| 2005/0112397 A1 | 5/2005 | Rolfe et al. |
| 2005/0113919 A1 | 5/2005 | Cragg et al. |
| 2005/0124993 A1 | 6/2005 | Chappuis |
| 2005/0131409 A1 | 6/2005 | Chervitz et al. |
| 2005/0137605 A1 | 6/2005 | Assell et al. |
| 2005/0143837 A1 | 6/2005 | Ferree |
| 2005/0149192 A1 | 7/2005 | Zucherman et al. |
| 2005/0159749 A1 | 7/2005 | Levy et al. |
| 2005/0159812 A1 | 7/2005 | Dinger et al. |
| 2005/0165398 A1 | 7/2005 | Reiley |
| 2005/0192572 A1 | 9/2005 | Abdelgany et al. |
| 2005/0216082 A1 | 9/2005 | Wilson et al. |
| 2005/0228384 A1 | 10/2005 | Zucherman et al. |
| 2005/0246021 A1 | 11/2005 | Ringeisen et al. |
| 2005/0251146 A1 | 11/2005 | Martz et al. |
| 2005/0273101 A1 | 12/2005 | Schumacher |
| 2005/0277940 A1 | 12/2005 | Neff |
| 2006/0004396 A1* | 1/2006 | Easley .............. A61B 17/1659 606/169 |
| 2006/0036247 A1 | 2/2006 | Michelson |
| 2006/0036251 A1 | 2/2006 | Reiley |
| 2006/0036252 A1 | 2/2006 | Baynham et al. |
| 2006/0054171 A1 | 3/2006 | Dall |
| 2006/0058793 A1 | 3/2006 | Michelson |
| 2006/0058800 A1 | 3/2006 | Ainsworth et al. |
| 2006/0062825 A1 | 3/2006 | Maccecchini |
| 2006/0084986 A1 | 4/2006 | Grinberg et al. |
| 2006/0089656 A1 | 4/2006 | Allard et al. |
| 2006/0111779 A1 | 5/2006 | Petersen |
| 2006/0129247 A1 | 6/2006 | Brown et al. |
| 2006/0142772 A1 | 6/2006 | Ralph et al. |
| 2006/0161163 A1 | 7/2006 | Shino |
| 2006/0178673 A1 | 8/2006 | Curran |
| 2006/0195094 A1 | 8/2006 | McGraw et al. |
| 2006/0217717 A1 | 9/2006 | Whipple |
| 2006/0241776 A1 | 10/2006 | Brown et al. |
| 2006/0271054 A1 | 11/2006 | Sucec et al. |
| 2006/0293662 A1 | 12/2006 | Boyer, II et al. |
| 2007/0027544 A1 | 2/2007 | McCord et al. |
| 2007/0038219 A1 | 2/2007 | Matthis et al. |
| 2007/0049933 A1 | 3/2007 | Ahn et al. |
| 2007/0066977 A1 | 3/2007 | Assell et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0093898 A1 | 4/2007 | Schwab et al. |
| 2007/0106383 A1 | 5/2007 | Abdou |
| 2007/0149976 A1 | 6/2007 | Hale et al. |
| 2007/0156144 A1 | 7/2007 | Ulrich et al. |
| 2007/0156241 A1 | 7/2007 | Reiley et al. |
| 2007/0156246 A1 | 7/2007 | Meswania et al. |
| 2007/0161985 A1 | 7/2007 | Demakas et al. |
| 2007/0161989 A1 | 7/2007 | Heinz et al. |
| 2007/0173820 A1 | 7/2007 | Trieu |
| 2007/0219634 A1 | 9/2007 | Greenhalgh et al. |
| 2007/0233080 A1 | 10/2007 | Na et al. |
| 2007/0233146 A1 | 10/2007 | Henniges et al. |
| 2007/0233247 A1 | 10/2007 | Schwab |

(56) References Cited

U.S. PATENT DOCUMENTS

| | | |
|---|---|---|
| 2007/0250166 A1 | 10/2007 | McKay |
| 2007/0270879 A1 | 11/2007 | Isaza et al. |
| 2007/0282443 A1 | 12/2007 | Globerman et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0021480 A1 | 1/2008 | Chin et al. |
| 2008/0065093 A1 | 3/2008 | Assell et al. |
| 2008/0065215 A1 | 3/2008 | Reiley |
| 2008/0071356 A1 | 3/2008 | Greenhalgh et al. |
| 2008/0109083 A1 | 5/2008 | Van Hoeck et al. |
| 2008/0125868 A1 | 5/2008 | Branemark et al. |
| 2008/0132901 A1 | 6/2008 | Recoules-Arche et al. |
| 2008/0140082 A1 | 6/2008 | Erdem et al. |
| 2008/0147079 A1 | 6/2008 | Chin et al. |
| 2008/0154374 A1 | 6/2008 | Labrom |
| 2008/0161810 A1 | 7/2008 | Melkent |
| 2008/0183204 A1 | 7/2008 | Greenhalgh et al. |
| 2008/0234758 A1 | 9/2008 | Fisher et al. |
| 2008/0255562 A1 | 10/2008 | Gil et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0294202 A1 | 11/2008 | Peterson et al. |
| 2008/0306554 A1 | 12/2008 | McKinley |
| 2009/0012529 A1 | 1/2009 | Blain et al. |
| 2009/0018660 A1 | 1/2009 | Roush |
| 2009/0024174 A1 | 1/2009 | Stark |
| 2009/0036927 A1 | 2/2009 | Vestgaarden |
| 2009/0037148 A1 | 2/2009 | Lin et al. |
| 2009/0043393 A1 | 2/2009 | Duggal et al. |
| 2009/0082810 A1 | 3/2009 | Bhatnagar et al. |
| 2009/0082869 A1 | 3/2009 | Slemker et al. |
| 2009/0099602 A1 | 4/2009 | Aflatoon |
| 2009/0099610 A1 | 4/2009 | Johnson et al. |
| 2009/0105770 A1 | 4/2009 | Berrevooets et al. |
| 2009/0118771 A1 | 5/2009 | Gonzalez-Hernandez |
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0187247 A1 | 7/2009 | Metcalf, Jr. et al. |
| 2009/0216238 A1 | 8/2009 | Stark |
| 2009/0270929 A1 | 10/2009 | Suddaby |
| 2009/0287254 A1 | 11/2009 | Nayet et al. |
| 2009/0312798 A1 | 12/2009 | Varela |
| 2009/0319043 A1 | 12/2009 | McDevitt et al. |
| 2009/0324678 A1 | 12/2009 | Thorne et al. |
| 2010/0003638 A1 | 1/2010 | Collins et al. |
| 2010/0022535 A1 | 1/2010 | Lee et al. |
| 2010/0076502 A1 | 3/2010 | Guyer et al. |
| 2010/0081107 A1 | 4/2010 | Bagambisa et al. |
| 2010/0094290 A1 | 4/2010 | Vaidya |
| 2010/0094295 A1 | 4/2010 | Schnieders et al. |
| 2010/0094420 A1 | 4/2010 | Grohowski |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0131011 A1 | 5/2010 | Stark |
| 2010/0137990 A1 | 6/2010 | Apatsidis et al. |
| 2010/0145461 A1 | 6/2010 | Landry et al. |
| 2010/0160977 A1 | 6/2010 | Gephart et al. |
| 2010/0168798 A1 | 7/2010 | Clineff et al. |
| 2010/0191292 A1 | 7/2010 | DeMeo et al. |
| 2010/0262242 A1 | 10/2010 | Chavatte et al. |
| 2010/0268228 A1 | 10/2010 | Petersen |
| 2010/0280619 A1 | 11/2010 | Yuan et al. |
| 2010/0280622 A1 | 11/2010 | McKinley |
| 2010/0286778 A1 | 11/2010 | Eisermann et al. |
| 2010/0331851 A1 | 12/2010 | Huene |
| 2010/0331893 A1 | 12/2010 | Geist et al. |
| 2011/0009869 A1 | 1/2011 | Marino et al. |
| 2011/0022089 A1 | 1/2011 | Assell et al. |
| 2011/0029019 A1 | 2/2011 | Ainsworth et al. |
| 2011/0040362 A1 | 2/2011 | Godara et al. |
| 2011/0046737 A1 | 2/2011 | Teisen |
| 2011/0060373 A1 | 3/2011 | Russell et al. |
| 2011/0060375 A1 | 3/2011 | Bonutti |
| 2011/0066190 A1 | 3/2011 | Schaller et al. |
| 2011/0082551 A1 | 4/2011 | Kraus |
| 2011/0093020 A1 | 4/2011 | Wu |
| 2011/0098747 A1 | 4/2011 | Donner et al. |
| 2011/0098816 A1 | 4/2011 | Jacob et al. |
| 2011/0098817 A1 | 4/2011 | Eckhardt et al. |
| 2011/0106175 A1 | 5/2011 | Rezach |
| 2011/0153018 A1 | 6/2011 | Walters et al. |
| 2011/0160866 A1 | 6/2011 | Laurence et al. |
| 2011/0178561 A1 | 7/2011 | Roh |
| 2011/0184417 A1 | 7/2011 | Kitch et al. |
| 2011/0184518 A1 | 7/2011 | Trieu |
| 2011/0184519 A1 | 7/2011 | Trieu |
| 2011/0184520 A1 | 7/2011 | Trieu |
| 2011/0196372 A1 | 8/2011 | Murase |
| 2011/0213432 A1 | 9/2011 | Geist et al. |
| 2011/0230966 A1 | 9/2011 | Trieu |
| 2011/0238074 A1 | 9/2011 | Ek |
| 2011/0238124 A1 | 9/2011 | Richelsoph |
| 2011/0238181 A1 | 9/2011 | Trieu |
| 2011/0245930 A1 | 10/2011 | Alley et al. |
| 2011/0257755 A1 | 10/2011 | Bellemere et al. |
| 2011/0264229 A1 | 10/2011 | Donner |
| 2011/0276098 A1 | 11/2011 | Biedermann et al. |
| 2011/0295272 A1 | 12/2011 | Assell et al. |
| 2011/0295370 A1 | 12/2011 | Suh et al. |
| 2011/0313471 A1 | 12/2011 | McLean et al. |
| 2011/0313532 A1 | 12/2011 | Hunt |
| 2011/0319995 A1 | 12/2011 | Voellmicke et al. |
| 2012/0004730 A1 | 1/2012 | Castro |
| 2012/0083887 A1 | 4/2012 | Purcell et al. |
| 2012/0095560 A1 | 4/2012 | Donner |
| 2012/0179256 A1 | 7/2012 | Reiley |
| 2012/0191191 A1 | 7/2012 | Trieu |
| 2012/0215315 A1 | 8/2012 | Hochschuler et al. |
| 2012/0226318 A1 | 9/2012 | Wenger et al. |
| 2012/0253398 A1 | 10/2012 | Metcalf et al. |
| 2012/0259372 A1 | 10/2012 | Glazer et al. |
| 2012/0271424 A1 | 10/2012 | Crawford |
| 2012/0277866 A1 | 11/2012 | Kalluri et al. |
| 2012/0296428 A1 | 11/2012 | Donner |
| 2012/0323285 A1 | 12/2012 | Assell et al. |
| 2013/0018427 A1 | 1/2013 | Pham et al. |
| 2013/0030456 A1 | 1/2013 | Assell et al. |
| 2013/0030529 A1 | 1/2013 | Hunt |
| 2013/0035727 A1 | 2/2013 | Datta |
| 2013/0053852 A1 | 2/2013 | Greenhalgh et al. |
| 2013/0053854 A1 | 2/2013 | Schoenefeld et al. |
| 2013/0053902 A1 | 2/2013 | Trudeau |
| 2013/0053963 A1 | 2/2013 | Davenport |
| 2013/0072984 A1 | 3/2013 | Robinson |
| 2013/0085535 A1 | 4/2013 | Greenhalgh et al. |
| 2013/0096683 A1 | 4/2013 | Kube |
| 2013/0116793 A1 | 5/2013 | Kloss |
| 2013/0123850 A1 | 5/2013 | Schoenefeld et al. |
| 2013/0123935 A1 | 5/2013 | Hunt et al. |
| 2013/0131678 A1 | 5/2013 | Dahners |
| 2013/0144343 A1 | 6/2013 | Arnett et al. |
| 2013/0158609 A1 | 6/2013 | Mikhail et al. |
| 2013/0172736 A1 | 7/2013 | Abdou |
| 2013/0197590 A1 | 8/2013 | Assell et al. |
| 2013/0203088 A1 | 8/2013 | Baerlecken et al. |
| 2013/0218215 A1 | 8/2013 | Ginn et al. |
| 2013/0218282 A1 | 8/2013 | Hunt |
| 2013/0231746 A1 | 9/2013 | Ginn et al. |
| 2013/0237988 A1 | 9/2013 | Mauldin |
| 2013/0238093 A1* | 9/2013 | Mauldin ............ A61B 17/1671 623/16.11 |
| 2013/0245703 A1 | 9/2013 | Warren et al. |
| 2013/0245763 A1 | 9/2013 | Mauldin |
| 2013/0267836 A1 | 10/2013 | Mauldin et al. |

(56) References Cited

U.S. PATENT DOCUMENTS

| | | |
|---|---|---|
| 2013/0267961 A1 | 10/2013 | Mauldin et al. |
| 2013/0267989 A1 | 10/2013 | Mauldin et al. |
| 2013/0274890 A1 | 10/2013 | McKay |
| 2013/0325129 A1 | 12/2013 | Huang |
| 2014/0012334 A1 | 1/2014 | Armstrong et al. |
| 2014/0012340 A1 | 1/2014 | Beck et al. |
| 2014/0031934 A1 | 1/2014 | Trieu |
| 2014/0031935 A1 | 1/2014 | Donner et al. |
| 2014/0031938 A1 | 1/2014 | Lechmann et al. |
| 2014/0031939 A1 | 1/2014 | Wolfe et al. |
| 2014/0046380 A1 | 2/2014 | Asfora |
| 2014/0074175 A1 | 3/2014 | Ehler et al. |
| 2014/0088596 A1 | 3/2014 | Assell et al. |
| 2014/0088707 A1 | 3/2014 | Donner et al. |
| 2014/0121776 A1 | 5/2014 | Hunt |
| 2014/0135927 A1 | 5/2014 | Pavlov et al. |
| 2014/0142700 A1 | 5/2014 | Donner et al. |
| 2014/0172027 A1 | 6/2014 | Biedermann et al. |
| 2014/0200618 A1 | 7/2014 | Donner et al. |
| 2014/0207240 A1 | 7/2014 | Stoffman et al. |
| 2014/0257294 A1 | 9/2014 | Gedet et al. |
| 2014/0257408 A1 | 9/2014 | Trieu et al. |
| 2014/0276846 A1 | 9/2014 | Mauldin et al. |
| 2014/0276851 A1 | 9/2014 | Schneider et al. |
| 2014/0277139 A1 | 9/2014 | Vrionis et al. |
| 2014/0277165 A1 | 9/2014 | Katzman et al. |
| 2014/0277460 A1 | 9/2014 | Schifano et al. |
| 2014/0277462 A1 | 9/2014 | Yerby et al. |
| 2014/0277463 A1 | 9/2014 | Yerby et al. |
| 2014/0288649 A1 | 9/2014 | Hunt |
| 2014/0288650 A1 | 9/2014 | Hunt |
| 2014/0296982 A1 | 10/2014 | Cheng |
| 2014/0330382 A1 | 11/2014 | Mauldin |
| 2014/0364917 A1 | 12/2014 | Sandstrom et al. |
| 2015/0012051 A1 | 1/2015 | Warren et al. |
| 2015/0039037 A1 | 2/2015 | Donner et al. |
| 2015/0080951 A1 | 3/2015 | Yeh |
| 2015/0080972 A1 | 3/2015 | Chin et al. |
| 2015/0094765 A1 | 4/2015 | Donner et al. |
| 2015/0112444 A1 | 4/2015 | Aksu |
| 2015/0147397 A1 | 5/2015 | Altschuler |
| 2015/0150683 A1 | 6/2015 | Donner et al. |
| 2015/0173805 A1 | 6/2015 | Donner et al. |
| 2015/0173904 A1 | 6/2015 | Stark |
| 2015/0182268 A1 | 7/2015 | Donner et al. |
| 2015/0190149 A1 | 7/2015 | Assell et al. |
| 2015/0190187 A1 | 7/2015 | Parent et al. |
| 2015/0209094 A1 | 7/2015 | Anderson |
| 2015/0216566 A1 | 8/2015 | Mikhail et al. |
| 2015/0238203 A1 | 8/2015 | Asfora |
| 2015/0250513 A1 | 9/2015 | De Lavigne Sainte |
| 2015/0250611 A1 | 9/2015 | Schifano et al. |
| 2015/0250612 A1 | 9/2015 | Schifano et al. |
| 2015/0257892 A1 | 9/2015 | Lechmann et al. |
| 2015/0313720 A1 | 11/2015 | Lorio |
| 2015/0320450 A1 | 11/2015 | Mootien et al. |
| 2015/0320451 A1 | 11/2015 | Mootien et al. |
| 2015/0320469 A1 | 11/2015 | Biedermann et al. |
| 2015/0342753 A1 | 12/2015 | Donner et al. |
| 2016/0000488 A1 | 1/2016 | Cross, III |
| 2016/0022429 A1 | 1/2016 | Greenhalgh et al. |
| 2016/0095711 A1 | 4/2016 | Castro |
| 2016/0095721 A1 | 4/2016 | Schell et al. |
| 2016/0100870 A1 | 4/2016 | Lavigne et al. |
| 2016/0106477 A1 | 4/2016 | Hynes et al. |
| 2016/0106479 A1 | 4/2016 | Hynes et al. |
| 2016/0120661 A1 | 5/2016 | Schell et al. |
| 2016/0143671 A1 | 5/2016 | Jimenez |
| 2016/0157908 A1 | 6/2016 | Cawley et al. |
| 2016/0166301 A1 | 6/2016 | Papangelou et al. |
| 2016/0175113 A1 | 6/2016 | Lins |
| 2016/0184103 A1 | 6/2016 | Fonte et al. |
| 2016/0213487 A1 | 7/2016 | Wilson et al. |
| 2016/0242820 A1 | 8/2016 | Whipple et al. |
| 2016/0242912 A1 | 8/2016 | Lindsey et al. |
| 2016/0249940 A1 | 9/2016 | Stark |
| 2016/0287171 A1 | 10/2016 | Sand et al. |
| 2016/0287301 A1 | 10/2016 | Mehl et al. |
| 2016/0310188 A1 | 10/2016 | Marino et al. |
| 2016/0310197 A1 | 10/2016 | Black et al. |
| 2016/0324643 A1 | 11/2016 | Donner et al. |
| 2016/0324656 A1 | 11/2016 | Morris et al. |
| 2016/0374727 A1 | 12/2016 | Greenhalgh et al. |
| 2017/0014235 A1 | 1/2017 | Jones et al. |
| 2017/0020573 A1 | 1/2017 | Cain et al. |
| 2017/0020585 A1 | 1/2017 | Harshman et al. |
| 2017/0049488 A1 | 2/2017 | Vestgaarden |
| 2017/0086885 A1 | 3/2017 | Duncan et al. |
| 2017/0128083 A1 | 5/2017 | Germain |
| 2017/0128214 A1 | 5/2017 | Mayer |
| 2017/0135733 A1 | 5/2017 | Donner et al. |
| 2017/0135737 A1 | 5/2017 | Krause |
| 2017/0143513 A1 | 5/2017 | Sandstrom et al. |
| 2017/0156879 A1 | 6/2017 | Janowski |
| 2017/0156880 A1 | 6/2017 | Halverson et al. |
| 2017/0202511 A1 | 7/2017 | Chang et al. |
| 2017/0209155 A1 | 7/2017 | Petersen |
| 2017/0216036 A1 | 8/2017 | Cordaro |
| 2017/0224393 A1 | 8/2017 | Lavigne et al. |
| 2017/0246000 A1 | 8/2017 | Pavlov et al. |
| 2017/0258498 A1 | 9/2017 | Redmond et al. |
| 2017/0258506 A1 | 9/2017 | Redmond et al. |
| 2017/0258606 A1 | 9/2017 | Afzal |
| 2017/0266007 A1 | 9/2017 | Gelaude et al. |
| 2017/0296344 A1 | 10/2017 | Souza et al. |
| 2017/0303938 A1 | 10/2017 | Rindal et al. |
| 2017/0333205 A1 | 11/2017 | Joly et al. |
| 2017/0348034 A1 | 12/2017 | LaPierre et al. |
| 2017/0360570 A1 | 12/2017 | Berndt et al. |
| 2018/0008256 A1 | 1/2018 | Fallin et al. |
| 2018/0036041 A1 | 2/2018 | Pham et al. |
| 2018/0042652 A1 | 2/2018 | Mari et al. |
| 2018/0042735 A1 | 2/2018 | Schell et al. |
| 2018/0200063 A1 | 7/2018 | Kahmer et al. |
| 2018/0228617 A1 | 8/2018 | Srour et al. |
| 2018/0228621 A1 | 8/2018 | Reiley et al. |
| 2018/0235643 A1 | 8/2018 | Lins et al. |
| 2018/0256232 A1 | 9/2018 | Russell |
| 2018/0296227 A1 | 10/2018 | Meek et al. |
| 2018/0296347 A1 | 10/2018 | Hamzey et al. |
| 2018/0360512 A1 | 12/2018 | Mari |
| 2018/0368894 A1 | 12/2018 | Wieland et al. |
| 2019/0046684 A1 | 2/2019 | Roth |
| 2019/0133613 A1 | 5/2019 | Reiley et al. |
| 2019/0133783 A1 | 5/2019 | Unger et al. |
| 2019/0142606 A1 | 5/2019 | Freudenberger |
| 2019/0247094 A1 | 8/2019 | Yacoub et al. |
| 2019/0298528 A1 | 10/2019 | Lindsey et al. |
| 2019/0298542 A1 | 10/2019 | Kloss |
| 2019/0343640 A1 | 11/2019 | Donner et al. |
| 2019/0343641 A1 | 11/2019 | Mauldin et al. |
| 2019/0343653 A1 | 11/2019 | McKay |
| 2019/0388228 A1 | 12/2019 | Donner et al. |
| 2020/0000595 A1 | 1/2020 | Jones et al. |
| 2020/0008817 A1 | 1/2020 | Reiley et al. |
| 2020/0069431 A1 | 3/2020 | Boehm et al. |
| 2020/0222195 A1 | 7/2020 | Assell et al. |
| 2020/0246158 A1 | 8/2020 | Bergey |
| 2020/0315647 A1 | 10/2020 | Fojtik et al. |
| 2020/0315666 A1 | 10/2020 | Nichols et al. |
| 2020/0345507 A1 | 11/2020 | Reiley |
| 2020/0345508 A1 | 11/2020 | Reiley |
| 2020/0345509 A1 | 11/2020 | Reiley |
| 2020/0345510 A1 | 11/2020 | Reiley |
| 2021/0153911 A1 | 5/2021 | Stuart et al. |
| 2021/0169660 A1 | 6/2021 | Reckling et al. |
| 2021/0212734 A1 | 7/2021 | Mesiwala et al. |
| 2021/0228360 A1 | 7/2021 | Hunt et al. |
| 2021/0338454 A1 | 11/2021 | Afzal |
| 2021/0393408 A1 | 12/2021 | Ginn |
| 2021/0393409 A1 | 12/2021 | Ginn |
| 2022/0031474 A1 | 2/2022 | Reckling et al. |
| 2022/0096098 A1 | 3/2022 | Sand et al. |
| 2022/0117640 A1 | 4/2022 | Schneider et al. |

(56) References Cited

U.S. PATENT DOCUMENTS

| | | |
|---|---|---|
| 2022/0151668 A1 | 5/2022 | Mauldin et al. |
| 2022/0249146 A1 | 8/2022 | Mauldin et al. |
| 2022/0273447 A1 | 9/2022 | Ginn |
| 2022/0273448 A1 | 9/2022 | Ginn et al. |
| 2022/0296377 A1 | 9/2022 | Ginn et al. |
| 2022/0296378 A1 | 9/2022 | Ginn |
| 2022/0304813 A1 | 9/2022 | Ginn et al. |
| 2022/0304814 A1 | 9/2022 | Ginn |

FOREIGN PATENT DOCUMENTS

| | | |
|---|---|---|
| CN | 1909848 A | 2/2007 |
| CN | 101795632 A | 8/2010 |
| CN | 102361601 A | 2/2012 |
| DE | 102011001264 A1 | 9/2012 |
| DE | 102012106336 A1 | 1/2014 |
| EP | 1287796 A1 | 3/2003 |
| EP | 2070481 B1 | 2/2012 |
| EP | 2796104 A1 | 10/2014 |
| EP | 2590576 B1 | 10/2015 |
| EP | 2749238 B1 | 3/2017 |
| EP | 288789981 | 8/2017 |
| EP | 2341852 B1 | 8/2018 |
| EP | 2496162 B1 | 10/2018 |
| EP | 3616634 A1 | 3/2020 |
| EP | 2408389 B1 | 4/2021 |
| JP | 59200642 A | 11/1984 |
| JP | 05-176942 A | 7/1993 |
| JP | 05184615 A | 7/1993 |
| JP | 09149906 A | 10/1997 |
| JP | 10-85231 A | 4/1998 |
| JP | 11318931 A | 11/1999 |
| JP | 2002509753 A | 4/2002 |
| JP | 2003511198 A | 3/2003 |
| JP | 2003533329 A | 11/2003 |
| JP | 2003534046 A | 11/2003 |
| JP | 2004121841 | 4/2004 |
| JP | 2004512895 | 4/2004 |
| JP | 2004516866 | 6/2004 |
| JP | 2006506181 | 2/2006 |
| JP | 2007535973 A | 12/2007 |
| JP | 2008540036 A | 11/2008 |
| JP | 2009521990 A | 6/2009 |
| JP | 2009533159 A | 9/2009 |
| JP | 2010137016 A | 6/2010 |
| JP | 2015510506 A | 4/2015 |
| WO | WO97/31517 A2 | 8/1997 |
| WO | WO01/17445 A1 | 3/2001 |
| WO | WO02/38054 | 5/2002 |
| WO | WO03/007839 A2 | 1/2003 |
| WO | WO04/02344 | 1/2004 |
| WO | WO2004/043277 A1 | 5/2004 |
| WO | WO2005/009729 A2 | 2/2005 |
| WO | WO2006/003316 | 1/2006 |
| WO | WO2006/023793 A2 | 3/2006 |
| WO | WO2006/074321 A2 | 7/2006 |
| WO | WO2009/025884 A2 | 2/2009 |
| WO | WO2009/029074 A1 | 3/2009 |
| WO | WO2010/105196 A1 | 9/2010 |
| WO | WO2011/010463 A1 | 1/2011 |
| WO | WO2011/110865 A2 | 9/2011 |
| WO | WO2011/124874 A1 | 10/2011 |
| WO | WO2011/149557 A1 | 12/2011 |
| WO | WO2012/015976 A1 | 2/2012 |
| WO | WO2012/048008 A1 | 4/2012 |
| WO | WO2013/000071 A1 | 1/2013 |
| WO | WO2013/052807 A2 | 4/2013 |
| WO | WO2013/119907 A1 | 8/2013 |
| WO | WO2014/145902 A1 | 9/2014 |
| WO | WO2017/147140 A1 | 8/2017 |
| WO | WO2017/147537 A1 | 8/2017 |

OTHER PUBLICATIONS

Al-Khayer et al.; Percutaneous sacroiliac joint arthrodesis, a novel technique; J Spinal Disord Tech; vol. 21; No. 5; pp. 359-363; Jul. 2008.

Khurana et al.; Percutaneous fusion of the sacroiliac joint with hollow modular anchorage screws, clinical and radiological outcome; J Bone Joint Surg; vol. 91-B; No. 5; pp. 627-631; May 2009.

Lu et al.; Mechanical properties of porous materials; Journal of Porous Materials; 6(4); pp. 359-368; Nov. 1, 1999.

Peretz et al.; The internal bony architecture of the sacrum; Spine; 23(9); pp. 971-974; May 1, 1998.

Richards et al.; Bone density and cortical thickness in normal, osteopenic, and osteoporotic sacra; Journal of Osteoporosis; 2010(ID 504078); 5 pgs; Jun. 9, 2010.

Wise et al.; Minimally invasive sacroiliac arthrodesis, outcomes of a new technique; J Spinal Disord Tech; vol. 21; No. 8; pp. 579-584; Dec. 2008.

Mesiwala et al.; U.S. Appl. No. 17/649,265 entitled "Implants for spinal fixation and or fusion," filed Jan. 28, 2022.

Mesiwala et al.; U.S. Appl. No. 17/649,296 entitled "Implants for spinal fixation and or fusion," filed Jan. 28, 2022.

Follini et al.; U.S. Appl. No. 17/777,679 entitled "Rod coupling assemblies for bone stabilization constructs," filed May 18, 2022.

Stuart et al.; U.S. Appl. No. 17/664,353 entitled "Bone stabilizing implants and methods of placement across SI joints," filed May 20, 2022.

Mauldin et al.; U.S. Appl. No. 17/664,582 entitled "Integrated implant," filed May 23, 2022.

Stuart et al.; U.S. Appl. No. 17/812,945 entitled "Sacro-iliac joint stabilizing implants and methods of implantation," filed Jul. 15, 2022.

Mauldin et al.; U.S. Appl. No. 17/822,360 entitled "Fenestrated implant," filed Aug. 25, 2022.

\* cited by examiner

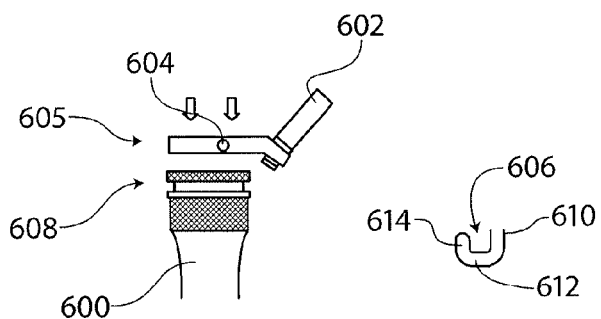
FIG. 6A   FIG. 6B
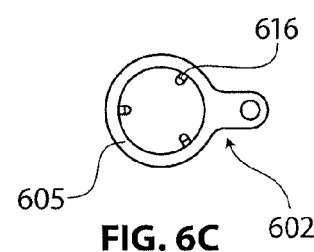
FIG. 6C
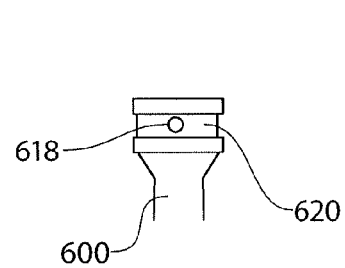
FIG. 6D
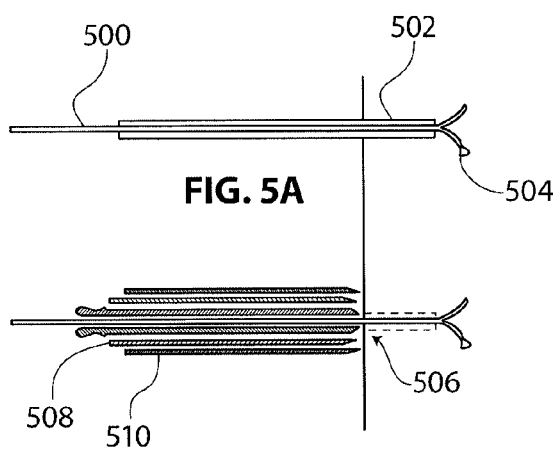
FIG. 5A
FIG. 5B
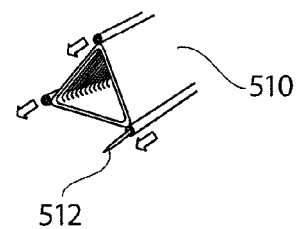
FIG. 5C

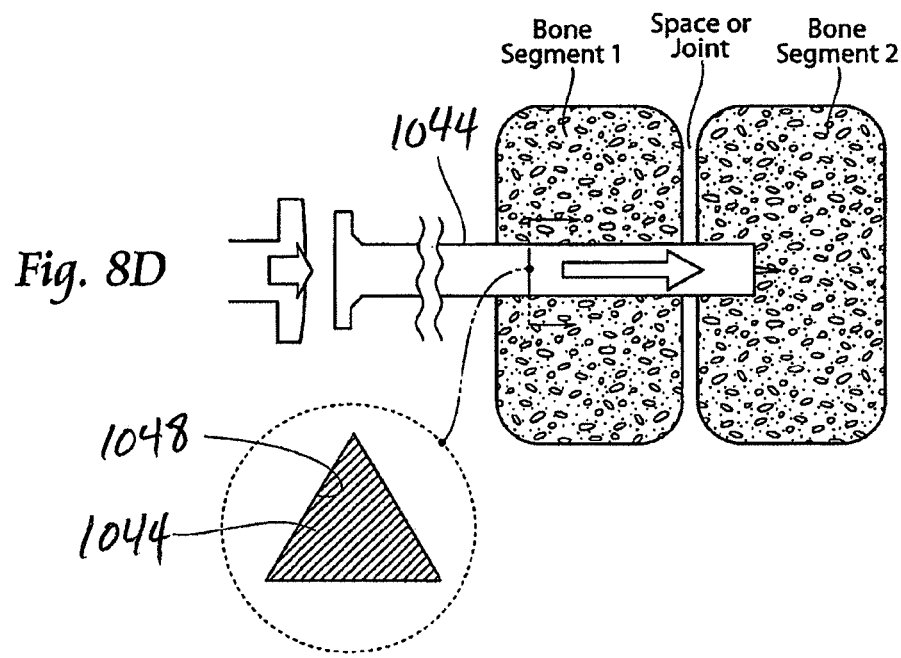

*(Anterior)*

*(Posterior)*

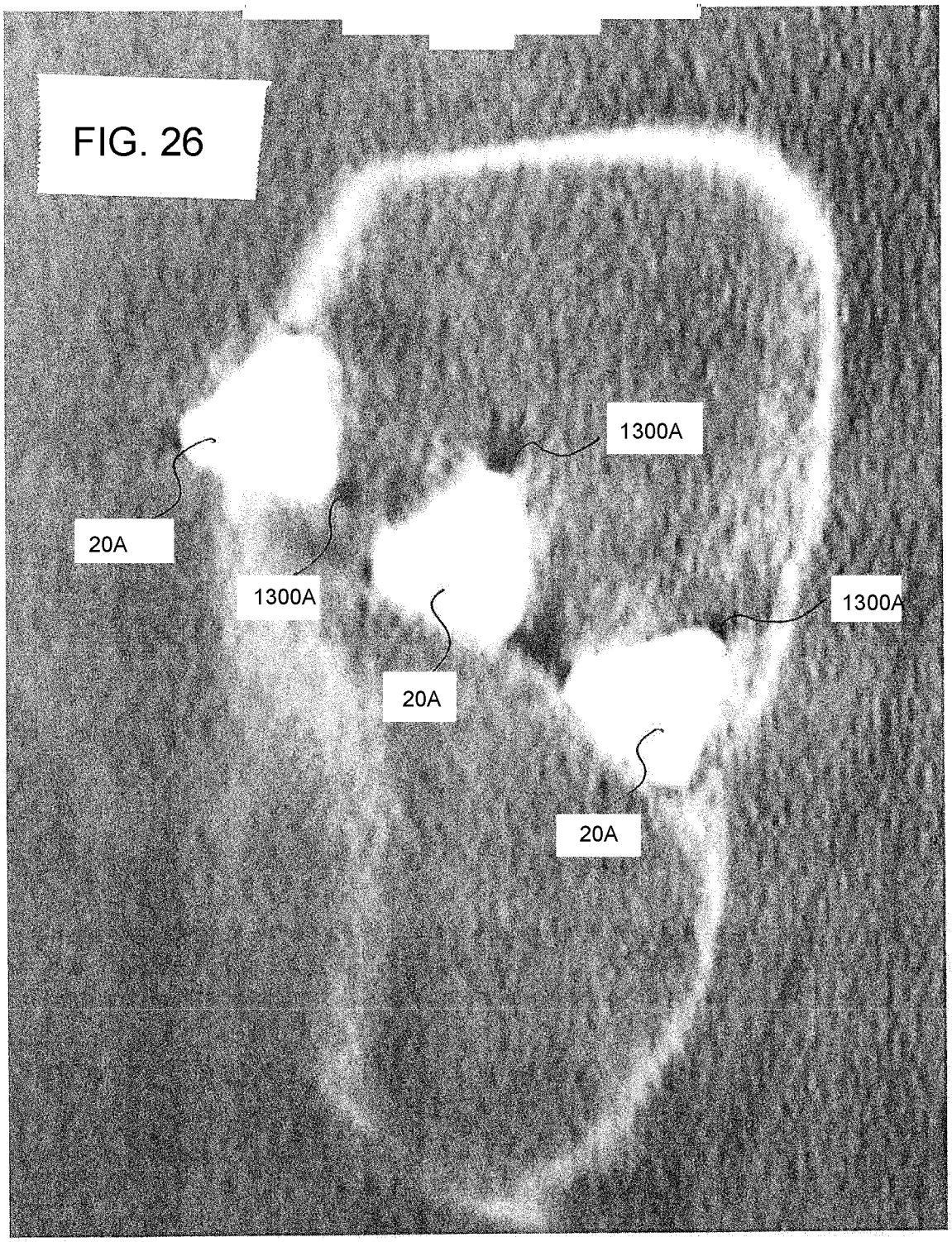

Translaminar Lumbar Fusion (Posterior Approach)

LUMBAR FACET FUSION
(POSTERIOR APPROACH)

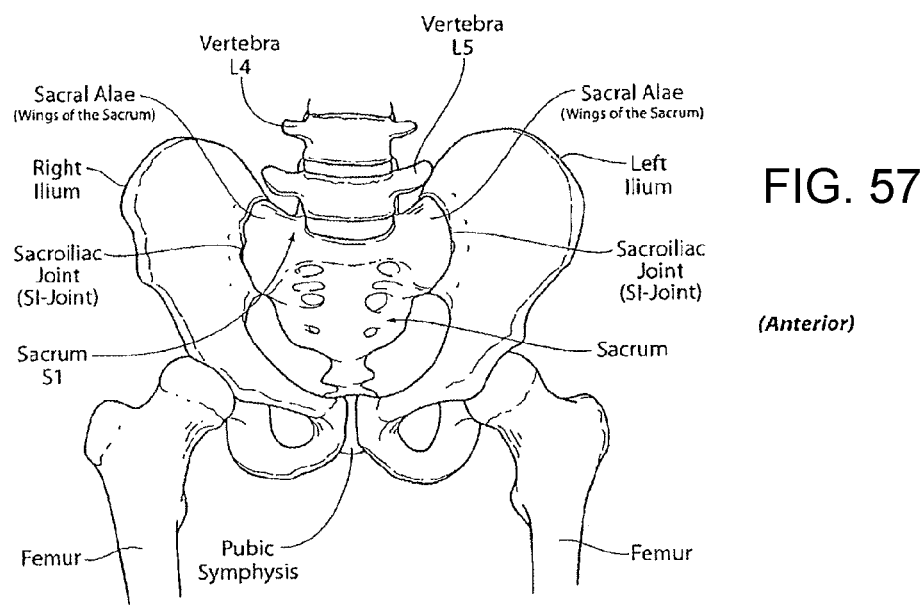
FIG. 57 (Anterior)
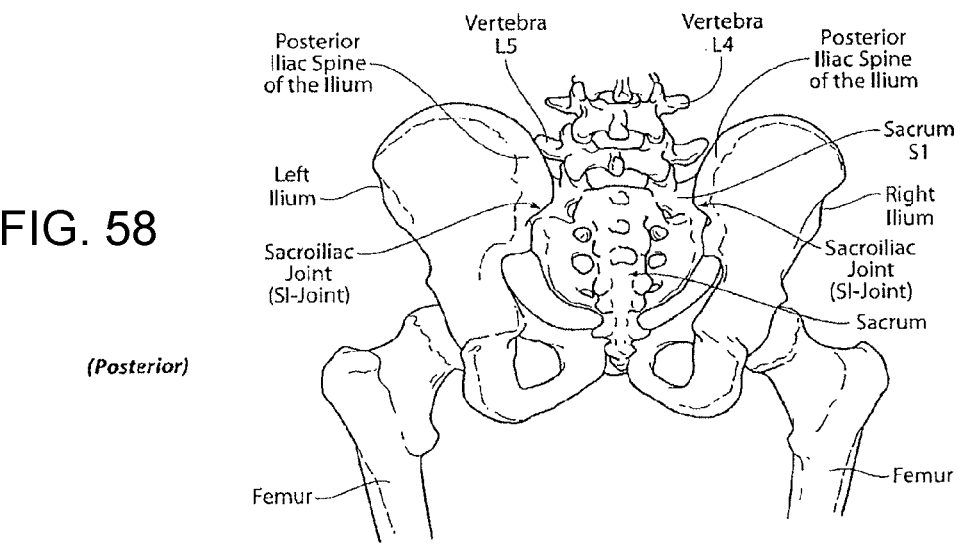
FIG. 58 (Posterior)

Translaminar Lumbar Fusion (Posterior Approach)

Lumbar Facet Fusion (Posterior Approach)

SYSTEMS, DEVICES, AND METHODS FOR JOINT FUSION

CROSS REFERENCE TO RELATED APPLICATIONS

This application is a continuation of U.S. application Ser. No. 16/523,992, filed Jul. 26, 2019, which is a divisional of U.S. application Ser. No. 15/208,588, filed Jul. 12, 2016, now U.S. Pat. No. 10,363,140, titled "SYSTEMS, DEVICE, AND METHODS FOR JOINT FUSION," which is a continuation-in-part of U.S. application Ser. No. 13/794,542, filed Mar. 11, 2013, titled "TISSUE DILATOR AND PROTECTOR,", which claims priority to U.S. Patent Application No. 61/609,043, filed Mar. 9, 2012, titled "TISSUE DILATOR AND PROTECTOR," which is hereby incorporated by reference in its entirety.

Said application Ser. No. 15/208,588 is also a continuation-in-part of U.S. application Ser. No. 14/216,790, filed Mar. 17, 2014, titled "SYSTEMS AND METHODS FOR IMPLANTING BONE GRAFT AND IMPLANT,", which claims priority to U.S. Provisional Application No. 61/793,357, filed Mar. 15, 2013, and titled "SYSTEMS AND METHODS FOR IMPLANTING BONE GRAFT AND IMPLANT," which is hereby incorporated by reference in its entirety.

Said application Ser. No. 15/208,588 is also a continuation-in-part of U.S. application Ser. No. 14/216,938, filed Mar. 17, 2014, titled "IMPLANTS FOR FACET FUSION,", which claims priority to U.S. Provisional Application No. 61/793,576 filed Mar. 15, 2013, and titled "IMPLANTS FOR FACET FUSION," which is hereby incorporated by reference in its entirety.

Said application Ser. No. 15/208,588 is also a continuation-in-part of U.S. application Ser. No. 14/217,008, filed Mar. 17, 2014, titled "SYSTEMS AND METHODS FOR REMOVING AN IMPLANT,", which claims priority to U.S. Patent Application No. 61/800,966 filed Mar. 15, 2013, and titled "SYSTEMS AND METHODS FOR REMOVING AN IMPLANT," which is hereby incorporated by reference in its entirety.

Said application Ser. No. 15/208,588 is also a continuation-in-part of U.S. application Ser. No. 14/217,089, filed Mar. 17, 2014, titled "LONG IMPLANT FOR SACROILIAC JOINT FUSION", which claims priority to U.S. Application No. 61/798,267 filed Mar. 15, 2013, and titled "LONG IMPLANT FOR SACROILIAC JOINT FUSION," which is hereby incorporated by reference in its entirety.

Said application Ser. No. 15/208,588 is related to U.S. Application Publication No. 2011/0125268 titled "APPARATUS, SYSTEMS, AND METHODS FOR ACHIEVING LUMBAR FACET FUSION," which is hereby incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference. For example, this application incorporates by reference in their entireties U.S. Patent Publication No. 2011/0087294 and U.S. Patent Publication No. 2011/0118785.

FIELD

This application relates generally to implants and tools for the fixation or fusion of joints or bone segments.

BACKGROUND

Many types of hardware are available both for the fixation of bones that are fractured and for the fixation of bones that are to be fused (arthrodesed).

For example, the human hip girdle is made up of three large bones joined by two relatively immobile joints. One of the bones is called the sacrum and it lies at the bottom of the lumbar spine, where it connects with the L5 vertebra. The other two bones are commonly called "hip bones" and are technically referred to as the right ilium and the left ilium. The sacrum connects with both hip bones at the sacroiliac joint (in shorthand, the SI-Joint).

The SI-Joint functions in the transmission of forces from the spine to the lower extremities, and vice-versa. The SI-Joint has been described as a pain generator for up to 22% of lower back pain.

To relieve pain generated from the SI Joint, sacroiliac joint fusion is typically indicated as surgical treatment, e.g., for degenerative sacroiliitis, inflammatory sacroiliitis, iatrogenic instability of the sacroiliac joint, osteitis condensans ilii, or traumatic fracture dislocation of the pelvis. Currently, screws and screws with plates are used for sacro-iliac fusion. At the same time the cartilage is removed from the "synovial joint" portion of the SI joint. This requires a large incision to approach the damaged, subluxed, dislocated, fractured, or degenerative joint.

Tissue Dilator and Protector

To reduce soft tissue damage, a tissue dilator can be used to provide access to the surgical site. One common type of tissue dilator system includes a plurality of tubular sleeves of increasing diameter that are designed to slide over a guide pin or guide wire. As dilators of increasing diameters are sequentially slid over the guide pin, the tissue surrounding the guide pin is gradually pushed away from the guide pin, resulting in an opening in the tissue.

Systems and Methods for Implanting Bone Graft and Implant

An alternative implant that is not based on the screw design can also be used to fuse the SI-Joint. Such an implant can have a triangular cross-section, for example, as further described below. To insert the implant, a cavity can be formed into the bone, and the implant can then be inserted into the cavity using a tool such as an impactor.

To improve integration of the implant with the bone, bone graft material can be applied to the implant before insertion into the bore or during the implantation procedure. Therefore, it would be desirable to provide systems, devices and methods for incorporating bone graft materials with the implant at the implantation site.

In addition, some methods of implantation of the implant require one or more drilling steps to form the bone cavity for receiving the implant. To reduce the number of drilling steps and simplify the procedure, it would be desirable to provide a modified broach that can efficiently cut the bone cavity with less drilling.

Implants for Facet Fusion

The spine (see FIG. 27) is a complex interconnecting network of nerves, joints, muscles, tendons and ligaments, and all are capable of producing pain.

The spine is made up of small bones, called vertebrae. The vertebrae protect and support the spinal cord. They also bear the majority of the weight put upon the spine.

Between each vertebra is a soft, gel-like "cushion," called an intervertebral disc. These flat, round cushions act like shock absorbers by helping absorb pressure and keep the bones from rubbing against each other. The intervertebral disc also binds adjacent vertebrae together. The intervertebral discs are a type of joint in the spine. Intervertebral disc joints can bend and rotate a bit but do not slide as do most body joints.

Each vertebra has two other sets of joints, called facet joints (see FIG. 28). The facet joints are located at the back of the spine (posterior). There is one facet joint on each lateral side (right and left). One pair of facet joints faces upward (called the superior articular facet) and the other pair of facet joints faces downward (called the inferior articular facet). The inferior and superior facet joints mate, allowing motion (articulation), and link vertebrae together. Facet joints are positioned at each level to provide the needed limits to motion, especially to rotation and to prevent forward slipping (spondylolisthesis) of that vertebra over the one below.

In this way, the spine accommodates the rhythmic motions required by humans to walk, run, swim, and perform other regular movements. The intervertebral discs and facet joints stabilize the segments of the spine while preserving the flexibility needed to turn, look around, and get around.

Degenerative changes in the spine can adversely affect the ability of each spinal segment to bear weight, accommodate movement, and provide support. When one segment deteriorates to the point of instability, it can lead to localized pain and difficulties. Segmental instability allows too much movement between two vertebrae. The excess movement of the vertebrae can cause pinching or irritation of nerve roots. It can also cause too much pressure on the facet joints, leading to inflammation. It can cause muscle spasms as the paraspinal muscles try to stop the spinal segment from moving too much. The instability eventually results in faster degeneration in this area of the spine. Degenerative changes in the spine can also lead to spondylolysis and spondylolisthesis. Spondylolisthesis is the term used to describe when one vertebra slips forward on the one below it. This usually occurs because there is a spondylolysis (defect) in the vertebra on top. For example, a fracture or a degenerative defect in the interarticular parts of lumbar vertebra L1 may cause a forward displacement of the lumbar vertebra L5 relative to the sacral vertebra S1 (called L5-S1 pondylolisthesis). When a spondylolisthesis occurs, the facet joint can no longer hold the vertebra back. The intervertebral disc may slowly stretch under the increased stress and allow other upper vertebra to slide forward.

An untreated persistent, episodic, severely disabling back pain problem can easily ruin the active life of a patient. In many instances, pain medication, splints, or other normally-indicated treatments can be used to relieve intractable pain in a joint. However, in for severe and persistent problems that cannot be managed by these treatment options, degenerative changes in the spine may require a bone fusion surgery to stop both the associated disc and facet joint problems.

A fusion is an operation where two bones, usually separated by a joint, are allowed to grow together into one bone. The medical term for this type of fusion procedure is arthrodesis.

Lumbar fusion procedures have been used in the treatment of pain and the effects of degenerative changes in the lower back. A lumbar fusion is a fusion in the S1-L5-L4 region in the spine.

One conventional way of achieving a lumbar fusion is a procedure called anterior lumbar interbody fusion (ALIF). In this procedure, the surgeon works on the spine from the front (anterior) and removes a spinal disc in the lower (lumbar) spine. The surgeon inserts a bone graft into the space between the two vertebrae where the disc was removed (the interbody space). The goal of the procedure is to stimulate the vertebrae to grow together into one solid bone (known as fusion). Fusion creates a rigid and immovable column of bone in the problem section of the spine. This type of procedure is used to try and reduce back pain and other symptoms.

Facet joint fixation procedures have also been used for the treatment of pain and the effects of degenerative changes in the lower back. These procedures take into account that the facet joint is the only true articulation in the lumbosacral spine. In one conventional procedure for achieving facet joint fixation, the surgeon works on the spine from the back (posterior). The surgeon passes screws from the spinous process through the lamina and across the mid-point of one or more facet joints.

Conventional treatment of spondylolisthesis may include a laminectomy to provide decompression and create more room for the exiting nerve roots. This can be combined with fusion using, e.g., an autologous fibular graft, which may be performed either with or without fixation screws to hold the bone together. In some cases the vertebrae are moved back to the normal position prior to performing the fusion, and in others the vertebrae are fused where they are after the slip, due to the increased risk of injury to the nerve with moving the vertebra back to the normal position.

Currently, these procedures entail invasive open surgical techniques (anterior and/or posterior). Further, ALIF entails the surgical removal of the disc. Like all invasive open surgical procedures, such operations on the spine risk infections and require hospitalization. Invasive open surgical techniques involving the spine continue to be a challenging and difficult area.

Systems and Methods for Removing An Implant

An alternative implant that is not based on the screw design can also be used to fuse the SI-Joint and/or the spine. Such an implant can have a triangular cross-section, for example, as further described below. To insert the implant, a cavity can be formed into the bone, and the implant can then be inserted into the cavity using a tool such as an impactor. The implants can then be stabilized together, if desired, by connected with implants with a crossbar or other connecting device.

Therefore, it would be desirable to provide systems, devices and methods for SI-Joint and/or spinal fixation and/or fusion.

Long Implant for Sacroiliac Joint Fusion

An alternative implant that is not based on the screw design can also be used to fuse the SI-Joint and/or the spine. Such an implant can have a triangular cross-section, for example, as further described below. To insert the implant, a cavity can be formed into the bone, and the implant can then be inserted into the cavity using a tool such as an impactor. The implants can then be stabilized together, if desired, by connected with implants with a crossbar or other connecting device.

Therefore, it would be desirable to provide systems, devices and methods for SI-Joint and/or spinal fixation and/or fusion.

SUMMARY OF THE DISCLOSURE

Tissue Dilator and Protector

Some embodiments of the present invention relate generally to tissue dilators and protectors. More specifically, some embodiments relate to tissue dilators and protectors used in medical procedures such as bone fixation or fusion.

In some embodiments, a soft tissue protector system for coating an implant with a biologic aid is provided. The system includes a longitudinal body having a distal end, a proximal end and a wall with an inner surface that defines a passage extending through the longitudinal body, wherein the passage is configured to receive the implant; at least one port located on the inner surface of the wall proximal the distal end of the longitudinal body; and at least one channel in fluid communication with the at least one port, wherein the at least one channel is configured to contain the biologic aid.

In some embodiments, the system further includes a pusher, wherein the pusher is configured to be inserted into both the passage and the at least one channel such that the pusher is capable of pushing out the implant from within the passage and pushing out the biologic aid from at least one channel through the at least one port to coat the implant as the implant is pushed out of the passage.

In some embodiments, the inner surface defines a passage having a rectilinear transverse cross-sectional profile that is configured to receive an implant having a corresponding rectilinear transverse cross-sectional profile. In some embodiments, the passage and the implant each have a transverse triangular cross-sectional profile.

In some embodiments, the inner surface comprises a plurality of planar surfaces, each planar surface defining one side of the rectilinear cross-sectional profile of the passage, wherein each of the plurality of planar surfaces comprises at least one port located proximal to the distal end of the longitudinal body and configured to deliver the biologic aid.

In some embodiments, the port is a slot oriented transversely to the longitudinal body.

In some embodiments, the channel is pre-loaded with the biologic aid. In some embodiments, the biologic aid is selected from the group consisting of bone morphogenetic proteins, hydroxyapatite, demineralized bone, morselized autograft bone, morselized allograft bone, analgesics, antibiotics, and steroids. In some embodiments, the biologic aid is incorporated into a controlled release formulation to provide sustained release of the biologic aid over time.

In some embodiments, an expandable dilator for dilating soft tissue is provided. The expandable dilator includes a longitudinal body having a distal end, a proximal end and a wall with an inner surface that defines a passage extending through the longitudinal body; wherein the wall comprises a plurality of longitudinal wall segments, each longitudinal wall segment slidably connected to two other longitudinal wall segments; wherein the longitudinal body has a compressed configuration with a first transverse cross-sectional area and an expanded configuration with a second transverse cross-sectional area, wherein the first transverse cross-sectional area is less than the second transverse cross sectional area.

In some embodiments, the longitudinal wall segments have a greater amount of overlap between adjacent longitudinal wall segments in the compressed configuration than in the expanded configuration.

In some embodiments, the first transverse cross-sectional area and the second transverse cross-sectional area are rectilinear.

In some embodiments, the transverse first cross-sectional area and the second transverse cross-sectional area are triangular.

In some embodiments, the first transverse cross-sectional area and the second transverse cross-sectional area are curvilinear.

In some embodiments, a delivery sleeve for delivering an implant to a delivery site is provided. The delivery sleeve includes a longitudinal body having a distal end, a proximal end and a wall with an inner surface that defines a passage extending through the longitudinal body, the passage configured to receive the implant; wherein the longitudinal body includes a flexible tapered distal portion having a plurality of longitudinal slits that divide the tapered distal portion into at least two expandable blade portions, the expandable blade portions configured to rotate outwards upon the application of force on the inner surface of the expandable blade portions.

In some embodiments, the delivery sleeve further includes an inner tube that is slidably disposed within the passage of the longitudinal body, wherein the inner tube is configured to apply force on the inner surface of the expandable blade portions.

In some embodiments, each longitudinal slit terminates at a stress relief cutout.

In some embodiments, the longitudinal body has a rectilinear transverse cross-section.

In some embodiments, the longitudinal body has a triangular transverse cross-section.

In some embodiments, the delivery sleeve further includes an adjusting sleeve that is controllably disposed within the passage of the longitudinal body to extend the length of the passage.

In some embodiments, a dilator system is provided. The system includes a guide pin configured to be inserted within bone, the guide pin having a distal portion comprising a plurality of outwardly biased prongs; a retractable cannula disposed around the outwardly biased prongs to keep the outwardly biased prongs in a collapsed configuration; one or more dilators that are configured to be sequentially disposed over the guide pin; and an outer cannula configured to be disposed over the one or more of dilators, the outer cannula having a plurality of stabilizing pins disposed around the circumference of the outer cannula, wherein the stabilizing pins are configured to be inserted within bone.

In some embodiments, the one or more dilators includes a drill dilator and a broach dilator.

In some embodiments, the broach dilator has a rectilinear transverse cross-section and the outer cannula has a rectilinear transverse cross-section.

In some embodiments, the plurality of stabilizing pins are slidably disposed within channels located around the circumference of the outer cannula.

In some embodiments, the one or more dilators and outer cannula are radiolucent and the guide pin and the stabilizing pins are radiopaque.

In some embodiments, a quick connect system is provided. The system includes a dilator having a proximal end and a distal end, the proximal end of the dilator having a first quick connect feature; and a handle having a proximal end and a distal end, the distal end of the handle having a second quick connect feature, wherein the first quick connect feature is configured to reversibly connect with the second quick connect feature.

In some embodiments, the first quick connect feature is an L or J shaped slot and the second quick connect feature is a pin, wherein the L or J shaped slot is configured to receive the pin.

In some embodiments, the first quick connect feature comprises a groove and at least one pin or bearing receptacle and the second quick connect feature comprises a collar with at least one spring loaded pin or bearing.

In some embodiments, a method of inserting an implant into a bone cavity is provided. The method includes providing an implant loaded into a lumen of a dilator having a proximal end and a distal end, the lumen of the dilator defined by a wall having an interior surface with one or more ports located proximal to distal end of the dilator, the one or more ports in communication with one or more channels within the wall, the one or more channels containing a biologic aid; positioning the distal end of the dilator adjacent to the bone cavity; advancing a pusher simultaneously through the lumen of the dilator and the one or more channels to simultaneously advance the implant into the bone cavity and eject the biologic aid out of the one or more ports, thereby coating the implant with the biologic aid as the implant is advanced into the bone cavity.

In some embodiments, a method of inserting an implant into a bone cavity is provided. The method includes providing an implant loaded into the lumen of a dilator having a proximal end and a distal end, the dilator including a reservoir of biologic aid; positioning the distal end of the dilator adjacent to the bone cavity; and advancing the implant into the bone cavity while simultaneously coating the implant with the biologic aid.

In some embodiments, a method of inserting an implant into bone is provided. The method includes inserting a guide pin into the bone; disposing an expandable dilator over the guide pin and against the bone; disposing a drill bit over the guide pin; drilling a hole in the bone with the drill bit to form a channel in the bone; withdrawing the drill bit from the channel; expanding the expandable dilator from a contracted configuration to an expanded configuration; disposing a broach over the guide pin and inserting the broach into the channel to enlarge and reshape the channel into a bone cavity; and inserting the implant over the guide pin and into the bone cavity.

In some embodiments, the bone cavity has a rectilinear transverse cross-section.

In some embodiments, the method further includes retracting a sleeve from a distal portion of the guide pin to deploy a plurality of outward biased prongs that form the distal portion or the guide pin.

In some embodiments, the method further includes inserting into the bone one or more stabilizing pins to secure the expandable dilator to the bone.

In some embodiments, the method further includes attaching a handle to the expandable dilator using a quick connect mechanism.

Systems and Methods for Implanting Bone Graft and Implant

Some embodiments relate generally to broaches. More specifically, some embodiments relate to broaches used to shape bores in bone. The broaches can shape the bores to receive an implant and also cut additional tubes or channels for receiving bone graft material and/or biologic aids.

In general, in one embodiment, a broach for shaping a bore in bone to receive an implant includes an elongate body with a proximal end, a distal end, at least three faces between the distal end and the proximal end, a plurality of apices formed at the junctions between adjacent faces, and a longitudinal axis. A lumen extends throughout the elongate body about the longitudinal axis, and the lumen is sized and shaped for receiving a guide pin. A plurality of cutting surfaces are located on the distal end of the elongate body for shaping the bore to receive the implant, and the plurality of cutting surfaces are oriented along the plurality of apices and become progressively smaller in size towards the distal end. A plurality of additional cutting surfaces is aligned with the plurality of apices for cutting channels in the bore to receive a bone graft material.

This and other embodiments can include one or more of the following features. Each face of the elongate body can include a channel extending along at least a portion of the longitudinal length of the elongate body. The elongate body can include three faces that define a substantially triangular cross-sectional profile transverse to the longitudinal axis. The plurality of cutting surfaces can be angled towards the distal end of the elongate body. The plurality of additional cutting surfaces can be partially circular. The plurality of additional cutting surfaces can be partially rectilinear.

In general, in one embodiment, a method for inserting an implant in bone includes: (1) drilling a bore into the bone; (2) inserting a broach to shape the bore to receive the implant and to form channels for receiving a bone graft material; (3) inserting the implant into the shaped bore; and (4) filling the channels with a bone graft material.

This and other embodiments can include one or more of the following features. The shaped bore can be rectilinear with a plurality of apices, and the channels can be formed at the apices of the shaped bore. The shaped bore can be triangular. The method can include inserting a guide pin into the bone. The steps of drilling a bore, inserting a broach, and inserting the implant all can be performed over the guide pin.

In general, in one embodiment, a broach for shaping a bore in bone to receive an implant includes an elongate body with a proximal end, a distal end, at least three faces between the distal end and the proximal end, a plurality of apices formed at the junctions between adjacent faces, and a longitudinal axis. A lumen extends throughout the elongate body about the longitudinal axis, and the lumen is sized and shaped for receiving a guide pin. A plurality of cutting surfaces is located on the distal end of the elongate body for shaping the bore to receive the implant. The plurality of cutting surfaces are oriented along the plurality of apices and become progressively smaller in size towards the distal end. A tapered distal tip portion at the distal end of the elongate body tapers to a distal opening of the lumen.

This and other embodiments can include one or more of the following features. The tapered distal tip portion can form a cutting surface around the opening of the lumen. The tapered distal tip portion can include a plurality of beveled faces that are angled towards the distal end. The tapered distal tip portion can include a smooth tapering surface that reaches the distal opening of the lumen. The elongate body can include three faces that define a substantially triangular cross-sectional profile transverse to the longitudinal axis. The plurality of cutting surfaces can be angled towards the distal end of the elongate body. Each face of the elongate body can include a channel extending along at least a portion of the longitudinal length of the elongate body.

In general, in one embodiment, a method for inserting an implant in bone includes: (1) inserting a guide pin into the bone; (2) inserting a sharp tipped broach over the guide pin to create a cavity for receiving the implant, wherein the cavity can be formed without first drilling a bore into the bone over the guide pin; and (3) inserting the implant into the cavity.

This and other embodiments can include one or more of the following features. The step of inserting a sharp tipped broach over the guide pin to create a cavity can include cutting the bone adjacent to the guide pine with one or more cutting edges at a distal end of the sharp tipped broach, and driving the sharp tipped broach further into the bone until a plurality of cutting surfaces on the sharp tipped broach can cut into and remove the bone surrounding the guide pin to form the cavity.

Implants for Facet Fusion

Embodiments of the present invention relate to apparatus, systems, and methods for the fusion and/or stabilization of the lumbar spine. The apparatus, systems, and methods include one or more elongated, stem-like implant structures sized and configured for the fusion or stabilization of adjacent bone structures in the lumbar region of the spine, either across the intervertebral disc or across one or more facet joints. Each implant structure can include a region formed along at least a portion of its length to promote bony in-growth onto or into surface of the structure and/or bony growth entirely through all or a portion of the structure. The bony in-growth or through-growth region along the surface of the implant structure accelerates bony in-growth or through-growth onto, into, or through the implant structure 20. The implant structure therefore provides extra-articular/intra osseous fixation, when bone grows in and around the bony in-growth or through-growth region. Bony in-growth or through-growth onto, into, or through the implant structure helps speed up the fusion and/or stabilization process of the adjacent bone regions fixated by the implant structure. The implant structure can also be curved.

The assemblies of one or more implant structures make possible the achievement of diverse interventions involving the fusion and/or stabilization of lumbar and sacral vertebra in a non-invasive manner, with minimal incision, and without the necessitating the removing the intervertebral disc. The representative lumbar spine interventions, which can be performed on adults or children, include, but are not limited to, lumbar interbody fusion; translaminar lumbar fusion; lumbar facet fusion; trans-iliac lumbar fusion; and the stabilization of a spondylolisthesis.

In some embodiments, an implant for fusing a facet joint of a patient is provided. The implant can include an elongate body having a proximal end, a distal end and a lumen extending between the proximal end and the distal end, wherein the elongate body has a curvature extending from the proximal end to the distal end and a rectilinear or curvilinear transverse cross-sectional profile.

In some embodiments, the elongate body is sized and configured to fuse the facet joint of the patient.

In some embodiments, the elongate body is formed of a shape memory material having a straight configuration and a curved configuration.

In some embodiments, the elongate body is formed of a plurality of interlocking segments.

In some embodiments, the elongate body is inflatable with a curable material.

In some embodiments, the elongate body comprises a valve.

In some embodiments, the elongate body is made of an inelastic material that cannot stretch.

In some embodiments, the elongate body is made of an elastic material that can stretch.

In some embodiments, the curvature is constant.

In some embodiments, the curvature is variable.

In some embodiments, the transverse cross-sectional profile is triangular.

In some embodiments, the transverse cross-sectional profile is circular.

In some embodiments, the elongate body has an exterior surface treated to promote bony in-growth.

In some embodiments, the exterior surface has a rough texture.

In some embodiments, a method for lumbar facet fusion is provided. The method can include creating a curved insertion path that extends from an inferior articular process of a selected lumbar vertebra in a caudal direction through the adjoining facet capsule into a corresponding superior articular process of an adjacent lumbar vertebra and into a pedicle of the adjacent lumbar vertebra; providing a curved bone fixation implant comprising a curved elongated implant structure having a longitudinal axis and a rectilinear cross section transverse to the longitudinal axis and including an exterior surface region treated to provide bony in-growth or through-growth along the implant structure; and inserting the curved bone fixation implant through the insertion path from the inferior articular process of the selected lumbar vertebra, in a caudal direction through the adjoining facet capsule into the corresponding superior articular process of the adjacent lumbar vertebra and into a pedicle of the adjacent lumbar vertebra.

In some embodiments, a method for translaminar lumbar fusion is provided. The method can include creating a curved insertion path that extends from a superior articular process of a selected lumbar vertebra, cranially through the adjoining facet capsule into a corresponding inferior articular process of an adjacent lumbar vertebra, and, from there, further through the lamina of the adjacent vertebra into an interior opposite posterolateral region adjacent the spinous process of the adjacent vertebra; providing a curved bone fixation implant comprising a curved elongated implant structure having a rectilinear cross section including an exterior surface region treated to provide bony in-growth or through-growth along the implant structure; and inserting the curved bone fixation implant through the insertion path from the superior articular process of the selected lumbar vertebra, cranially through the adjoining facet capsule into the inferior articular process of the adjacent lumbar vertebra, and, from there, further through the lamina of the adjacent vertebra into an interior opposite posterolateral region adjacent the spinous process of the adjacent vertebra.

In some embodiments, the step of creating a curved insertion path further includes inserting a curved guide pin into the superior articular process of a selected lumbar vertebra along the curved insertion path; and advancing a drill or cutting device over the curved guidewire along the curved insertion path.

In some embodiments, the step of inserting the curved guide pin includes rotating the curved guide pin about an axis.

In some embodiments, the step of creating a curved insertion path further includes advancing a drill or cutting device along the curved insertion path.

In some embodiments, a method for translaminar lumbar fusion of a superior vertebra to an inferior vertebrae is provided. The method can include creating a curved insertion path that starts in the lamina of the superior vertebra, extends distally and laterally to the inferior articular process of the superior vertebra, through the joint between the superior vertebra and the inferior vertebrae, and into the superior articular process of the inferior vertebra; providing a curved bone fixation implant comprising a curved elongated implant structure having a rectilinear cross section including an exterior surface region treated to provide bony in-growth or through-growth along the implant structure; and inserting the curved bone fixation implant through the insertion path from the lamina of the superior vertebra, extending distally and laterally to the inferior articular process of the superior vertebra, through the joint between the superior vertebra and the inferior vertebrae, and into the superior articular process of the inferior vertebra.

Systems and Methods for Removing an Implant

Embodiments of the present invention relate generally to systems and methods for removing an implant from bone.

In some embodiments, a system for removing an implant from bone, wherein the implant has a plurality of sides and a rectilinear cross-section, is provided. The system includes a guidepin; an osteotome having a flat, elongate body with proximal end, a distal end, and a sharp, blade portion for cutting bone located at the distal end of the elongate body; an osteotome guide having an elongate body having a plurality of planar faces and a rectilinear cross-section that corresponds in shape to the rectilinear cross-section of the implant, a lumen extending through the elongate body of the osteotome for receiving the guidepin, and a plurality of channels for receiving the osteotome, wherein one of the plurality of channels is disposed along each one of the plurality of planar faces.

In some embodiments, the guidepin has a distal end comprising a male connector for attachment into a corresponding female connector of the implant.

In some embodiments, the sharp, blade portion of the osteotome has a width that is equal to the width of one of the sides of the implant.

In some embodiments, the sharp, blade portion of the osteotome has a width that is greater than the width of one of the sides of the implant.

In some embodiments, the system further includes a dilator having a proximal end and a distal end, wherein the distal end of the dilator comprises at least one cutout.

In some embodiments, the system further includes an adjustable stop attached to the osteotome guide for limiting the depth of insertion of the osteotome guide within the dilator.

In some embodiments, the system further includes a blank having a flat elongate body with a blade portion for cutting bone located at the distal end of the elongate body, the blank sized and shaped to be disposed into the plurality of channels, the blank configured to be tapped into the bone to secure the osteotome guide in place.

In some embodiments, the blank comprises a receptacle extending through the flat elongate body for receiving a stop, wherein the stop is configured to reversibly hold the blank in place with respect to the osteotome.

In some embodiments, the guidepin has a threaded distal end for attachment to corresponding internal threads of the implant.

In some embodiments, the guidepin has a threaded proximal end that can be reversibly connected to a pull handle or pull shaft.

In some embodiments, a system for removing an implant from bone, wherein the implant has a plurality of sides and a rectilinear cross-section, is provided. The system includes a guidepin; an osteotome having a V-shaped elongate body with a proximal end, a distal end, a sharp, V-shaped blade portion for cutting bone located at the distal end of the elongate body, and a lumen extending through a portion of the elongate body for receiving the guidepin, wherein the angle of the V-shaped blade portion is the same as the angle between two sides of the implant.

In some embodiments, the V-shaped blade portion comprises a first planar section having a width equivalent to the width of a first side of the implant, and a second planar section having a width equivalent to the width of a second side of the implant.

In some embodiments, the V-shaped blade portion comprises a first planar section having a width that is between about half the width to the full width of a first side of the implant, and a second planar section having a width that is between about half the width to the full width of a second side of the implant.

In some embodiments, a system for removing an implant from bone, wherein the implant has a plurality of sides and a rectilinear cross-section, is provided. The system can include a guidepin; an osteotome having a V-shaped elongate body with a proximal end, a distal end, a sharp, and a V-shaped blade portion for cutting bone located at the distal end of the elongate body, wherein the angle of the V-shaped blade portion is the same as the angle between two sides of the implant; and an osteotome guide having an elongate body having a plurality of planar faces and a rectilinear cross-section that corresponds in shape to the rectilinear cross-section of the implant, a lumen extending through the elongate body of the osteotome for receiving the guidepin, and at least one channel for receiving the osteotome, wherein the at least one channel is V-shaped and is disposed along two adjacent planar faces.

In some embodiments, a method for removing an implant having a rectilinear cross-section from a bone matrix is provided. The method can include attaching a guidepin to the implant; disposing an osteotome guide over the guidepin; aligning the osteotome guide with the implant; inserting an osteotome into a channel in the osteotome guide; cutting the bone matrix away from the implant with the osteotome; and pulling on the guidepin to remove the implant from the bone matrix and leave a cavity in the bone matrix.

In some embodiments, the method further includes inserting a replacement implant having a larger cross-sectional profile than the removed implant into the cavity.

In some embodiments, the method further includes disposing a dilator over the guidepin, wherein the dilator has a proximal end and a distal end having at least one cutout, and wherein the osteotome guide is inserted within the dilator.

In some embodiments, the method further includes aligning the at least one cutout of the dilator over a second implant in the bone matrix.

In some embodiments, the method further includes limiting the depth in which the osteotome guide is inserted within the dilator by adjusting a stop attached to the osteotome guide.

In some embodiments, the method further includes attaching a pull handle to the guidepin.

In some embodiments, the osteotome guide has at least two channels.

In some embodiments, the method further includes inserting a blank into one of the channels of the osteotome guide; and tapping the blank into the bone matrix to secure the osteotome guide in place.

In some embodiments, the method further includes securing the blank in place in the channel of the osteotome guide.

In some embodiments, a method for removing an implant having a rectilinear cross-section from a bone matrix is provided. The method includes attaching a guidepin to the implant; disposing over the guidepin an osteotome having a V-shaped elongate body with a proximal end, a distal end, a V-shaped blade portion for cutting bone located at the distal end of the elongate body, and a lumen extending through a portion of the elongate body for receiving the guidepin; aligning the V-shaped blade portion with two adjacent faces of the rectilinear implant; driving the V-shaped blade portion into the bone matrix to cut away the bone matrix from two adjacent faces of the rectilinear implant; and pulling on the guidepin to remove the implant from the bone matrix and leave a cavity in the bone matrix.

In some embodiments, the method further includes removing the V-shaped blade portion from the bone matrix; aligning the V-shaped blade portion with at least one remaining uncut face of the rectilinear implant; and driving the V-shaped blade portion into the bone matrix to cut away the bone matrix from the at least one remaining uncut face of the rectilinear implant.

In some embodiments, a system for removing an implant from bone, wherein the implant has a plurality of sides and a rectilinear cross-section, is provided. The system can include an osteotome having a flat, elongate body with proximal end, a distal end, and a sharp, blade portion for cutting bone located at the distal end of the elongate body; and an osteotome guide having an elongate body having a plurality of planar faces and a rectilinear cross-section that corresponds in shape to the rectilinear cross-section of the implant, and a plurality of channels for receiving the osteotome, wherein one of the plurality of channels is disposed along each one of the plurality of planar faces.

In some embodiments, a device for removing an implant from bone, wherein the implant has a plurality of sides and a rectilinear cross-section, is provided. The system can include an elongate body with a proximal end, a distal end, a sharp, V-shaped blade portion for cutting bone located at the distal end of the elongate body, wherein the angle of the V-shaped blade portion is the same as the angle between two sides of the implant.

Long Implant for Sacroiliac Joint Fusion

Embodiments of the present invention relate generally to an implant for SI-Joint fusion.

In some embodiments, a system for the fusion of the sacroiliac joint is provided. The system includes a guide pin having a length greater than the width of a patient's pelvis, the guide pin having a proximal end with a first alignment feature and a distal end with a second alignment feature; a broach having a lumen for receiving the guide pin, the lumen having a complementary alignment feature that is configured to interact with the first alignment feature and the second alignment feature to register the broach with the guide pin in a predetermined orientation, the broach configured to form a rectilinear cavity in bone; and an implant having a rectilinear cross-section transverse to a longitudinal axis of the implant, the implant having a length greater than the width between a surface of the patient's right ilium and a surface of the patient's left ilium, the implant sized to fit through a cavity formed by the broach.

In some embodiments, the implant has a rough surface.

In some embodiments, the implant has a triangular cross-section transverse to the longitudinal axis of the implant.

In some embodiments, the implant has a rectangular or square cross-section transverse to the longitudinal axis of the implant.

In some embodiments, the first alignment feature and the second alignment feature are selected from the group consisting of lines, ridges, slots, and pins.

In some embodiments, a system for the fusion of the sacroiliac joint is provided. The system can include a guide pin having a length greater than the width of a patient's pelvis; a broach having a lumen for receiving the guide pin, the broach configured to form a rectilinear cavity in bone; and an implant having a rectilinear cross-section transverse to a longitudinal axis of the implant, the implant having a length greater than the width between a surface of the patient's right ilium and a surface of the patient's left ilium, the implant sized to fit through the rectilinear cavity formed by the broach.

In some embodiments, the implant has a length greater than the width between a surface of the patient's right ilium and a surface of the patient's left ilium by about 2 to 20 mm.

In some embodiments, the implant has a length between about 100 mm to 300 mm.

In some embodiments, the guide pin has an alignment feature that extends across the length of the guide pin.

In some embodiments, a method for fusing both sacroiliac joints of a patient is provided. The method can include inserting a guide pin through the first ilium and across the first SI-Joint, through the sacrum and above the S1 foramen, across the second SI-Joint, and through the second ilium; forming a first rectilinear cavity through the first ilium and the first SI-Joint; forming a second rectilinear cavity through the second ilium and the second SI-Joint, wherein the first rectilinear cavity and the second rectilinear cavity are aligned; and inserting an implant through the first cavity, across the first SI-Joint, through the sacrum, across the second SI-Joint, and through the second cavity, wherein the implant has a rectilinear cross-section transverse to a longitudinal axis of the implant that corresponds to the first rectilinear cavity and the second rectilinear cavity.

In some embodiments, the step of forming the first rectilinear cavity includes aligning a broach with an alignment feature on the guide pin.

In some embodiments, the step of forming the second rectilinear cavity includes aligning the broach with the alignment feature of the guide pin.

In some embodiments, the step of forming the second rectilinear cavity includes aligning the broach with a second alignment feature on the guide pin.

In some embodiments, the step of forming the second rectilinear cavity includes aligning a broach with an image of the first rectilinear cavity under fluoroscopy.

In some embodiments, the method further includes determining a length of the guide pin residing between the surface of the first ilium and the surface of the second ilium; and sizing the implant based on the determined length of the guide pin residing between the surface of the first ilium and the surface of the second ilium.

In some embodiments, the step of determining the length of the guide pin residing between the surface of the first ilium and the surface of the second ilium includes measuring the length of the guide pin extending from the surface of the first ilium and the surface of the second ilium.

In some embodiments, the implant has a length that is about 2 to 20 mm greater than the determined length of the guide pin residing between the surface of the first ilium and the surface of the second ilium.

In some embodiments, the step of forming the first rectilinear cavity includes drilling a first bore over the guide pin in the first ilium; and shaping the first bore with a broach.

In some embodiments, a method for fusing both sacroiliac joints of a patient is provided. The method includes inserting a guide pin through the first ilium and across the first SI-Joint, through the sacrum between the S1 and S2 foramen, across the second SI-Joint, and through the second ilium; forming a first rectilinear cavity through the first ilium and the first SI-Joint; forming a second rectilinear cavity through the second ilium and the second SI-Joint, wherein the first rectilinear cavity and the second rectilinear cavity are aligned; and inserting an implant through the first cavity, across the first SI-Joint, through the sacrum, across the second SI-Joint, and through the second cavity.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 5A-5C illustrate an embodiment of a sequential dilation system.

FIGS. 6A-6D illustrate embodiments of a quick change mechanism that allows two instruments or components to be quickly and reversibly connected together.

FIGS. 8A-8D are side section views of the formation of a broached bore in bone according to one embodiment of the invention.

FIG. 26 illustrates a CT scan with haloing artifacts around the implant.

FIGS. 57 and 58 are, respectively, anterior and posterior anatomic views of the human hip girdle comprising the sacrum and the hip bones (the right ilium, and the left ilium), the sacrum being connected with both hip bones at the sacroiliac joint (in shorthand, the SI-Joint).

DETAILED DESCRIPTION

Tissue Dilator and Protector

Figure 1A:
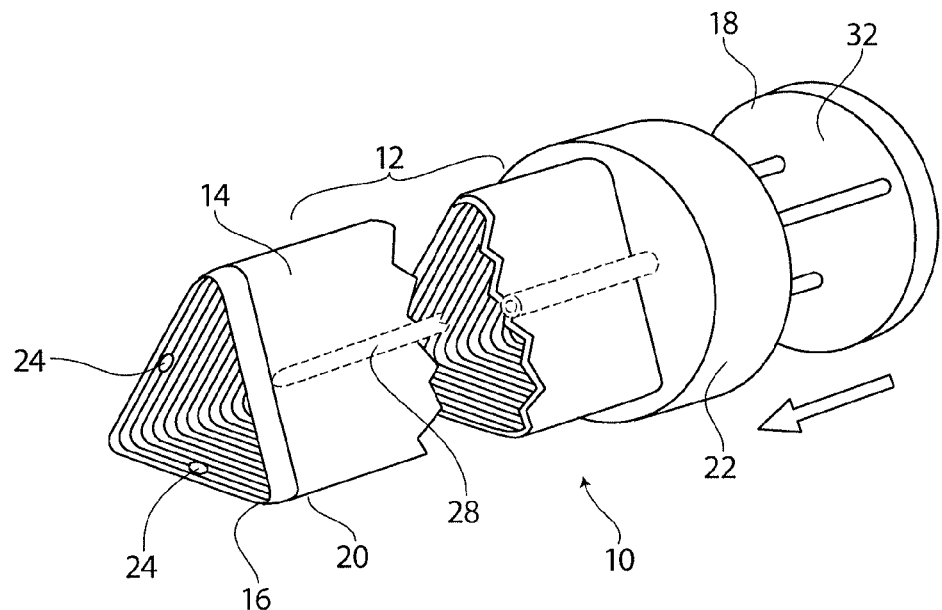
FIG. 1A is a perspective view of an embodiment of a dilator with an integrated infusion system.
Figure 1B:
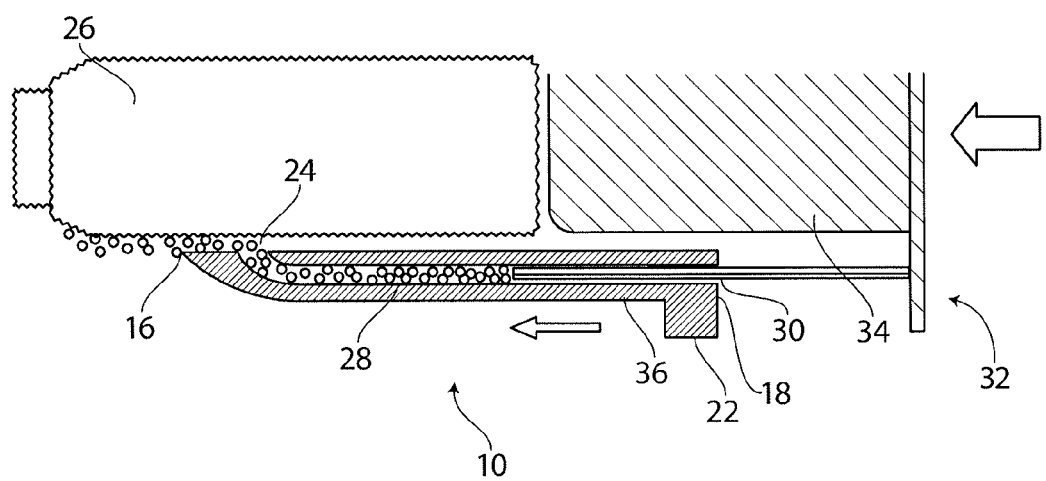
FIG. 1B is a longitudinal cross-sectional view of the dilator shown in FIG. 1A.

FIGS. 1A and 1B are a perspective view and a longitudinal cross-sectional view, respectively, of an embodiment of a dilator 10 with an integrated infusion system. In some embodiments, the dilator 10 can be used as a soft tissue protector in addition to or in place of its function as a dilator 10. In some embodiments, the dilator 10 has a longitudinal body 12 with a wall 14 that can be shaped to match the cross-sectional profile of an implant 26. The wall 14 can define a passage that extends through the longitudinal body. For example, if the implant 26 has a triangular cross-section, then the hollow interior of the dilator 10 can have a triangular cross-section that matches the implant geometry, such that the implant 26 can pass through the interior of the dilator 10. In other embodiments, the implant 26 can have other cross-sectional geometries, such as a square implant, a hexagonal implant and the like, and the cross-sectional shape of the interior of the dilator is designed to match the implant 26. The hollow interior cross-sectional area of the dilator is sized to be slightly larger than the cross-sectional area of the implant 26, which allows the implant 26 to pass through the dilator with little lateral movement within the dilator 10.

In some embodiments, the exterior cross-sectional shape of the dilator 10 can also match the implant 26 cross-sectional shape. In the case of a triangular implant and most non-circular implants, this allows the surgeon to easily and accurately control the orientation that the implant 26 will ultimately be inserted into the patient. For example, the surgeon can align the vertices of the triangular dilator in the desired orientation and be assured that the implant 26 will be implanted in the same orientation. In other embodiments, the exterior cross-sectional shape of the dilator 10 does not match the implant 26 cross-sectional shape.

The dilator 10 has a distal end 16 and a proximal end 18, where the terms distal and proximal are used in relation to the operator of the dilator 10. In some embodiments, the distal end 16 of the dilator 10 has a beveled edge 20. The beveled edge 20, which can be formed on the interior surface and/or the exterior surface of the distal end 16 of the wall 14, is designed to aid in the insertion of the dilator 10 through soft tissue, as well as providing a way for stabilizing the dilator 10 by being able to bite into the bone around the implant site. For example, once the dilator 10 is place against the bone in the correct orientation, the surgeon can tap the dilator 10 so that the beveled edge 20 bites into the bone, thereby anchoring the dilator 10 in place.

The proximal end 18 of the dilator 10 can have a collar 22 that is attached to the longitudinal body 12. The collar 22 can be knurled to provide a better grip for the operator. In addition, the collar 22 can have an attachment feature, such as a threaded hole for example, to allow the attachment of a handle, with for example a corresponding threaded end portion. In some embodiments, the attachment feature can be oriented such that the handle extends both axially and radially away in the proximal direction from the longitudinal axis of the dilator 10.

In some embodiments, as illustrated in FIGS. 1A and 1B, the dilator 10 includes one or more ports 24 that can be used for infusing and/or coating a liquid, gel, slurry, paste, powder or other material onto and/or into the implant 26 as the implant 26 is advanced through the dilator 10 and inserted into the patient. The ports 24 can be located on the interior surface of the distal end 16 or distal portion of the dilator 10 such that the ports 24 face the implant 26 as the implant 26 passes through the dilator 10. The ports 24 can have circular openings, oval openings, square openings, rectangular or slot openings, or any other suitably shaped opening that is capable of coating the implant surfaces as the implant 26 passes through the dilator 10. The number of ports 24 can vary. For example, for a triangular dilator 10 with a wall 14 with three planar surfaces, the dilator 10 can have one port 24 for each planar surface, for a total of three ports 24. In other embodiments, each planar surface can have two or three or more ports 24. In some embodiments, the one or more ports 24 can be spaced evenly around the circumference of the distal portion of the dilator 10. In some embodiments, the openings of the ports 24 extend around at least 5%, 10%, 25%, 50%, 75% or 90% of the circumference of the dilator 10. For example, one or more slit type openings can be used to extend substantially around the circumference of the dilator 10, which will enable the implant surfaces to be coated substantially with the coating material.

In some embodiments, the ports 24 can be connected to and/or are in fluid communication with one or more reservoirs 28, such as a hollow tube or channel for example, that contains the coating material. The reservoirs 28 can be integrated within the wall 14 of the dilator 10 such that the reservoirs 28 are located between the inner and outer surfaces of the wall 14. The reservoirs 28 also may be connected to and/or are in fluid communication with one or more openings 30 on the proximal end 18 of the dilator 10, as shown. These openings 30 can be loading ports used for loading the coating material into the reservoir 28. In addition, these openings 30 can be configured to receive, for example, a pusher and plunger device 32 that can be inserted into the openings 30 and push the coating material out of the reservoir 28 and out of the ports 24 to coat the implant 26. The pusher and plunger device 32 can also be referred to as an impactor. The pusher and plunger device 32 includes a pusher portion 34 that is configured to be inserted into the dilator 10 to push the implant 26 into the patient and a plunger portion 36 that is configured to be inserted into the reservoir 28 to push the coating material out of the dilator 10. The pusher and plunger device 32 can be integrated as a single device so that a single pushing action by the operator will cause the pusher and plunger device 32 to simultaneously push out the implant 26 and push out the coating material, thereby coating and/or infusing the implant 26 with the coating material as the implant 26 is advanced out of the dilator 10 and inserted into the patient.

In some embodiments, the coating material can include a biologic aid that can promote and/or enhance bony ingrowth, tissue repair, and/or reduce inflammation, infection and pain. For example, the biologic aid can include growth factors, such as bone morphogenetic proteins (BMPs), hydroxyapatite in, for example, a liquid or slurry carrier, demineralized bone, morselized autograft or allograft bone, medications to reduce inflammation, infection or pain such as analgesics, antibiotics and steroids. In some embodiments, the growth factors can be human recombinant growth factors, such as hr-BMP-2 and/or hr-BMP-7, or any other human recombinant form of BMP, for example. The carrier for the biologic aid can be a liquid or gel such as saline or a collagen gel, for example. The biologic aid can also be encapsulated or incorporated in a controlled released formulation so that the biologic aid is released to the patient at the implant site over a longer duration. For example, the controlled release formulation can be configured to release the biologic aid over the course of days or weeks or months, and can be configured to release the biologic aid over estimated time it would take for the implant site to heal. The amount of biologic aid delivered to the implant 26 can be controlled using a variety of techniques, such as controlling or varying the amount of coating material applied to the implant and/or controlling or varying the amount of biologic aid incorporated into the coating material. In some embodiments, in may be important to control the amount of biologic aid delivered because excessive use of certain biologic aids can result in negative effects such as radicular pain, for example.

The dilator 10 can be made of a variety of materials, such as metals and metal alloys. For example, the dilator 10 can be made of a stainless steel or titanium alloy. In addition, the dilator 10 or parts of the dilator 10 can be made of other materials such as polymers and carbon fibers, for example.

Figure 2A:
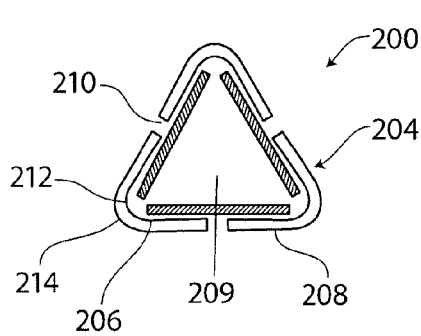
FIGS. 2A-2G illustrate embodiments of an expandable dilator.
Figure 2B:
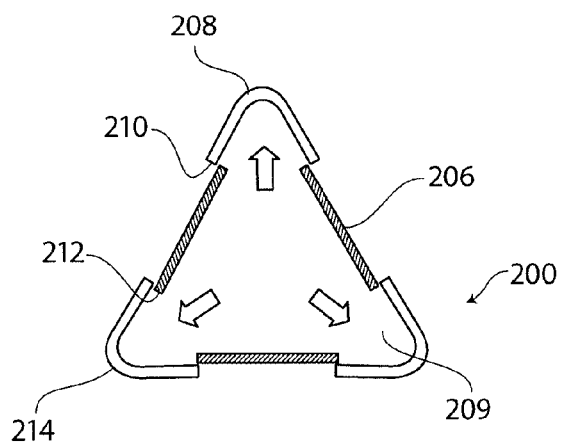

FIGS. 2A and 2B are cross-sectional views that illustrate an embodiment of an expandable dilator 200. For example, in one embodiment of the expandable dilator 200, the longitudinal body 202 of the dilator 200 is made of a plurality of interconnected and slidable wall portions 204. In the collapsed or non-expanded configuration, the expandable dilator 200 has a smaller cross-sectional area which facilitates insertion of the dilator 200 through soft tissues, causing less soft tissue damage than a larger device, and therefore, reducing pain and recovery time for the patient. In addition, in some embodiments the smaller cross-sectional area in the collapsed configuration allows the dilator 200 to be used in minimally invasive procedures. In the collapsed configuration, the cross-sectional area of the expandable dilator 200 can be less than the cross-sectional area of the implant. In the expanded configuration, the cross-sectional area of the expandable dilator 200 can be slightly greater than the cross-sectional area of the implant. The expandable dilator 200 can be expanded only when needed during the various steps of the overall procedure, such as during the insertion of the broach and implant 26, thereby reducing or minimizing the time the soft tissue is fully expanded.

As illustrated in FIGS. 2A and 2B, some embodiments of the expandable dilator 200 have a triangular cross-section area. The interconnected and slidable wall portions 204 can include three inner wall portions 206 and three outer wall portions 208. The inner wall portions 206 can be substantially planar while the outer wall portions 208 can be angled at, for example, approximately 60 degrees to form vertices of a triangle. In other embodiments, the outer wall portions can be substantially planar while the inner wall portions can be angled to form vertices of a triangle. For example, the inner wall portions 206 of the embodiment illustrated in FIGS. 2A and 2B can be moved to the outside of the dilator, while the outer wall portions 208 can be moved to the inside.

In the collapsed configuration, the inner wall portions 206 can be arranged in a triangular orientation with the outer wall portions 208 placed around the outside of the inner wall portions 206 to form the vertices of the triangle. Each outer wall portion 208 is connected to two inner wall portions 206, and each inner wall portion 206 is connected to two outer wall portions 208. In the collapsed configuration, the overlap of the inner wall portion 206 with the outer wall portion 208 is at its greatest or maximum amount, with the longitudinal edges 210 of the outer wall portion 208 near or at the central portion of the inner wall portion 206, and the longitudinal edges 212 of the inner wall portion near or at the vertices 214 of the outer wall portions 208.

In some embodiments, the inner wall portions 206 and the outer wall portions 208 of the dilator 200 define a lumen 209 that is configured to receive a plurality of different surgical tools and devices, such as a guide pin and guide pin sleeve. In some embodiments, the guide pin sleeve has a similar cross-sectional shape and size as the lumen 209 of the expandable dilator 200, which allows the guide pin sleeve to fit securely within the lumen 209. Additional surgical tools and devices can be inserted into the dilator 200 over the guide pin and/or guide pin sleeve, causing the dilator 200 to expand to accommodate the additional tools and devices.

Figure 2C:
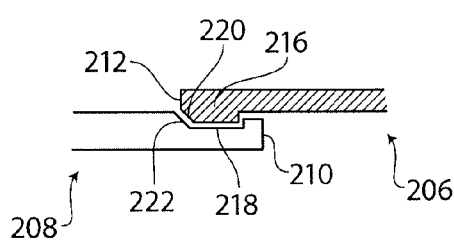

An outward force applied to the inner surfaces of the dilator 200 can be used to expand the collapsed configuration to the expanded configuration via a slide and lock mechanism, for example. The inner wall portions 206 can be slidably secured to the outer wall portions 208 by a variety of techniques, such as a dovetail fit between the wall portions. As illustrated in FIG. 2C, a locking mechanism can be used to keep the wall portions from over expanding and separating. For example, the longitudinal edges 212 of the inner wall portions 206 can have a latch portion 216 while the longitudinal edges 210 of the outer wall portions 208 can have a corresponding groove portion 218. When the dilator 200 is fully expanded, the latch portions 216 fall or snap into the corresponding groove portions 218 and stop or inhibit further expansion of the dilator. The latch portion 216 and groove portions 218 can have corresponding bevels that allow the dilator 200 to be collapsed back into the collapsed configuration from the fully expanded configuration. For example, a bevel 220 on the outer longitudinal edge of the latch portion 216 and a bevel 222 on the inner longitudinal edge of the groove portion will allow the dilator 200 to collapse from the fully expanded configuration.

Figures 2F, 2G:
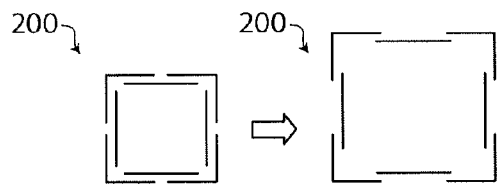
Figures 2D, 2E:
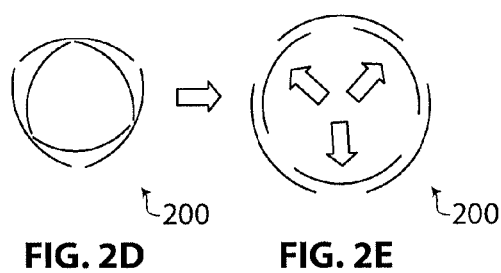

Other dilator 200 geometries can be used in place of the triangular dilator 200 illustrated in FIGS. 2A and 2B. For example, FIGS. 2D and 2E illustrate an expandable dilator 200 with a substantially circular cross-sectional area when expanded. FIGS. 2F and 2G illustrate an expandable dilator 200 with a substantially square cross-sectional area when expanded. Similarly, other geometries can be used, such as a rectangle, oval, hexagon, and the like.

Figure 3A:
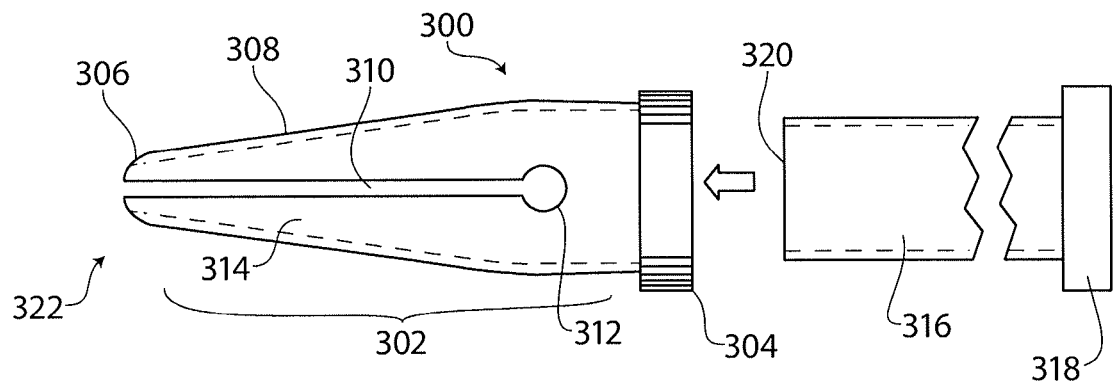
FIGS. 3A-3C illustrate additional embodiments of the dilator.
Figure 3B:
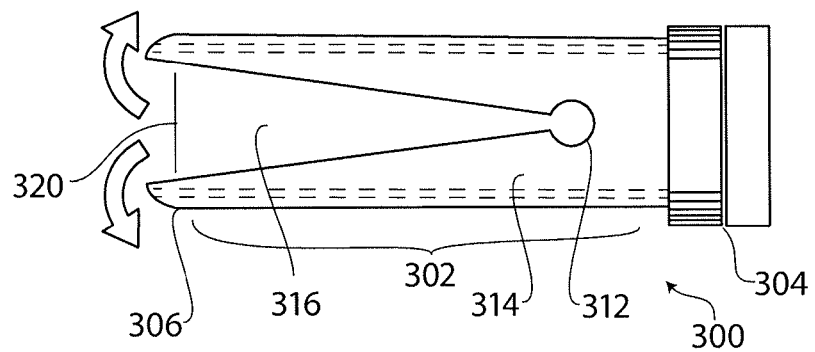

FIGS. 3A and 3B illustrate another embodiment of the dilator 300. The dilator 300 comprises a longitudinal body 302 with a proximal end 304 and a distal end 306. The longitudinal body 302 gradually tapers to a rounded portion 322 or a narrow portion at the distal end 306, thereby forming a tapered portion 308. The rounded portion 322 or narrow portion at the distal end 306 is more easily pushed over the guide pin or guide wire through the soft tissue, reducing the possible tissue damage that can be caused by pushing a larger diameter or larger cross-sectional area dilator through the soft tissue. As the dilator 300 is pushed further into the soft tissue, the widening cross-sectional area of the tapered portion 308 gradually pushes the soft tissue apart.

The tapered portion 308 of the longitudinal body 302 has a plurality of slits 310 that extend from the distal end 306 to a stress relief portion 312 on the proximal end of the tapered portion 308. The plurality of slits 310 divide the tapered portion into expandable blade portions 314 that can be pushed, moved, actuated or rotated outwards to expand the interior diameter and cross-sectional area of the tapered portion 308. In some embodiments, the dilator 300 has two slits, while in other embodiments, the dilator 300 has 3, 4, or more slits which can be evenly spaced around the circumference of the tapered portion 308. In some embodiments, the slits can be aligned with the corners of the longitudinal body 302, such as the apexes of a triangular shaped longitudinal body 302. In other embodiments, the slits can be aligned in between the corners of the longitudinal body 302. For example, in some embodiments, a triangular dilator 300 with three sides can have three slits to divide the tapered portion into three blade portions. The rounded portion 322 or narrow portion can have a hole or cutout at the central and distal most point or portion that aligns with the longitudinal axis of the dilator 300 in order to facilitate the passage of a guide pin or guide wire through the dilator 300.

In some embodiments, the stress relief portion 312 can be a cutout or hole in the longitudinal body 302 that facilitates the movement of the blade portions 314 from a non-expanded configuration to an expanded configuration. The blade portions 314 can be pushed apart into the expanded configuration by mechanical means, such as by the insertion of an inner tube 316 that slides into the interior of the dilator 300. In some embodiments, the inner tube 316 is a guide tube that facilitates the passage of another device, such as a drill bit or broach or implant, through the dilator 300. As the inner tube is advanced through the interior of the dilator 300, the distal end of the inner tube 316 contacts the inner surface of the blade portions 314 and progressively pushes the blade portions 314 apart until the inner diameter of the dilator 300 is at least as great as the outer diameter of the inner tube 316. The inner tube 316 can have a collar portion 318 that is configured to abut against the proximal end 304 of the dilator 300 when the inner tube 316 is fully inserted into the dilator 300. At full insertion, the distal end 320 of the inner tube 316 can extend to the distal end 306 of the dilator 300, or extend to a point just proximal the distal end 306 of the dilator 300.

In some embodiments, the expandable dilator 300 can be made of metals or polymers, for example. The material of the blade portions 314 that bends and/or deforms can be resiliently or non-resiliently flexible. In addition, in some embodiments, the deformation of the blade portions 314 can be substantially permanent in the sense that once expanded, the blade portions 314 tend to stay in the expanded configuration and resist compression even if the inner tube 316 is removed. In other embodiments, the deformation of the blade portions 314 can be substantially reversible in the sense that once expanded, the blade portions 314 tend to want to return to the original non-expanded configuration.

Figure 3C:
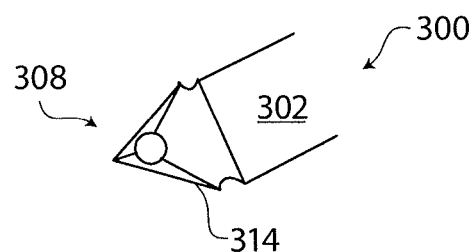

In other embodiments, as illustrated in FIG. 3C, the blade portions 314 can be attached or connected to the longitudinal body 302 with a hinge or other mechanical means that allows the blade portions 314 to bend outwards. As mentioned above, the blade portions can also or alternatively be made of a flexible material. Also, the tapered portion 308 can be of different lengths, and illustrated in FIGS. 3A to 3C. FIG. 3A illustrates a relatively longer tapered portion 308 that forms at least half of the overall length of the longitudinal body 302. In contrast, FIG. 3C illustrates a relatively short tapered portion 308 that is only located on the distal portion of the device, and forms less than half of the overall length of the longitudinal body 302, such as less than about 30%, less than about 20% or less than about 10% of the overall length of the longitudinal body 302.

In some embodiments, the dilator 300 can instead be used as a delivery sheath or sleeve that covers the implant 26. The sheath or sleeve embodiment can be used, for example, when the implant 26 includes an integrated broach portion on the distal end of the implant 26. In some embodiments, the sheath or sleeve embodiment has a tapered portion 308 that substantially matches the taper of the broach. In some embodiments, the implant 26, rather than an inner tube 316, is used to push open the blade portions 314. In some embodiments, the broach portion of an implant 26 with an integrated broach portion is used to push open the blade portions 314.

Figure 4A:
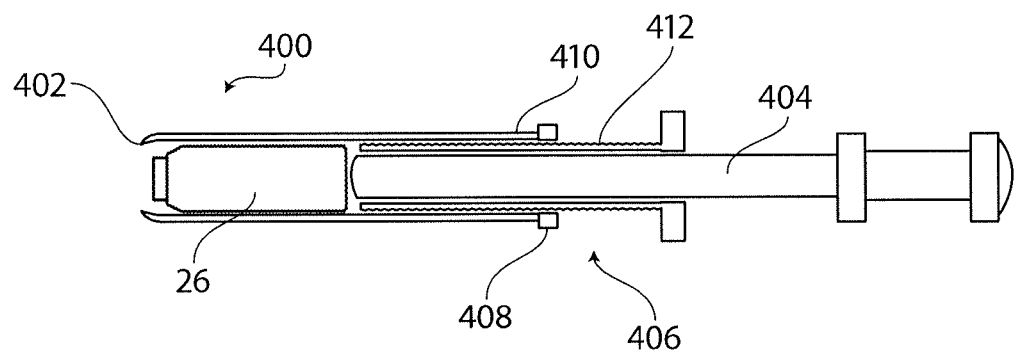
FIGS. 4A and 4B show an embodiment of a delivery sleeve that can be used in place of a dilator.
Figure 4B:
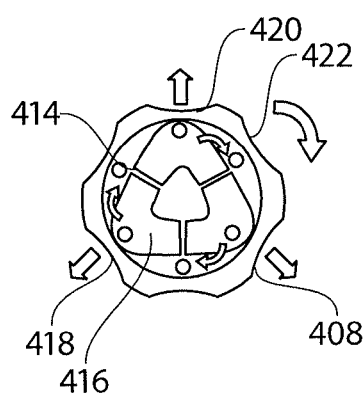

FIGS. 4A and 4B show an embodiment of a delivery sleeve 400 that can be used in place of a dilator and/or soft tissue protector. The delivery sleeve 400 can be made to fit over the implant 26 and have a tapered distal end 402 that can expand outwards to allow the implant 26 to pass through the delivery sleeve 400. The delivery sleeve 400 can be flexible so that the tapered distal end 402 can be expanded to allow the implant 26 to pass through. The tapered distal end 402 can include a plurality of slits 414 that divide the tapered distal end into blade portions 416 in a similar manner as described above for the dilators. The slits 414 can be aligned in a variety of ways, such as being aligned with the vertices or being aligned between the vertices. A variety of flexible materials can be used to fabricate the delivery sleeve 400, such as nitinol or another flexible metal or metal allow, or flexible nonmetal materials such as polymers. The delivery sleeve 400 can be shaped as described herein for dilators and other delivery sleeves. For example, the delivery sleeve 400 can be triangular shaped with a triangular cross-section for a triangular shaped implant 26 with a triangular cross-section. An impactor 404 sized to fit within the delivery sleeve 400 can be used to push the implant 26 out of the delivery sleeve 400 and into the implant site. In some embodiments, the delivery sleeve 400 is used to cover the implant 26 only during insertion of the implant 26 into the implant site.

In addition, in some embodiments, an adjusting sleeve 406 is configured to fit within the delivery sleeve 400 so that a variety of different length implants 26 can be used with a single length delivery sleeve 400. In some embodiments, the delivery sleeve 400 can have a threaded nut 408 located on the proximal end 410 of the delivery sleeve 400. The adjusting sleeve 406 can have corresponding external threads 412 on its outer surface and be sized to fit through the inner diameter of the nut 408 so that the external threads 412 on the adjusting sleeve 406 engage the internal threads on the nut 408. Once the threads are engaged, the adjusting sleeve 406 can be rotated relative to the nut 408 in order to advance or retract the adjusting sleeve 406 through the delivery sleeve 400. In other embodiments, the adjusting sleeve 406 can be adjusted with a ratcheting mechanism that is advanced via translation, such as pushing or pulling, as opposed to rotation. For example, the ratcheting mechanism can include a plurality of teeth on the adjusting sleeve 406 and a pawl on the delivery sleeve.

The adjusting sleeve 406 can be advanced to the implant 26 so that the distal end of the adjusting sleeve 406 abuts against the proximal end of the implant 26. In addition, the adjusting sleeve 406 can be advanced so that the implant 26 is pushed to or near the distal end 402 of the delivery sleeve 400. In order to expand the tapered distal end 402 of the delivery sleeve 400, the adjusting sleeve 406 can be further advanced through the delivery sleeve 400, thereby pushing the implant 26 so that the distal end of the implant 26 pushes apart the tapered distal end 402 of the delivery sleeve 400. The impactor 404 can be sized to fit through the adjusting sleeve 406. In addition, the system as described can be used with one or more of the following: a guide pin or guide wire, drill sleeve, drill, broach sleeve and broach, for example.

In some embodiments, the triangular delivery sleeve 400 is designed to go over a guide pin and then expand to dilate the soft tissues. As illustrated in FIG. 4B, the distal portion of the delivery sleeve 400 can include three rigid blade portions or arms 416 that cover each apex of the triangular shape. These arms 416 move in the direction of the small outward arrows when the nut or dial 408 in the proximal portion of the delivery sleeve 400 rotates by a predetermined amount, for example, by about 15, 20, 25, 30, 35, 40, 45, 50, 55 or 60 degrees. The dial 408 has rigid pins 418 which engage a path on the rigid arms 416 that force the rigid arms 416 to expand or collapse when the dial 408 is rotated. Three of the small circles 420 represent the rigid pins 416 in position 1, where the delivery sleeve 400 is in the relaxed step, with the arms 416 in a collapsed configuration, during initial insertion. The three other circles 422 represent the rigid pins 416 in position 2 where they have expanded the rigid arms 416 (expansion of arms not shown).

FIGS. 5A-5C illustrate an embodiment of a sequential dilation system. A guide pin 500 can be placed into the bone. In some embodiments, the guide pin 500 can have a cannula 502 or sleeve that covers at least the distal portion of the guide pin 500 prior to insertion. After the guide pin 500 is inserted into the bone at the right location and depth, the cannula 502 can be removed from the guide pin 500. In some embodiments, the distal portion of the guide pin 500 can include a plurality of prongs 504 that expand or curl outwards once removed from the cannula 502. The prongs 504 can form an anchor in the bone that anchors and prevents or inhibits further advancement of the guide pin 500 within the bone.

After the guide pin 500 has been inserted into the bone and the cannula 502 has been removed, a sequence of dilators can be inserted over the guide pin 500 in order to gradually dilate the soft tissue and to serve later as a guide for insertion of additional instruments and devices. For example, in some embodiments a drill dilator 506 can be inserted over the guide pin 500 to dilate the soft tissue. Additional dilators include, for example, a broach dilator 508 that can be placed over the drill dilator 506 and be shaped to match the cross-sectional shape of the broach and implant. For example, the broach dilator 508 can have a triangular cross section for a triangular implant. Placement of the broach dilator 508 over the drill dilator 506 further dilates the soft tissue around the guide pin 500. In addition, an outer cannula 510 that is shaped and sized to fit over the broach dilator 508 can be placed over the broach dilator 508 to further dilate the soft tissue and to complete the dilator system assembly.

In order to drill a hole through the bone around the guide pin 500, the drill dilator 506 can be removed. The drill dilator 506 can be sized to correspond to the diameter of the drill bit. Once the drill dilator 506 is removed, the broach dilator 508 and the space vacated by the drill dilator 506 forms a guide for the drill bit. After the hole is drilled, the broach dilator 508 can be removed. The outer cannula 510 and the space vacated by the broach dilator 508 forms a guide for a broach which widens the hole drilled into the bone into a hole shaped to receive the implant.

In some embodiments, the outer cannula 510 can include one or more stabilizing pins 512 that can be located around the circumference of the outer cannula 510. For example, a triangular shaped outer cannula 510 can have three stabilizing pins 512, with one stabilizing pin 512 located at each apex of the triangular cannula 510. The stabilizing pins 512 are aligned longitudinally along the outer cannula, with for example, the apexes of the triangular outer cannula 510 and/or the faces or flat portions of the outer cannula 510. The stabilizing pins 512 can be located in a channel or tube on the outer cannula 510, for example, and can be deployed into the bone after the outer cannula 510 is positioned over the guide pin and other dilators and into contact with the bone around the implant site. In some embodiments, the channel or tubes holding the stabilizing pins 512 are located on the outer surface of the outer cannula 510, while in other embodiments the channel or tubes are embedded within the outer cannula 510 walls. Deployment of the stabilizing pins 512 into the bone around the implant site provides additional stability to the dilator system, thereby reducing unwanted or inadvertent movement of the system during the implant insertion process and resulting in accurate placement of the implant in bone.

In some embodiments, the dilators and cannulas can be radiolucent and be made from radiolucent materials such as polymers or a carbon fiber based material. In general, instruments and devices that do not substantially enter the bone can be radiolucent in some embodiments, while instruments and devices that do substantially enter the bone can be radiopaque. This property of being radiolucent or radiopaque is applicable to all the embodiments disclosed herein.

For example, the drill dilator 506, the broach dilator 508 and the outer cannula 510 can be radiolucent, while the guide pin 500 and the implant can be radiopaque. In some embodiments, the stabilizing pins 512 can also be radiopaque. This allows the surgeon to monitor using fluoroscopy, for example, the position of the guide pin 500 and implant in the bone during the insertion procedure without being obscured by the dilators and cannulas, thereby reducing the likelihood that the guide pin 500 or implant is inserted into the wrong location, which can damage sensitive tissues such as blood vessels and nerves, and require the removal and reinsertion of the implant.

FIGS. 6A-6D illustrate embodiments of a quick change mechanism that allows two instruments or components to be quickly and reversibly connected together. Although the quick change or quick connect mechanism will now be described for a handle and a dilator, it should be understood that the quick change or quick connect mechanism can be used to connect many other types of instruments or components together. As shown in FIGS. 6A and 6B, a dilator 600 can be attached to a handle 602 using a bayonet-type connector. The bayonet connector can include, for example, a pin 604 or tab located on the distally located handle attachment portion 605 that is configured to fit into an L or J shaped slot 606 in the proximally located dilator attachment portion 608. In other embodiments, the pin 604 can be located on the dilator 600 and the L shaped slot 606 can be located on the handle 602. The L shaped slot 606 has an axially aligned slot portion 610 that is configured to receive the pin 604, and a transversely aligned slot portion 612 that is configured to reversibly lock the pin 604 in place in some embodiments. In some embodiments, the transversely aligned slot portion 612 can be angled or curved towards the proximal end of the dilator. One end of the transversely aligned slot portion 612 is connected to the axially aligned slot portion 610. In some embodiments, a locking slot portion 614 is located on the other end of the transversely aligned slot portion 612. The locking slot portion 614 extends axially and towards the proximal end of the dilator 600 and is configured to securely and reversibly lock the pin 604 in place. In some embodiments where the transversely aligned slot portion 612 is angled or curved towards the proximal end of the dilator 600, the transversely aligned slot portion 612 can also function as the locking slot portion.

To connect the dilator 600 to the handle 602, the pin 604 is aligned with and then inserted into the axially aligned slot portion 610 of the slot 606. Once the pin 604 reaches the end of the axially aligned slot portion 610, the handle 602 is rotated or twisted relative to the dilator 600 about the longitudinal axis, thereby moving the pin 604 along the transversely aligned slot portion 612. Once the pin 604 reaches the end of the transversely aligned slot portion 612, a spring, which can be constantly applying a force or tension on the pin 604 towards the proximal end of the dilator 600, pushes and secures the pin 604 into the locking slot portion 614. Once in the locking slot portion 614, the pin 604 is restricted from moving in the transverse direction as well as in the axial direction towards the proximal end of the dilator.

To remove the dilator 600 from the handle 602, the pin 604 is pushed axially towards the distal end of the dilator, thereby moving the pin out 604 out of the locking slot portion 614. Next, the pin 604 is rotated along the transversely aligned slot portion 612 until the pin 604 reaches the axially aligned slot portion 610. Once the pin 604 reaches the axially aligned slot portion 610, the pin 604 can be removed from the L shaped slot, thereby disconnecting the handle 602 from the dilator 600. As mentioned above, portions of the dilator 600 and handle 602, such as collar portions, can be knurled to provide an enhanced gripping feature.

An embodiment of an alternative quick connect mechanism is illustrated in FIGS. 6C and 6D. In some embodiments, this mechanism includes at least one spring loaded pin 616 or spring loaded bearing that is located on the inner circumference of the handle attachment portion 605. In some embodiments, the mechanism includes a plurality of spring loaded pins 616, such as 2, 3 or 4 or more spring loaded pins 616. In some embodiments, the dilator 600 can include pin receptacles 618 that are configured to receive the spring loaded pins 616. In addition, the dilator 600 can include a pin groove 620 that is configured to receive the spring loaded pins 616. The pin groove 620 can be configured to align the spring loaded pins 616 with the pin receptacles 618. In some embodiments, the pin receptacles 618 are located along the pin groove 620, and the depth of the pin receptacles 618 is generally greater than the depth of the pin groove 620. In other embodiments, the spring loaded pins 616 can be located on the dilator 600 while the pin receptacles 618 and pin groove 620 can be located on the handle 602.

To connect the dilator 600 to the handle 602, the spring loaded pins 616 can be aligned with the pin receptacles 618. The handle 602 and dilator 600 can then be pushed together. As the handle 602 and dilator 600 are pushed together, the spring loaded pins 616 are initially pushed back into the handle 602 so that the handle 602 can slide over the dilator 600. Once the spring loaded pins 616 are aligned over the pin receptacles 618 or pin groove 620, the spring loaded pins 616 push back out from the handle and into the pin receptacles 618 or pin groove 620 on the dilator 600. If the spring loaded pins 616 are in the pin groove 620, the spring loaded pins 616 can be rotated along the pin groove 620 until the spring loaded pins 616 are aligned with the pin receptacles 618. Once aligned, the spring loaded pins 616 push into pin receptacles 618, thereby reversibly locking the dilator 600 and handle 602 together.

In some embodiments, to remove the dilator 600 from the handle 602, the dilator 600 and handle 602 can be simply be pulled apart, with or without rotation depending on the embodiment. As force is exerted on the spring loaded pins 616 in the pin receptacles 618, the spring loaded pins 616 begin to be pushed back into the handle 602. Once enough force is exerted on the spring loaded pins 616, from a pulling force and/or rotational force, the spring loaded pins 616 will retract back into the handle 606 and allow the dilator 600 to be separated from the handle 602. In other embodiments, the handle 602 can have a pin retractor that can be actuated to temporarily retract the spring loaded pins 616 into the handle 602. The pin retractor can be actuated prior to either handle 602 connection or handle 602 removal to ease connection and removal of the handle 602 from the dilator.

The soft tissue protectors, dilators, delivery sleeves and quick connect mechanisms described above can be used with a variety of implants in a variety of implant procedures, examples of which are further described below.

Figure 7:
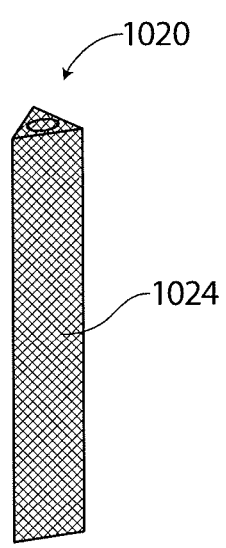
FIG. 7 illustrates an embodiment of an implant structure.
Figure 9:
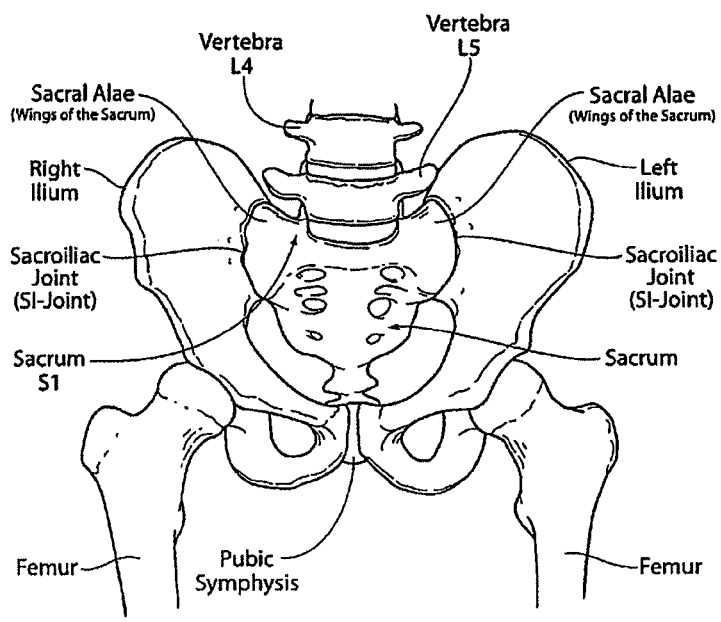
FIGS. 9 and 10 are, respectively, anterior and posterior anatomic views of the human hip girdle comprising the sacrum and the hip bones (the right ilium, and the left ilium), the sacrum being connected with both hip bones at the sacroiliac joint (in shorthand, the SI-Joint).
Figure 10:
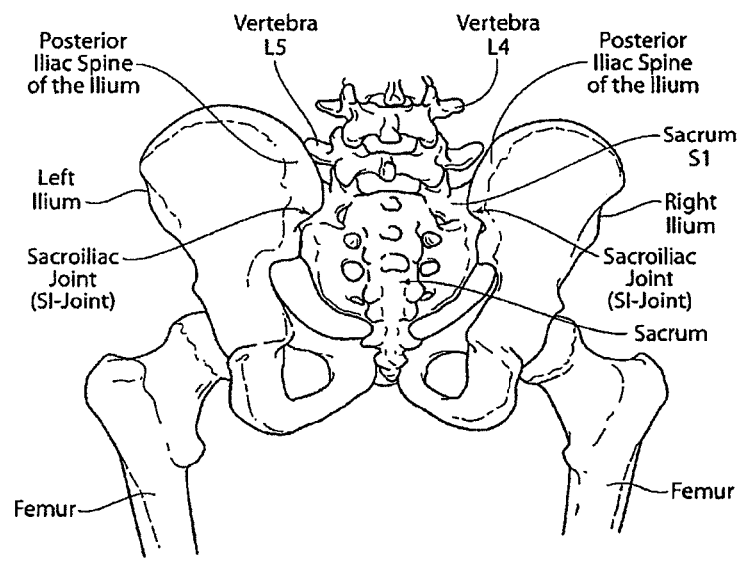

Elongated, stem-like implant structures 1020 like that shown in FIG. 7 make possible the fixation of the SI-Joint (shown in anterior and posterior views, respectively, in FIGS. 9 and 10) in a minimally invasive manner. These implant structures 1020 can be effectively implanted through the use a lateral surgical approach. The procedure is desirably aided by conventional lateral and/or anterior-posterior (A-P) visualization techniques, e.g., using X-ray image intensifiers such as a C-arms, intraoperative CT scanners, or fluoroscopes to produce a live image feed which is displayed on a TV screen.

In one embodiment of a lateral approach (see FIGS. 11, 12, and 13A/B), one or more implant structures 1020 are introduced laterally through the ilium, the SI-Joint, and into the sacrum. This path and resulting placement of the implant structures 1020 are best shown in FIGS. 12 and 13A/B. In the illustrated embodiment, three implant structures 1020 are placed in this manner. Also in the illustrated embodiment, the implant structures 1020 are rectilinear in cross section and triangular in this case, but it should be appreciated that implant structures 1020 of other cross sections can be used. For example, the implant structures can have a square cross-section. In some embodiments, the implant structures can have a curvilinear cross-section, such as circular, oval or elliptical. The cross-sections discussed above refer to the transverse cross-section of the implant rather than a longitudinal cross-section taken along the longitudinal axis of the implant structure. In addition, the term rectilinear describes a device that is defined or substantially defined by straight lines. This includes, for example, triangles, squares, and other polygons, and also includes triangles, squares and other polygons having rounded corners. In contrast, the term curvilinear is meant to describe devices that are defined by only curved lines, such as a circle or ellipse, for example.

Before undertaking a lateral implantation procedure, the physician identifies the SI-Joint segments that are to be fixated or fused (arthrodesed) using, e.g., the Fortin finger test, thigh thrust, FABER, Gaenslen's, compression, distraction, and diagnostic SI joint injection.

Figure 8A:
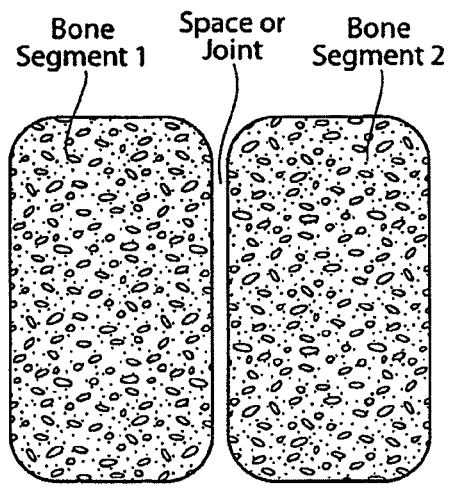
Figure 8B:
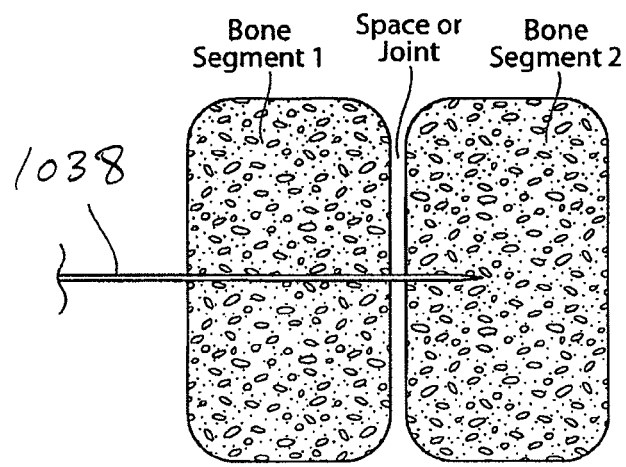

Aided by lateral and anterior-posterior (A-P) c-arm images, and with the patient lying in a prone position, the physician aligns the greater sciatic notches (using lateral visualization) to provide a true lateral position. A 3 cm incision is made starting aligned with the posterior cortex of the sacral canal, followed by blunt tissue separation to the ilium. From the lateral view, the guide pin 1038 (with sleeve (not shown)) (e.g., a Steinmann Pin) is started resting on the ilium at a position inferior to the sacrum end plate and just anterior to the sacral canal. In A-P and lateral views, the guide pin 1038 should be parallel to the sacrum end plate at a shallow angle anterior (e.g., 15.degree. to 20.degree. off horizontal, as FIG. 13A shows). In a lateral view, the guide pin 1038 should be posterior to the sacrum anterior wall. In the A-P view, the guide pin 1038 should be superior to the sacral inferior foramen and lateral of mid-line. This corresponds generally to the sequence shown diagrammatically in FIGS. 8A and 8B. A soft tissue protector (not shown) is desirably slipped over the guide pin 1038 and firmly against the ilium before removing the guide pin sleeve (not shown).

Figure 8C:
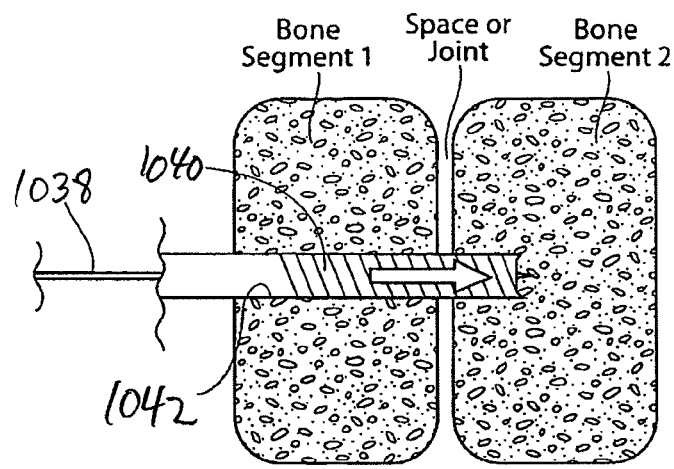

Over the guide pin 1038 (and through the soft tissue protector), the pilot bore 1042 is drilled in the manner previously described, as is diagrammatically shown in FIG. 8C. The pilot bore 1042 extends through the ilium, through the SI-Joint, and into the S1. The drill bit 1040 is removed.

The shaped broach 1044 is tapped into the pilot bore 1042 over the guide pin 1038 (and through the soft tissue protector) to create a broached bore 1048 with the desired profile for the implant structure 1020, which, in the illustrated embodiment, is triangular. This generally corresponds to the sequence shown diagrammatically in FIG. 8D. The triangular profile of the broached bore 1048 is also shown in FIG. 11.

Figure 8E:
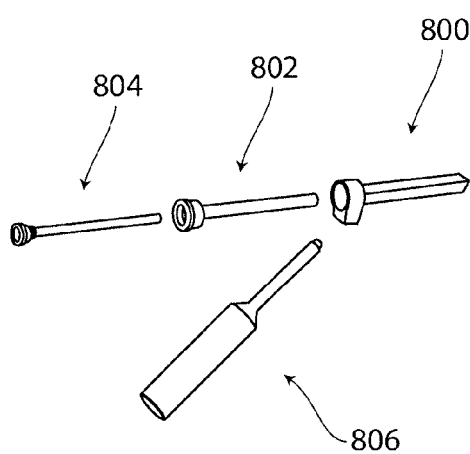
FIGS. 8E and 8F illustrate an embodiment of the assembly of a soft tissue protector or dilator with a drill sleeve and a guide pin sleeve.
Figure 8F:
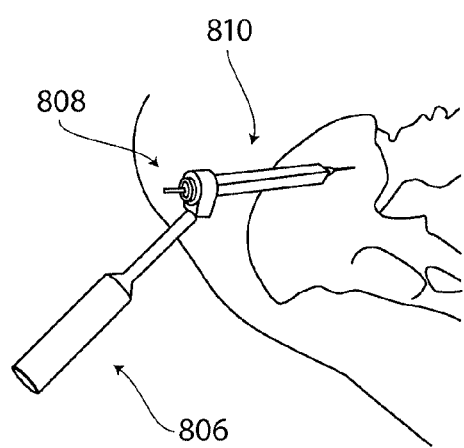

FIGS. 8E and 8F illustrate an embodiment of the assembly of a soft tissue protector or dilator or delivery sleeve 800 with a drill sleeve 802, a guide pin sleeve 804 and a handle 806. In some embodiments, the drill sleeve 802 and guide pin sleeve 804 can be inserted within the soft tissue protector 800 to form a soft tissue protector assembly 810 which can slide over the guide pin 808 until bony contact is achieved. The soft tissue protector 800 can be any one of the soft tissue protectors or dilators or delivery sleeves disclosed herein. In some embodiments, an expandable dilator or delivery sleeve 800 as disclosed herein can be used in place of a conventional soft tissue dilator. In the case of the expandable dilator, in some embodiments, the expandable dilator can be slid over the guide pin and then expanded before the drill sleeve 802 and/or guide pin sleeve 804 are inserted within the expandable dilator. In other embodiments, insertion of the drill sleeve 802 and/or guide pin sleeve 804 within the expandable dilator can be used to expand the expandable dilator.

In some embodiments, a dilator can be used to open a channel though the tissue prior to sliding the soft tissue protector assembly 810 over the guide pin. The dilator(s) can be placed over the guide pin, using for example a plurality of sequentially larger dilators or using an expandable dilator. After the channel has been formed through the tissue, the dilator(s) can be removed and the soft tissue protector assembly can be slid over the guide pin. In some embodiments, the expandable dilator can serve as a soft tissue protector after being expanded. For example, after expansion the drill sleeve and guide pin sleeve can be inserted into the expandable dilator.

Figure 11:
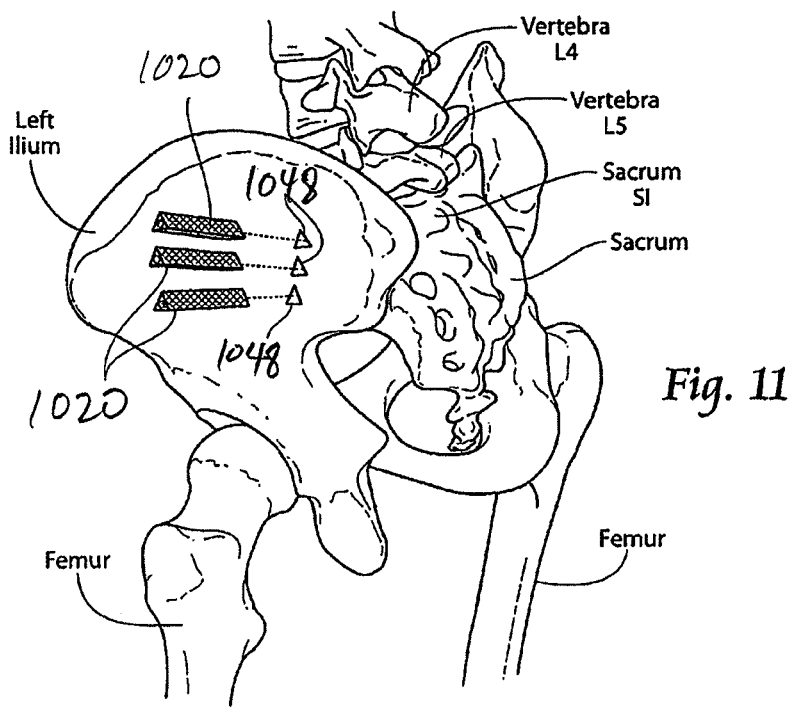
FIGS. 11, 12, 13A and 13B are anatomic views showing, respectively, a pre-implanted perspective, implanted perspective, implanted anterior view, and implanted craniocaudal section view, the implantation of three implant structures for the fixation of the SI-Joint using a lateral approach through the ilium, the SI-Joint, and into the sacrum.
Figure 12:
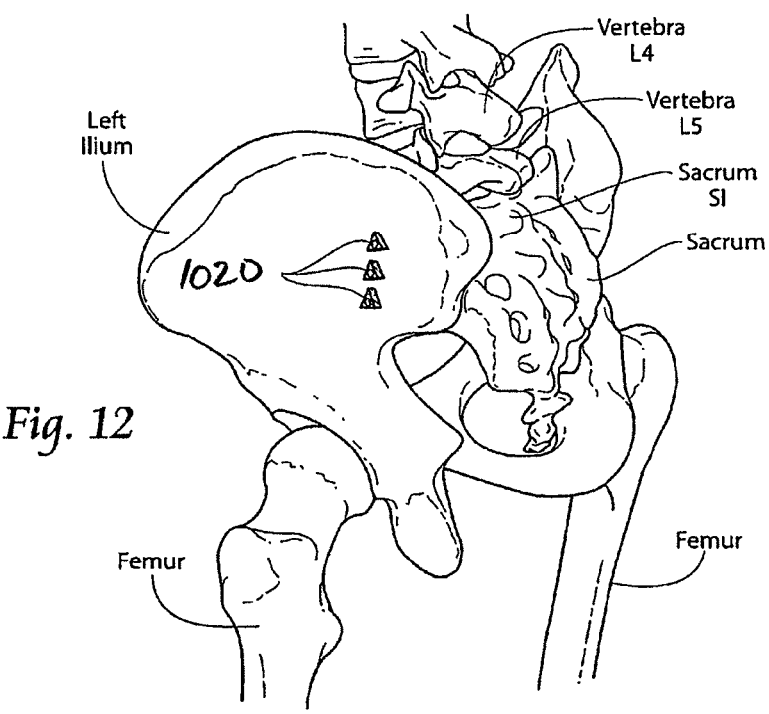
Figure 13A:
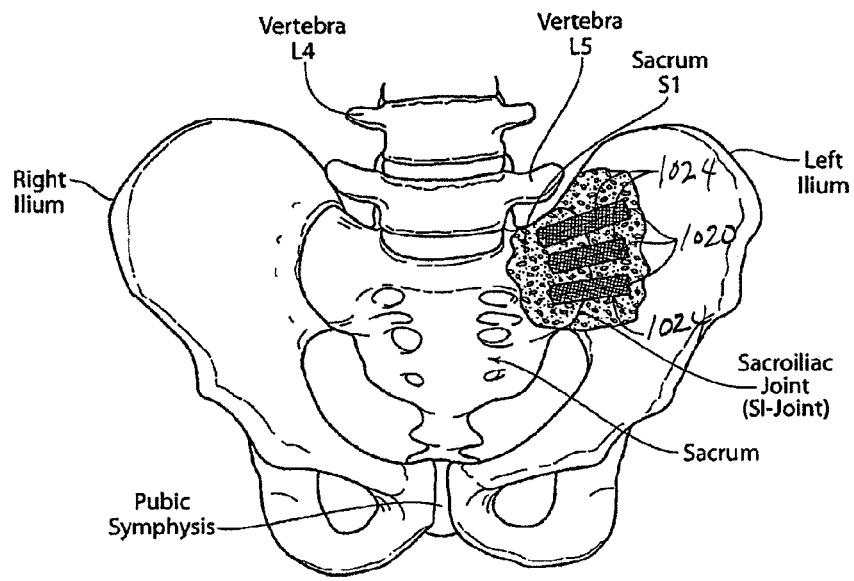
Figure 13B:
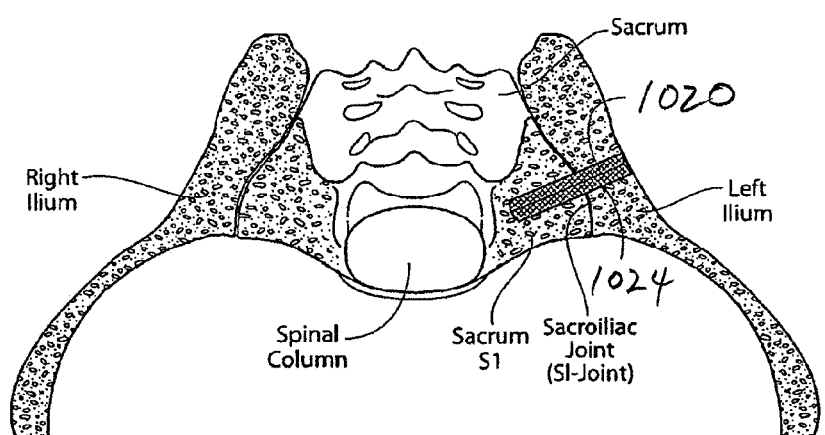

As shown in FIGS. 11 and 12, a triangular implant structure 1020 can be now tapped through the soft tissue protector over the guide pin 1038 through the ilium, across the SI-Joint, and into the sacrum, until the proximal end of the implant structure 1020 is flush against the lateral wall of the ilium (see also FIGS. 13A and 13B). The guide pin 1038 and soft tissue protector are withdrawn, leaving the implant structure 1020 residing in the broached passageway, flush with the lateral wall of the ilium (see FIGS. 13A and 13B). In the illustrated embodiment, two additional implant structures 1020 are implanted in this manner, as FIG. 12 best shows. In other embodiments, the proximal ends of the implant structures 1020 are left proud of the lateral wall of the ilium, such that they extend 1, 2, 3 or 4 mm outside of the ilium. This ensures that the implants 1020 engage the hard cortical portion of the ilium rather than just the softer cancellous portion, through which they might migrate if there was no structural support from hard cortical bone. The hard cortical bone can also bear the loads or forces typically exerted on the bone by the implant 1020.

The implant structures 1020 are sized according to the local anatomy. For the SI-Joint, representative implant structures 1020 can range in size, depending upon the local anatomy, from about 35 mm to about 60 mm in length, and about a 7 mm inscribed diameter (i.e. a triangle having a height of about 10.5 mm and a base of about 12 mm). The morphology of the local structures can be generally understood by medical professionals using textbooks of human skeletal anatomy along with their knowledge of the site and its disease or injury. The physician is also able to ascertain the dimensions of the implant structure 1020 based upon prior analysis of the morphology of the targeted bone using, for example, plain film x-ray, fluoroscopic x-ray, or MRI or CT scanning.

Using a lateral approach, one or more implant structures 1020 can be individually inserted in a minimally invasive fashion across the SI-Joint, as has been described. Conventional tissue access tools, obturators, cannulas, and/or drills can be used for this purpose. Alternatively, the novel tissue access tools described above and in FIGS. 1-6 can also be used. No joint preparation, removal of cartilage, or scraping are required before formation of the insertion path or insertion of the implant structures 1020, so a minimally invasive insertion path sized approximately at or about the maximum outer diameter of the implant structures 1020 can be formed.

The implant structures 1020 can obviate the need for autologous bone graft material, additional pedicle screws and/or rods, hollow modular anchorage screws, cannulated compression screws, threaded cages within the joint, or fracture fixation screws. Still, in the physician's discretion, bone graft material and other fixation instrumentation can be used in combination with the implant structures 20.

In a representative procedure, one to six, or perhaps up to eight, implant structures 1020 can be used, depending on the size of the patient, the number of SI Joints treated, and the size of the implant structures 1020. After installation, the patient would be advised to prevent or reduce loading of the SI-Joint while fusion occurs. This could be about a three to twelve week period or more, depending on the health of the patient and his or her adherence to post-op protocol.

The implant structures 1020 make possible surgical techniques that are less invasive than traditional open surgery with no extensive soft tissue stripping. The lateral approach to the SI-Joint provides a straightforward surgical approach that complements the minimally invasive surgical techniques. The profile and design of the implant structures 1020 minimize or reduce rotation and micromotion. Rigid implant structures 1020 made from titanium provide immediate post-op SI Joint stability. A bony in-growth region 1024 comprising a porous plasma spray coating with irregular surface supports stable bone fixation/fusion. The implant structures 1020 and surgical approaches make possible the placement of larger fusion surface areas designed to maximize post-surgical weight bearing capacity and provide a biomechanically rigorous implant designed specifically to stabilize the heavily loaded SI-Joint.

Systems and Methods for Implanting Bone Graft and Implant

Figure 14:
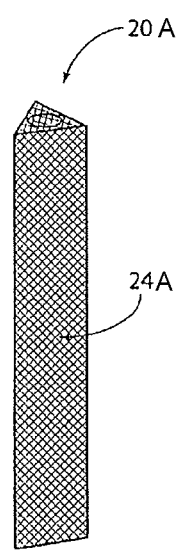
FIG. 14 illustrates an embodiment of an implant structure.
Figure 16:
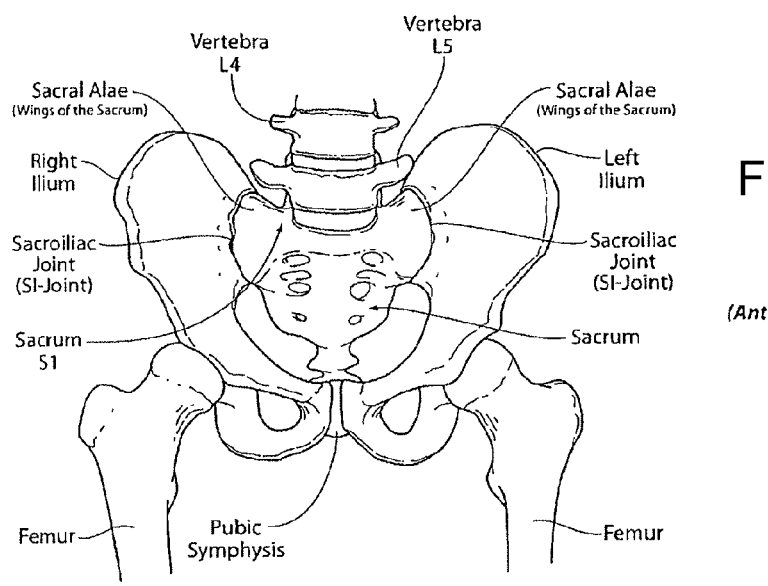
FIGS. 16 and 17 are, respectively, anterior and posterior anatomic views of the human hip girdle comprising the sacrum and the hip bones (the right ilium, and the left ilium), the sacrum being connected with both hip bones at the sacroiliac joint (in shorthand, the SI-Joint).
Figure 17:
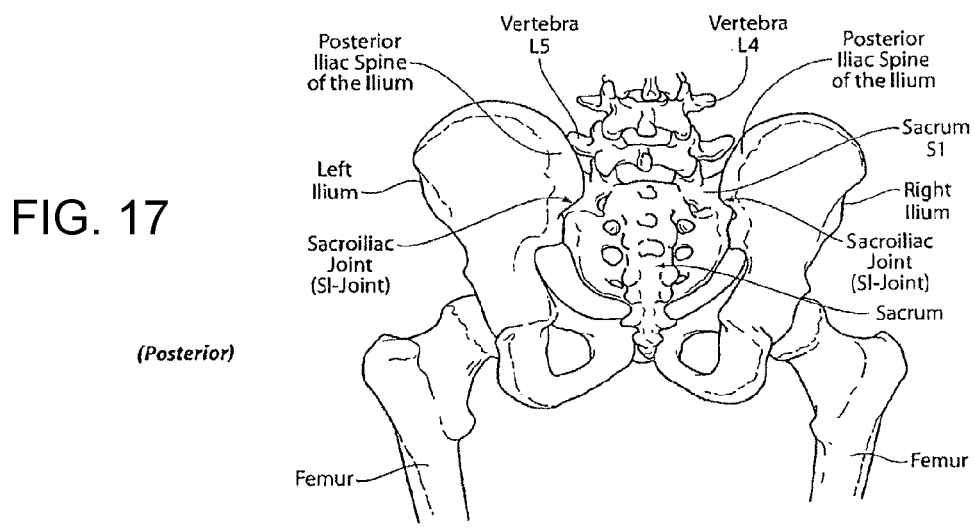

Elongated, stem-like implant structures 20A like that shown in FIG. 14 make possible the fixation of the SI-Joint (shown in anterior and posterior views, respectively, in FIGS. 16 and 17) in a minimally invasive manner. These implant structures 20A can be effectively implanted through the use a lateral surgical approach. The procedure is desirably aided by conventional lateral, inlet, and outlet visualization techniques, e.g., using X-ray image intensifiers such as a C-arms or fluoroscopes to produce a live image feed, which is displayed on a TV screen.

In one embodiment of a lateral approach (see FIGS. 18, 19, and 20A/B), one or more implant structures 20A are introduced laterally through the ilium, the SI-Joint, and into the sacrum. This path and resulting placement of the implant structures 20A are best shown in FIGS. 19 and 20A/B. In the illustrated embodiment, three implant structures 20A are placed in this manner. Also in the illustrated embodiment, the implant structures 20A are rectilinear in cross section and triangular in this case, but it should be appreciated that implant structures 20A of other rectilinear cross sections can be used.

Before undertaking a lateral implantation procedure, the physician identifies the SI-Joint segments that are to be fixated or fused (arthrodesed) using, e.g., the Fortin finger test, thigh thrust, FABER, Gaenslen's, compression, distraction, and diagnostic SI joint injection . . . .

Figure 15A:
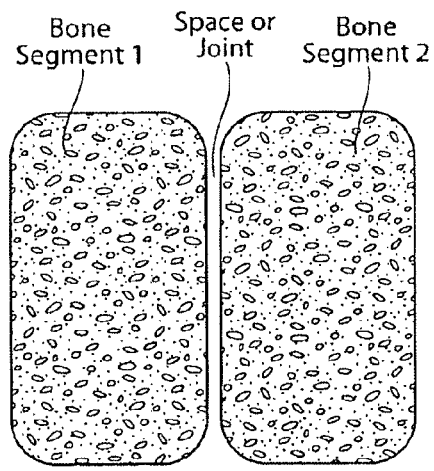
FIGS. 15A-15D are side section views of the formation of a broached bore in bone according to one embodiment of the invention.
Figure 15B:
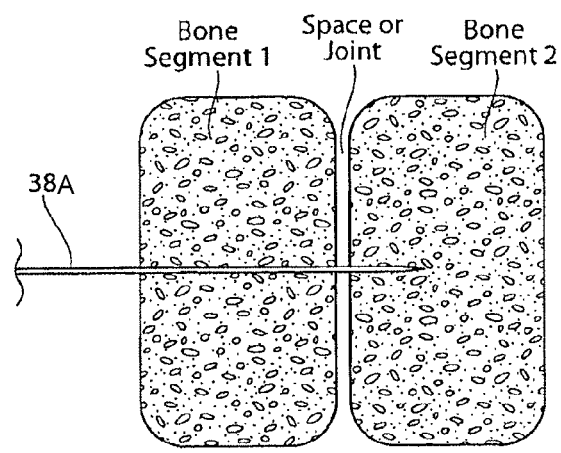

Aided by lateral, inlet, and outlet C-arm views, and with the patient lying in a prone position, the physician aligns the greater sciatic notches and then the alae (using lateral visualization) to provide a true lateral position. A 3 cm incision is made starting aligned with the posterior cortex of the sacral canal, followed by blunt tissue separation to the ilium. From the lateral view, the guide pin 38A (with sleeve (not shown)) (e.g., a Steinmann Pin) is started resting on the ilium at a position inferior to the sacrum end plate and just anterior to the sacral canal. In the outlet view, the guide pin 38A should be parallel to the sacrum end plate at a shallow angle anterior (e.g., 15.degree. to 20.degree. off the floor, as FIG. 20A shows). In a lateral view, the guide pin 38A should be posterior to the sacrum anterior wall. In the outlet view, the guide pin 38A should be superior to the first sacral foramen and lateral of mid-line. This corresponds generally to the sequence shown diagrammatically in FIGS. 15A and 15B. A soft tissue protector (not shown) is desirably slipped over the guide pin 38A and firmly against the ilium before removing the guide pin sleeve (not shown).

Figure 15C:
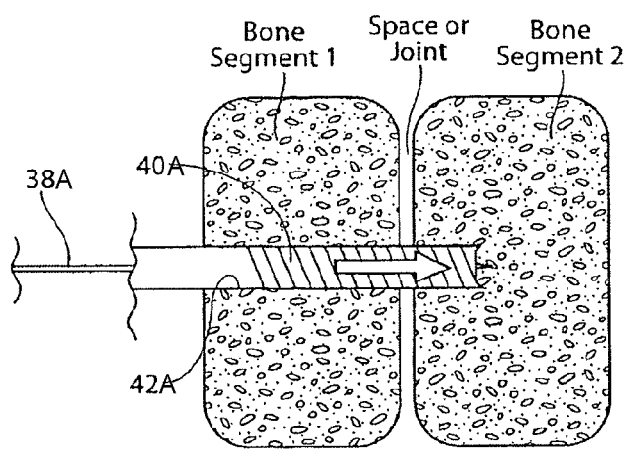

Over the guide pin 38A (and through the soft tissue protector), the pilot bore 42A is drilled in the manner previously described, as is diagrammatically shown in FIG. 15C. The pilot bore 42A extends through the ilium, through the SI-Joint, and into the S1. The drill bit 40A is removed.

Figure 15D:
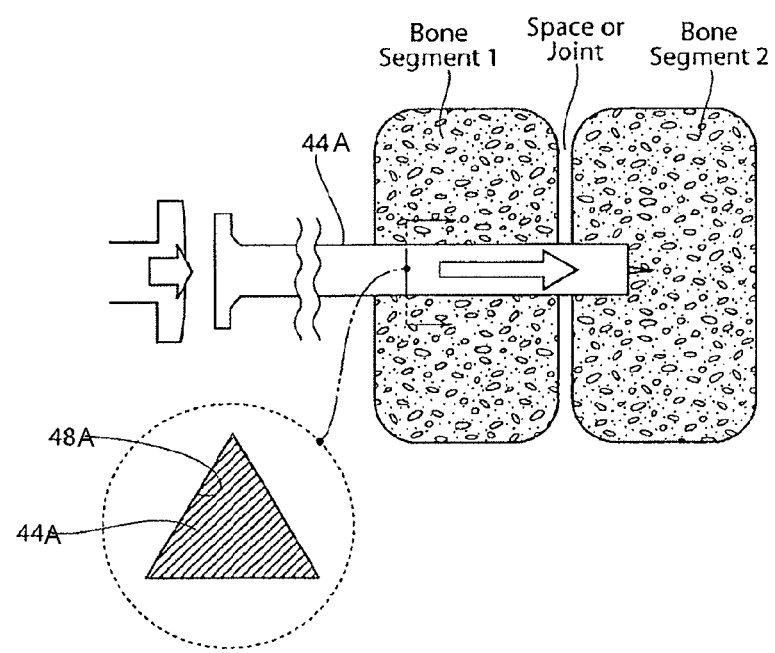

The shaped broach 44A is tapped into the pilot bore 42A over the guide pin 38A (and through the soft tissue protector) to create a broached bore 48A with the desired profile for the implant structure 20A, which, in the illustrated embodiment, is triangular. This generally corresponds to the sequence shown diagrammatically in FIG. 15D. The triangular profile of the broached bore 48A is also shown in FIG. 18.

Figure 15E:
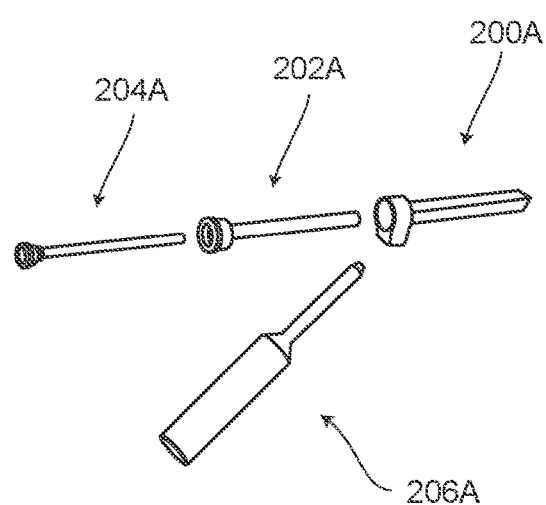
FIGS. 15E and 15F illustrate the assembly of a soft tissue protector system for placement over a guide wire.
Figure 15F:
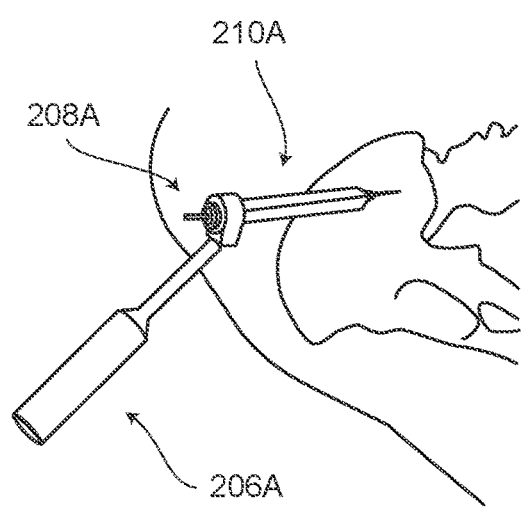

FIGS. 15E and 15F illustrate an embodiment of the assembly of a soft tissue protector or dilator or delivery sleeve 200A with a drill sleeve 202A, a guide pin sleeve 204A and a handle 206A. In some embodiments, the drill sleeve 202A and guide pin sleeve 204A can be inserted within the soft tissue protector 200A to form a soft tissue protector assembly 210A that can slide over the guide pin 208A until bony contact is achieved. The soft tissue protector 200A can be any one of the soft tissue protectors or dilators or delivery sleeves disclosed herein. In some embodiments, an expandable dilator or delivery sleeve 200A as disclosed herein can be used in place of a conventional soft tissue dilator. In the case of the expandable dilator, in some embodiments, the expandable dilator can be slid over the guide pin and then expanded before the drill sleeve 202A and/or guide pin sleeve 204A are inserted within the expandable dilator. In other embodiments, insertion of the drill sleeve 202A and/or guide pin sleeve 204A within the expandable dilator can be used to expand the expandable dilator.

In some embodiments, a dilator can be used to open a channel though the tissue prior to sliding the soft tissue protector assembly 210A over the guide pin. The dilator(s) can be placed over the guide pin, using for example a plurality of sequentially larger dilators or using an expandable dilator. After the channel has been formed through the tissue, the dilator(s) can be removed and the soft tissue protector assembly can be slid over the guide pin. In some embodiments, the expandable dilator can serve as a soft tissue protector after being expanded. For example, after expansion the drill sleeve and guide pin sleeve can be inserted into the expandable dilator.

Figure 18:
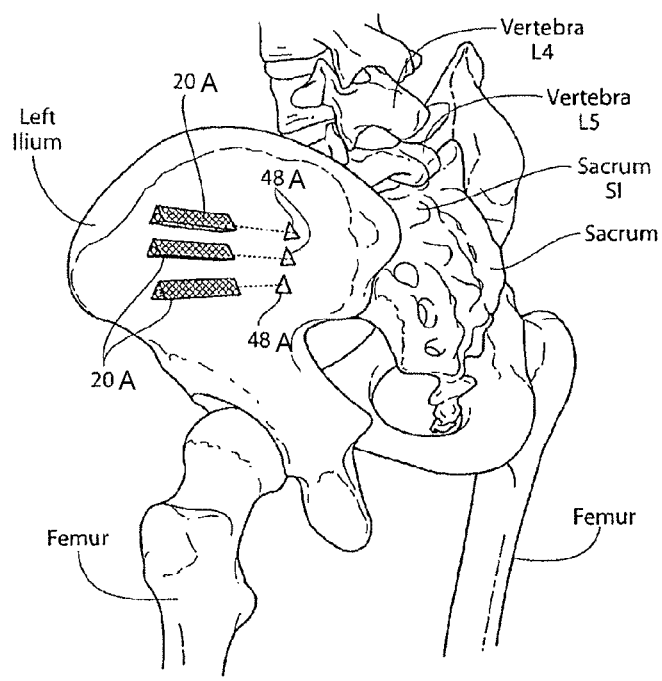
FIGS. 18, 19, 20A and 20B are anatomic views showing, respectively, a pre-implanted perspective, implanted perspective, implanted anterior view, and implanted craniocaudal section view, the implantation of three implant structures for the fixation of the SI-Joint using a lateral approach through the ilium, the SI-Joint, and into the sacrum.
Figure 19:
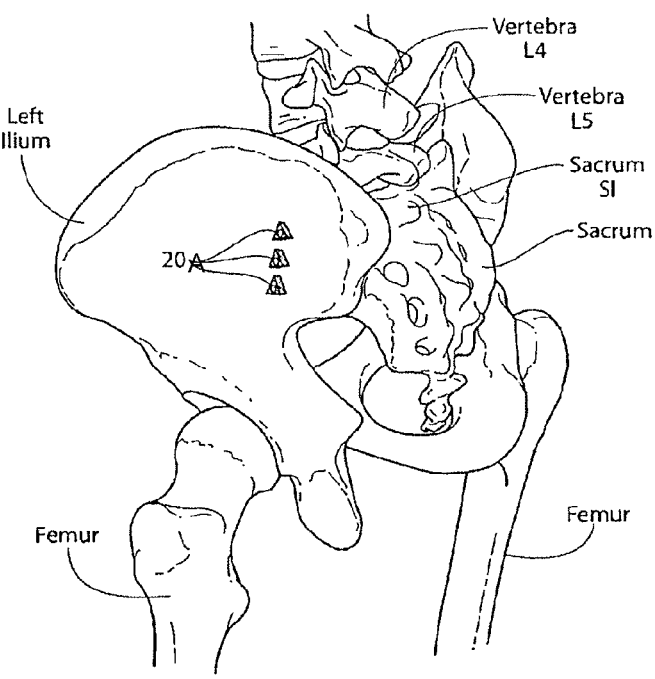
Figure 20A:
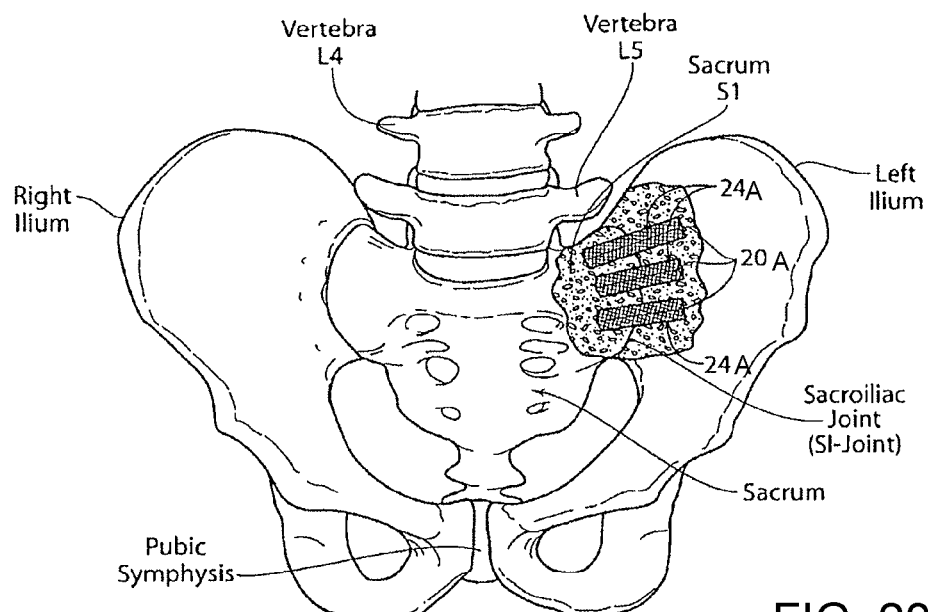
Figure 20B:
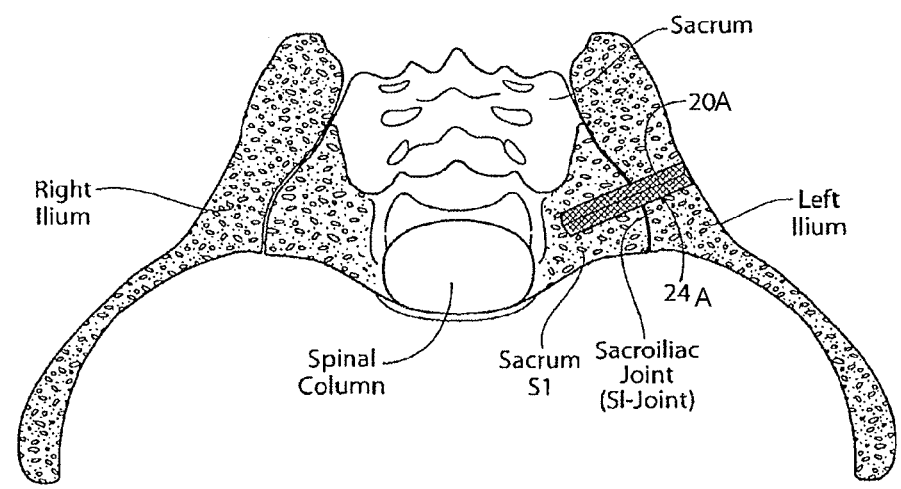

As shown in FIGS. 18 and 19, a triangular implant structure 20A can be now tapped through the soft tissue protector over the guide pin 38A through the ilium, across the SI-Joint, and into the sacrum, until the proximal end of the implant structure 20A is flush against the lateral wall of the ilium (see also FIGS. 20A and 20B). The guide pin 38A and soft tissue protector are withdrawn, leaving the implant structure 20 residing in the broached passageway, flush with the lateral wall of the ilium (see FIGS. 13A and 13B). In the illustrated embodiment, two additional implant structures 20A are implanted in this manner, as FIG. 19 best shows. In other embodiments, the proximal ends of the implant structures 20A are left proud of the lateral wall of the ilium, such that they extend 1, 2, 3 or 4 mm outside of the ilium. This ensures that the implants 20A engage the hard cortical portion of the ilium rather than just the softer cancellous portion, through which they might migrate if there was no structural support from hard cortical bone. The hard cortical bone can also bear the loads or forces typically exerted on the bone by the implant 20A.

The implant structures 20A are sized according to the local anatomy. For the SI-Joint, representative implant structures 20A can range in size, depending upon the local anatomy, from about 35 mm to about 60 mm in length, and about a 7 mm inscribed diameter (i.e. a triangle having a height of about 10.5 mm and a base of about 12 mm). The morphology of the local structures can be generally understood by medical professionals using textbooks of human skeletal anatomy along with their knowledge of the site and its disease or injury. The physician is also able to ascertain the dimensions of the implant structure 20A based upon prior analysis of the morphology of the targeted bone using, for example, plain film x-ray, fluoroscopic x-ray, or MRI or CT scanning.

Using a lateral approach, one or more implant structures 20A can be individually inserted in a minimally invasive fashion across the SI-Joint, as has been described. Conventional tissue access tools, obturators, cannulas, and/or drills can be used for this purpose. Alternatively, the novel tissue access tools described above and in U.S. Application No. 61/609,043, titled "TISSUE DILATOR AND PROTECTER" and filed Mar. 9, 2012, which is hereby incorporated by reference in its entirety, can also be used. No joint preparation, removal of cartilage, or scraping are required before formation of the insertion path or insertion of the implant structures 20A, so a minimally invasive insertion path sized approximately at or about the maximum outer diameter of the implant structures 20A can be formed.

The implant structures 20A can obviate the need for autologous bone graft material, additional pedicle screws and/or rods, hollow modular anchorage screws, cannulated compression screws, threaded cages within the joint, or fracture fixation screws. Still, in the physician's discretion, bone graft material and other fixation instrumentation can be used in combination with the implant structures 20A.

In a representative procedure, one to six, or perhaps up to eight, implant structures 20A can be used, depending on the size of the patient and the size of the implant structures 20A. After installation, the patient would be advised to prevent or reduce loading of the SI-Joint while fusion occurs. This could be about a six to twelve week period or more, depending on the health of the patient and his or her adherence to post-op protocol.

The implant structures 20A make possible surgical techniques that are less invasive than traditional open surgery with no extensive soft tissue stripping. The lateral approach to the SI-Joint provides a straightforward surgical approach that complements the minimally invasive surgical techniques. The profile and design of the implant structures 20A minimize or reduce rotation and micromotion. Rigid implant structures 20A made from titanium provide immediate post-op SI Joint stability. A bony in-growth region 24A comprising a porous plasma spray coating with irregular surface supports stable bone fixation/fusion. The implant structures 20A and surgical approaches make possible the placement of larger fusion surface areas designed to maximize post-surgical weight bearing capacity and provide a biomechanically rigorous implant designed specifically to stabilize the heavily loaded SI-Joint.

To improve the stability and weight bearing capacity of the implant, the implant can be inserted across three or more cortical walls. For example, after insertion the implant can traverse two cortical walls of the ilium and at least one cortical wall of the sacrum. The cortical bone is much denser and stronger than cancellous bone and can better withstand the large stresses found in the SI-Joint. By crossing three or more cortical walls, the implant can spread the load across more load bearing structures, thereby reducing the amount of load borne by each structure. In addition, movement of the implant within the bone after implantation is reduced by providing structural support in three locations around the implant versus two locations.

Figure 21A:
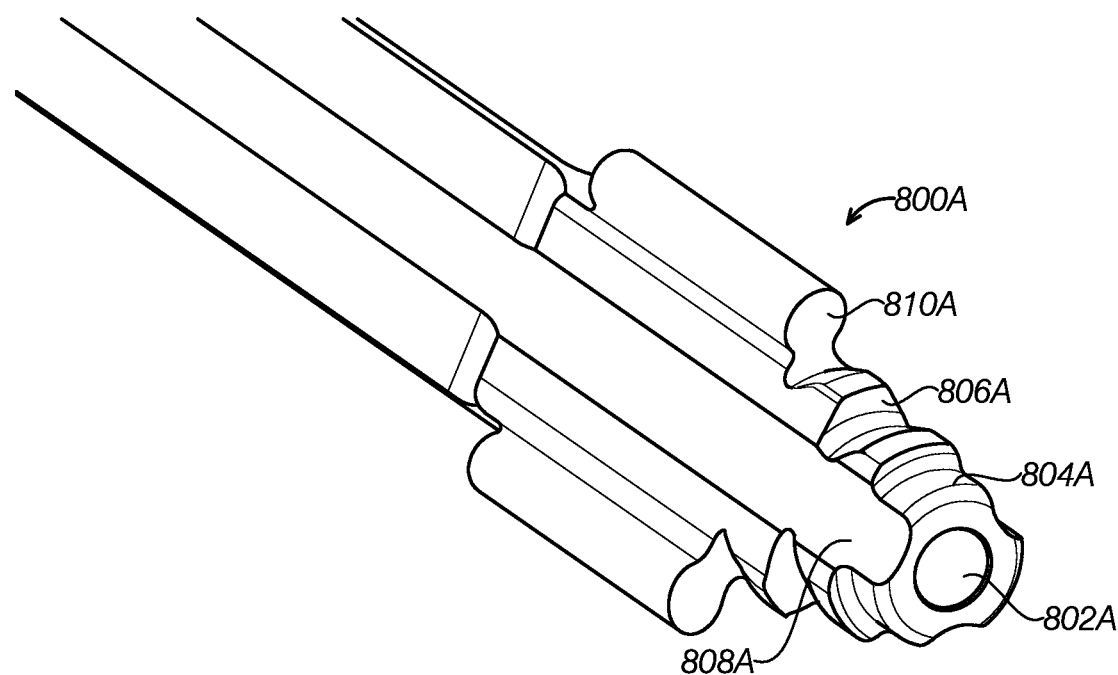
FIGS. 21A-21E illustrate embodiments of a modified broach for removing additional bone from a bore so that a bone graft or other material can be added with the implant.
Figure 21B:
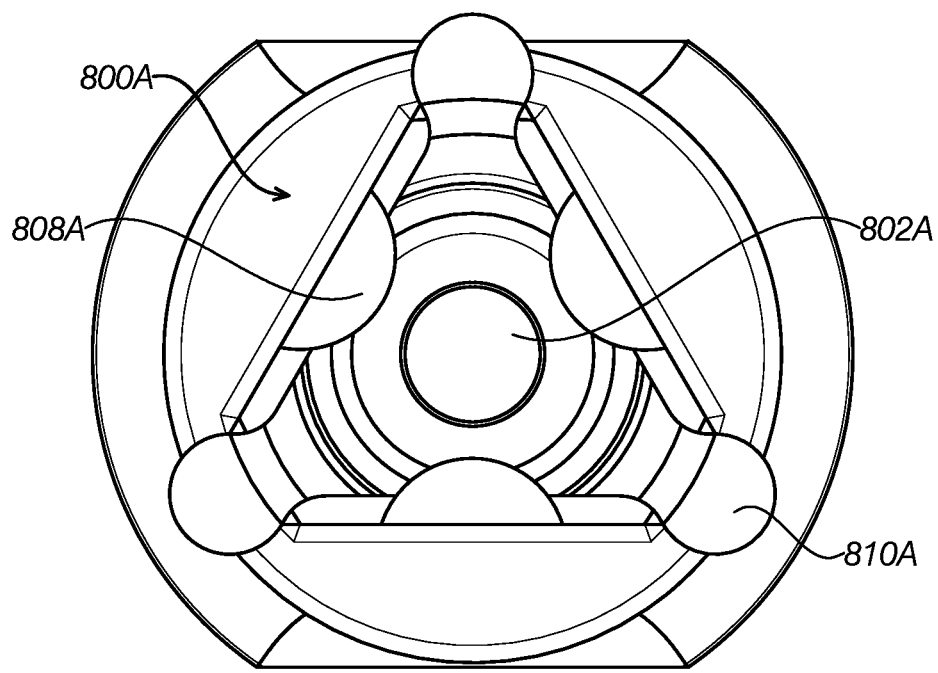

In some embodiments, it may be desirable to add a bone graft material and/or biologic aid along with the implant in order to promote bone growth around and/or into the implant. An embodiment of a modified broach 800A is illustrated in FIGS. 21A and 21B. The modified broach 800A can be used in place of the broach 44A illustrated in FIG. 15D to create a shaped bore with channels for receiving a bone graft material and/or biologic aid.

The modified broach 800A can have a cross-sectional profile that generally matches the shape of the implant. For example, for a triangular shaped implant, the modified broach 800A can have a generally triangular shaped cross-sectional profile. Likewise, for an implant with a rectangular, square, or any other rectilinear shape, the modified broach 800A can have a generally matching cross-sectional profile. In some embodiments, as illustrated in FIG. 21B, the modified broach 800A has a generally triangular cross-sectional profile. The modified broach 800A can have a lumen or channel 802A extending along its entire longitudinal length and sized and shaped so that the modified broach 800A can be placed over a guide pin. The distal end 804A of the modified broach 800A can be tapered and have a plurality of cutting surfaces 806A that function to chisel away bone from the bore. The cutting surfaces 806A can be angled slightly towards the distal end 804A with the more proximal cutting surfaces 806A larger than the more distal cutting surfaces 806A. In some embodiments, the cutting surfaces 806A are oriented with each apex of the modified broach 800A. This configuration allows the modified broach 800A to progressively chisel away bone as the modified broach 800A is inserted into the bore. In some embodiments, the modified broach can also include one or more channels 808A that extend longitudinally along the sides of the modified broach 800A that aid in the removal of bone fragments from the bore. The channels 808A can be located along the center of each face of the modified broach 800A, and can have a curved surface or be formed from two or more flat surfaces.

Figure 21C:
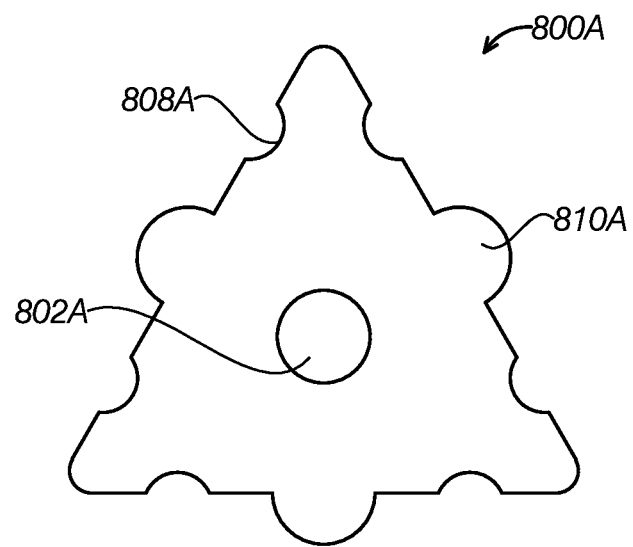
Figure 21D:
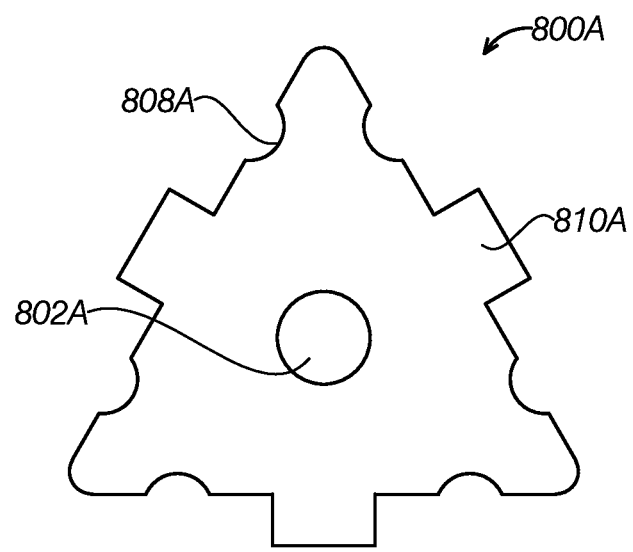
Figure 21E:
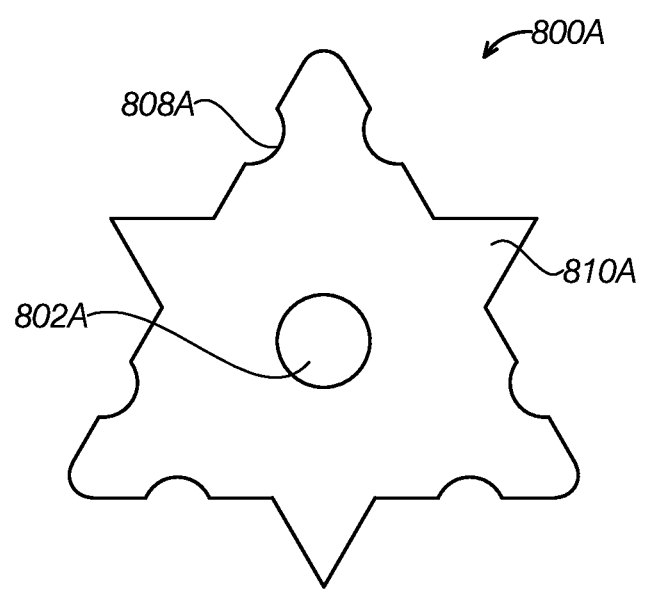

In some embodiments as illustrated in FIGS. 21A and 21B, the modified broach 800A can have additional cutting surfaces 810A located at each apex of the modified broach 800A. In some embodiments, the additional cutting surfaces 810A can be located on one or more of the apices of the modified broach 800A. In some embodiments, the additional cutting surfaces 810A can be located on each of the faces of the modified broach 800A, such as where the channels 808A are shown in FIGS. 21A and 21B. In some embodiments as illustrated in FIGS. 21C-21E, the additional cutting surfaces 810A, which can be circular, rectangular, triangular or any other suitable shape, can be located on one or more of the faces of the modified broach 800A. In some embodiments, the additional cutting surfaces 810A can be located in a combination of one or more of the apices and faces of the modified broach 800A. The additional cutting surfaces 810A can be angled slightly distally so that the cutting surfaces can chisel away bone fragments as the modified broach 800A is advanced into the bore. As described above, the additional cutting surfaces 810A can have circular shaped cutting surfaces or be any other shape, such as triangular, square, rectilinear, oval and the like. The channels can be sized to have a width or diameter of about 0.1 to 0.5 the width of a face or side of the bore.

The additional cutting surfaces 810A can cut tubes or channels from the shaped bore that can be filled bone graft material and/or a biologic aid. In some embodiments, the drilled bore can be enlarged using the modified broach 800A to shape the bore into a general shape that matches the implant while also cutting out bone graft channels that extend beyond the general implant profile. In some embodiments, the bone graft channels can be located at the apexes of the shaped bore.

In some embodiments, a standard broach can be used to shape the bore while additional tubes or channels can be made separately with a drill and specialized drill bit or drill fixture. In some embodiments, a standard broach can be used to initially shape the bore while a second broach can be used to cut out the additional tubes or channels.

As described above, the implant can be inserted into the shaped bore while bone graft material and/or a biologic aid can be inserted into the additional cut tubes or channels. In some embodiments, the bone graft material and/or biologic aids can be formed into solid rods, with shapes matching the cut tubes or channels, which can be impacted into each cut tube or channel. In other embodiments, the bone graft material and/or biologic aids can be injected with a specialized syringe or other injection device into each of the cut tubes or channels. In some embodiments, the bone graft material and/or biologic aids can also be smeared or coated onto the implant either before or as the implant in inserted into the shaped bore.

The bone graft materials can be a liquid, gel, slurry, paste, powder, solid structure, matrix of granular material or other form, and can include a biologic aid that can promote and/or enhance bony ingrowth, tissue repair, and/or reduce inflammation, infection and pain. For example, the bone graft materials and/or biologic aid can include growth factors, such as bone morphogenetic proteins (BMPs), hydroxyapatite in, for example, a liquid or slurry carrier, demineralized bone, morselized autograft or allograft bone, bone fragments, medications to reduce inflammation, infection or pain such as analgesics, antibiotics and steroids. In addition, a blood pellet formed by centrifugation of the patient's blood, for example, can be included in the bone graft materials. In some embodiments, the blood pellet can be added in pellet form to the bone graft materials, while in other embodiments, the blood pellet can be disassociated and mixed or incorporated with other bone graft materials and/or biologic aids. In some embodiments, the growth factors can be human recombinant growth factors, such as hr-BMP-2 and/or hr-BMP-7, or any other human recombinant form of BMP, for example. The carrier for the biologic aid can be a liquid or gel such as saline or a collagen gel, for example. The biologic aid can also be encapsulated or incorporated in a controlled released formulation so that the biologic aid is released to the patient at the implant site over a longer duration. For example, the controlled release formulation can be configured to release the biologic aid over the course of days or weeks or months, and can be configured to release the biologic aid over the estimated time it would take for the implant site to heal. The amount of biologic aid delivered to the implant structure can be controlled using a variety of techniques, such as controlling or varying the amount of coating material applied to the implant and/or controlling or varying the amount of biologic aid incorporated into the coating material. In some embodiments, in may be important to control the amount of biologic aid delivered because excessive use of certain biologic aids can result in negative effects such as radicular pain, for example.

In some embodiments, the filling of the cutting tubes or channels with bone graft material at the apices around the implant helps reduce haloing artifacts around the implant. As shown in FIG. 26, haloing refers to CT imaging artifacts 1300A that generally occur around corners of the implant 20A which can cause confusion in interpreting the CT image. Replacing the relatively sharp corners and apices with circular channels or tube can help to reduce the haloing artifacts.

Figure 22A:
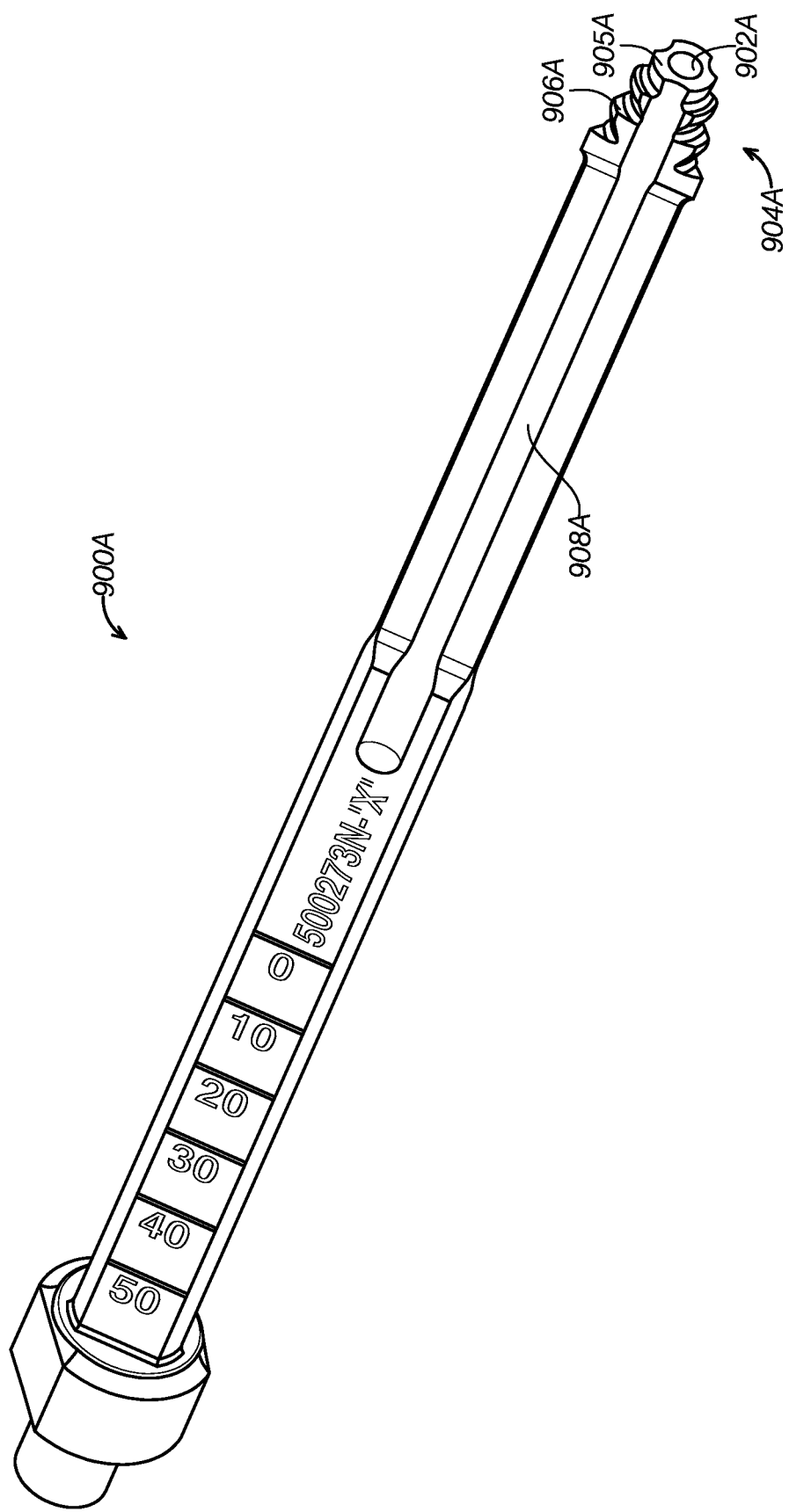
FIGS. 22A and 22B illustrate an embodiment of a standard broach with a flat distal face.
Figure 22B:
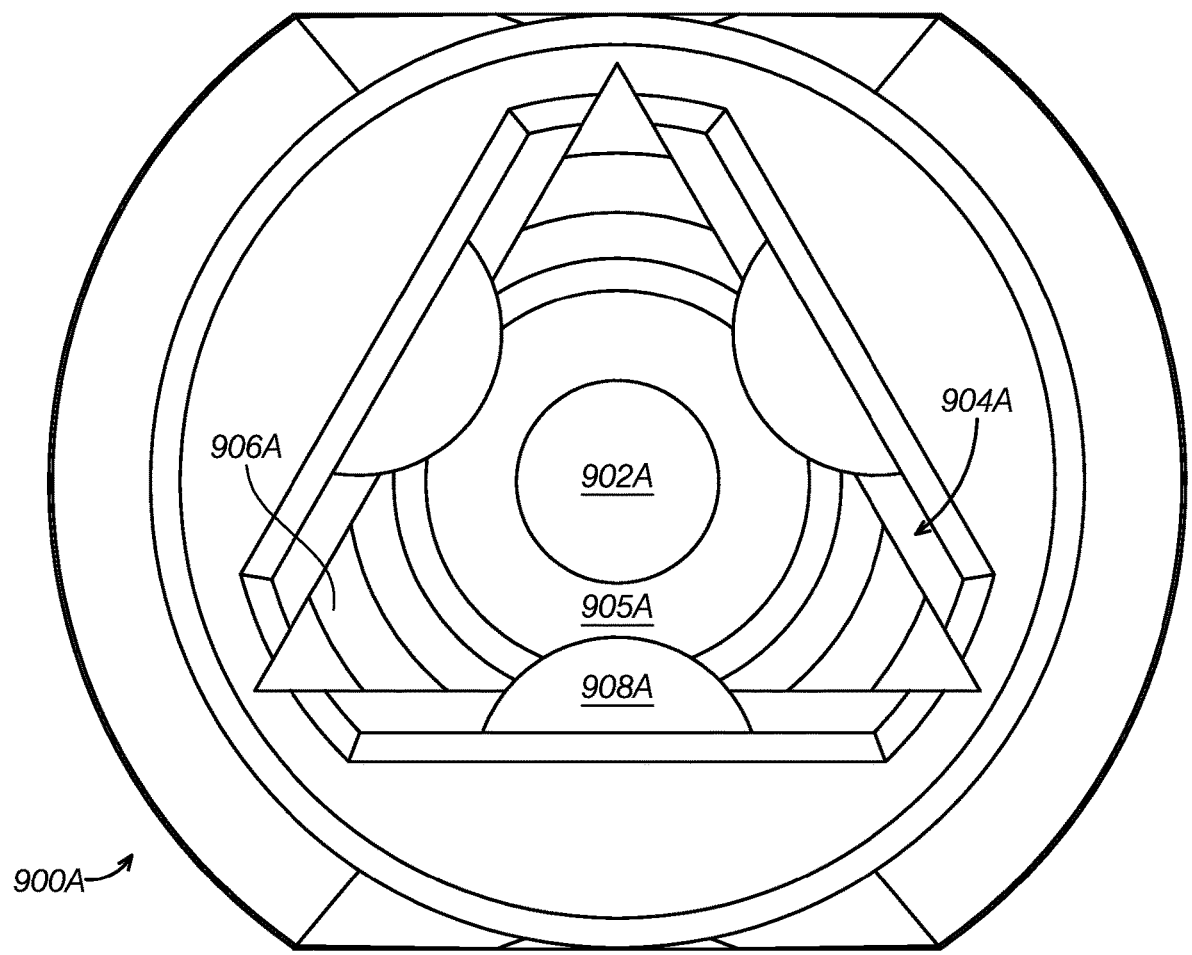

FIGS. 22A and 22B illustrate a broach 900A without the additional cutting surfaces for cutting out additional tubes or channels. The broach 900A can have a cross-sectional profile that generally matches the shape of the implant. For example, for a triangular shaped implant, the broach 900A can have a generally triangular shaped cross-sectional profile, as illustrated in FIGS. 22A and 22B. Likewise, for an implant with a rectangular, square, or any other rectilinear shape, the broach can have a generally matching cross-sectional profile. The broach 900A can have a lumen or channel 902A extending along its entire longitudinal length and sized and shaped so that the broach 900A can be placed over a guide pin. The distal end 904A of the broach 900A can be tapered and have a plurality of cutting surfaces 906A that function to chisel away bone from the bore. The cutting surfaces 906A can be angled slightly towards the distal end 904A with the more proximal cutting surfaces 906A larger than the more distal cutting surfaces 906A. In some embodiments, the cutting surfaces 906A are oriented with each apex of the broach 900A. This configuration allows the broach 900A to progressively chisel away bone as the broach 900A is inserted into the bore. In some embodiments, the broach 900A can also include one or more channels 908A that extend longitudinally along the sides of the broach 900A that aid in the removal of bone fragments from the bore. The channels 908A can be located along the center of each face of the broach 900A, and can have a curved surface or be formed from two or more flat surfaces. In some embodiments, the distal face 905A of the distal end 904A can be flat or blunt and be shaped generally like a ring with cutouts along the perimeter for the channels 908A.

Figure 23A:
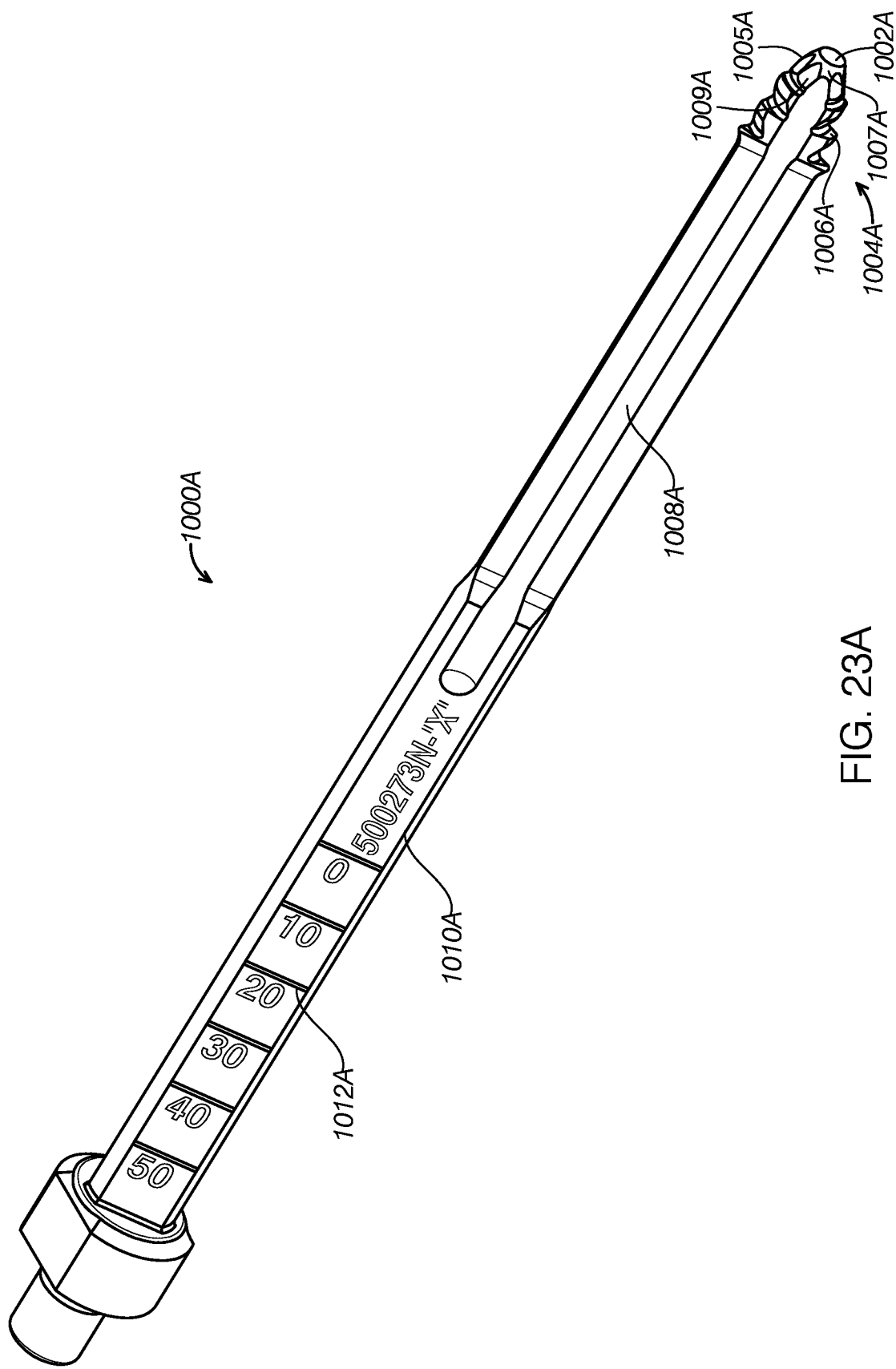
FIGS. 23A and 23B illustrate an embodiment of the broach with a pointed distal tip portion.
Figure 23B:
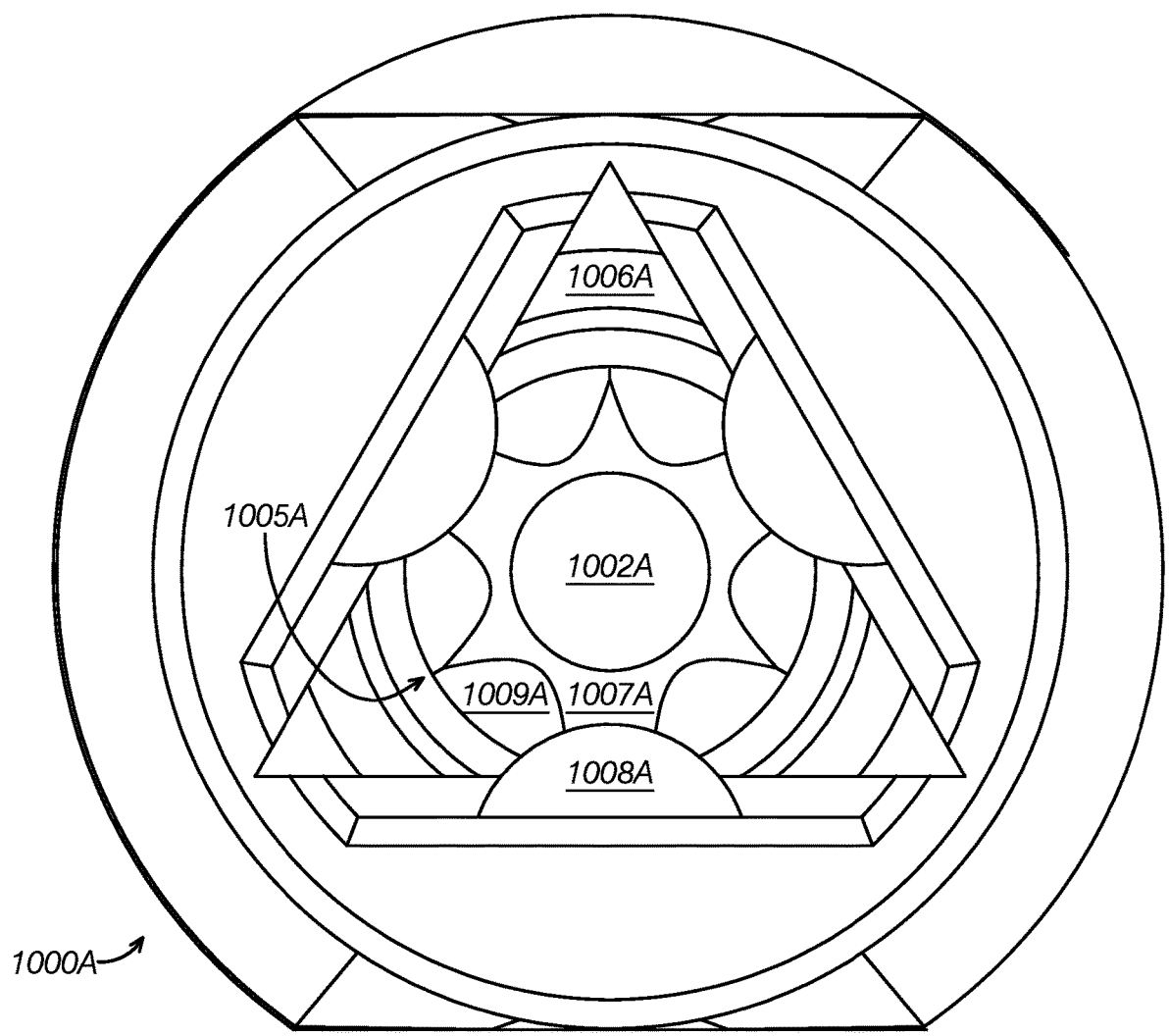

FIGS. 23A and 23B illustrate another embodiment of a broach 1000A with a similar design to the broach illustrated in FIGS. 22A and 22B, except that the broach 1000A illustrated in FIGS. 23A and 23B has a distal end 1004A that tapers into a pointed or bullet shaped tip rather than a flat surface. Like the broach 900A illustrated in FIGS. 22A and 22B, the broach 1000A illustrated in FIGS. 23A and 23B can have a cross-sectional profile that generally matches the shape of the implant. For example, for a triangular shaped implant, the broach 1000A can have a generally triangular shaped cross-sectional profile, as illustrated in FIGS. 23A and 23B. Likewise, for an implant with a rectangular, square, or any other rectilinear shape, the broach can have a generally matching cross-sectional profile. The broach 1000A can have a lumen or channel 1002A extending along its entire longitudinal length and sized and shaped so that the broach 1000A can be placed over a guide pin. The distal end 1004A of the broach 1000A can be tapered and have a plurality of cutting surfaces 1006A that function to chisel away bone from the bore. The cutting surfaces 1006A can be angled slightly towards the distal end 1004A with the more proximal cutting surfaces 1006A larger than the more distal cutting surfaces 1006A. In some embodiments, the cutting surfaces 1006A are oriented with each apex of the broach 1000A. This configuration allows the broach 1000A to progressively chisel away bone as the broach 1000A is inserted into the bore. In some embodiments, the broach 1000A can also include one or more channels 1008A that extend longitudinally along the sides of the broach 1000A that aid in the removal of bone fragments from the bore. The channels 1008A can be located along the center of each face of the broach 1000A, and can have a curved surface or be formed from two or more flat surfaces. The proximal portion of the broach shaft 1010A can have markings 1012A that can provide indicators to the operator regarding the depth of penetration of the broach 1000A into the bone. The markings 1012A can be a transverse line and can include numerical indications of penetration depth.

However, in contrast to the embodiment of the broach illustrated in FIGS. 22A and 22B, the embodiment of the broach 1000A illustrated in FIGS. 23A and 23B has a pointed tip 1005A with a diameter at the distal end that is equal to the diameter of the lumen or channel 1002A, and the diameter of the pointed tip 1005A can gradually increase in the proximal direction. The pointed tip 1005A can comprise a plurality of beveled faces 1009A angled towards the distal end 1004A. The distal portion of the pointed tip 1005A can be formed into a smooth tapering surface 1007A that narrows until it reaches the lumen or channel 1002A at the distal end 1004A. The smooth tapering surface 1007A can act as a cutting surface around the opening of the lumen 1002A to remove bone around the guide pin. As the broach 1000A traverses over the guide pin and is forced into the bone, the pointed tip 1005A can penetrate into the bone around the guide pin until the cutting surfaces 1006A can engage and chisel away the bone around the guide pin. Such a design can reduce or eliminate the need for additional drilling after the guide pin is place in the bone. The broach 1000A can be simply placed over the guide pin to form the bore into the bone without the need of placing a drill bit over the guide pin and drilling a bore and then using the broach to shape the circular bore into a triangular or rectilinear bore.

Figure 24A:
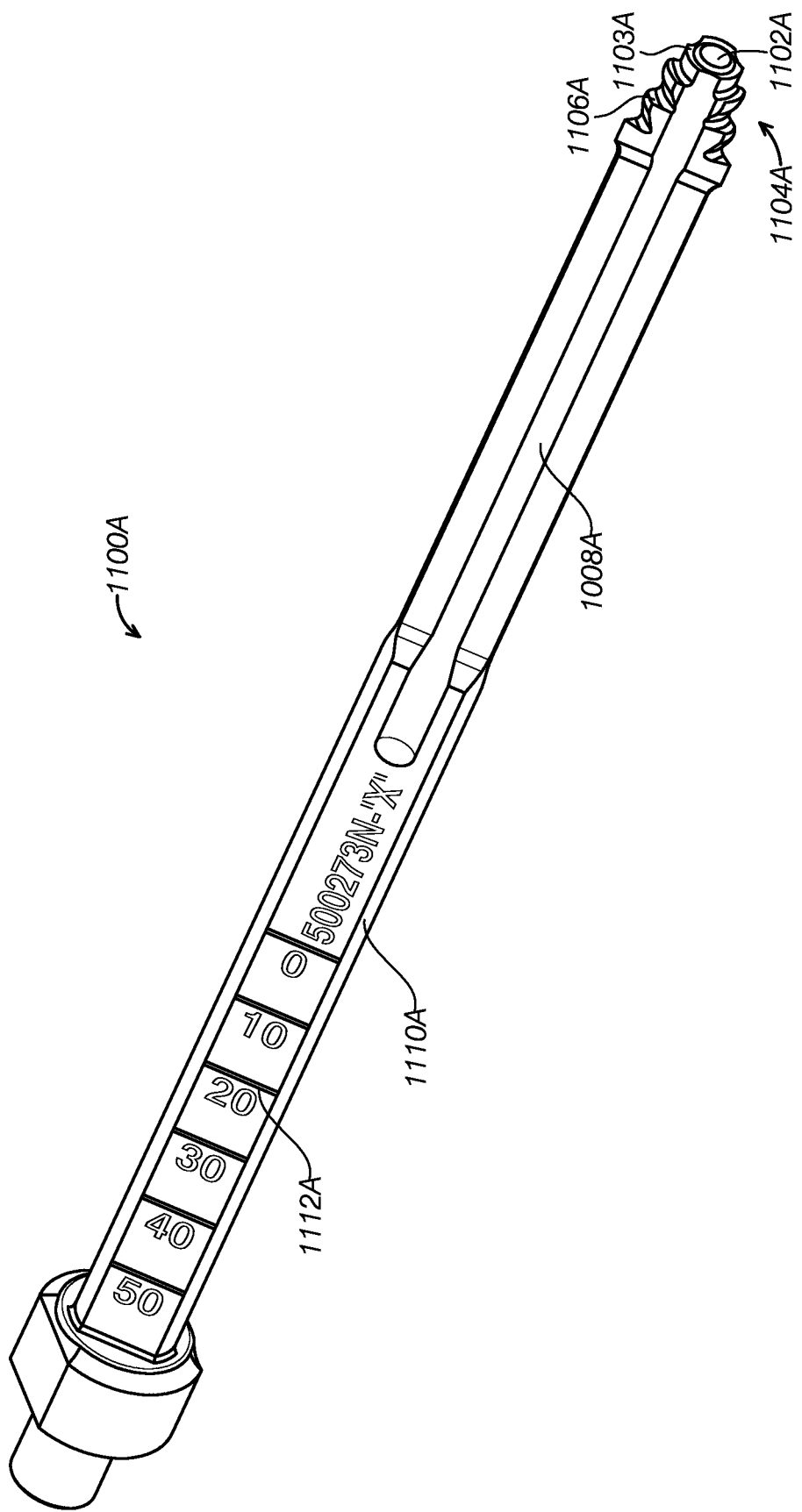
FIGS. 24A and 24B illustrate an embodiment of the broach with an additional cutting surface located at the distal end of the broach.
Figure 24B:
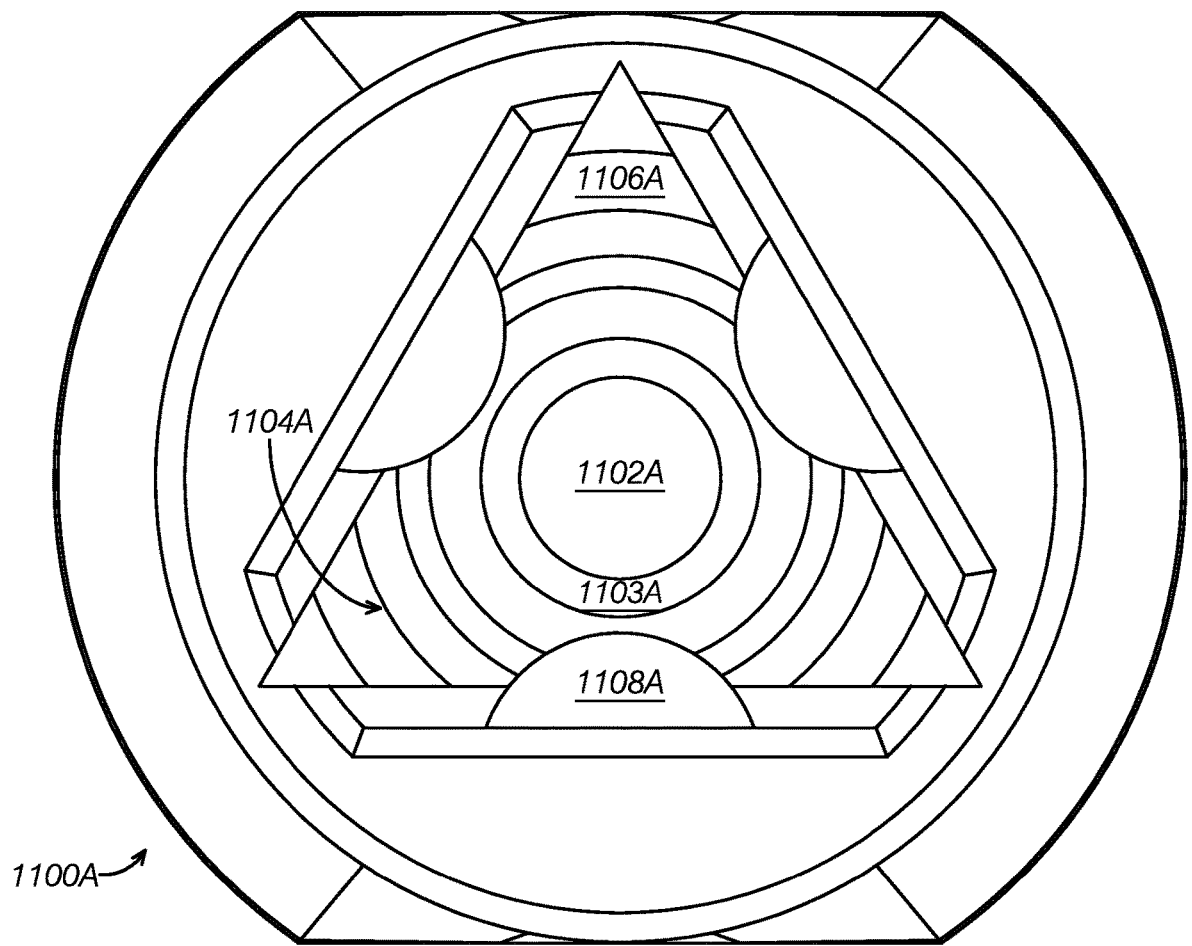

FIGS. 24A and 24B illustrate another embodiment of a broach 1100A with a similar design to the broach illustrated in FIGS. 22A and 22B, except that the broach 1100A illustrated in FIGS. 24A and 24B has a distal end 1104A with an additional distal cutting surface 1103A adjacent to and surrounding the opening of the lumen or channel 1102A that forms the most distal part of the broach 1100A. Like the broach 900A illustrated in FIGS. 22A and 22B, the broach 1100A illustrated in FIGS. 24A and 24B can have a cross-sectional profile that generally matches the shape of the implant. For example, for a triangular shaped implant, the broach 1100A can have a generally triangular shaped cross-sectional profile, as illustrated in FIGS. 24A and 24B. Likewise, for an implant with a rectangular, square, or any other rectilinear shape, the broach can have a generally matching cross-sectional profile. The broach 1100A can have a lumen or channel 1102A extending along its entire longitudinal length and sized and shaped so that the broach 1100A can be placed over a guide pin. The distal end 1104A of the broach 1100A can be tapered and have a plurality of cutting surfaces 1106A that function to chisel away bone from the bore. The cutting surfaces 1106A can be angled slightly towards the distal end 1104A with the more proximal cutting surfaces 1106A larger than the more distal cutting surfaces 1106A. In some embodiments, the cutting surfaces 1106A are oriented with each apex of the broach 1100A. This configuration allows the broach 1100A to progressively chisel away bone as the broach 1100A is inserted into the bore. In some embodiments, the broach 1100A can also include one or more channels 1108A that extend longitudinally along the sides of the broach 1100A that aid in the removal of bone fragments from the bore. The channels 1108A can be located along the center of each face of the broach 1100A, and can have a curved surface or be formed from two or more flat surfaces. The proximal portion of the broach shaft 1110A can have markings 1112A that can provide indicators to the operator regarding the depth of penetration of the broach 1100A into the bone. The markings 1112A can be a transverse line and can include numerical indications of penetration depth.

However, as discussed briefly above, in contrast to the embodiment of the broach illustrated in FIGS. 22A and 22B, the embodiment of the broach 1100A illustrated in FIGS. 24A and 24B has a distal end 1104A with an additional distal cutting surface 1103A adjacent to and surrounding the opening of the lumen or channel 1102A that forms the most distal part of the broach 1100A. As the broach 1100A traverses over the guide pin and is forced into the bone, the distal cutting surface 1103A engages the bone around the guide pin and begins cutting, chiseling and removing the bone from around the guide pin, thereby starting the bore to receive the implant. As the broach 1100A penetrates further into the bone, the primary cutting surfaces 1106A can engage and chisel away additional bone around the guide pin, thereby enlarging the bore. Such a design can reduce or eliminate the need for additional drilling after the guide pin is place in the bone. The broach 1100A can be simply placed over the guide pin to form the bore into the bone without the need of placing a drill bit over the guide pin and drilling a bore and then using the broach to shape the circular bore into a triangular or rectilinear bore.

Figure 25A:
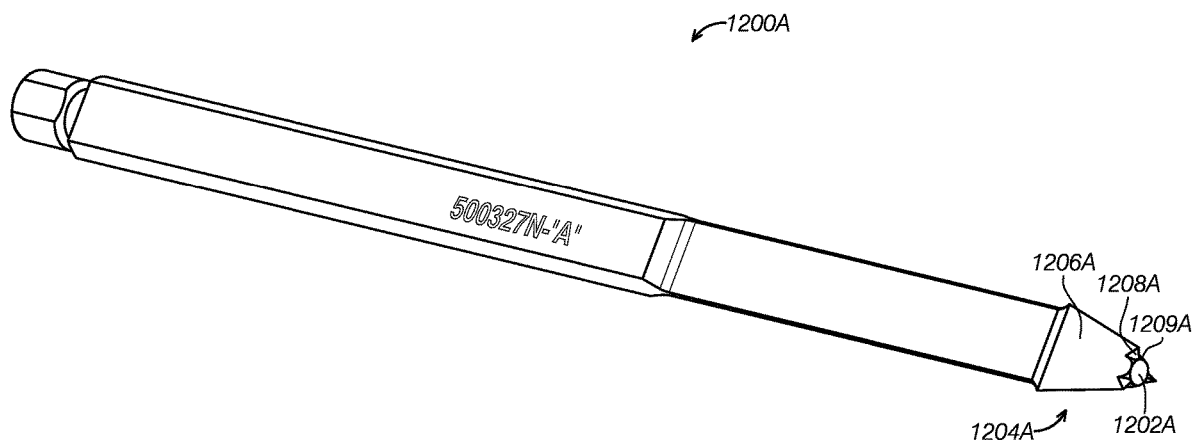
FIGS. 25A and 25B illustrate an embodiment of the broach with a pyramid shaped distal tip.
Figure 25B:
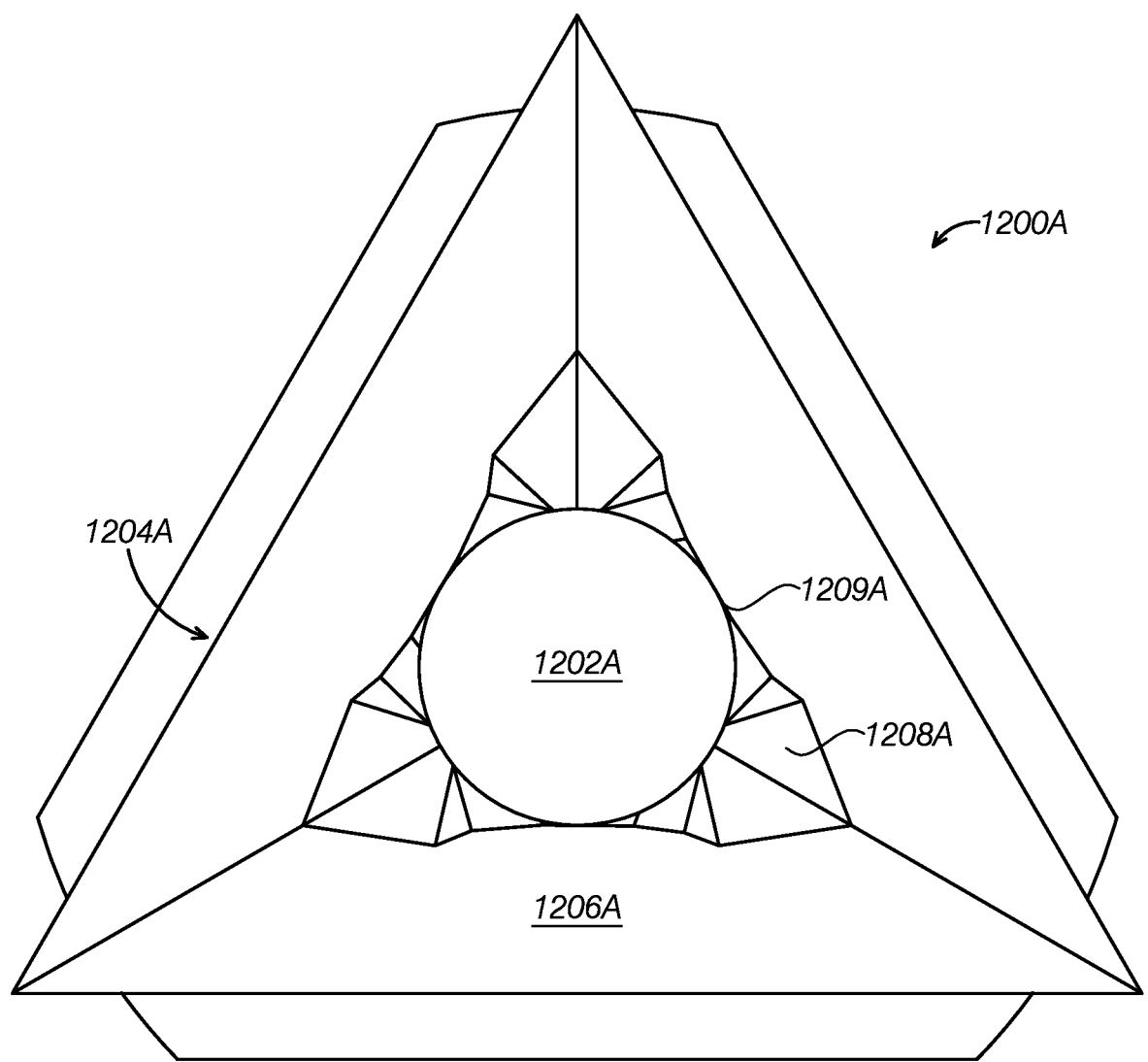
Figure 27:
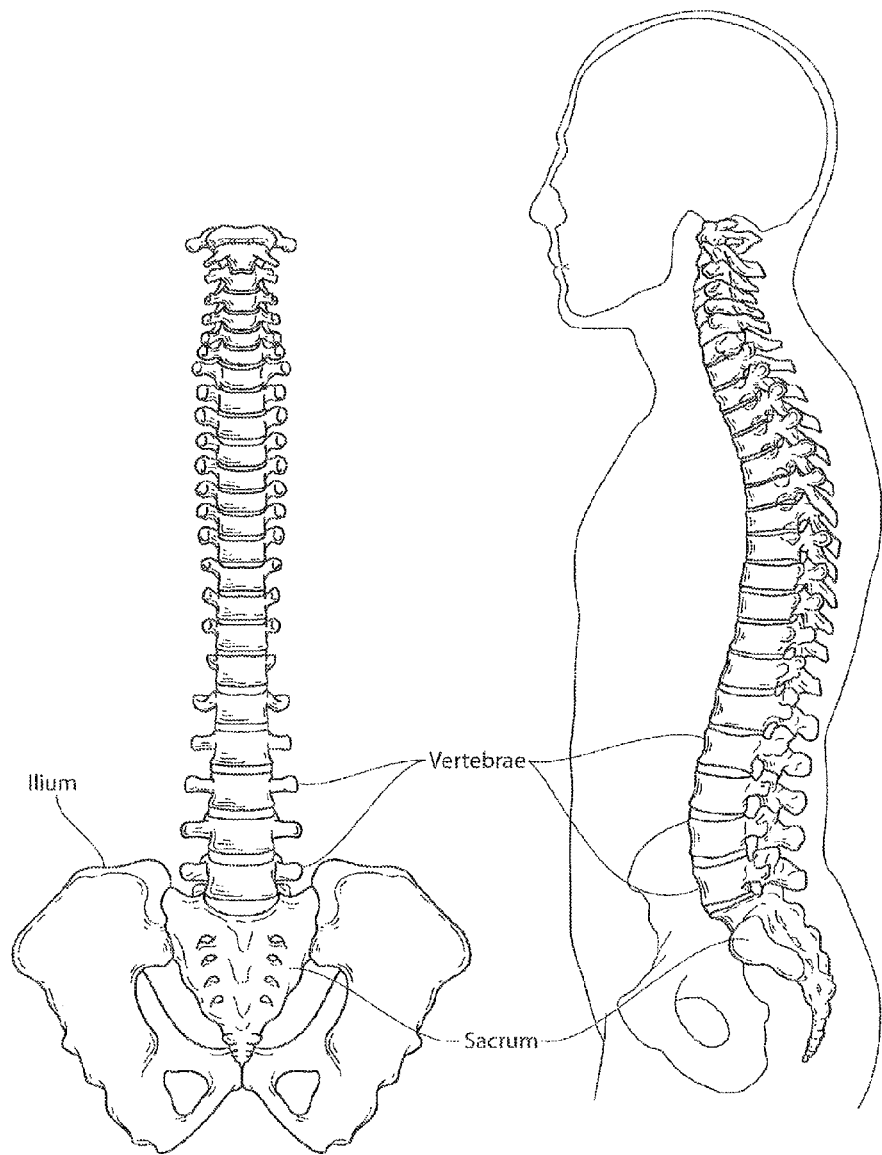
FIG. 27 is an anatomic anterior and lateral view of a human spine.
Figure 28:
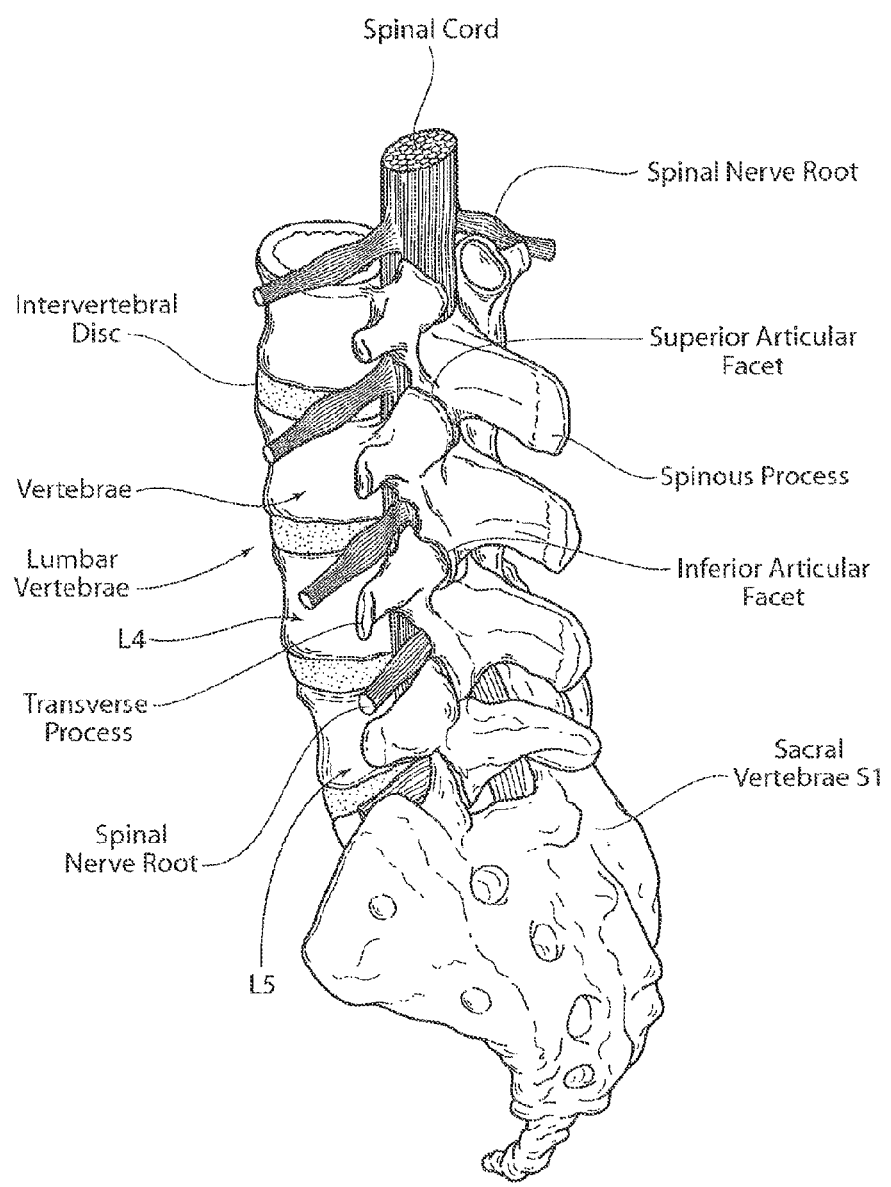
FIG. 28 is an anatomic posterior perspective view of the lumbar region of a human spine, showing lumbar vertebrae L2 to L5 and the sacral vertebrae.
Figure 29:
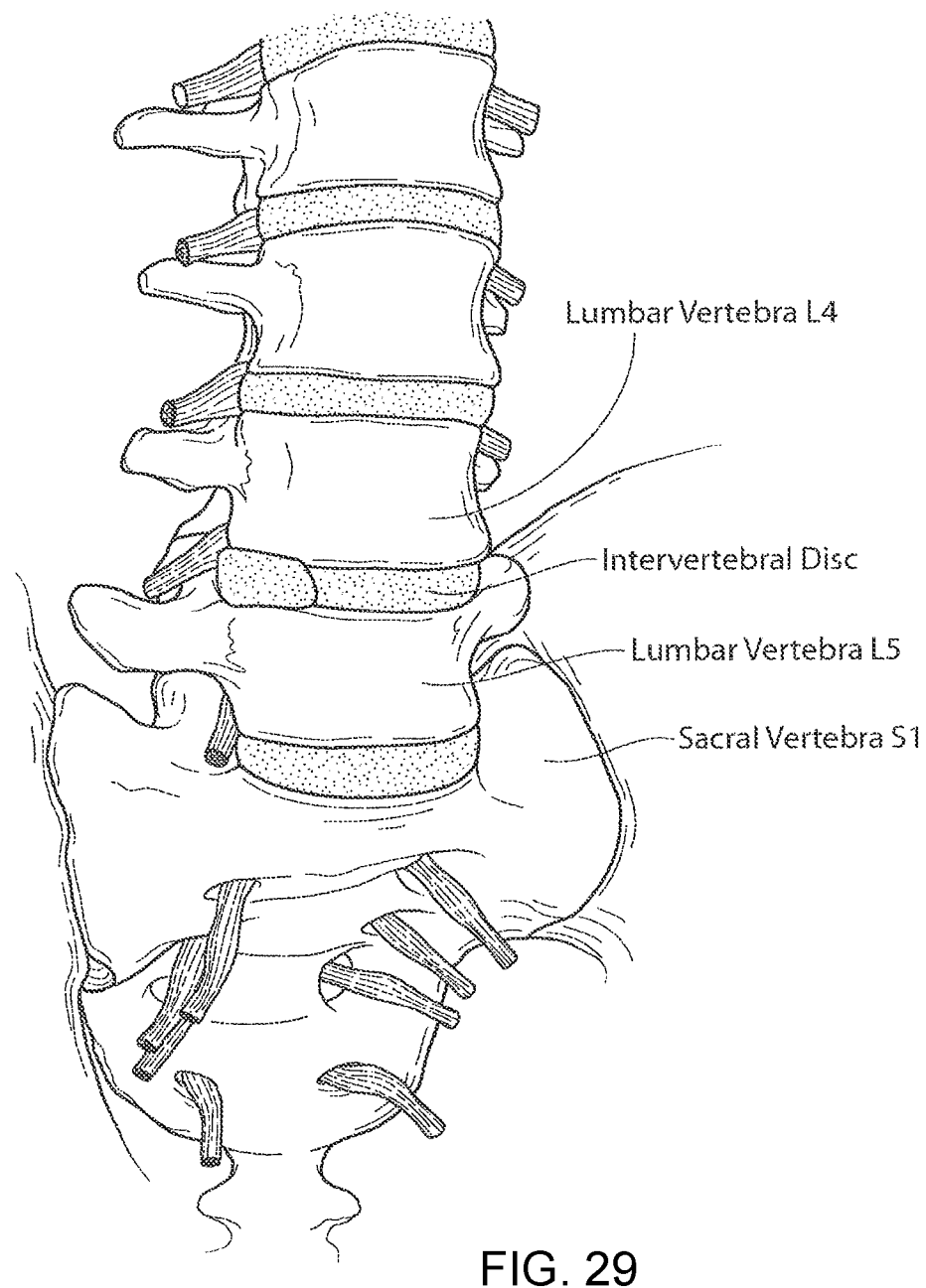
FIG. 29 is an anatomic anterior perspective view of the lumbar region of a human spine, showing lumbar vertebrae L2 to L5 and the sacral vertebrae.

FIGS. 25A and 25B illustrate another embodiment of a broach 1200A having a pyramid shaped tip 1204A. Like the broach 900A illustrated in FIGS. 22A and 22B, the broach 1200A illustrated in FIGS. 25A and 25B can have a cross-sectional profile that generally matches the shape of the implant. For example, for a triangular shaped implant, the broach 1200A can have a generally triangular shaped cross-sectional profile, as illustrated in FIGS. 25A and 25B. Likewise, for an implant with a rectangular, square, or any other rectilinear shape, the broach can have a generally matching cross-sectional profile. In some embodiments, the broach 1200A can have a lumen or channel 1202A extending along its entire longitudinal length and sized and shaped so that the broach 1200A can be placed over a guide pin.

The pyramid shaped tip 1204A can comprise three faces 1206A that taper towards the distal end of the broach 1200A. At the distal end of the broach 1200A can be an opening to the lumen 1202A. Surround the opening can be a plurality of cutting surfaces 1208A, 1209A located at both the apices between the faces 1206A and along the distal end of each face 1206A between the apices. The cutting surfaces 1208A, 1209A are configured to cut and chisel out the bone around the guide pin to form the bore for the implant. Furthermore, the cutting surfaces 1208 located at the apices can be arranged to form teeth with a pointed tip that can penetrate into and cut and chisel the bone surrounding the guide pin.
Implants for Facet Fusion Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

I. The Implant Structure

Figure 30:
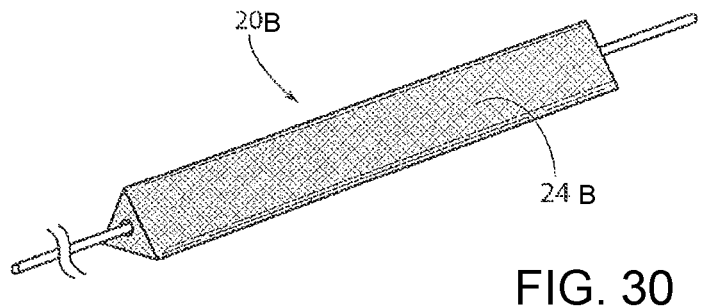
FIG. 30 is a perspective view of a representative embodiment of an elongated, stem-like, cannulated implant structure well suited for the fusion or stabilization of adjacent bone structures in the lumbar region of the spine, either across the intervertebral disc or across one or more facet joints.

FIG. 30 shows a representative embodiment of an elongated, stem-like, cannulated implant structure 20B. As will be described in greater detail later, the implant structure 20B is sized and configured for the fixation of bones which are to be fused (arthrodesed) (i.e. fixation of two or more individual bones that are adjacent and/or jointed) and/or the stabilization of adjacent bone structures. In particular, and as will be demonstrated, the implant structure is well suited for the fusion or stabilization of adjacent bone structures in the lumbar region of the spine, either across the intervertebral disc or across one or more facet joints.

The implant structure 20B can be formed—e.g., by machining, molding, or extrusion—from a durable material usable in the prosthetic arts that is not subject to significant bio-absorption or resorption by surrounding bone or tissue over time. The implant structure 20B, is intended to remain in place for a time sufficient to stabilize a bone fracture or fusion site. Such materials include, but are not limited to, titanium, titanium alloys, tantalum, tivanium (aluminum, vanadium, and titanium), chrome cobalt, surgical steel, or any other total joint replacement metal and/or ceramic, sintered glass, artificial bone, any uncemented metal or ceramic surface, or a combination thereof.

Alternatively, the implant structure 20B may be formed from a suitable durable biologic material or a combination of metal and biologic material, such as a biocompatible bone-filling material. The implant structure 20B may be molded from a flowable biologic material, e.g., acrylic bone cement, that is cured, e.g., by UV light, to a non-flowable or solid material.

The implant structure 20B is sized according to the local anatomy. The morphology of the local structures can be generally understood by medical professionals using textbooks of human skeletal anatomy along with their knowledge of the site and its disease or injury. The physician is also able to ascertain the dimensions of the implant structure 20B based upon prior analysis of the morphology of the targeted bone region using, for example, plain film x-ray, fluoroscopic x-ray, or MRI or CT scanning.

Figures 31, 32, 33:
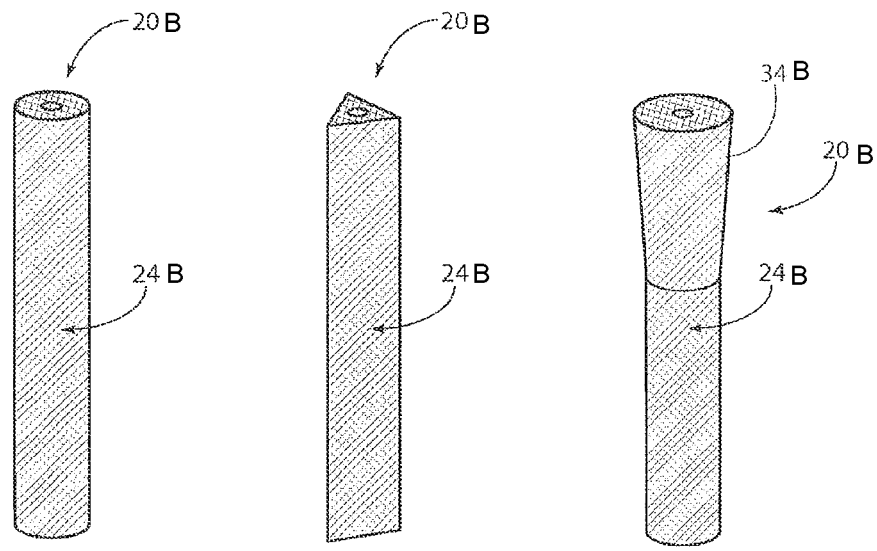
FIGS. 31, 32, 33 and 34 are perspective views of other representative embodiments of implant structures well suited for the fusion or stabilization of adjacent bone structures in the lumbar region of the spine, either across the intervertebral disc or across one or more facet joints.

As FIGS. 31 to 34 show, the implant structure 20B can take various shapes and have various cross-sectional geometries. The implant structure 20B can have, e.g., a generally curvilinear (i.e., round or oval) cross-section—as FIG. 31 shows for purposes of illustration—or a generally rectilinear cross section (i.e., square or rectangular or hexagon or H-shaped or triangular—as FIG. 32 shows for purposes of illustration—or combinations thereof. In FIG. 30, the implant structure 20B is shown to be triangular in cross section, which effectively resists rotation and micromotion once implanted.

Figure 34:
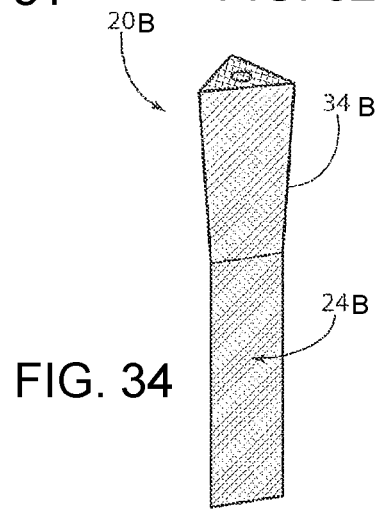

As FIGS. 33 and 34 show, the implant structure 20B, whether curvilinear (FIG. 33) or rectilinear (FIG. 34) can include a tapered region 34B at least along a portion of its axial length, meaning that the width or diameter of the implant structure 20B incrementally increases along its axial length. Desirably, the tapered region 34B corresponds with, in use, the proximal region of the implant structure 20B (i.e., the last part of the implant structure 20B to enter bone). The amount of the incremental increase in width or diameter can vary. As an example, for an implant structure 20B having a normal diameter of 7 mm, the magnitude of the incremental increase at its maximum can range between about 0.25 mm to 1.25 mm. The tapered region 34 enhances the creation and maintenance of compression between bone segments or regions.

As FIG. 30 shows, the implant structure 20B includes a region 24B formed along at least a portion of its length to promote bony in-growth onto or into surface of the structure and/or bony growth entirely through all or a portion of the structure. The bony in-growth or through-growth region 24B along the surface of the implant structure 20B accelerates bony in-growth or through-growth onto, into, or through the implant structure 20B. Bony in-growth or through-growth onto, into, or through the implant structure 20B helps speed up the fusion process of the adjacent bone regions fixated by the implant structure 20B.

The bony in-growth or through-growth region 24B desirably extends along the entire outer surface of the implant structure 20B, as shown in FIGS. 30 to 34. The bony in-growth region 24B or through-growth can comprise, e.g., through holes, and/or various surface patterns, and/or various surface textures, and/or pores, or combinations thereof. The configuration of the bony in-growth or through-growth region 24B can, of course, vary. By way of examples, the bony in-growth or through-growth region 24B can comprise an open mesh configuration; or beaded configuration; or a trabecular configuration; or include holes or fenestrations. Any configuration conducive to bony in-growth and/or bony through-growth will suffice.

The bony in-growth or through-growth region 24B can be coated or wrapped or surfaced treated to provide the bony in-growth or through-growth region, or it can be formed from a material that itself inherently possesses a structure conducive to bony in-growth or through-growth, such as a porous mesh, hydroxyapatite, or other porous surface. The bony in-growth or through-growth region can includes holes that allow bone to grow throughout the region.

In a preferred embodiment, the bony in-growth region or through-growth region 24B comprises a porous plasma spray coating on the implant structure 20B. This creates a biomechanically rigorous fixation/fusion system, designed to support reliable fixation/fusion and acute weight bearing capacity.

The bony in-growth or through-growth region 24B may further be covered with various other coatings such as antimicrobial, antithrombotic, and osteoinductive agents, or a combination thereof. The entire implant structure 20B may be impregnated with such agents, if desired.

The implant structure includes an interior bore that accommodates its placement in a non-invasive manner by sliding over a guide pin, as will be described in greater detail later.

As before stated, the implant structure 20B is well suited for the fusion and/or stabilization of adjacent bone structures in the lumbar region of the spine. Representative examples of the placement of the implant structure 20B in the lumbar region of the spine will now be described.

A. Use of the Implant Structures to Achieve Anterior Lumbar Interbody Fusion

Figure 35:
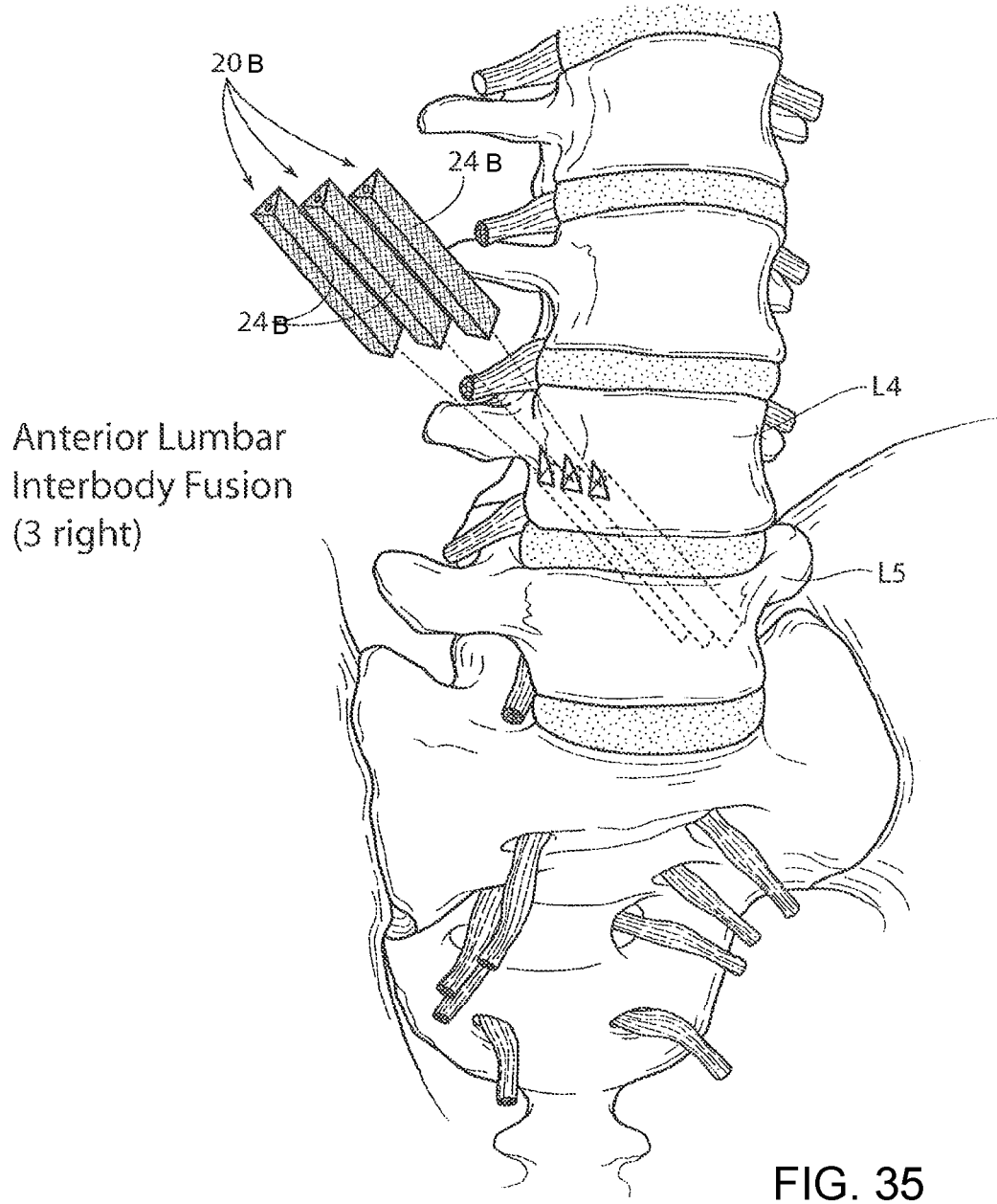
FIG. 35 is an anatomic anterior perspective view showing, in an exploded view prior to implantation, a representative configuration of an assembly of one or more implant structures as shown in FIG. 30, sized and configured to achieve anterior lumbar interbody fusion, in a non-invasive manner and without removal of the intervertebral disc.
Figure 36:
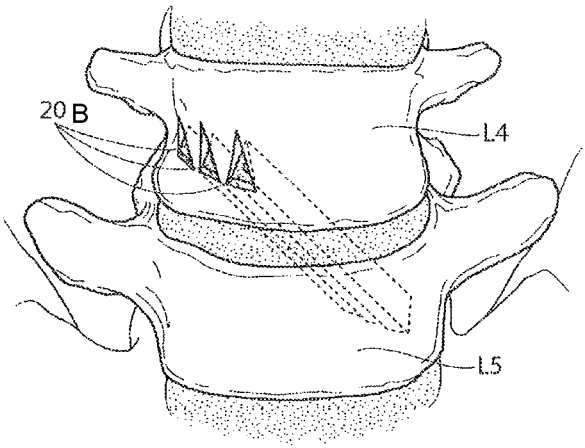
FIG. 36 is an anatomic anterior perspective view showing the assembly shown in FIG. 35 after implantation.
Figure 37:
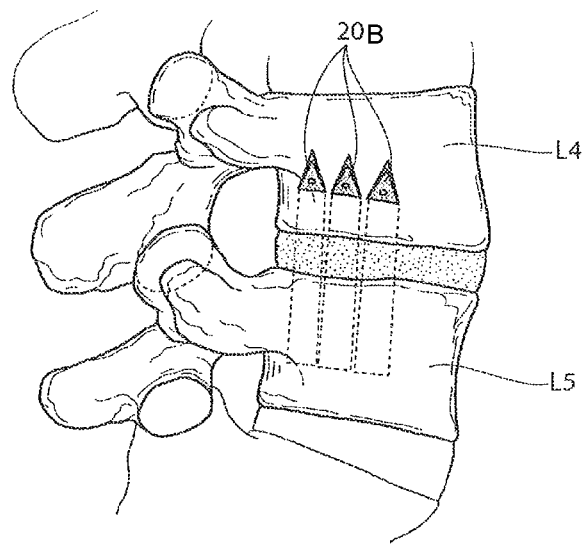
FIG. 37 is an anatomic right lateral perspective view showing the assembly shown in FIG. 35 after implantation.
Figure 38:
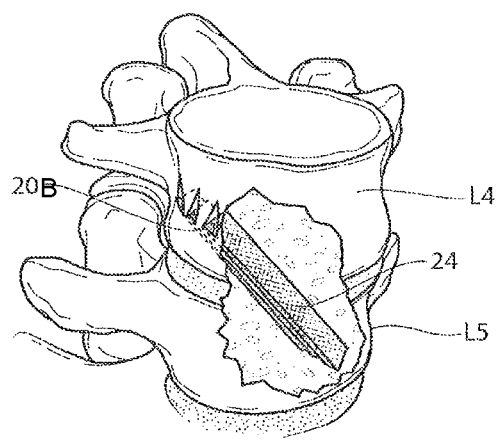
FIG. 38 is an anatomic superior left lateral perspective view showing the assembly shown in FIG. 35 after implantation.

FIG. 35 shows, in an exploded view prior to implantation, a representative configuration of an assembly of one or more implant structures 20B sized and configured to achieve anterior lumbar interbody fusion, in a non-invasive manner and without removal of the intervertebral disc. FIGS. 36 to 38 show the assembly after implantation, respectively, in an anterior view, a right lateral view, and a superior left lateral perspective view.

In the representative embodiment illustrated in FIGS. 36 to 38, the assembly comprises three implant structures 20B. It should be appreciated, however, that a given assembly can include a greater or lesser number of implant structures 20B.

In the representative embodiment shown in FIGS. 36 to 38, the three implant structures 20B are spaced in an adjacent lateral array. The implant structures 20B extend from an anterolateral region of a selected vertebral body (i.e., a lateral region anterior to a transverse process), across the intervertebral disc into an opposite anterolateral region of an adjacent caudal (inferior) vertebra. As shown in FIGS. 36 to 38, the array of implant structures 20B extends in an angled path (e.g., about 20.degree. to about 40.degree. off horizontal) through the cranial (superior) lumbar vertebral body (shown as L4) in an inferior direction, through the adjoining intervertebral disc, and terminates in the next adjacent caudal (inferior) lumbar vertebral body (shown as L5).

More particularly, in the representative embodiment shown in FIGS. 35 to 38, the implant structures 20B enter the right anterolateral region of vertebra L4 and terminate within the left anterolateral interior of vertebra L5, spanning the intervertebral disc between L4 and L5.

Alternatively, or in combination, an array of implant structures 20B can likewise extend between L5 and S1 in the same trans-disc formation.

The implant structures 20B are sized according to the local anatomy. The implant structures 20B can be sized differently, e.g., 3 mm, 4 mm, 6 mm, etc.), to accommodate anterolateral variations in the anatomy. The implant structures 20B can be sized for implantation in adults or children.

The intimate contact created between the bony in-growth or through-growth region 24B along the surface of the implant structure 20B accelerates bony in-growth or through-growth onto, into, or through the implant structure 20B, to accelerate trans-disc fusion between these lumbar vertebrae.

FIGS. 39A to 39G diagrammatically show, for purposes of illustration, a representative lateral (or posterolateral) procedure for implanting the assembly of implant structures 20B shown in FIGS. 36 to 38.

The physician identifies the vertebrae of the lumbar spine region that are to be fused using, e.g., the Faber Test, or CT-guided injection, or X-ray/MRI of the lumbar spine. Aided by lateral and anterior-posterior (A-P) c-arms, and with the patient lying in a prone position (on their stomach), the physician makes a 3 mm incision laterally or posterolaterally from the side (see FIG. 39A). Aided by conventional visualization techniques, e.g., using X-ray image intensifiers such as a C-arms or fluoroscopes to produce a live image feed which is displayed on a TV screen, a guide pin 38B is introduced by conventional means into L4 (see FIG. 39B) for the first, most anterolateral implant structure (closest to the right transverse process of L4), in the desired angled inferiorly-directed path through the intervertebral disc and into the interior left anterolateral region of vertebra L5.

When the guide pin 38B is placed in the desired orientation, the physician desirable slides a soft tissue protector over the guide pin 38B before proceeding further. To simplify the illustration, the soft tissue protector is not shown in the drawings.

Figure 39A:
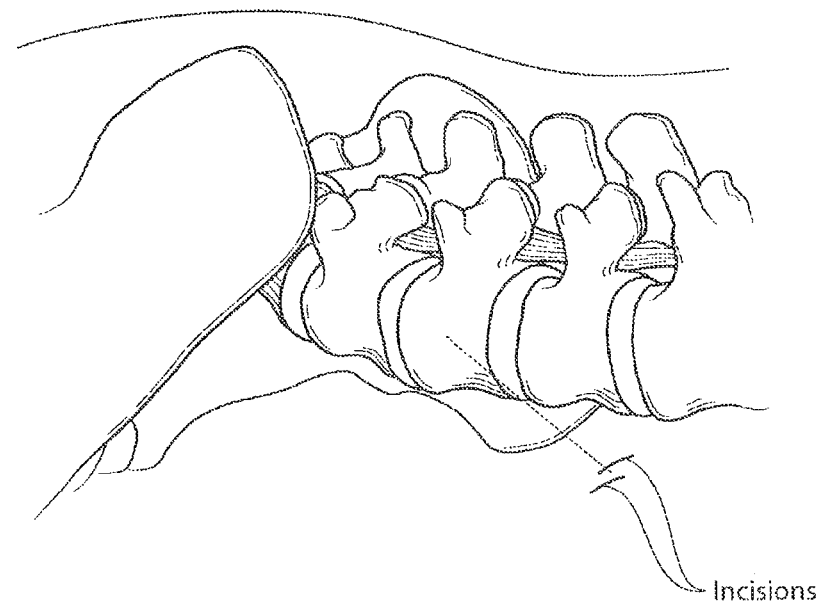
FIGS. 39A to 39G are diagrammatic views showing, for purposes of illustration, a representative lateral (or posterolateral) procedure for implanting the assembly of implant structures shown in FIGS. 36 to 38.
Figure 39B:
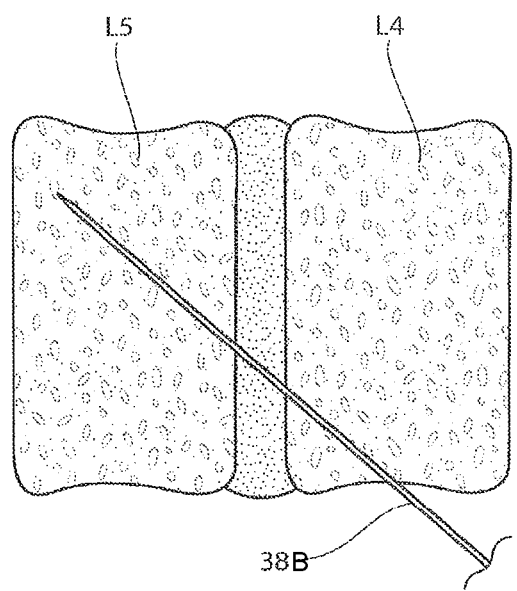
Figure 39C:
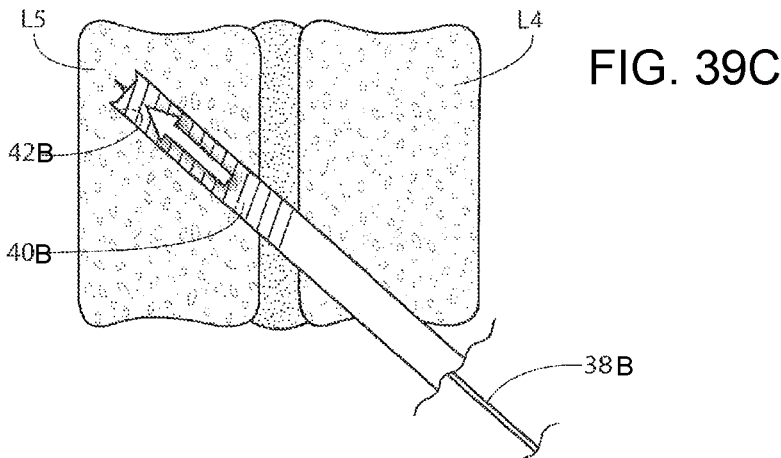
Figure 39D:
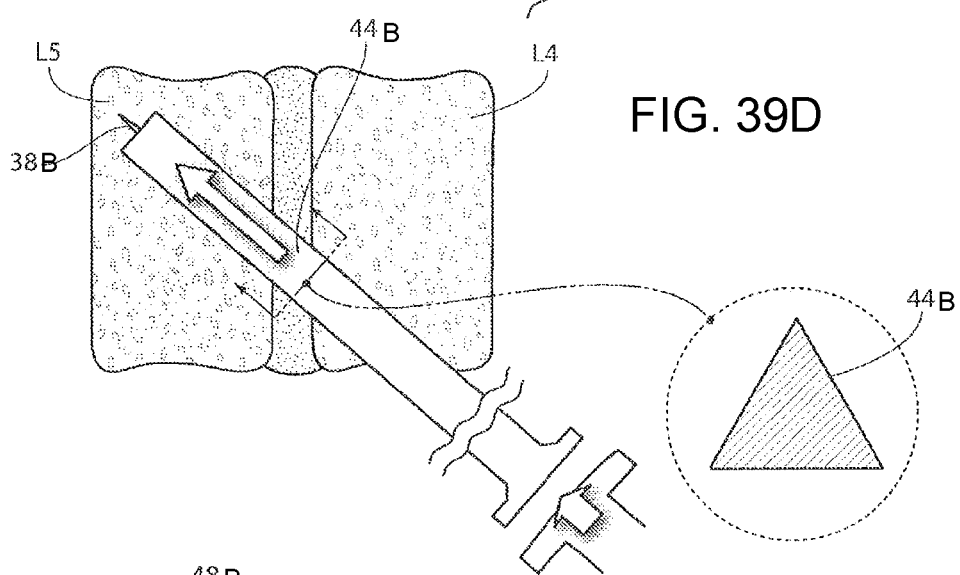
Figure 39E:
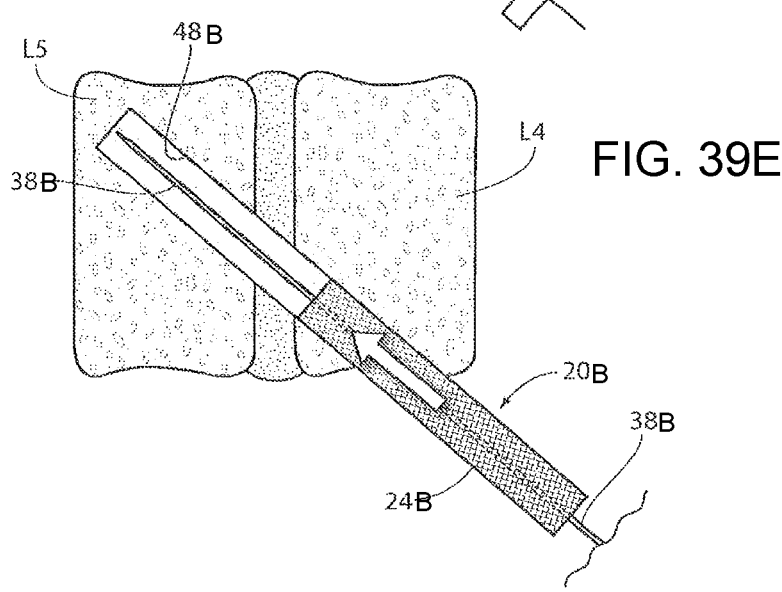

Through the soft tissue protector, a cannulated drill bit 40B is next passed over the guide pin 38B (see FIG. 39C). The cannulated drill bit 40B forms a pilot insertion path or bore 42B along the first angled path defined by the guide pin 38B. A single drill bit or multiple drill bits 40B can be employed to drill through bone fragments or bone surfaces to create a pilot bore 42B of the desired size and configuration.

When the pilot bore 42B is completed, the cannulated drill bit 40B is withdrawn over the guide pin 38B.

Through the soft tissue protector, a broach 44B having the external geometry and dimensions matching the external geometry and dimensions of the implant structure 20B (which, in the illustrated embodiment, is triangular) (see FIG. 39D) is tapped through the soft tissue protector over the guide pin 38B and into the pilot bore 42B. The shaped broach 44B cuts along the edges of the pilot bore 42B to form the desired profile (which, in the illustrated embodiment, is triangular) to accommodate the implant structure 20B.

The broach 44B is withdrawn (see FIG. 39E), and the first, most anterolateral implant structure 20B is passed over the guide pin 38B through the soft tissue protector into the broached bore 48B. The guide pin 38B and soft tissue protector are withdrawn from the first implant structure 20B.

Figure 39F:
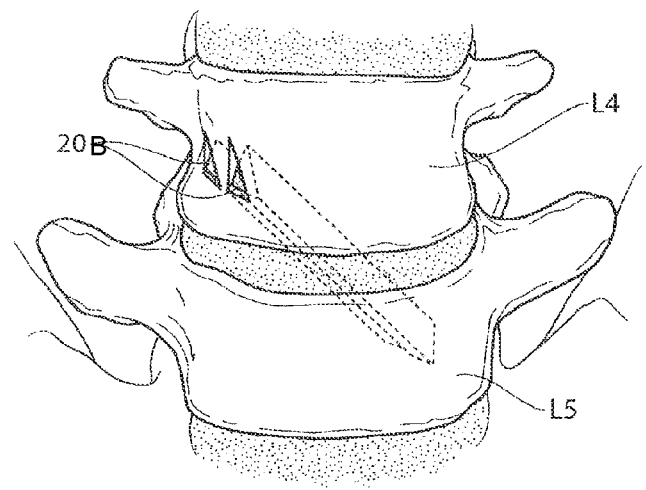
Figure 39G:
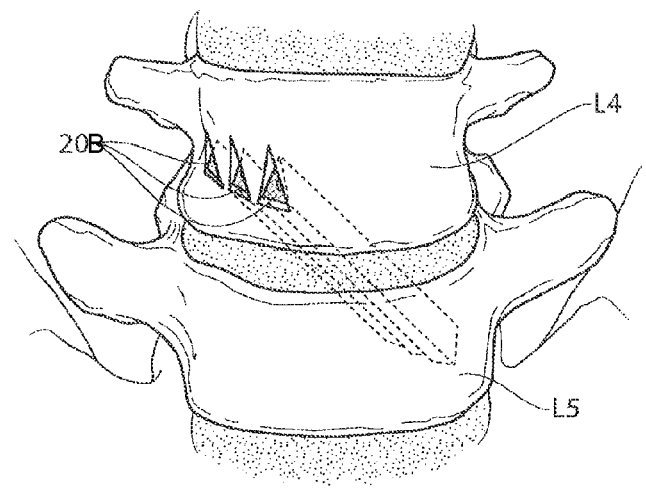

The physician repeats the above-described procedure sequentially for the next anterolateral implant structures 20B: for each implant structure, inserting the guide pin 38B, forming the pilot bore, forming the broached bore, inserting the respective implant structure, withdrawing the guide pin, and then repeating the procedure for the next implant structure, and so on until all implant structures 20B are placed (as FIGS. 39F and 39G indicate). The incision site(s) are closed.

In summary, the method for implanting the assembly of the implant structures 20B comprises (i) identifying the bone structures to be fused and/or stabilized; (ii) opening an incision; (iii) using a guide pin to established a desired implantation path through bone for the implant structure 20B; (iv) guided by the guide pin, increasing the cross section of the path; (v) guided by the guide pin, shaping the cross section of the path to correspond with the cross section of the implant structure 20B; (vi) inserting the implant structure 20B through the path over the guide pin; (vii) withdrawing the guide pin; (viii) repeating, as necessary, the procedure sequentially for the next implant structure(s) until all implant structures 20B contemplated are implanted; and (ix) closing the incision.

Figure 40:
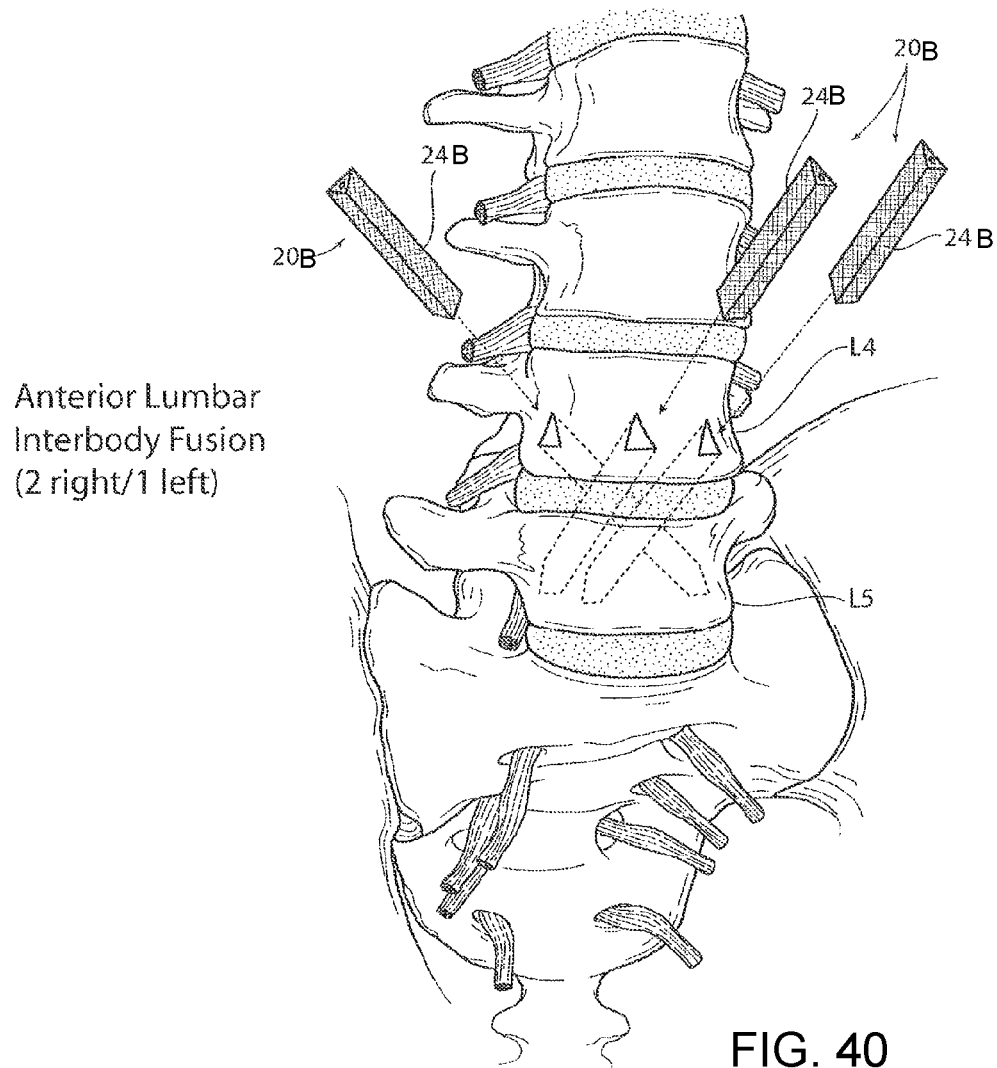
FIG. 40 is an anatomic anterior perspective view showing, in an exploded view prior to implantation, assemblies comprising one or more implant structures like that shown in FIG. 30 inserted from left and/or right anterolateral regions of a given lumbar vertebra, in an angled path through the intervertebral disc and into an opposite anterolateral interior region of the next inferior lumbar vertebra, FIG. 40 showing in particular two implant structures entering on the right anterolateral side of L4, through the intervertebral disc and into the left anterolateral region of L5, and one implant structure entering on the left anterolateral side of L4, through the intervertebral disc and into the right anterolateral region of L5, the left and right implant structures crossing each other in transit through the intervertebral disc.
Figure 41:
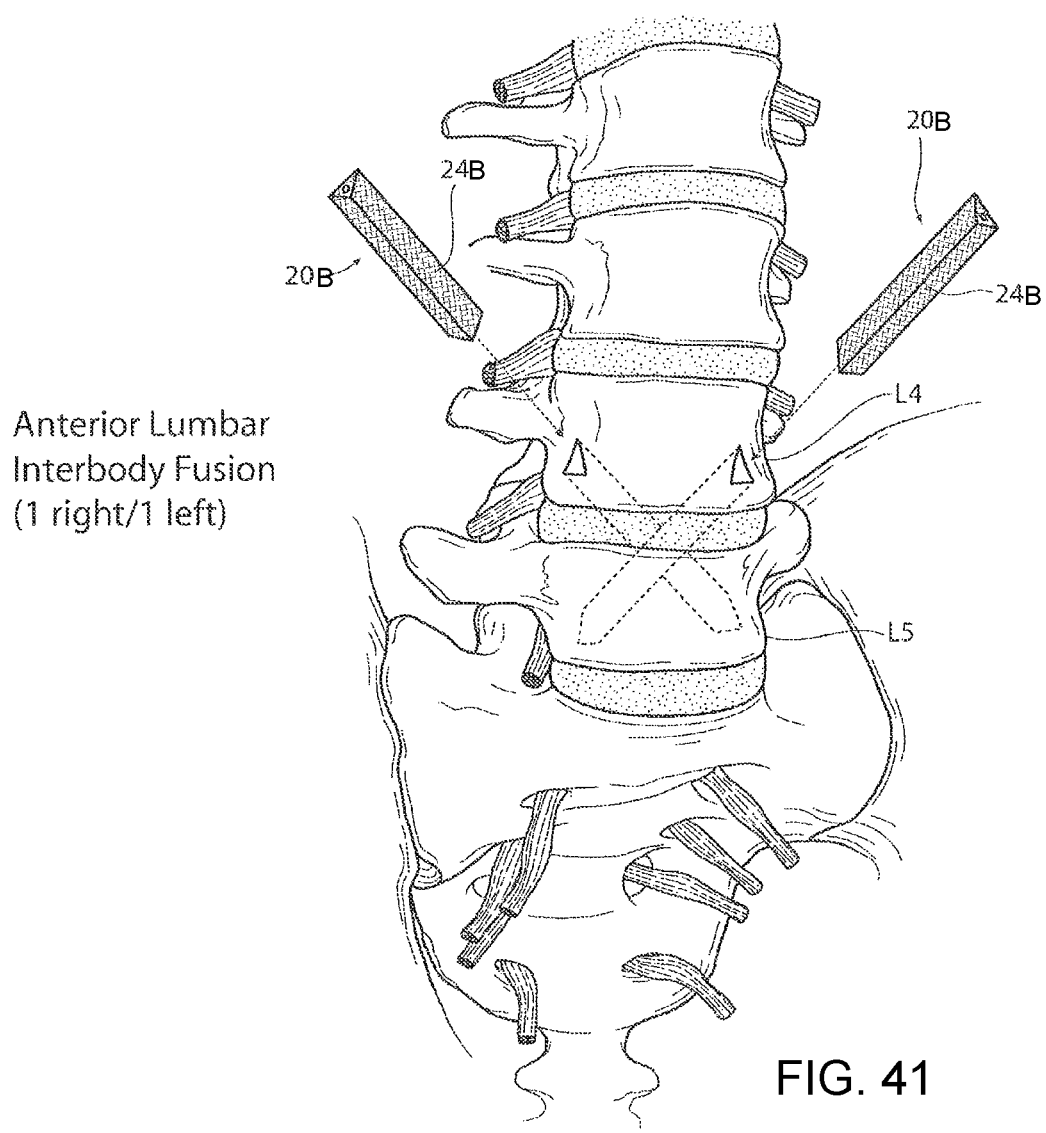
FIG. 41 is an anatomic anterior perspective view showing, in an exploded view prior to implantation, assemblies comprising one or more implant structures like that shown in FIG. 30 inserted from left and/or right anterolateral regions of a given lumbar vertebra, in an angled path through the intervertebral disc and into an opposite anterolateral interior region of the next inferior lumbar vertebra, FIG. 40 showing in particular one implant structure entering on the right anterolateral side of L4, through the intervertebral disc and into the left anterolateral region of L5, and one implant structure entering on the left anterolateral side of L4, through the intervertebral disc and into the right anterolateral region of L5, the left and right implant structures crossing each other in transit through the intervertebral disc.

As FIGS. 40 and 41 show, assemblies comprising one or more implant structures 20B can be inserted from left and/or right anterolateral regions of a given lumbar vertebra, in an angled path through the intervertebral disc and into an opposite anterolateral interior region of the next inferior lumbar vertebra.

For purposes of illustration, FIG. 40 shows two implant structures 20B entering on the right anterolateral side of L4, through the intervertebral disc and into the left anterolateral region of L5, and one implant structure 20B entering on the left anterolateral side of L4, through the intervertebral disc and into the right anterolateral region of L5. In this arrangement, the left and right implant structures 20B cross each other in transit through the intervertebral disc.

As another illustration of a representative embodiment, FIG. 41 shows one implant structure 20B entering on the right anterolateral side of L4, through the intervertebral disc and into the left anterolateral region of L5, and one implant structure 20B entering on the left anterolateral side of L4, through the intervertebral disc and into the right anterolateral region of L5. In this arrangement as well, the left and right implant structures 20B cross each other in transit through the intervertebral disc.

B. Use of Implant Structures to Achieve Translaminar Lumbar Fusion (Posterior Approach)

Figure 42:
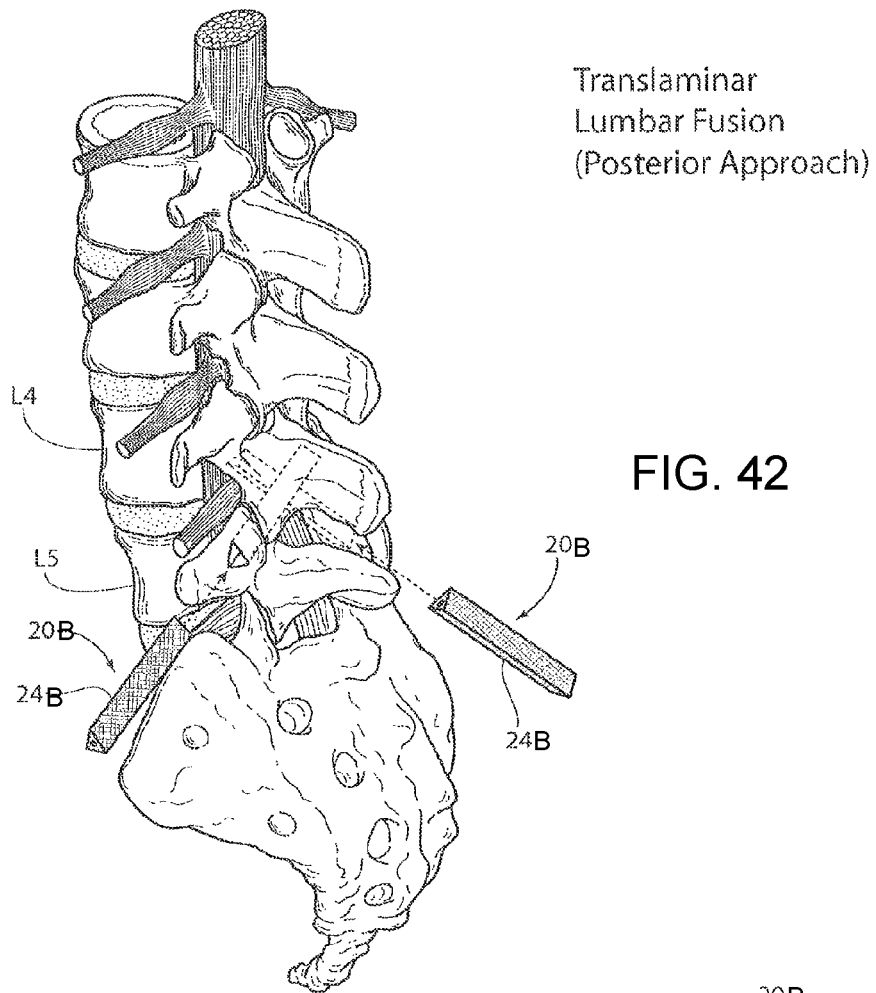
FIG. 42 is an anatomic posterior perspective view, exploded prior to implantation, of a representative configuration of an assembly of one or more implant structures like that shown in FIG. 30, sized and configured to achieve translaminar lumbar fusion in a non-invasive manner and without removal of the intervertebral disc.
Figure 43:
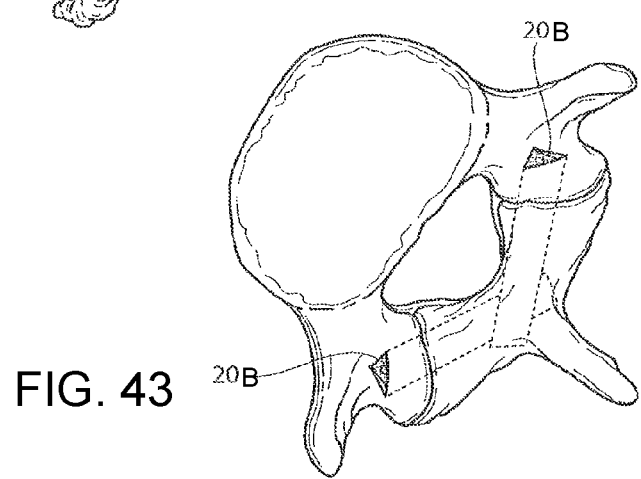
FIG. 43 is an anatomic inferior transverse plane view showing the assembly shown in FIG. 42 after implantation.

FIG. 42 shows, in an exploded view prior to implantation, a representative configuration of an assembly of one or more implant structures 20B sized and configured to achieve translaminar lumbar fusion in a non-invasive manner and without removal of the intervertebral disc. FIG. 43 shows the assembly after implantation, respectively, in an inferior transverse plane view. The implant structures illustrated in FIGS. 47-49 can also be used to achieve translaminar lumbar fusion as described herein.

As can be seen in the representative embodiment illustrated in FIGS. 42 and 43, the assembly comprises two implant structures 20B. The first implant structure 20B extends from the left superior articular process of vertebra L5, through the adjoining facet capsule into the left inferior articular process of vertebra L4, and, from there, further through the lamina of vertebra L4 into an interior right posterolateral region of vertebra L4 adjacent the spinous process. The second implant structure 20B extends from the right superior articular process of vertebra L5, through the adjoining facet capsule into the right inferior articular process of vertebra L4, and, from there, further through the lamina of vertebra L4 into an interior left posterolateral region of vertebra L4 adjacent the spinous process. The first and second implant structures 20B cross each other within the medial lamina of vertebra L4.

The first and second implant structures 20B are sized and configured according to the local anatomy. The selection of a translaminar lumbar fusion (posterior approach) is indicated when the facet joints are aligned with the sagittal plane. Removal of the intervertebral disc is not required, unless the condition of the disc warrants its removal.

A procedure incorporating the technical features of the procedure shown in FIGS. 39A to 39G can be tailored to a posterior procedure for implanting the assembly of implant structures 20B shown in FIGS. 42 and 43. The method comprises (i) identifying the vertebrae of the lumbar spine region that are to be fused; (ii) opening an incision, which comprises, e.g., with the patient lying in a prone position (on their stomach), making a 3 mm posterior incision; and (iii) using a guide pin to established a desired implantation path through bone for the first (e.g., left side) implant structure 20B, which, in FIGS. 42 and 43, traverses through the left superior articular process of vertebra L5, through the adjoining facet capsule into the left inferior articular process of vertebra L4, and then through the lamina of vertebra L4 into an interior right posterolateral region of vertebra L4 adjacent the spinous process. The method further includes (iv) guided by the guide pin, increasing the cross section of the path; (v) guided by the guide pin, shaping the cross section of the path to correspond with the cross section of the implant structure; (vi) inserting the implant structure 20B through the path over the guide pin; (vii) withdrawing the guide pin; and (viii) using a guide pin to established a desired implantation path through bone for the second (e.g., right side) implant structure 20B, which, in FIGS. 42 and 43, traverses through the right superior articular process of vertebra L5, through the adjoining facet capsule into the right inferior articular process of vertebra L4, and through the lamina of vertebra L4 into an interior left posterolateral region of vertebra L4 adjacent the spinous process. The physician repeats the remainder of the above-described procedure sequentially for the right implant structure 20B as for the left, and, after withdrawing the guide pin, closes the incision.

The intimate contact created between the bony in-growth or through-growth region 24B along the surface of the implant structure 20B across the facet joint accelerates bony in-growth or through-growth onto, into, or through the implant structure 20B, to accelerate fusion of the facets joints between L4 and L5. Of course, translaminar lumbar fusion between L5 and S1 can be achieved using first and second implant structures in the same manner.

C. Use of Implant Structures to Achieve Lumbar Facet Fusion (Posterior Approach)

Figure 44:
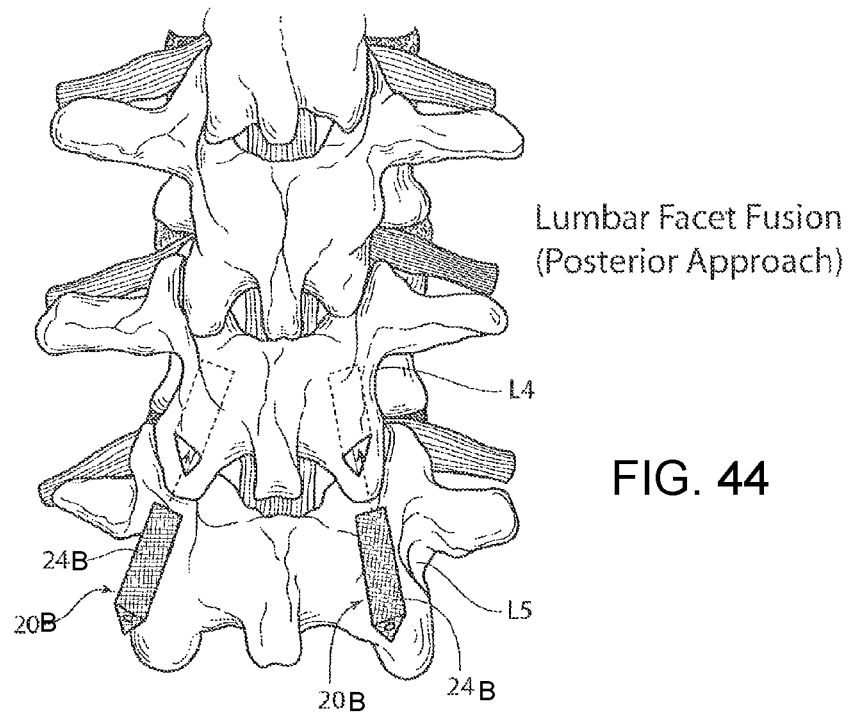
FIG. 44 is an anatomic posterior perspective view, exploded prior to implantation, of a representative configuration of an assembly of one or more implant structures like that shown in FIG. 30, sized and configured to achieve lumbar facet fusion, in a non-invasive manner and without removal of the intervertebral disc.
Figure 45:
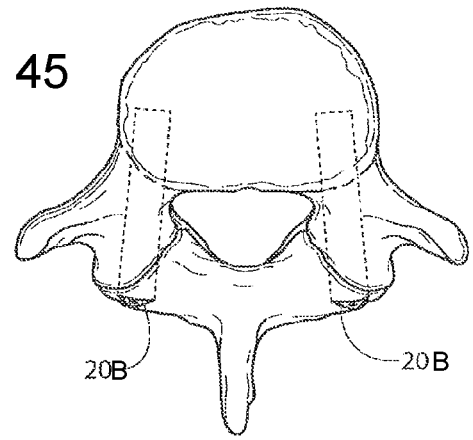
FIG. 45 is an anatomic inferior transverse plane view showing the assembly shown in FIG. 44 after implantation.
Figure 46:
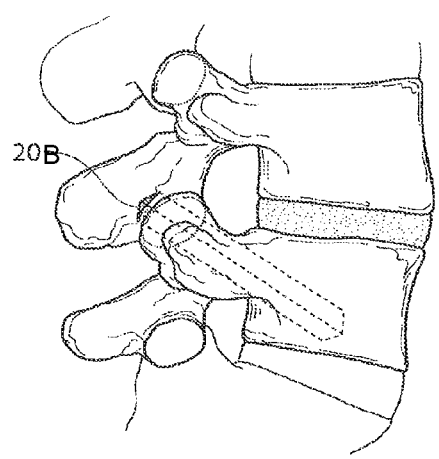
FIG. 46 is an anatomic lateral view showing the assembly shown in FIG. 44 after implantation.

FIG. 44 shows, in an exploded view prior to implantation, a representative configuration of an assembly of one or more implant structures 20B sized and configured to lumbar facet fusion, in a non-invasive manner and without removal of the intervertebral disc. FIGS. 45 and 46 show the assembly after implantation, respectively, in an inferior transverse plane view and a lateral view. The implant structures illustrated in FIGS. 47-49 can also be used to achieve lumbar facet fusion as described herein.

As can be seen in the representative embodiment illustrated in FIGS. 44 and 46, the assembly comprises two implant structures 20B. The first implant structure 20B extends from the left inferior articular process of vertebra L4, through the adjoining facet capsule into the left superior articular process of vertebra L5 and into the pedicle of vertebra L5. The second implant structure 20B extends from the right inferior articular process of vertebra L5, through the adjoining facet capsule into the right superior articular process of vertebra L5 and into the pedicle of vertebra L5. In this arrangement, the first and second implant structures 20B extend in parallel directions on the left and right pedicles of vertebra L5. The first and second implant structures 20B are sized and configured according to the local anatomy. The selection of lumbar facet fusion (posterior approach) is indicated when the facet joints are coronally angled. Removal of the intervertebral disc is not necessary, unless the condition of the disc warrants its removal.

A procedure incorporating the technical features of the procedure shown in FIGS. 39A to 39G can be tailored to a posterior procedure for implanting the assembly of implant structures 20B shown in FIGS. 44 to 46. The method comprises (i) identifying the vertebrae of the lumbar spine region that are to be fused; (ii) opening an incision, which comprises, e.g., with the patient lying in a prone position (on their stomach), making a 3 mm posterior incision; and (iii) using a guide pin to established a desired implantation path through bone for the first (e.g., left side) implant structure 20B, which, in FIGS. 44 to 46, traverses through the left inferior articular process of vertebra L4, through the adjoining facet capsule into the left superior articular process of vertebra L5 and into the pedicle of vertebra L5. The method further includes (iv) guided by the guide pin, increasing the cross section of the path; (v) guided by the guide pin, shaping the cross section of the path to correspond with the cross section of the implant structure 20B; (vi) inserting the implant structure 20B through the path over the guide pin; (vii) withdrawing the guide pin; and (viii) using a guide pin to established a desired implantation path through bone for the second (e.g., right side) implant structure 20B, which, in FIGS. 44 to 46, traverses through the right inferior articular process of vertebra L5, through the adjoining facet capsule into the right superior articular process of vertebra L5 and into the pedicle of vertebra L5. The physician repeats the remainder of the above-described procedure sequentially for the right implant structure 20B as for the left and, withdrawing the guide pin, closes the incision.

The intimate contact created between the bony in-growth or through-growth region 24B along the surface of the implant structure 20B across the facet joint accelerates bony in-growth or through-growth onto, into, or through the implant structure 20B, to accelerate fusion of the facets joints between L4 and L5.

Of course, translaminar lumbar fusion between L5 and S1 can be achieved using first and second implant structures in the same manner.

Figure 47:
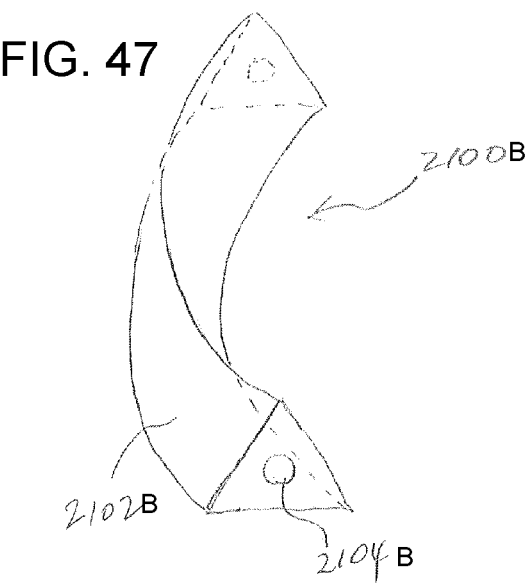
FIG. 47 is an embodiment of a curved implant structure.

FIG. 47 illustrates another embodiment of an implant structure 2100B which has a rectilinear cross-section and a curved elongate body 2102B having a lumen 2104B for receiving a guide wire or guide pin. In some embodiments, the curved elongate body 212B can have a constant curvature which can be particularly suited to facilitate insertion of a curved and rigid implant structure 210B into a curved bore or channel also with a matching constant curvature. In this context, constant curvature refers, for example, to a curvature of a circle or spiral. Although the implant structure 2100B is shown as having a rectilinear cross-section, and specifically a triangular cross-section, other rectilinear cross-sections are contemplated, include square, rectangular, rhomboid, trapezoidal, pentagonal, hexagonal and the like. In addition, the implant structure 2100B can alternatively have a curvilinear cross-section, such as circular, elliptical, oval, oblong, and the like. The primary new feature disclosed in FIG. 47 over the other embodiments of the implant structure described herein is the curved elongate body 2102B which can be implemented in any of the implanted structures disclosed and/or contemplated herein. In some embodiments, the implant structure can be made of a shape memory material, such as a nickel titanium alloy, that can adopt a predetermined curved configuration during and/or after implantation. In some embodiments, implant structures made of a shape memory material can have an initial delivery configuration that is straight, partially curved or curved, where the curvature can either be constant or variable.

Figure 48:
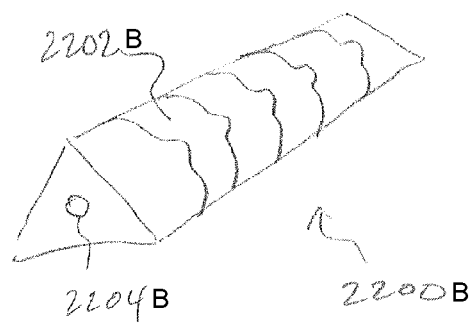
FIG. 48 is another embodiment of a curved implant structure formed from interconnected segments.

FIG. 48 illustrates another embodiment of an implant structure 2200B which has a rectilinear cross-section and an elongate body 2202B that can be made from a plurality of interlocking segments 2204B that allows the elongate body 2202B to bend and take on a variety of different configurations, from straight to curved with a constant curvature to curved with a variable curvature. The elongate body 2202B can also have a lumen 2204B for receiving a guidewire or guide pin. In some embodiments, the implant structure 2200B can be flexible and/or formed in-situ. In some embodiments, the implant structure can be made of a shape memory material, such as a nickel titanium alloy, that can adopt a predetermined curved configuration during and/or after implantation.

Figure 49:
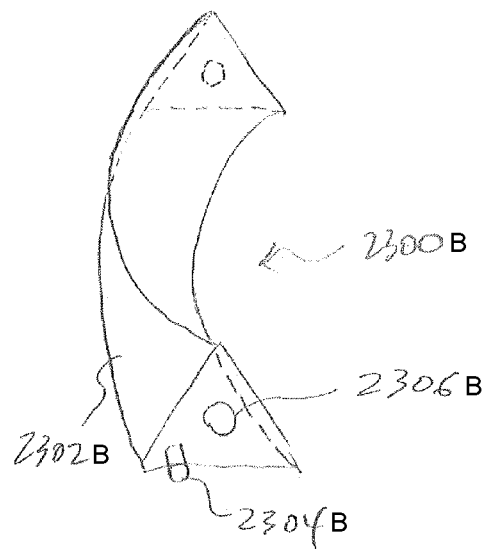
FIG. 49 is another embodiment of a curved implant structure that is inflatable.
Figure 50:
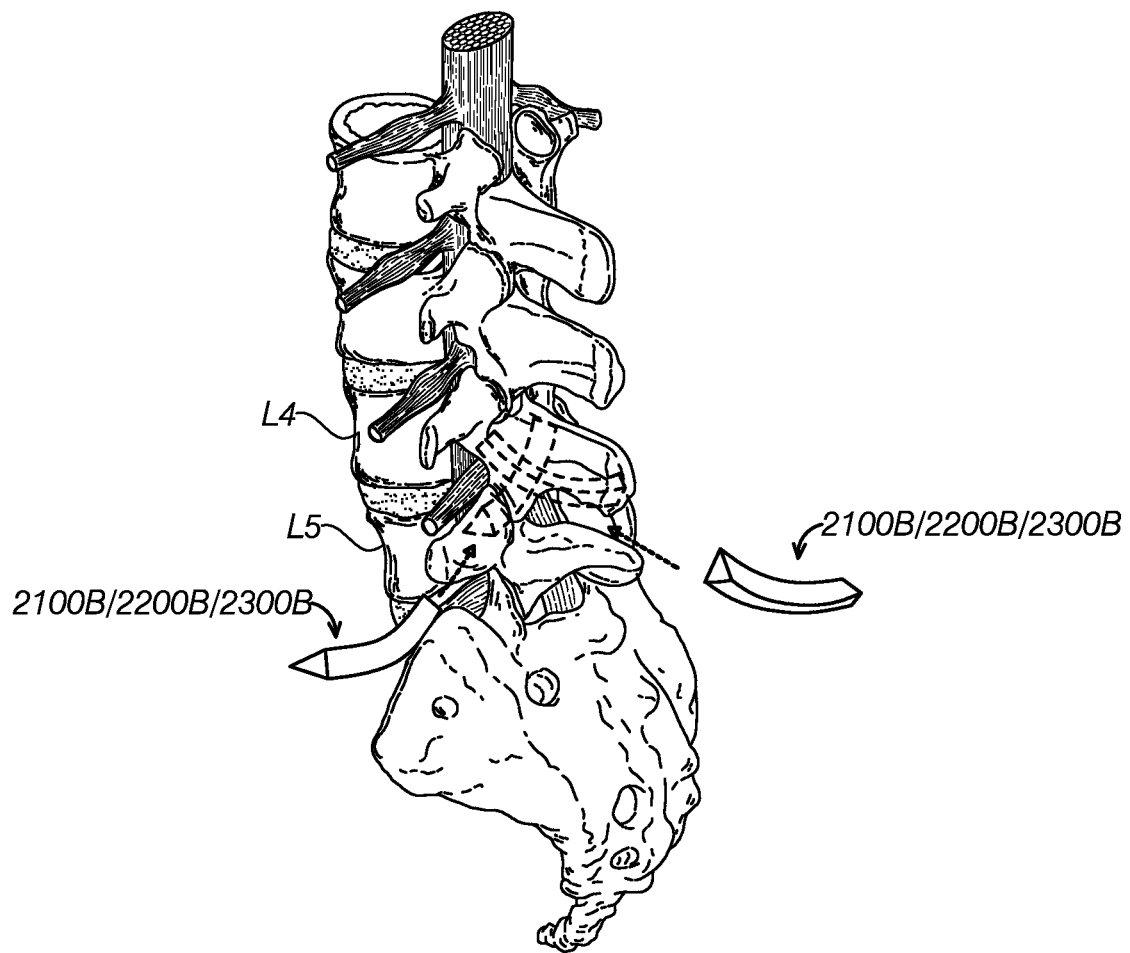
FIG. 50 is an anatomic posterior perspective view, exploded prior to implantation, of a representative configuration of an assembly of one or more implant structures like that shown in FIGS. 47-49, sized and configured to achieve translaminar lumbar fusion in a non-invasive manner and without removal of the intervertebral disc.
Figure 51:
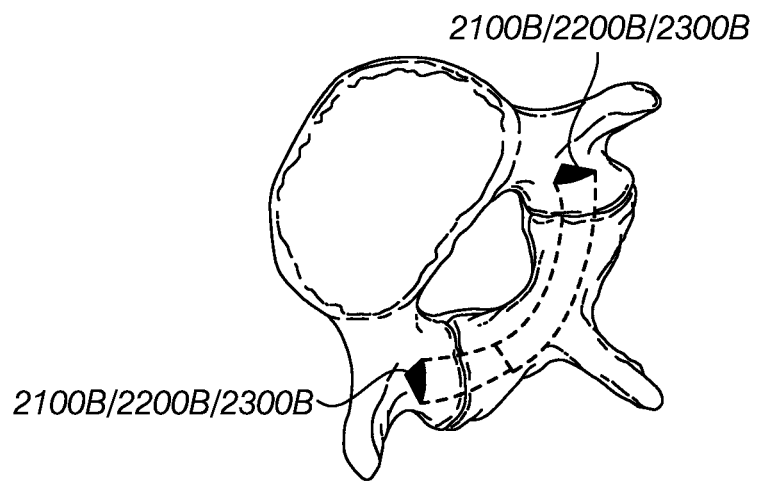
FIG. 51 is an anatomic inferior transverse plane view showing the assembly shown in FIG. 50 after implantation.
Figure 52:
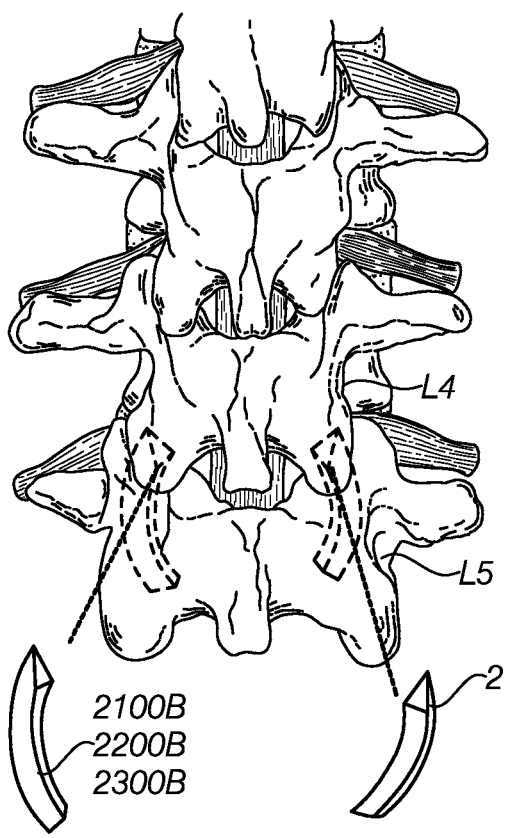
FIG. 52 is an anatomic posterior perspective view, exploded prior to implantation, of a representative configuration of an assembly of one or more implant structures like that shown in FIGS. 47-49, sized and configured to achieve lumbar facet fusion, in a non-invasive manner and without removal of the intervertebral disc.
Figure 53:
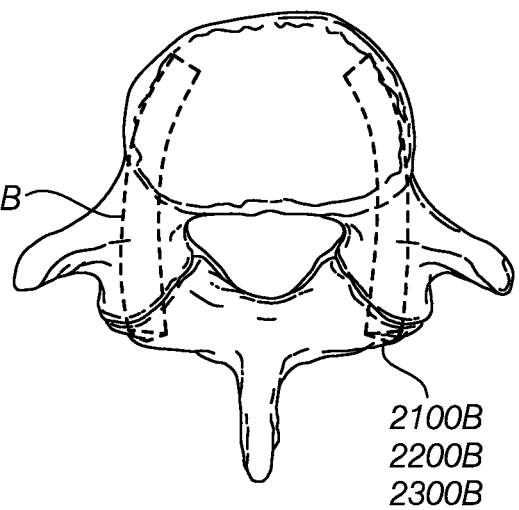
FIG. 53 is an anatomic inferior transverse plane view showing the assembly shown in FIG. 52 after implantation.
Figure 54:
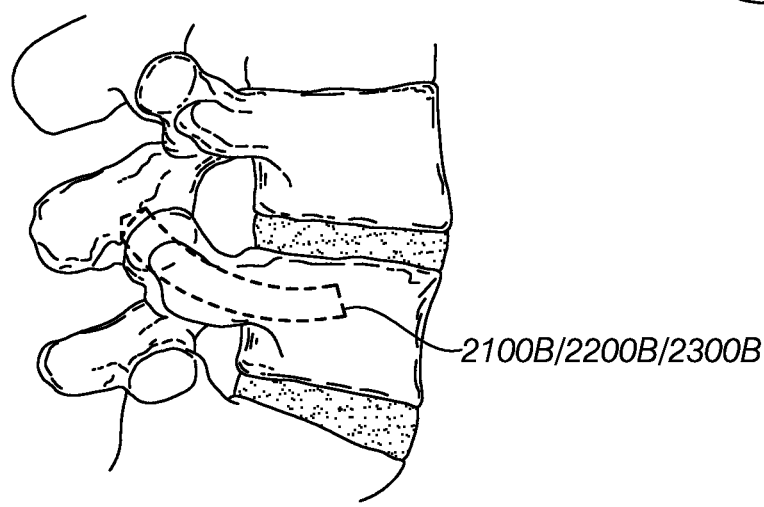
FIG. 54 is an anatomic lateral view showing the assembly shown in FIG. 52 after implantation.

FIG. 49 illustrates another embodiment of a curved implant structure 2300B that can be formed in-situ. The implant structure 2300B can be inflatable and can be filled with a curable polymer or resin or cement. The walls 2302B of the implant structure 2300B can be made of either an inelastic material that cannot stretch or an elastic material that can stretch. The implant structure 2300B can be delivered in a collapsed and uninflated state over a guidewire, and can then be filled with the curable material through, for example, a valve 2304B located on the proximal end of the implant structure 2300B. In the inflated configuration, the implant structure 2300B can take any of the configurations disclosed herein, such as having a rectilinear cross-section or a curvilinear cross-section and having a curved configuration or a straight configuration. The implant structure can have an elongate body with a lumen 2306B for receiving a guidewire or guide pin.

In some embodiments, the curved implant structures illustrated in FIGS. 47-49 can be used in one of the facet fusion procedures as shown and described, for example, above in reference to FIGS. 42-46. FIGS. 50-54 illustrate the same procedures as FIGS. 42-46 expect that a curved implant structure is used in place of a straight implant structure. In some embodiments, the transfacet fusion procedure, as illustrated in FIGS. 44-46, involves placing the implant structures such that the implant structures do not cross the spinal process. In contrast, translaminar facet fusion procedures generally involve placing the implant structures such that the implant structures cross the spinal process, as illustrated in FIGS. 42 and 43. The curved implant structure can provide improved transfacet fusion and translaminar facet fusion over a straight implant structure by curving around sensitive nerve tissue which can provide a larger safety margin and can allow a longer implant structure to be used. More generally, the curved implant structures can be advantageously used in any of the bone fusion or fixation procedures described herein, especially where a curved geometry is useful for maintaining the implant structure within bone tissue while avoiding sensitive tissues such as nerve tissue. The surfaces of the curved implant structures can be porous and/or textured and can be treated and/or coated with bone growth promoting materials or compounds, such as hydroxyapatite and bone morphogenetic proteins (BMPs).

To form the curved bore or channel a curved through bone such as the vertebrae, a curved guidewire or guide pin can be inserted into the bone by, for example, placing the curved guidewire or guide pin against the bone surface and rotating the curved guidewire or guide pin about an axis. Alternatively or in addition to the curved guidewire or guide pin, a steerable drill or cutting device can be used to create the bore or a pilot bore. In some embodiments, the steerable drill or cutting device can be advanced over, through or with a curved guide track or sheath to form the curved bore. In some embodiments, the drill bit or cutting device can be curved and can form the curved bore by placing the drill bit or cutting device against the bone surface and rotating the drill bit or cutting device about an axis. In some embodiments, the drill bit or cutting device can have a guidewire lumen that allows the drill bit or cutting device to be advanced over the curved guidewire. Similarly, a curved broach can be used to shape the curved bore into any cross-sectional shape described herein, such as rectilinear and triangular, in particular. In some embodiments, the curved broach can have a guidewire lumen that allows the curved broach to be advanced over the curved guidewire. In some embodiments, the curved broach can be rotated about an axis like the guidewire and cutting device.

Once the curved bore is formed, the implant structure can be inserted as described above. In some embodiments, the bore can be formed in a reverse fashion, by for example, creating a curved insertion path that starts in the lamina of the superior vertebra, extends distally and laterally to the inferior articular process of the superior vertebra, through the joint between the superior vertebra and the inferior vertebrae, and into the superior articular process of the inferior vertebra. The curved bone fixation implant can be inserted through the insertion path from the lamina of the superior vertebra, extending distally and laterally to the inferior articular process of the superior vertebra, through the joint between the superior vertebra and the inferior vertebrae, and into the superior articular process of the inferior vertebra II. Conclusion The various representative embodiments of the assemblies of the implant structures, as described, make possible the achievement of diverse interventions involving the fusion and/or stabilization of lumbar and sacral vertebra in a non-invasive manner, with minimal incision, and without the necessitating the removing the intervertebral disc. The representative lumbar spine interventions described can be performed on adults or children and include, but are not limited to, lumbar interbody fusion; translaminar lumbar fusion; lumbar facet fusion; trans-iliac lumbar fusion; and the stabilization of a spondylolisthesis. It should be appreciated that such interventions can be used in combination with each other and in combination with conventional fusion/fixation techniques to achieve the desired therapeutic objectives.

Significantly, the various assemblies of the implant structures as described make possible lumbar interbody fusion without the necessity of removing the intervertebral disc. For example, in conventional anterior lumbar interbody fusion procedures, the removal of the intervertebral disc is a prerequisite of the procedure. However, when using the assemblies as described to achieve anterior lumbar interbody fusion, whether or not the intervertebral disc is removed depends upon the condition of the disc, and is not a prerequisite of the procedure itself. If the disc is healthy and has not appreciably degenerated, one or more implant structures can be individually inserted in a minimally invasive fashion, across the intervertebral disc in the lumbar spine area, leaving the disc intact.

In all the representative interventions described, the removal of a disc, or the scraping of a disc, is at the physician's discretion, based upon the condition of the disc itself, and is not dictated by the procedure. The bony in-growth or through-growth regions of the implant structures described provide both extra-articular and intra osseous fixation, when bone grows in and around the bony in-growth or through-growth regions.

Conventional tissue access tools, obturators, cannulas, and/or drills can be used during their implantation. No disc preparation, removal of bone or cartilage, or scraping are required before and during formation of the insertion path or insertion of the implant structures, so a minimally invasive insertion path sized approximately at or about the maximum outer diameter of the implant structures need be formed. Still, the implant structures, which include the elongated bony in-growth or through-growth regions, significantly increase the size of the fusion area, from the relatively small surface area of a given joint between adjacent bones, to the surface area provided by an elongated bony in-growth or through-growth regions. The implant structures can thereby increase the surface area involved in the fusion and/or stabilization by 3-fold to 4-fold, depending upon the joint involved.

The implant structures can obviate the need for autologous grafts, bone graft material, additional pedicle screws and/or rods, hollow modular anchorage screws, cannulated compression screws, cages, or fixation screws. Still, in the physician's discretion, bone graft material and other fixation instrumentation can be used in combination with the implant structures.

The implant structures make possible surgical techniques that are less invasive than traditional open surgery with no extensive soft tissue stripping and no disc removal. The assemblies make possible straightforward surgical approaches that complement the minimally invasive surgical techniques. The profile and design of the implant structures minimize rotation and micro-motion. Rigid implant structures made from titanium provide immediate post-op fusion stability. A bony in-growth region comprising a porous plasma spray coating with irregular surface supports stable bone fixation/fusion. The implant structures and surgical approaches make possible the placement of larger fusion surface areas designed to maximize post-surgical weight bearing capacity and provide a biomechanically rigorous implant designed specifically to stabilize the heavily loaded lumbar spine.

Systems and Methods for Removing an Implant

Figure 55:
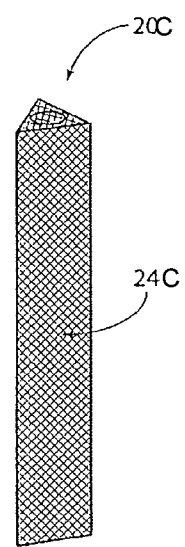
FIG. 55 illustrates an embodiment of an implant structure.

Elongated, stem-like implant structures 20C like that shown in FIG. 55 make possible the fixation of the SI-Joint (shown in anterior and posterior views, respectively, in FIGS. 57 and 58) in a minimally invasive manner. These implant structures 20C can be effectively implanted through the use a lateral surgical approach. The procedure is desirably aided by conventional lateral, inlet, and outlet visualization techniques, e.g., using X-ray image intensifiers such as a C-arms or fluoroscopes to produce a live image feed, which is displayed on a TV screen.

In one embodiment of a lateral approach (see FIGS. 59, 60, and 61A/B), one or more implant structures 20C are introduced laterally through the ilium, the SI-Joint, and into the sacrum. This path and resulting placement of the implant structures 20C are best shown in FIGS. 60 and 61A/B. In the illustrated embodiment, three implant structures 20C are placed in this manner. Also in the illustrated embodiment, the implant structures 20C are rectilinear in cross section and triangular in this case, but it should be appreciated that implant structures 20C of other rectilinear cross sections can be used.

Before undertaking a lateral implantation procedure, the physician identifies the SI-Joint segments that are to be fixated or fused (arthrodesed) using, e.g., the Fortin finger test, thigh thrust, FABER, Gaenslen's, compression, distraction, and diagnostic SI joint injection . . . .

Figure 56A:
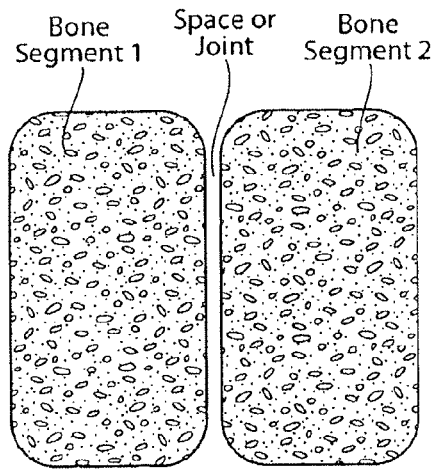
FIGS. 56A-56D are side section views of the formation of a broached bore in bone according to one embodiment of the invention.
Figure 56B:
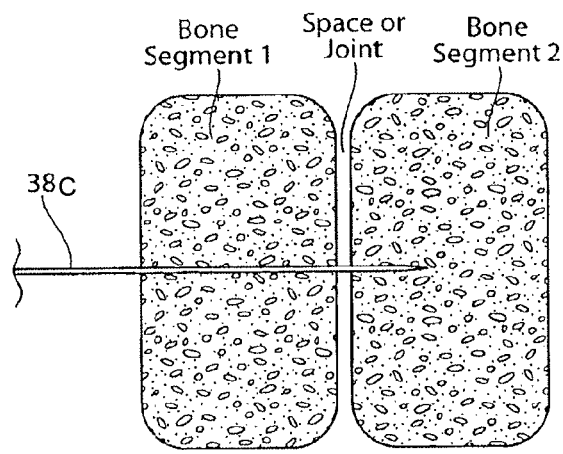

Aided by lateral, inlet, and outlet C-arm views, and with the patient lying in a prone position, the physician aligns the greater sciatic notches and then the alae (using lateral visualization) to provide a true lateral position. A 3 cm incision is made starting aligned with the posterior cortex of the sacral canal, followed by blunt tissue separation to the ilium. From the lateral view, the guide pin 38C (with sleeve (not shown)) (e.g., a Steinmann Pin) is started resting on the ilium at a position inferior to the sacrum end plate and just anterior to the sacral canal. In the outlet view, the guide pin 38C should be parallel to the sacrum end plate at a shallow angle anterior (e.g., 15.degree. to 20.degree. off the floor, as FIG. 61A shows). In a lateral view, the guide pin 38C should be posterior to the sacrum anterior wall. In the outlet view, the guide pin 38C should be superior to the first sacral foramen and lateral of mid-line. This corresponds generally to the sequence shown diagrammatically in FIGS. 56A and 56B. A soft tissue protector (not shown) is desirably slipped over the guide pin 38C and firmly against the ilium before removing the guide pin sleeve (not shown).

Figure 56C:
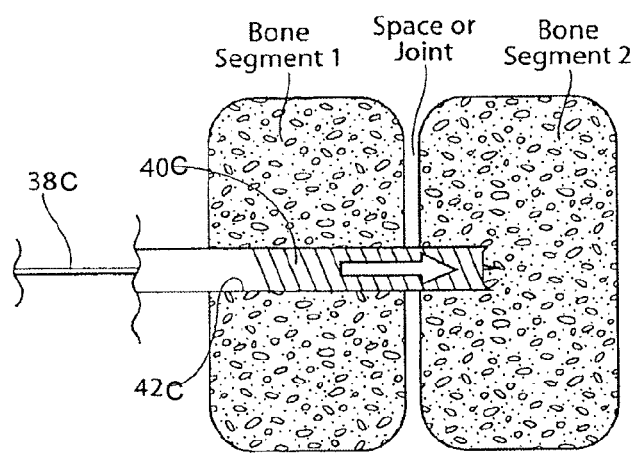

Over the guide pin 38C (and through the soft tissue protector), the pilot bore 42C is drilled in the manner previously described, as is diagrammatically shown in FIG. 56C. The pilot bore 42C extends through the ilium, through the SI-Joint, and into the S1. The drill bit 40C is removed.

Figure 56D:
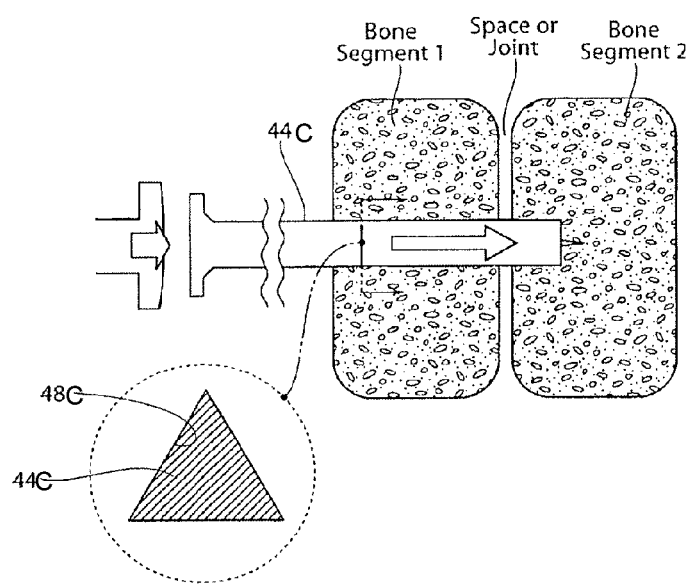

The shaped broach 44C is tapped into the pilot bore 42C over the guide pin 38C (and through the soft tissue protector) to create a broached bore 48 with the desired profile for the implant structure 20C, which, in the illustrated embodiment, is triangular. This generally corresponds to the sequence shown diagrammatically in FIG. 56D. The triangular profile of the broached bore 48C is also shown in FIG. 59.

Figure 56E:
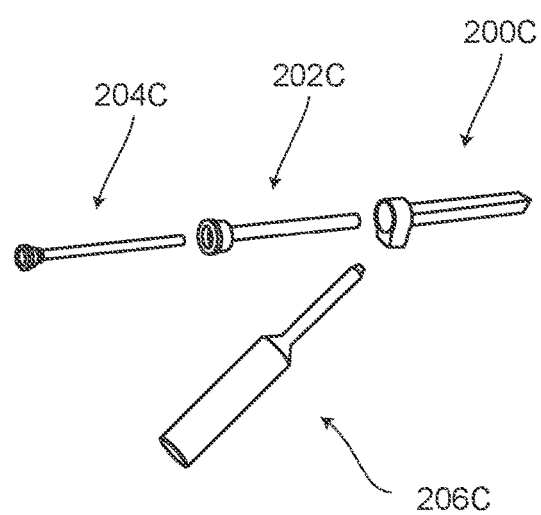
FIGS. 56E and 56F illustrate the assembly of a soft tissue protector system for placement over a guide wire.
Figure 56F:
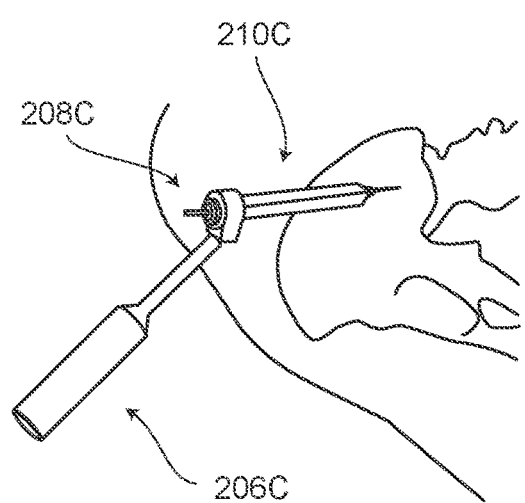

FIGS. 56E and 56F illustrate an embodiment of the assembly of a soft tissue protector or dilator or delivery sleeve 200C with a drill sleeve 202C, a guide pin sleeve 204C and a handle 206C. In some embodiments, the drill sleeve 202C and guide pin sleeve 204C can be inserted within the soft tissue protector 200C to form a soft tissue protector assembly 210C that can slide over the guide pin 208C until bony contact is achieved. The soft tissue protector 200C can be any one of the soft tissue protectors or dilators or delivery sleeves disclosed herein. In some embodiments, an expandable dilator or delivery sleeve 200C as disclosed herein can be used in place of a conventional soft tissue dilator. In the case of the expandable dilator, in some embodiments, the expandable dilator can be slid over the guide pin and then expanded before the drill sleeve 202C and/or guide pin sleeve 204C are inserted within the expandable dilator. In other embodiments, insertion of the drill sleeve 202C and/or guide pin sleeve 204C within the expandable dilator can be used to expand the expandable dilator.

In some embodiments, a dilator can be used to open a channel though the tissue prior to sliding the soft tissue protector assembly 210C over the guide pin. The dilator(s) can be placed over the guide pin, using for example a plurality of sequentially larger dilators or using an expandable dilator. After the channel has been formed through the tissue, the dilator(s) can be removed and the soft tissue protector assembly can be slid over the guide pin. In some embodiments, the expandable dilator can serve as a soft tissue protector after being expanded. For example, after expansion the drill sleeve and guide pin sleeve can be inserted into the expandable dilator.

Figure 59:
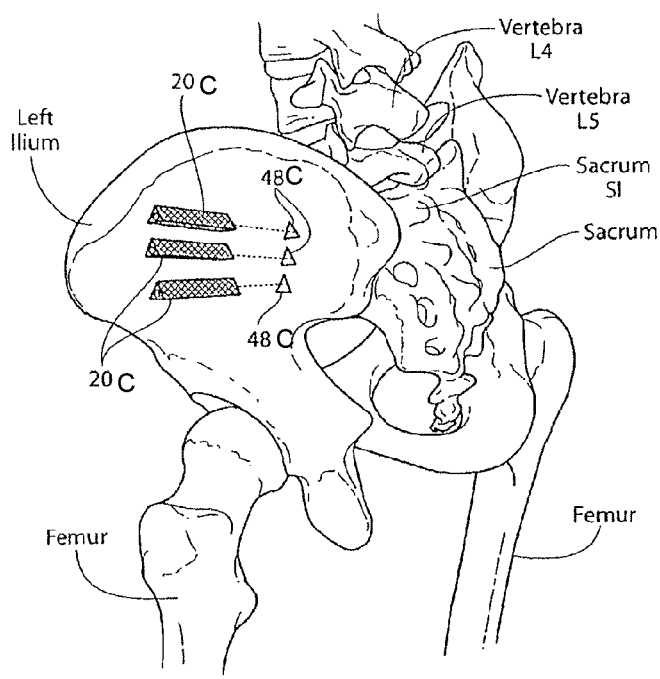
FIGS. 59, 60, 61A and 61B are anatomic views showing, respectively, a pre-implanted perspective, implanted perspective, implanted anterior view, and implanted craniocaudal section view, the implantation of three implant structures for the fixation of the SI-Joint using a lateral approach through the ilium, the SI-Joint, and into the sacrum.
Figure 60:
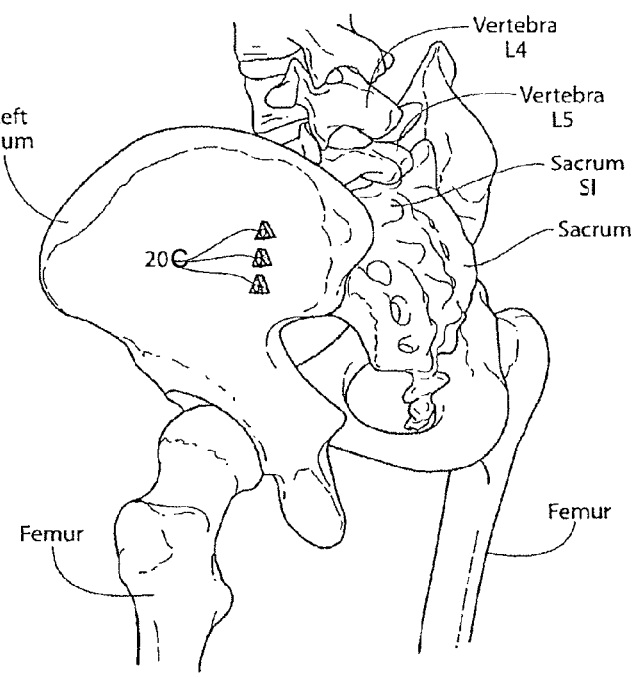
Figure 61A:
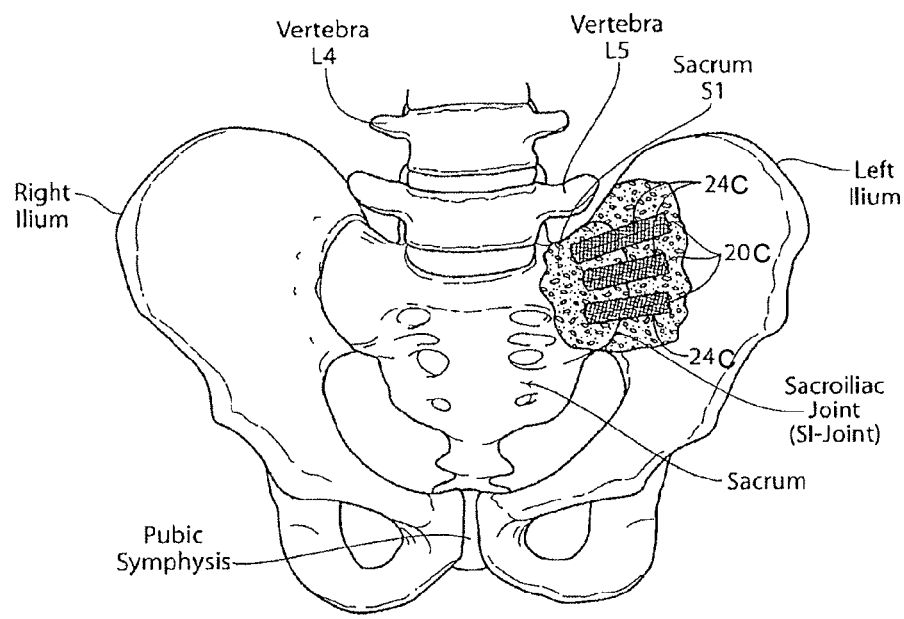
Figure 61B:
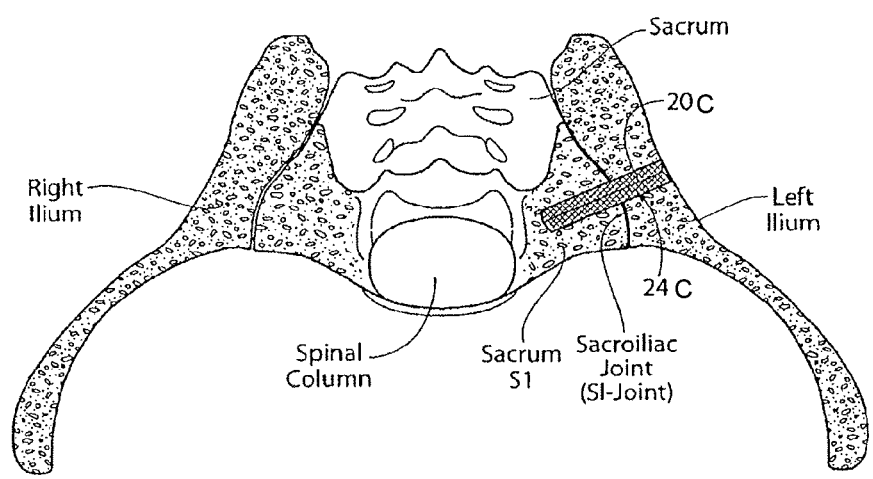

As shown in FIGS. 59 and 60, a triangular implant structure 20C can be now tapped through the soft tissue protector over the guide pin 38C through the ilium, across the SI-Joint, and into the sacrum, until the proximal end of the implant structure 20C is flush against the lateral wall of the ilium (see also FIGS. 61A and 61B). The guide pin 38C and soft tissue protector are withdrawn, leaving the implant structure 20C residing in the broached passageway, flush with the lateral wall of the ilium (see FIGS. 61A and 61B). In the illustrated embodiment, two additional implant structures 20C are implanted in this manner, as FIG. 60 best shows. In other embodiments, the proximal ends of the implant structures 20C are left proud of the lateral wall of the ilium, such that they extend 1, 2, 3 or 4 mm outside of the ilium. This ensures that the implants 20C engage the hard cortical portion of the ilium rather than just the softer cancellous portion, through which they might migrate if there was no structural support from hard cortical bone. The hard cortical bone can also bear the loads or forces typically exerted on the bone by the implant 20C.

The implant structures 20C are sized according to the local anatomy. For the SI-Joint, representative implant structures 20C can range in size, depending upon the local anatomy, from about 35 mm to about 60 mm in length, and about a 7 mm inscribed diameter (i.e. a triangle having a height of about 10.5 mm and a base of about 12 mm). The morphology of the local structures can be generally understood by medical professionals using textbooks of human skeletal anatomy along with their knowledge of the site and its disease or injury. The physician is also able to ascertain the dimensions of the implant structure 20C based upon prior analysis of the morphology of the targeted bone using, for example, plain film x-ray, fluoroscopic x-ray, or MRI or CT scanning.

Using a lateral approach, one or more implant structures 20C can be individually inserted in a minimally invasive fashion across the SI-Joint, as has been described. Conventional tissue access tools, obturators, cannulas, and/or drills can be used for this purpose. Alternatively, the novel tissue access tools described above and in U.S. Provisional Patent Application No. 61/609,043, titled "TISSUE DILATOR AND PROTECTER" and filed Mar. 9, 2012, which is hereby incorporated by reference in its entirety, can also be used. No joint preparation, removal of cartilage, or scraping are required before formation of the insertion path or insertion of the implant structures 20C, so a minimally invasive insertion path sized approximately at or about the maximum outer diameter of the implant structures 20C can be formed.

The implant structures 20C can obviate the need for autologous bone graft material, additional pedicle screws and/or rods, hollow modular anchorage screws, cannulated compression screws, threaded cages within the joint, or fracture fixation screws. Still, in the physician's discretion, bone graft material and other fixation instrumentation can be used in combination with the implant structures 20C.

In a representative procedure, one to six, or perhaps up to eight, implant structures 20C can be used, depending on the size of the patient and the size of the implant structures 20C. After installation, the patient would be advised to prevent or reduce loading of the SI-Joint while fusion occurs. This could be about a six to twelve week period or more, depending on the health of the patient and his or her adherence to post-op protocol.

The implant structures 20C make possible surgical techniques that are less invasive than traditional open surgery with no extensive soft tissue stripping. The lateral approach to the SI-Joint provides a straightforward surgical approach that complements the minimally invasive surgical techniques. The profile and design of the implant structures 20C minimize or reduce rotation and micromotion. Rigid implant structures 20C made from titanium provide immediate post-op SI Joint stability. A bony in-growth region 24C comprising a porous plasma spray coating with irregular surface supports stable bone fixation/fusion. The implant structures 20C and surgical approaches make possible the placement of larger fusion surface areas designed to maximize post-surgical weight bearing capacity and provide a biomechanically rigorous implant designed specifically to stabilize the heavily loaded SI-Joint.

To improve the stability and weight bearing capacity of the implant, the implant can be inserted across three or more cortical walls. For example, after insertion the implant can traverse two cortical walls of the ilium and at least one cortical wall of the sacrum. The cortical bone is much denser and stronger than cancellous bone and can better withstand the large stresses found in the SI-Joint. By crossing three or more cortical walls, the implant can spread the load across more load bearing structures, thereby reducing the amount of load borne by each structure. In addition, movement of the implant within the bone after implantation is reduced by providing structural support in three locations around the implant versus two locations.

Use of the Implant

Figure 62A:
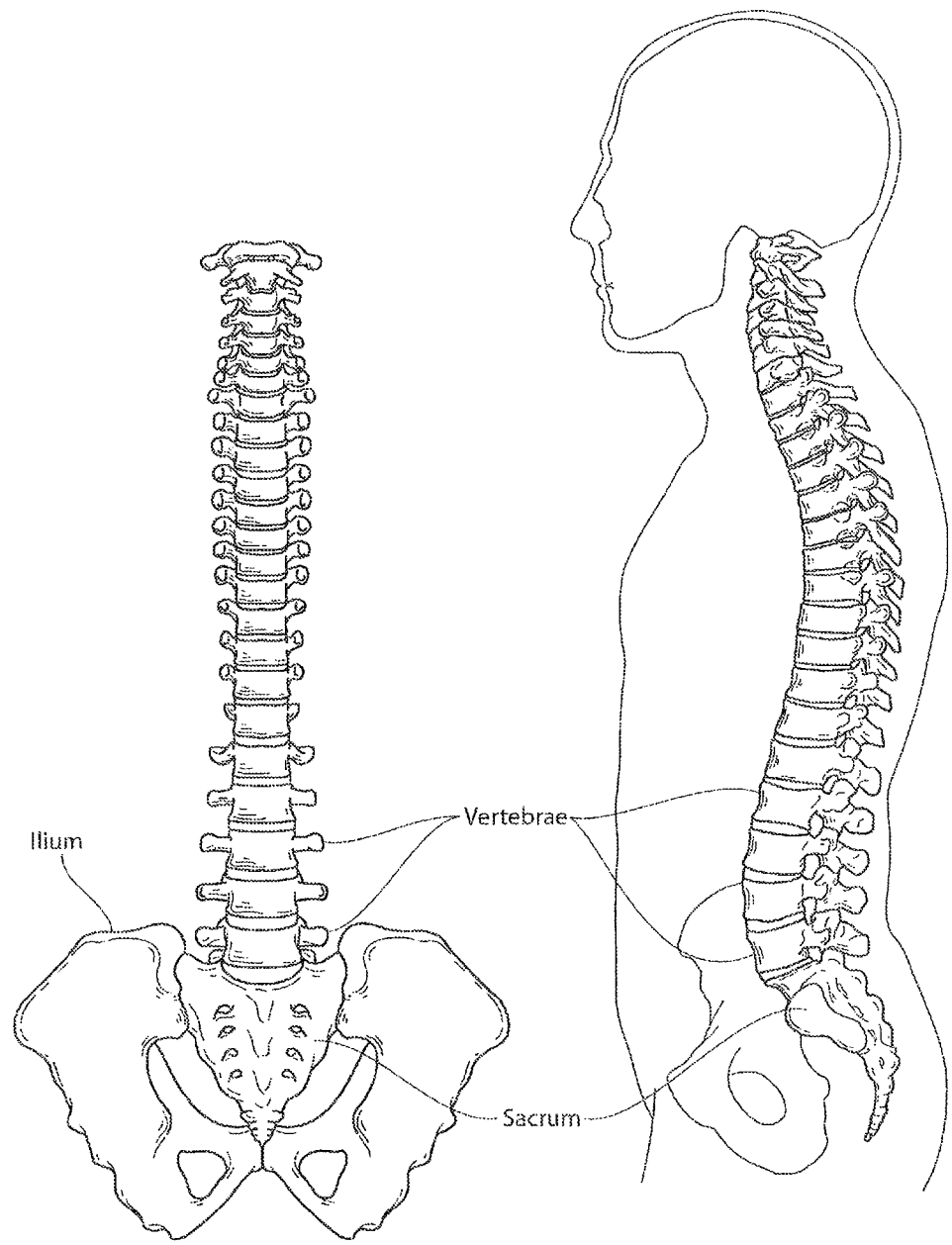
FIG. 62A is an anatomic anterior and lateral view of a human spine.

The spine (see FIGS. 62A-62C) is a complex interconnecting network of nerves, joints, muscles, tendons and ligaments, and all are capable of producing pain.

The spine is made up of small bones, called vertebrae. The vertebrae protect and support the spinal cord. They also bear the majority of the weight put upon the spine.

Between each vertebra is a soft, gel-like "cushion," called an intervertebral disc. These flat, round cushions act like shock absorbers by helping absorb pressure and keep the bones from rubbing against each other. The intervertebral disc also binds adjacent vertebrae together. The intervertebral discs are a type of joint in the spine. Intervertebral disc joints can bend and rotate a bit but do not slide as do most body joints.

Figure 62B:
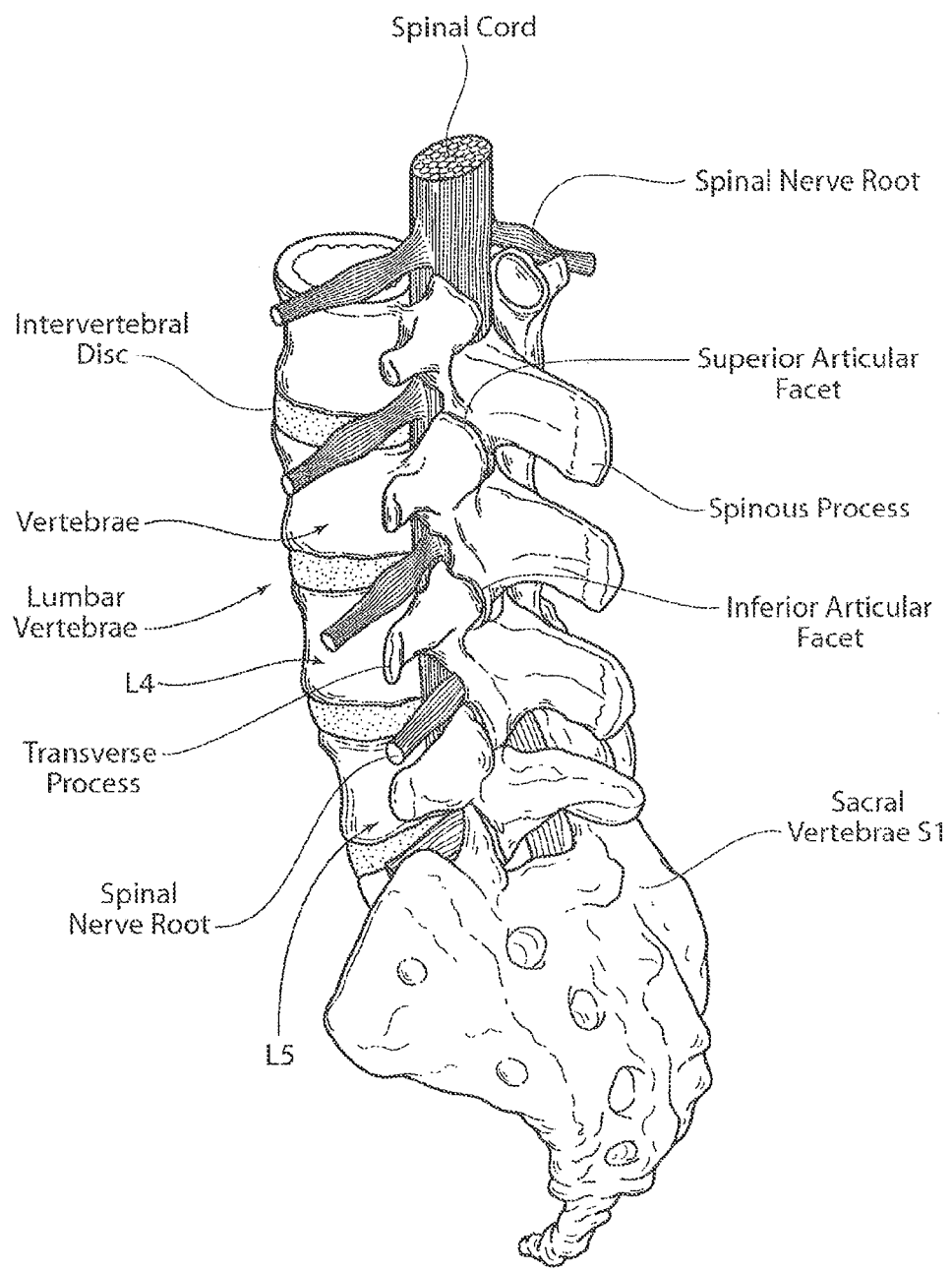
FIG. 62B is an anatomic posterior perspective view of the lumbar region of a human spine, showing lumbar vertebrae L2 to L5 and the sacral vertebrae.
Figure 62C:
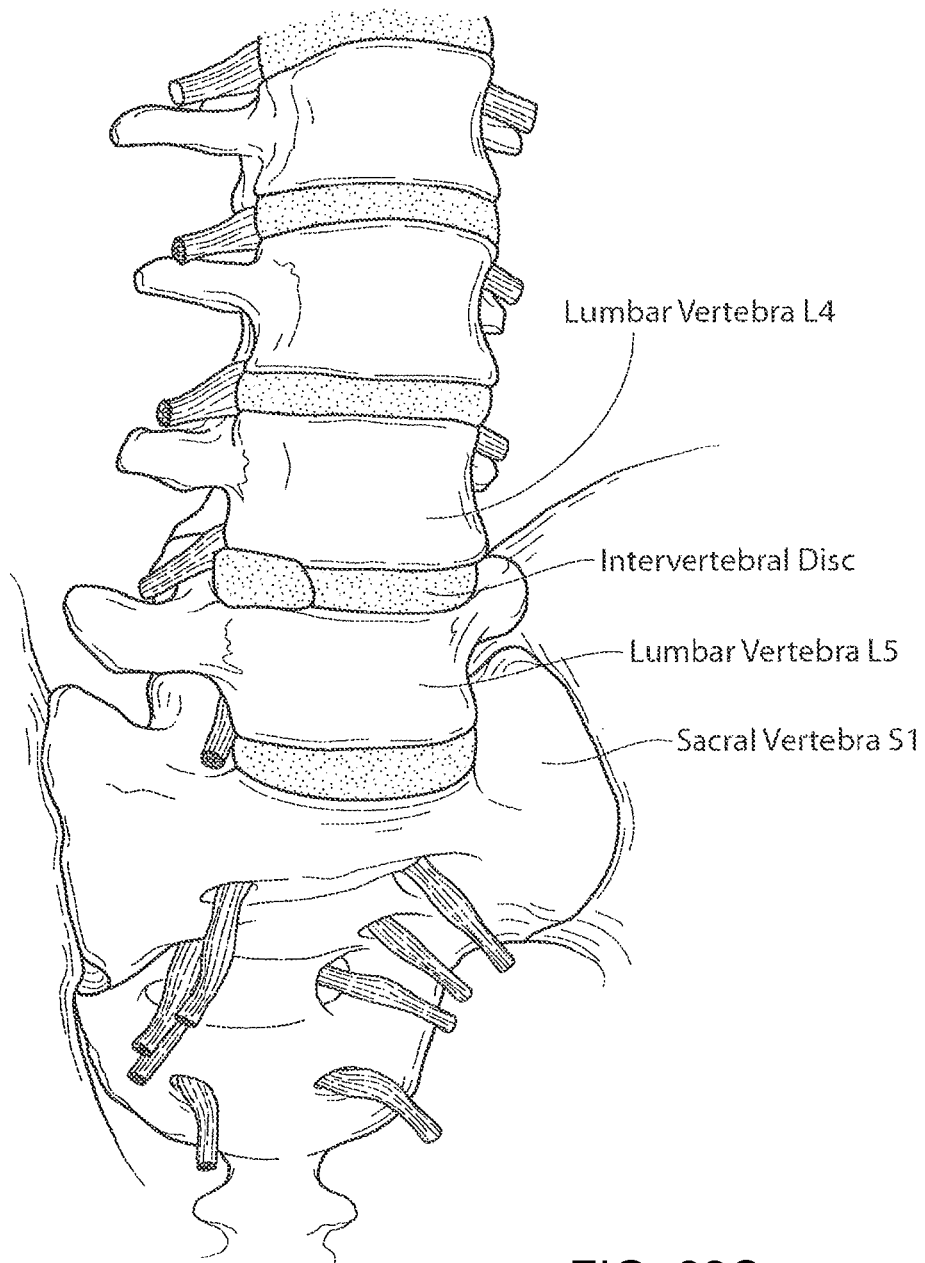
FIG. 62C is an anatomic anterior perspective view of the lumbar region of a human spine, showing lumbar vertebrae L2 to L5 and the sacral vertebrae.

Each vertebra has two other sets of joints, called facet joints (see FIG. 62B). The facet joints are located at the back of the spine (posterior). There is one facet joint on each lateral side (right and left). One pair of facet joints faces upward (called the superior articular facet) and the other pair of facet joints faces downward (called the inferior articular facet). The inferior and superior facet joints mate, allowing motion (articulation), and link vertebrae together. Facet joints are positioned at each level to provide the needed limits to motion, especially to rotation and to prevent forward slipping (spondylolisthesis) of that vertebra over the one below.

In this way, the spine accommodates the rhythmic motions required by humans to walk, run, swim, and perform other regular movements. The intervertebral discs and facet joints stabilize the segments of the spine while preserving the flexibility needed to turn, look around, and get around.

Degenerative changes in the spine can adversely affect the ability of each spinal segment to bear weight, accommodate movement, and provide support. When one segment deteriorates to the point of instability, it can lead to localized pain and difficulties. Segmental instability allows too much movement between two vertebrae. The excess movement of the vertebrae can cause pinching or irritation of nerve roots. It can also cause too much pressure on the facet joints, leading to inflammation. It can cause muscle spasms as the paraspinal muscles try to stop the spinal segment from moving too much. The instability eventually results in faster degeneration in this area of the spine. Degenerative changes in the spine can also lead to spondylolysis and spondylolisthesis. Spondylolisthesis is the term used to describe when one vertebra slips forward on the one below it. This usually occurs because there is a spondylolysis (defect) in the vertebra on top. For example, a fracture or a degenerative defect in the interarticular parts of lumbar vertebra L1 may cause a forward displacement of the lumbar vertebra L5 relative to the sacral vertebra S1 (called L5-S1 spondylolisthesis). When a spondylolisthesis occurs, the facet joint can no longer hold the vertebra back. The intervertebral disc may slowly stretch under the increased stress and allow other upper vertebra to slide forward.

An untreated persistent, episodic, severely disabling back pain problem can easily ruin the active life of a patient. In many instances, pain medication, splints, or other normally-indicated treatments can be used to relieve intractable pain in a joint. However, in for severe and persistent problems that cannot be managed by these treatment options, degenerative changes in the spine may require a bone fusion surgery to stop both the associated disc and facet joint problems.

A fusion is an operation where two bones, usually separated by a joint, are allowed to grow together into one bone. The medical term for this type of fusion procedure is arthrodesis.

Lumbar fusion procedures have been used in the treatment of pain and the effects of degenerative changes in the lower back. A lumbar fusion is a fusion in the S1-L5-L4 region in the spine.

One conventional way of achieving a lumbar fusion is a procedure called anterior lumbar interbody fusion (ALIF). In this procedure, the surgeon works on the spine from the front (anterior) and removes a spinal disc in the lower (lumbar) spine. The surgeon inserts a bone graft into the space between the two vertebrae where the disc was removed (the interbody space). The goal of the procedure is to stimulate the vertebrae to grow together into one solid bone (known as fusion). Fusion creates a rigid and immovable column of bone in the problem section of the spine. This type of procedure is used to try and reduce back pain and other symptoms.

Facet joint fixation procedures have also been used for the treatment of pain and the effects of degenerative changes in the lower back. These procedures take into account that the facet joint is the only true articulation in the lumbosacral spine. In one conventional procedure for achieving facet joint fixation, the surgeon works on the spine from the back (posterior). The surgeon passes screws from the spinous process through the lamina and across the mid-point of one or more facet joints.

Conventional treatment of spondylolisthesis may include a laminectomy to provide decompression and create more room for the exiting nerve roots. This can be combined with fusion using, e.g., an autologous fibular graft, which may be performed either with or without fixation screws to hold the bone together. In some cases the vertebrae are moved back to the normal position prior to performing the fusion, and in others the vertebrae are fused where they are after the slip, due to the increased risk of injury to the nerve with moving the vertebra back to the normal position.

Currently, these procedures entail invasive open surgical techniques (anterior and/or posterior). Further, ALIF entails the surgical removal of the disc. Like all invasive open surgical procedures, such operations on the spine risk infections and require hospitalization. Invasive open surgical techniques involving the spine continue to be a challenging and difficult area.

A. Use of the Implant Structures to Achieve Anterior Lumbar Interbody Fusion

Figure 63:
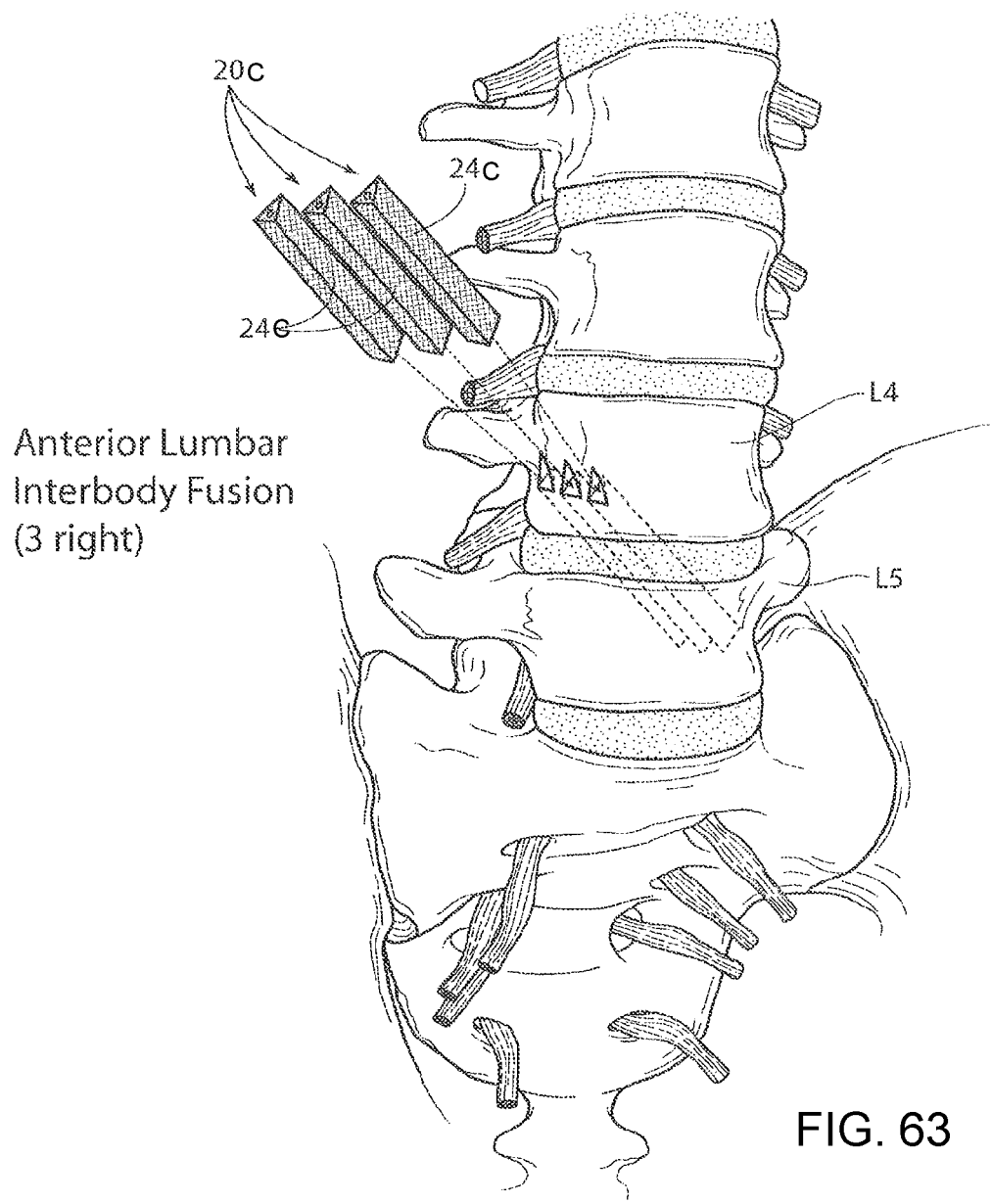
FIG. 63 is an anatomic anterior perspective view showing, in an exploded view prior to implantation, a representative configuration of an assembly of one or more implant structures as shown in FIG. 55, sized and configured to achieve anterior lumbar interbody fusion, in a non-invasive manner and without removal of the intervertebral disc.
Figure 64:
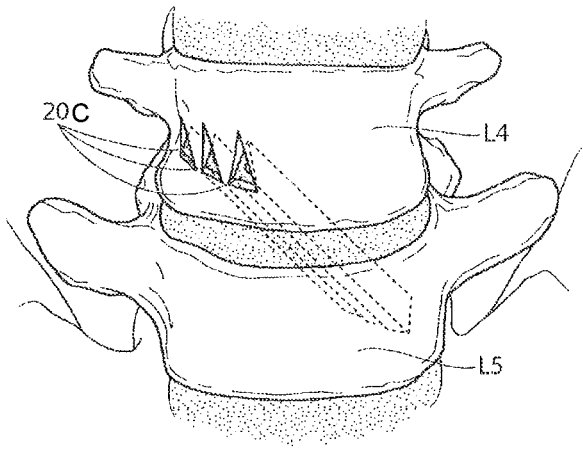
FIG. 64 is an anatomic anterior perspective view showing the assembly shown in FIG. 63 after implantation.
Figure 65:
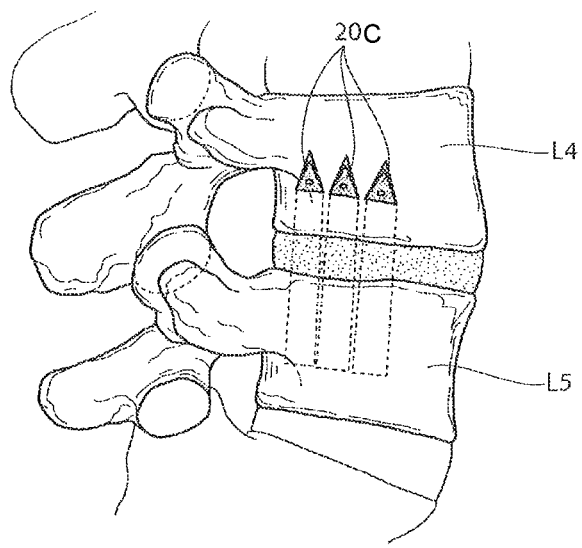
FIG. 65 is an anatomic right lateral perspective view showing the assembly shown in FIG. 63 after implantation.
Figure 66:
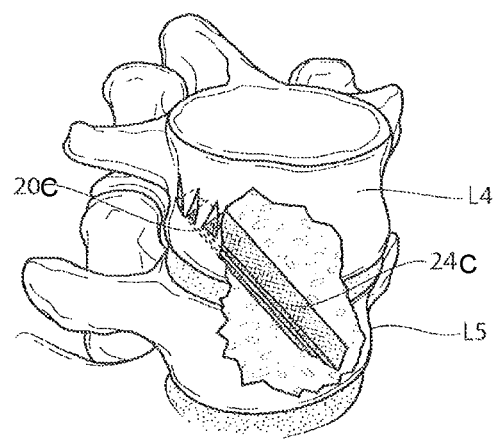
FIG. 66 is an anatomic superior left lateral perspective view showing the assembly shown in FIG. 63 after implantation.

FIG. 63 shows, in an exploded view prior to implantation, a representative configuration of an assembly of one or more implant structures 20C sized and configured to achieve anterior lumbar interbody fusion, in a non-invasive manner and without removal of the intervertebral disc. FIGS. 64 to 66 show the assembly after implantation, respectively, in an anterior view, a right lateral view, and a superior left lateral perspective view.

In the representative embodiment illustrated in FIGS. 64 to 66, the assembly comprises three implant structures 20C. It should be appreciated, however, that a given assembly can include a greater or lesser number of implant structures 20C.

In the representative embodiment shown in FIGS. 64 to 66, the three implant structures 20C are spaced in an adjacent lateral array. The implant structures 20C extend from an anterolateral region of a selected vertebral body (i.e., a lateral region anterior to a transverse process), across the intervertebral disc into an opposite anterolateral region of an adjacent caudal (inferior) vertebra. As shown in FIGS. 64 to 66, the array of implant structures 20C extends in an angled path (e.g., about 20° to about 40° off horizontal) through the cranial (superior) lumbar vertebral body (shown as L4) in an inferior direction, through the adjoining intervertebral disc, and terminates in the next adjacent caudal (inferior) lumbar vertebral body (shown as L5).

More particularly, in the representative embodiment shown in FIGS. 63 to 66, the implant structures 20C enter the right anterolateral region of vertebra L4 and terminate within the left anterolateral interior of vertebra L5, spanning the intervertebral disc between L4 and L5.

Alternatively, or in combination, an array of implant structures 20C can likewise extend between L5 and S1 in the same trans-disc formation.

The implant structures 20C are sized according to the local anatomy. The implant structures 20C can be sized differently, e.g., 3 mm, 4 mm, 6 mm, etc.), to accommodate anterolateral variations in the anatomy. The implant structures 20C can be sized for implantation in adults or children.

The intimate contact created between the bony in-growth or through-growth region 24C along the surface of the implant structure 20C accelerates bony in-growth or through-growth onto, into, or through the implant structure 20C, to accelerate trans-disc fusion between these lumbar vertebrae.

FIGS. 67A to 67G diagrammatically show, for purposes of illustration, a representative lateral (or posterolateral) procedure for implanting the assembly of implant structures 20C shown in FIGS. 64 to 66.

The physician identifies the vertebrae of the lumbar spine region that are to be fused using, e.g., the Faber Test, or CT-guided injection, or X-ray/MRI of the lumbar spine. Aided by lateral and anterior-posterior (A-P) c-arms, and with the patient lying in a prone position (on their stomach), the physician makes a 3 mm incision laterally or posterolaterally from the side (see FIG. 67A). Aided by conventional visualization techniques, e.g., using X-ray image intensifiers such as a C-arms or fluoroscopes to produce a live image feed which is displayed on a TV screen, a guide pin 38C is introduced by conventional means into L4 (see FIG. 67B) for the first, most anterolateral implant structure (closest to the right transverse process of L4), in the desired angled inferiorly-directed path through the intervertebral disc and into the interior left anterolateral region of vertebra L5.

When the guide pin 38C is placed in the desired orientation, the physician desirable slides a soft tissue protector over the guide pin 38C before proceeding further. To simplify the illustration, the soft tissue protector is not shown in the drawings.

Figure 67A:
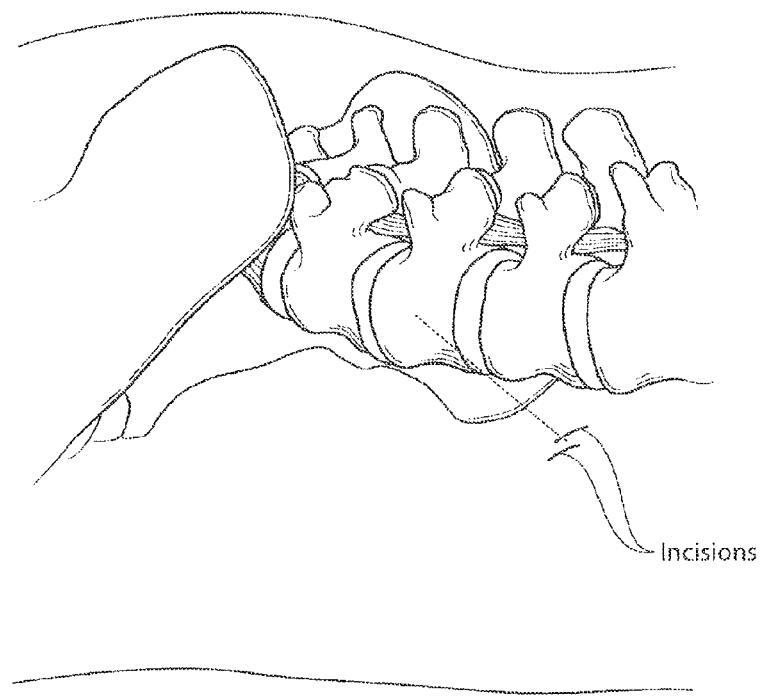
FIGS. 67A to 67G are diagrammatic views showing, for purposes of illustration, a representative lateral (or posterolateral) procedure for implanting the assembly of implant structures shown in FIGS. 64 to 66.
Figure 67B:
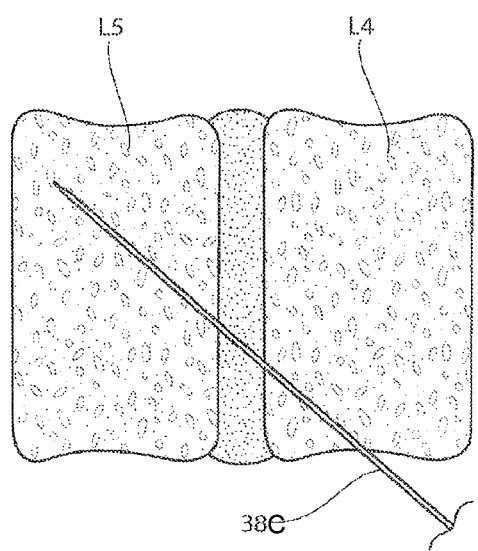
Figure 67C:
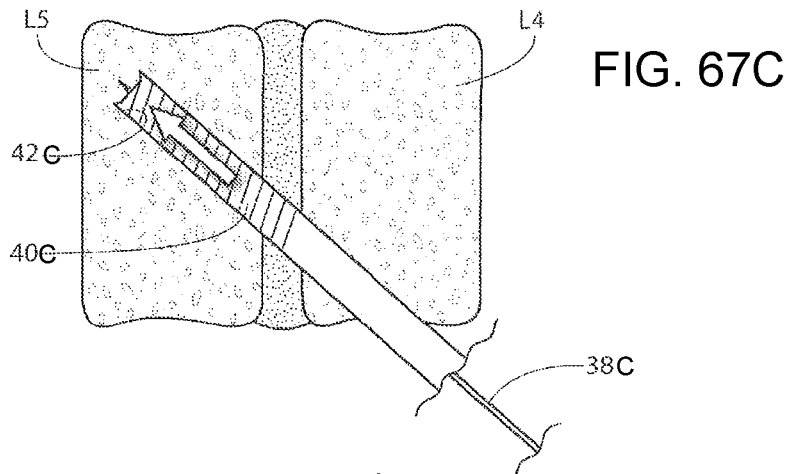
Figure 67D:
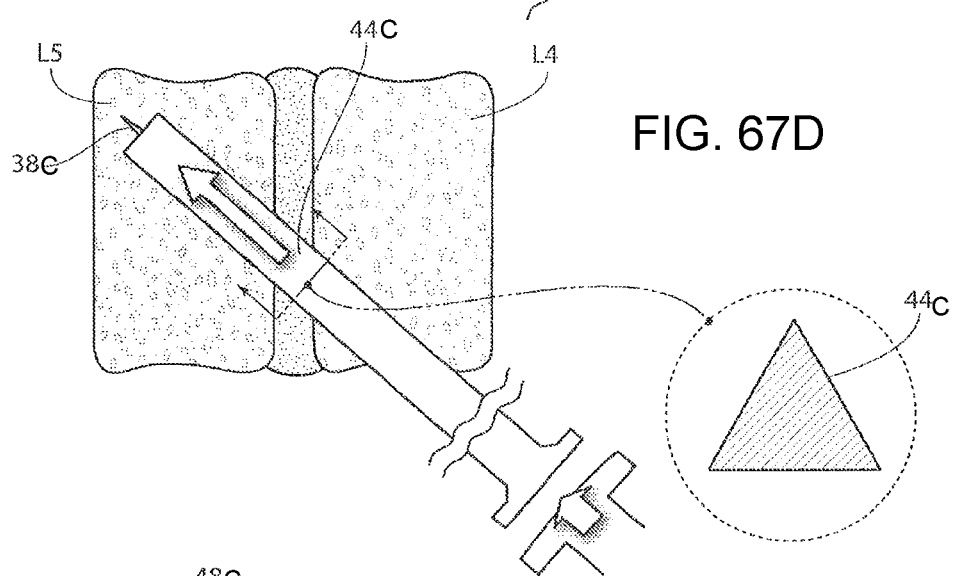
Figure 67E:
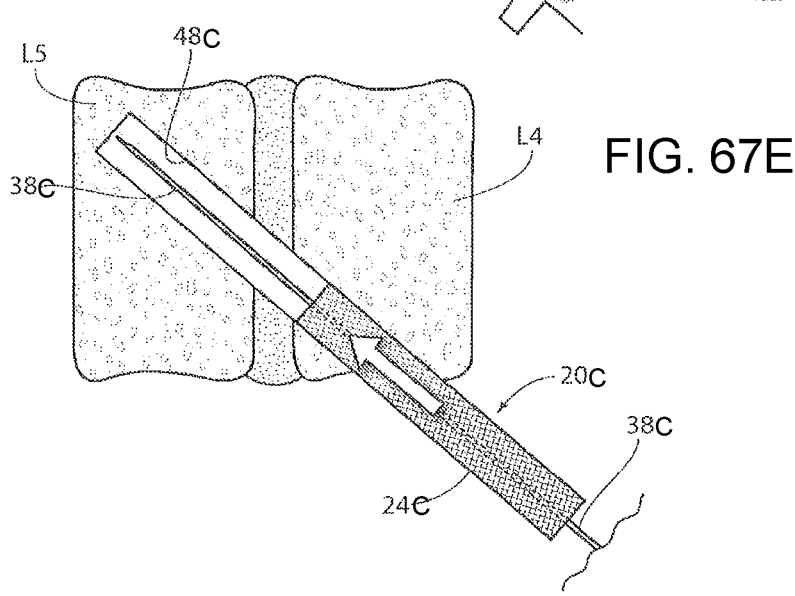

Through the soft tissue protector, a cannulated drill bit 40C is next passed over the guide pin 38C (see FIG. 67C). The cannulated drill bit 40C forms a pilot insertion path or bore 42C along the first angled path defined by the guide pin 38C. A single drill bit or multiple drill bits 40C can be employed to drill through bone fragments or bone surfaces to create a pilot bore 42C of the desired size and configuration.

When the pilot bore 42C is completed, the cannulated drill bit 40C is withdrawn over the guide pin 38C.

Through the soft tissue protector, a broach 44C having the external geometry and dimensions matching the external geometry and dimensions of the implant structure 20C (which, in the illustrated embodiment, is triangular) (see FIG. 67D) is tapped through the soft tissue protector over the guide pin 38C and into the pilot bore 42C. The shaped broach 44C cuts along the edges of the pilot bore 42C to form the desired profile (which, in the illustrated embodiment, is triangular) to accommodate the implant structure 20C.

The broach 44C is withdrawn (see FIG. 67E), and the first, most anterolateral implant structure 20C is passed over the guide pin 38C through the soft tissue protector into the broached bore 48C. The guide pin 38C and soft tissue protector are withdrawn from the first implant structure 20C.

Figure 67F:
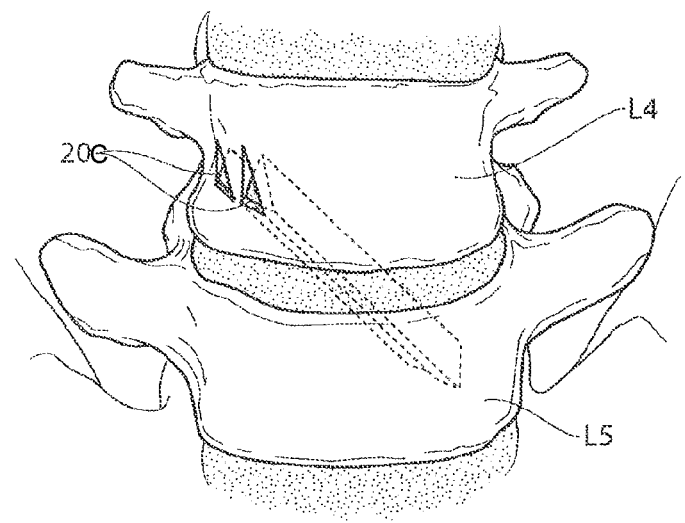
Figure 67G:
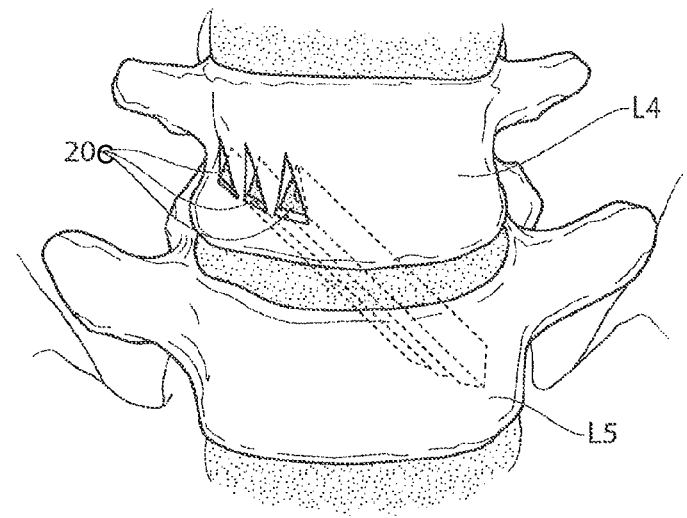

The physician repeats the above-described procedure sequentially for the next anterolateral implant structures 20C: for each implant structure, inserting the guide pin 38C, forming the pilot bore, forming the broached bore, inserting the respective implant structure, withdrawing the guide pin, and then repeating the procedure for the next implant structure, and so on until all implant structures 20C are placed (as FIGS. 67F and 67G indicate). The incision site(s) are closed.

In summary, the method for implanting the assembly of the implant structures 20C comprises (i) identifying the bone structures to be fused and/or stabilized; (ii) opening an incision; (iii) using a guide pin to established a desired implantation path through bone for the implant structure 20C; (iv) guided by the guide pin, increasing the cross section of the path; (v) guided by the guide pin, shaping the cross section of the path to correspond with the cross section of the implant structure 20C; (vi) inserting the implant structure 20C through the path over the guide pin; (vii) withdrawing the guide pin; (viii) repeating, as necessary, the procedure sequentially for the next implant structure(s) until all implant structures 20C contemplated are implanted; and (ix) closing the incision.

Figure 68:
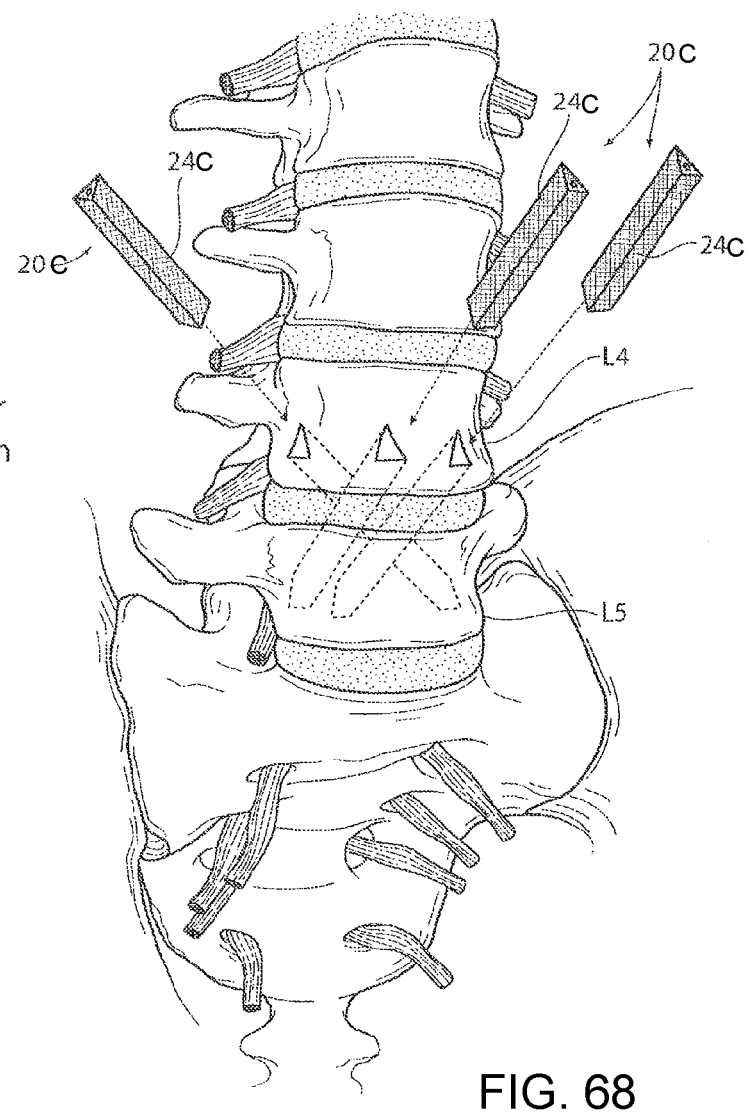
FIG. 68 is an anatomic anterior perspective view showing, in an exploded view prior to implantation, assemblies comprising one or more implant structures like that shown in FIG. 55 inserted from left and/or right anterolateral regions of a given lumbar vertebra, in an angled path through the intervertebral disc and into an opposite anterolateral interior region of the next inferior lumbar vertebra, FIG. 68 showing in particular two implant structures entering on the right anterolateral side of L4, through the intervertebral disc and into the left anterolateral region of L5, and one implant structure entering on the left anterolateral side of L4, through the intervertebral disc and into the right anterolateral region of L5, the left and right implant structures crossing each other in transit through the intervertebral disc.
Figure 69:
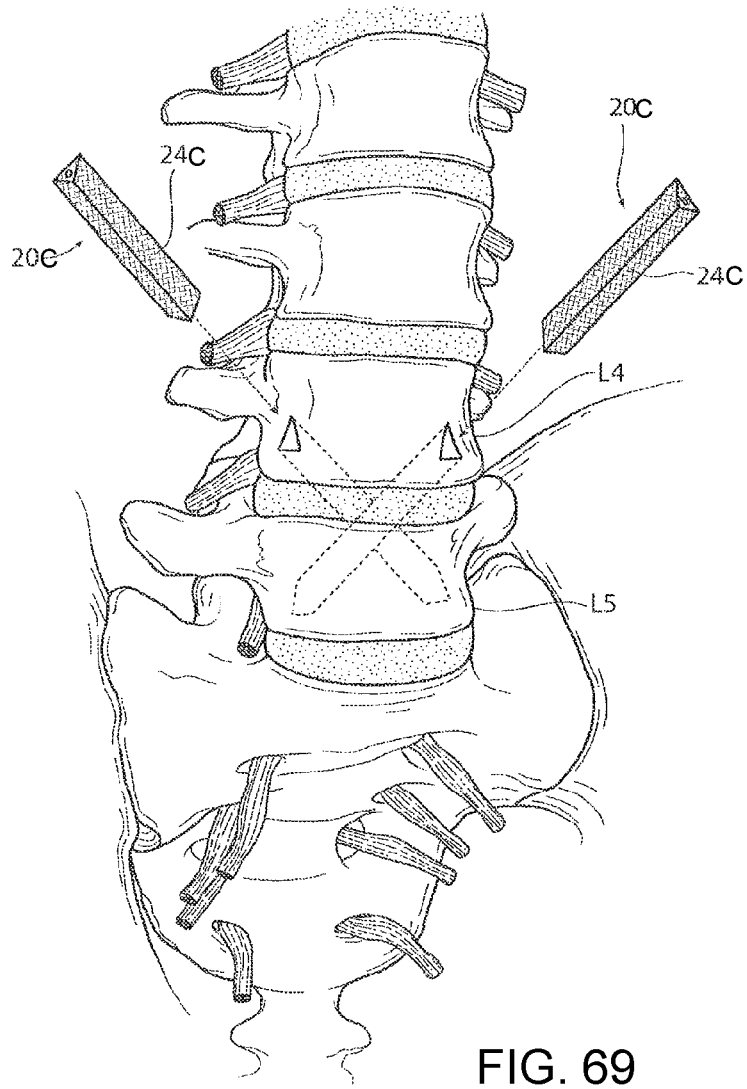
FIG. 69 is an anatomic anterior perspective view showing, in an exploded view prior to implantation, assemblies comprising one or more implant structures like that shown in FIG. 55 inserted from left and/or right anterolateral regions of a given lumbar vertebra, in an angled path through the intervertebral disc and into an opposite anterolateral interior region of the next inferior lumbar vertebra, FIG. 69 showing in particular one implant structure entering on the right anterolateral side of L4, through the intervertebral disc and into the left anterolateral region of L5, and one implant structure entering on the left anterolateral side of L4, through the intervertebral disc and into the right anterolateral region of L5, the left and right implant structures crossing each other in transit through the intervertebral disc.

As FIGS. 68 and 69 show, assemblies comprising one or more implant structures 20C can be inserted from left and/or right anterolateral regions of a given lumbar vertebra, in an angled path through the intervertebral disc and into an opposite anterolateral interior region of the next inferior lumbar vertebra.

For purposes of illustration, FIG. 68 shows two implant structures 20C entering on the right anterolateral side of L4, through the intervertebral disc and into the left anterolateral region of L5, and one implant structure 20C entering on the left anterolateral side of L4, through the intervertebral disc and into the right anterolateral region of L5. In this arrangement, the left and right implant structures 20C cross each other in transit through the intervertebral disc.

As another illustration of a representative embodiment, FIG. 69 shows one implant structure 20C entering on the right anterolateral side of L4, through the intervertebral disc and into the left anterolateral region of L5, and one implant structure 20C entering on the left anterolateral side of L4, through the intervertebral disc and into the right anterolateral region of L5. In this arrangement as well, the left and right implant structures 20C cross each other in transit through the intervertebral disc.

B. Use of Implant Structures to Achieve Translaminal Lumbar Fusion (Posterior Approach)

Figure 70:
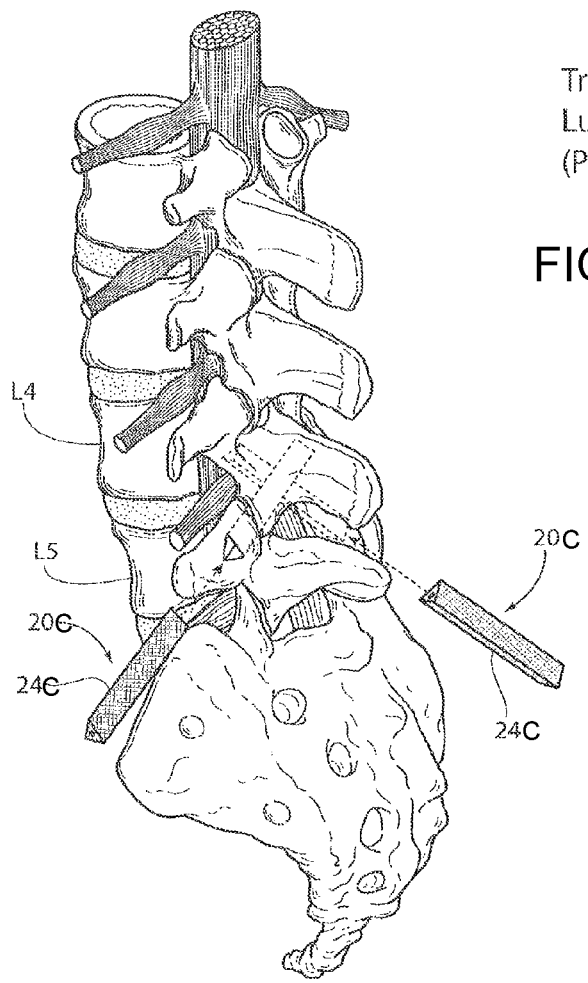
FIG. 70 is an anatomic posterior perspective view, exploded prior to implantation, of a representative configuration of an assembly of one or more implant structures like that shown in FIG. 55, sized and configured to achieve translaminar lumbar fusion in a non-invasive manner and without removal of the intervertebral disc.
Figure 71:
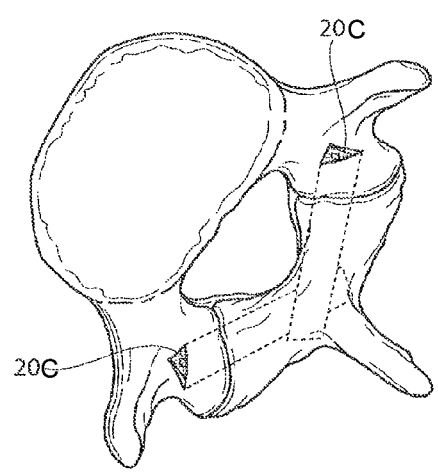
FIG. 71 is an anatomic inferior transverse plane view showing the assembly shown in FIG. 70 after implantation.

FIG. 70 shows, in an exploded view prior to implantation, a representative configuration of an assembly of one or more implant structures 20C sized and configured to achieve translaminal lumbar fusion in a non-invasive manner and without removal of the intervertebral disc. FIG. 71 shows the assembly after implantation, respectively, in an inferior transverse plane view.

As can be seen in the representative embodiment illustrated in FIGS. 70 and 71, the assembly comprises two implant structures 20C. The first implant structure 20C extends from the left superior articular process of vertebra L5, through the adjoining facet capsule into the left inferior articular process of vertebra L4, and, from there, further through the lamina of vertebra L4 into an interior right posterolateral region of vertebra L4 adjacent the spinous process. The second implant structure 20C extends from the right superior articular process of vertebra L5, through the adjoining facet capsule into the right inferior articular process of vertebra L4, and, from there, further through the lamina of vertebra L4 into an interior left posterolateral region of vertebra L4 adjacent the spinous process. The first and second implant structures 20C cross each other within the medial lamina of vertebra L4.

The first and second implant structures 20C are sized and configured according to the local anatomy. The selection of a translaminal lumbar fusion (posterior approach) is indicated when the facet joints are aligned with the sagittal plane. Removal of the intervertebral disc is not required, unless the condition of the disc warrants its removal.

A procedure incorporating the technical features of the procedure shown in FIGS. 67A to 67G can be tailored to a posterior procedure for implanting the assembly of implant structures 20C shown in FIGS. 70 and 71. The method comprises (i) identifying the vertebrae of the lumbar spine region that are to be fused; (ii) opening an incision, which comprises, e.g., with the patient lying in a prone position (on their stomach), making a 3 mm posterior incision; and (iii) using a guide pin to established a desired implantation path through bone for the first (e.g., left side) implant structure 20C, which, in FIGS. 70 and 71, traverses through the left superior articular process of vertebra L5, through the adjoining facet capsule into the left inferior articular process of vertebra L4, and then through the lamina of vertebra L4 into an interior right posterolateral region of vertebra L4 adjacent the spinous process. The method further includes (iv) guided by the guide pin, increasing the cross section of the path; (v) guided by the guide pin, shaping the cross section of the path to correspond with the cross section of the implant structure; (vi) inserting the implant structure 20C through the path over the guide pin; (vii) withdrawing the guide pin; and (viii) using a guide pin to established a desired implantation path through bone for the second (e.g., right side) implant structure 20C, which, in FIGS. 70 and 71, traverses through the right superior articular process of vertebra L5, through the adjoining facet capsule into the right inferior articular process of vertebra L4, and through the lamina of vertebra L4 into an interior left posterolateral region of vertebra L4 adjacent the spinous process. The physician repeats the remainder of the above-described procedure sequentially for the right implant structure 20C as for the left, and, after withdrawing the guide pin, closes the incision.

The intimate contact created between the bony in-growth or through-growth region 24C along the surface of the implant structure 20C across the facet joint accelerates bony in-growth or through-growth onto, into, or through the implant structure 20C, to accelerate fusion of the facets joints between L4 and L5. Of course, translaminar lumbar fusion between L5 and S1 can be achieved using first and second implant structures in the same manner.

C. Use of Implant Structures to Achieve Lumbar Facet Fusion (Posterior Approach)

Figure 72:
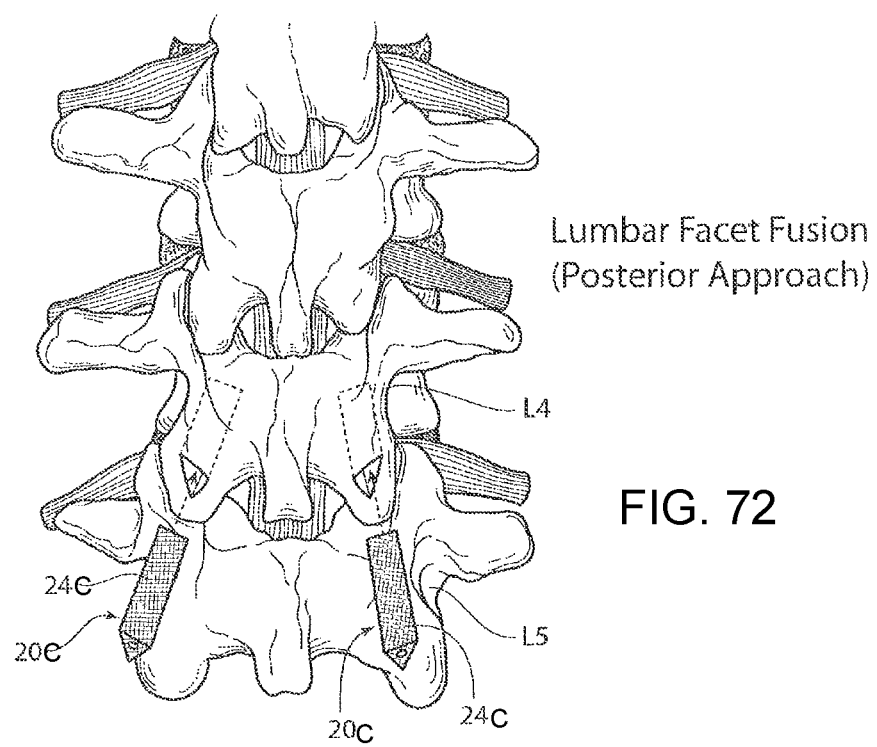
FIG. 72 is an anatomic posterior perspective view, exploded prior to implantation, of a representative configuration of an assembly of one or more implant structures like that shown in FIG. 55, sized and configured to achieve lumbar facet fusion, in a non-invasive manner and without removal of the intervertebral disc.
Figure 73:
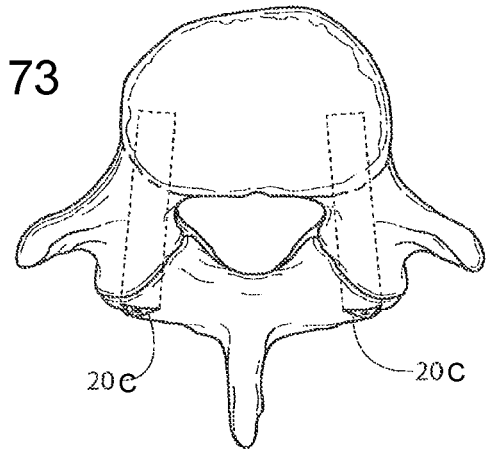
FIG. 73 is an anatomic inferior transverse plane view showing the assembly shown in FIG. 72 after implantation.
Figure 74:
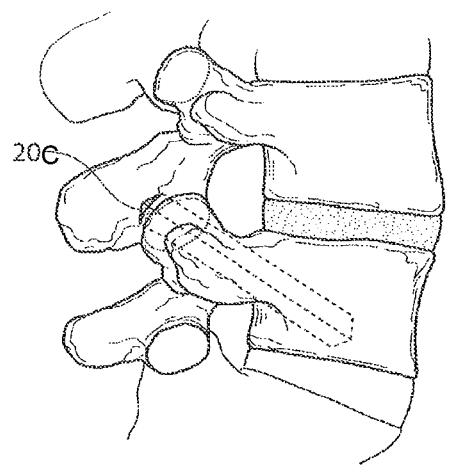
FIG. 74 is an anatomic lateral view showing the assembly shown in FIG. 72 after implantation.

FIG. 72 shows, in an exploded view prior to implantation, a representative configuration of an assembly of one or more implant structures 20C sized and configured to lumbar facet fusion, in a non-invasive manner and without removal of the intervertebral disc. FIGS. 73 and 74 show the assembly after implantation, respectively, in an inferior transverse plane view and a lateral view.

As can be seen in the representative embodiment illustrated in FIGS. 72 and 74, the assembly comprises two implant structures 20C. The first implant structure 20C extends from the left inferior articular process of vertebra L4, through the adjoining facet capsule into the left superior articular process of vertebra L5 and into the pedicle of vertebra L5. The second implant structure 20C extends from the right inferior articular process of vertebra L5, through the adjoining facet capsule into the right superior articular process of vertebra L5 and into the pedicle of vertebra L5. In this arrangement, the first and second implant structures 20C extend in parallel directions on the left and right pedicles of vertebra L5. The first and second implant structures 20C are sized and configured according to the local anatomy. The selection of lumbar facet fusion (posterior approach) is indicated when the facet joints are coronally angled. Removal of the intervertebral disc is not necessary, unless the condition of the disc warrants its removal.

A procedure incorporating the technical features of the procedure shown in FIGS. 67A to 67G can be tailored to a posterior procedure for implanting the assembly of implant structures 20C shown in FIGS. 72 to 74. The method comprises (i) identifying the vertebrae of the lumbar spine region that are to be fused; (ii) opening an incision, which comprises, e.g., with the patient lying in a prone position (on their stomach), making a 3 mm posterior incision; and (iii) using a guide pin to established a desired implantation path through bone for the first (e.g., left side) implant structure 20C, which, in FIGS. 72 to 74, traverses through the left inferior articular process of vertebra L4, through the adjoining facet capsule into the left superior articular process of vertebra L5 and into the pedicle of vertebra L5. The method further includes (iv) guided by the guide pin, increasing the cross section of the path; (v) guided by the guide pin, shaping the cross section of the path to correspond with the cross section of the implant structure 20; (vi) inserting the implant structure 20C through the path over the guide pin; (vii) withdrawing the guide pin; and (viii) using a guide pin to established a desired implantation path through bone for the second (e.g., right side) implant structure 20C, which, in FIGS. 72 to 74, traverses through the right inferior articular process of vertebra L5, through the adjoining facet capsule into the right superior articular process of vertebra L5 and into the pedicle of vertebra L5. The physician repeats the remainder of the above-described procedure sequentially for the right implant structure 20C as for the left and, withdrawing the guide pin, closes the incision.

The intimate contact created between the bony in-growth or through-growth region 24C along the surface of the implant structure 20C across the facet joint accelerates bony in-growth or through-growth onto, into, or through the implant structure 20C, to accelerate fusion of the facets joints between L4 and L5.

Of course, translaminar lumbar fusion between L5 and S1 can be achieved using first and second implant structures in the same manner.

D. Use of Implant Structures to Achieve Trans-Iliac Lumbar Fusion (Anterior Approach)

Figure 75A:
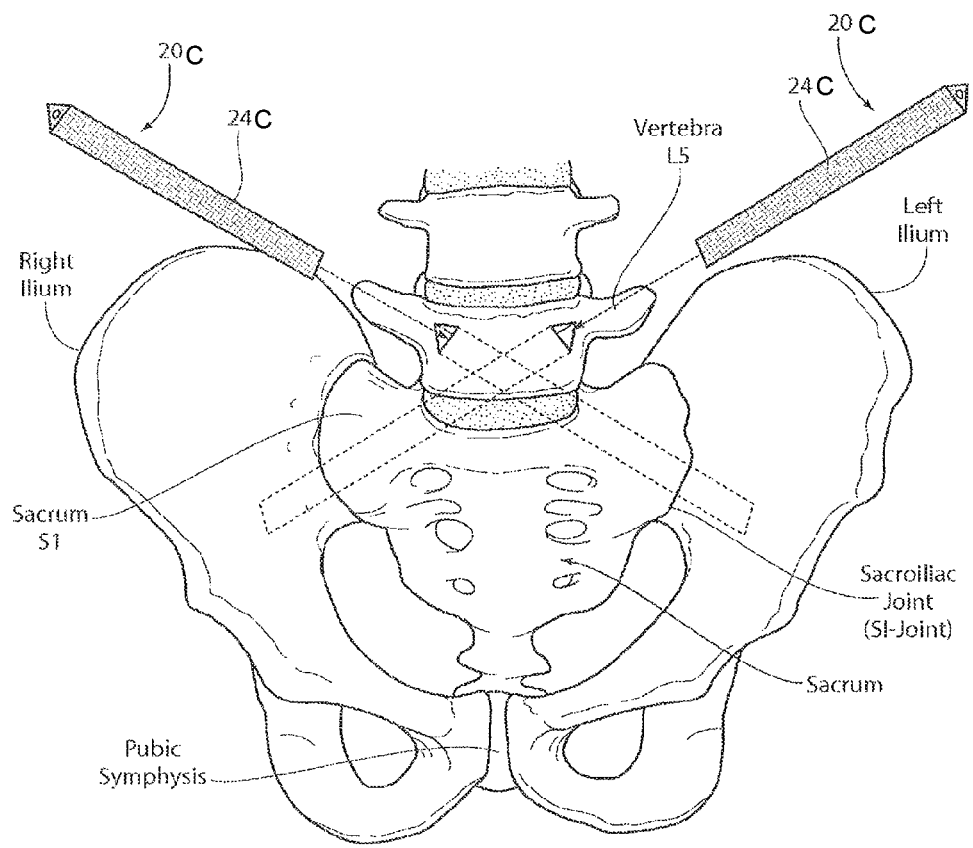
FIG. 75A is an anatomic anterior perspective view showing, in an exploded view prior to implantation, a representative configuration of an assembly of one or more implant structures like that shown in FIG. 55, sized and configured to achieve fusion between lumbar vertebra L5 and sacral vertebra S1, in a non-invasive manner and without removal of the intervertebral disc, using an anterior approach.
Figure 75B:
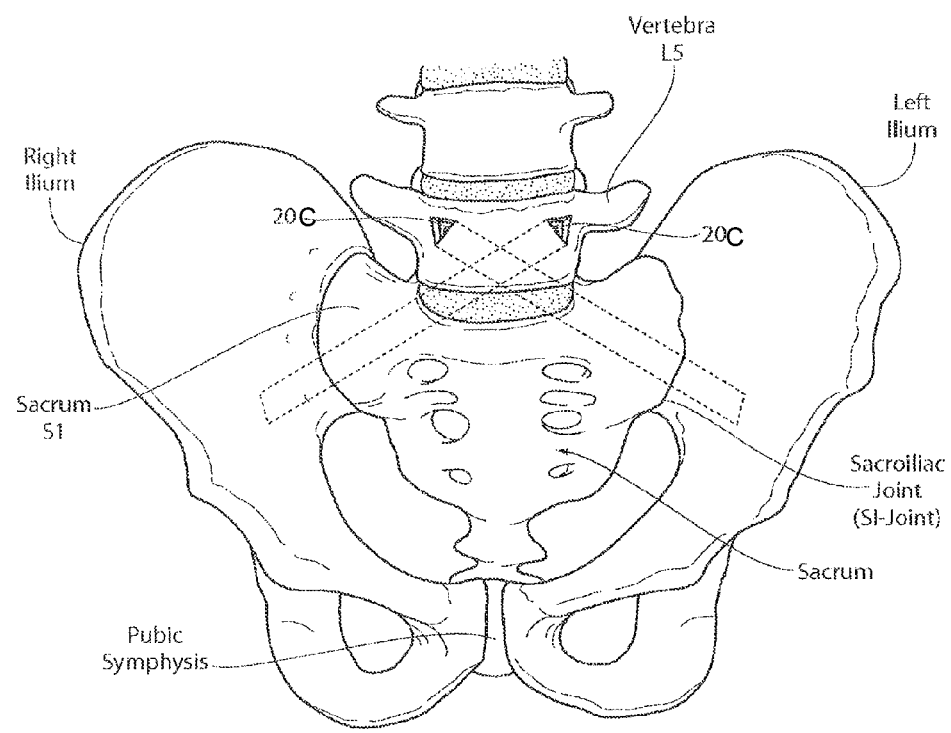
FIG. 75B is an anatomic anterior perspective view showing the assembly shown in FIG. 75A after implantation.

FIG. 75A shows, in an exploded view prior to implantation, a representative configuration of an assembly of one or more implant structures 20C sized and configured to achieve fusion between lumbar vertebra L5 and sacral vertebra S1, in a non-invasive manner and without removal of the intervertebral disc. FIG. 75B shows the assembly after implantation.

In the representative embodiment illustrated in FIGS. 75A and 75B, the assembly comprises two implant structures 20C. It should be appreciated, however, that a given assembly can include a greater or lesser number of implant structures 20C.

As FIGS. 75A and 75B show, the assembly comprises two implant structures 20C inserted from left and right anterolateral regions of lumbar vertebra L5, in an angled path (e.g., about 20.degree. to about 40.degree. off horizontal) through the intervertebral disc in an inferior direction, into and through opposite anterolateral interior regions of sacral vertebra S1, through the sacro-iliac joint, and terminating in the ilium. In this arrangement, the left and right implant structures 20C cross each other in transit through the intervertebral disc. As before described, the implant structures 20C are sized according to the local anatomy.

The intimate contact created between the bony in-growth or through-growth region 24C along the surface of the implant structure 20C accelerates bony in-growth or through-growth onto, into, or through the implant structure 20C, to accelerate lumbar trans-iliac fusion between vertebra L5 and S1.

A physician can employ the lateral (or posterolateral) procedure as generally shown in FIGS. 67A to 67G for implanting the assembly of implant structures 20C shown in FIGS. 75A and 75B, including forming a pilot bore over a guide pin inserted in the angled path, forming a broached bore, inserting the right implant 20C structure, withdrawing the guide pin, and repeating for the left implant structure 20C, or vice versa. The incision site(s) are closed.

The assembly as described makes possible the achievement of trans-iliac lumbar fusion using an anterior in a non-invasive manner, with minimal incision, and without necessarily removing the intervertebral disc between L5 and S1.

E. Use of Implant Structures to Achieve Trans-Iliac Lumbar Fusion (Postero-Lateral Approach from Posterior Iliac Spine)

Figure 76A:
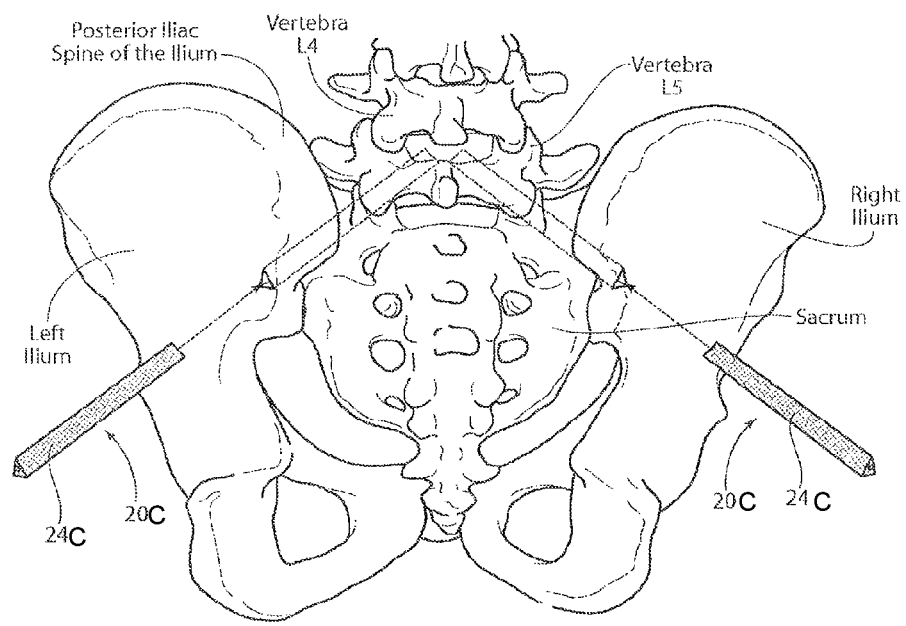
FIG. 76A is an anatomic posterior view showing, in an exploded view prior to implantation, another representative configuration of an assembly of one or more implant structures 20C sized and configured to achieve fusion between lumbar vertebra L5 and sacral vertebra S1, in a non-invasive manner and without removal of the intervertebral disc, using a postero-lateral approach entering from the posterior iliac spine of the ilium, angling through the SI-Joint, and terminating in the lumbar vertebra L5.
Figure 76B:
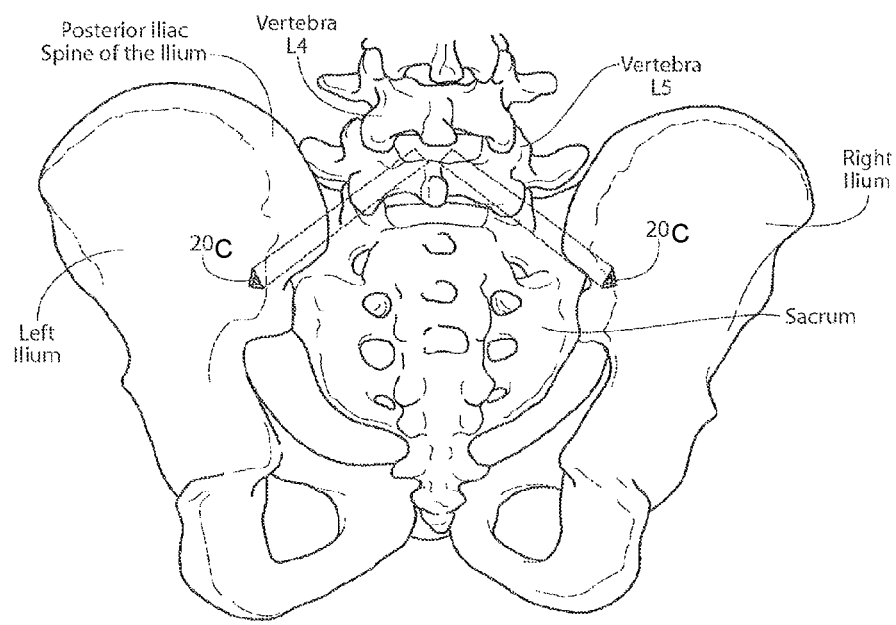
FIG. 76B is an anatomic posterior view showing the assembly shown in FIG. 76A after implantation.
Figure 76C:
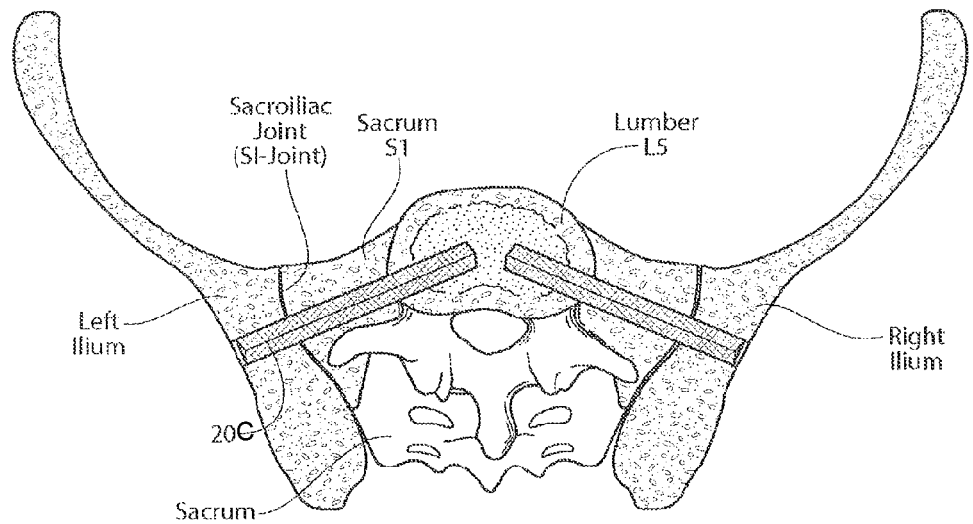
FIG. 76C is an anatomic superior view showing the assembly shown in FIG. 76B.

FIG. 76A shows, in an exploded view prior to implantation, another representative configuration of an assembly of one or more implant structures 20C sized and configured to achieve fusion between lumbar vertebra L5 and sacral vertebra S1, in a non-invasive manner and without removal of the intervertebral disc. FIGS. 76B and 76C show the assembly after implantation.

As FIGS. 76A and 76B show, the one or more implant structures are introduced in a postero-lateral approach entering from the posterior iliac spine of the ilium, angling through the SI-Joint into and through the sacral vertebra S1, and terminating in the lumbar vertebra L5. This path and resulting placement of the implant structures 20C are also shown in FIG. 76C. In the illustrated embodiment, two implant structures 20C are placed in this manner, but there can be more or fewer implant structures 20C. Also in the illustrated embodiment, the implant structures 20C are triangular in cross section, but it should be appreciated that implant structures 20C of other cross sections as previously described can be used.

The postero-lateral approach involves less soft tissue disruption that the lateral approach, because there is less soft tissue overlying the entry point of the posterior iliac spine of the ilium. Introduction of the implant structure 20C from this region therefore makes possible a smaller, more mobile incision.

The set-up for a postero-lateral approach is generally the same as for a lateral approach. It desirably involves the identification of the lumbar region that is to be fixated or fused (arthrodesed) using, e.g., the Faber Test, or CT-guided injection, or X-ray/MRI of SI Joint. It is desirable performed with the patient lying in a prone position (on their stomach) and is aided by lateral and anterior-posterior (A-P) c-arms. The same surgical tools are used to form the pilot bore over a guide pin (e.g., on the right side), except the path of the pilot bore now starts from the posterior iliac spine of the ilium, angles through the SI-Joint, and terminates in the lumbar vertebra L5. The broached bore is formed, and the right implant 20C structure is inserted. The guide pin is withdrawn, and the procedure is repeated for the left implant structure 20C, or vice versa. The incision site(s) are closed.

The assembly as described makes possible the achievement of trans-iliac lumbar fusion using a postero-lateral approach in a non-invasive manner, with minimal incision, and without necessarily removing the intervertebral disc between L5 and S1.

F. Use of Implant Structures to Stabilize a Spondylolisthesis

Figure 77:
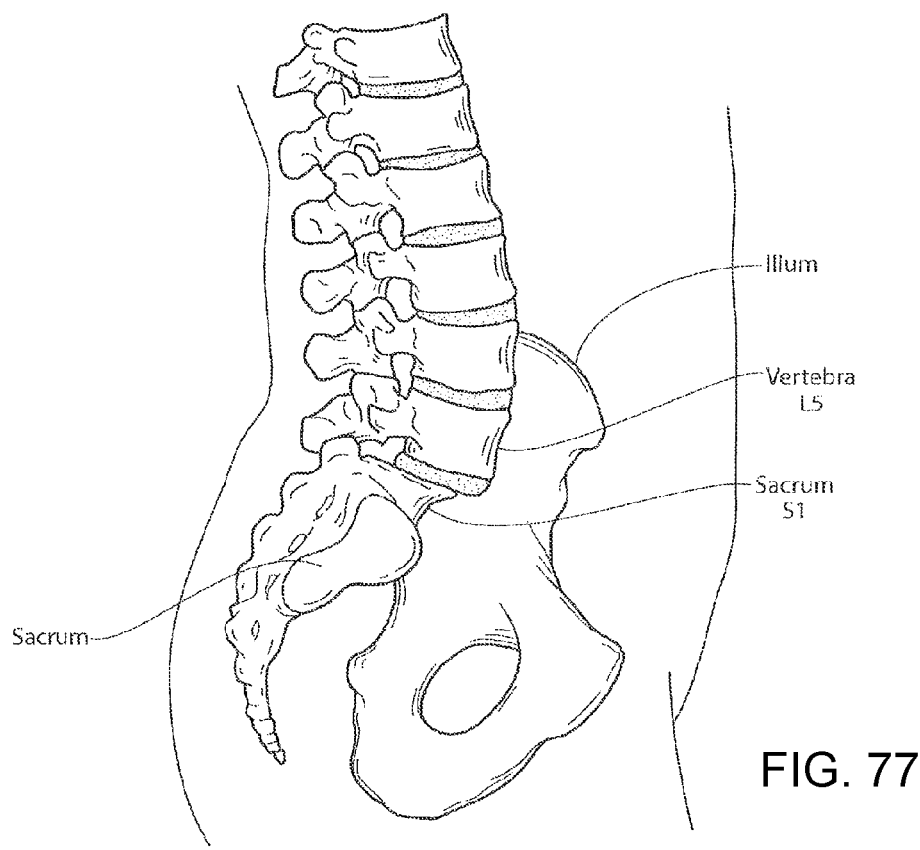
FIG. 77 is an anatomic lateral view showing a spondylolisthesis at the L5/S1 articulation, in which the lumbar vertebra L5 is displaced forward (anterior) of the sacral vertebra S1.

FIG. 77 shows a spondylolisthesis at the L5/S1 articulation, in which the lumbar vertebra L5 is displaced forward (anterior) of the sacral vertebra S1. As FIG. 77 shows, the posterior fragment of L5 remains in normal relation to the sacrum, but the anterior fragment and the L5 vertebral body has moved anteriorly. Spondylolisthesis at the L5/S1 articulation can result in pressure in the spinal nerves of the cauda equine as they pass into the superior part of the sacrum, causing back and lower limb pain.

Figure 78A:
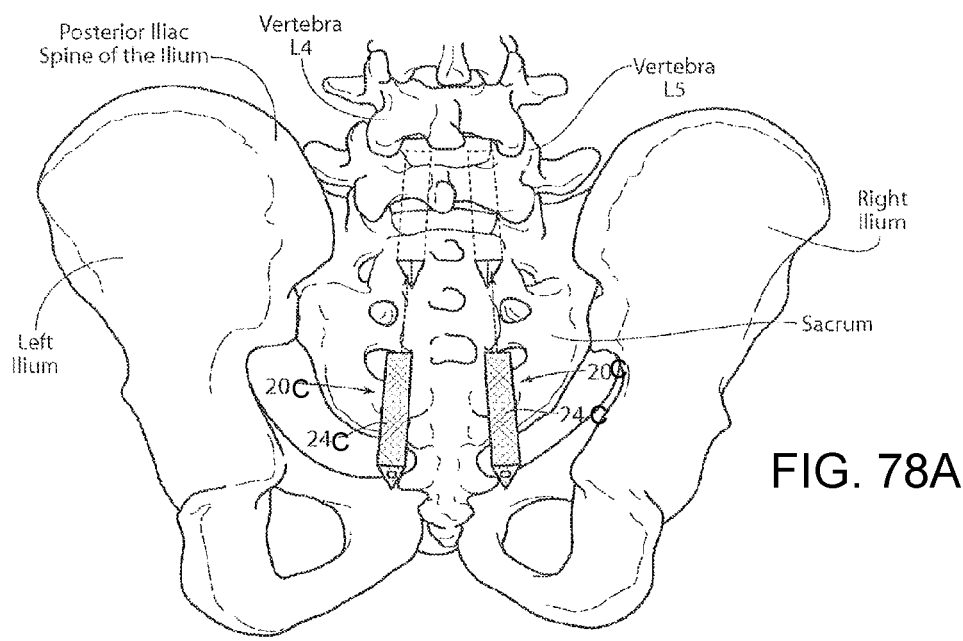
FIG. 78A is an anatomic anterior perspective view showing, in an exploded view prior to implantation, a representative configuration of an assembly of one or more implant structures like that shown in FIG. 55, sized and configured to stabilize a spondylolisthesis at the L5/S1 articulation.
Figure 78B:
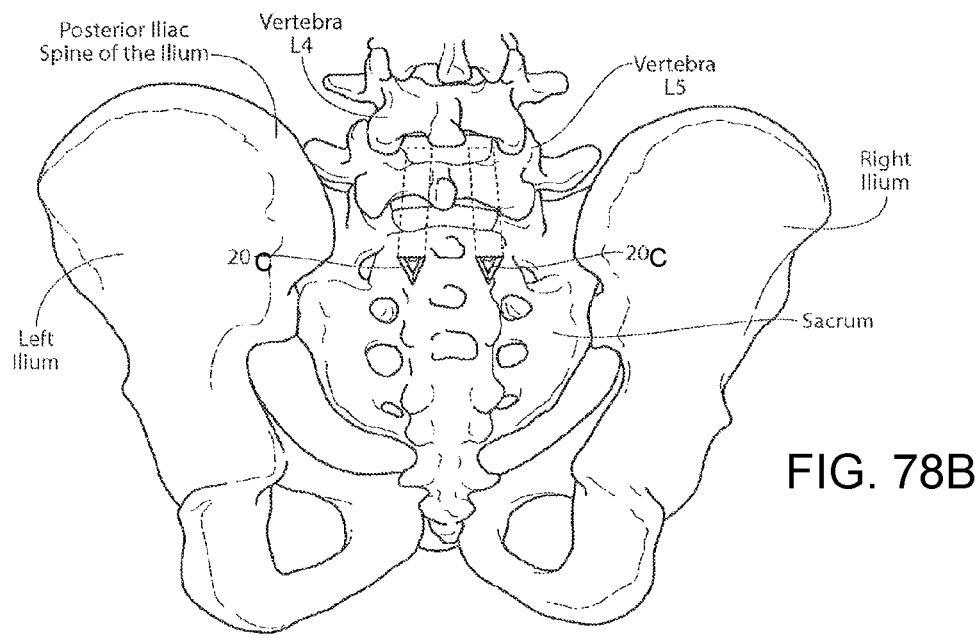
FIG. 78B is an anatomic anterior perspective view showing the assembly shown in FIG. 78A after implantation.
Figure 78C:
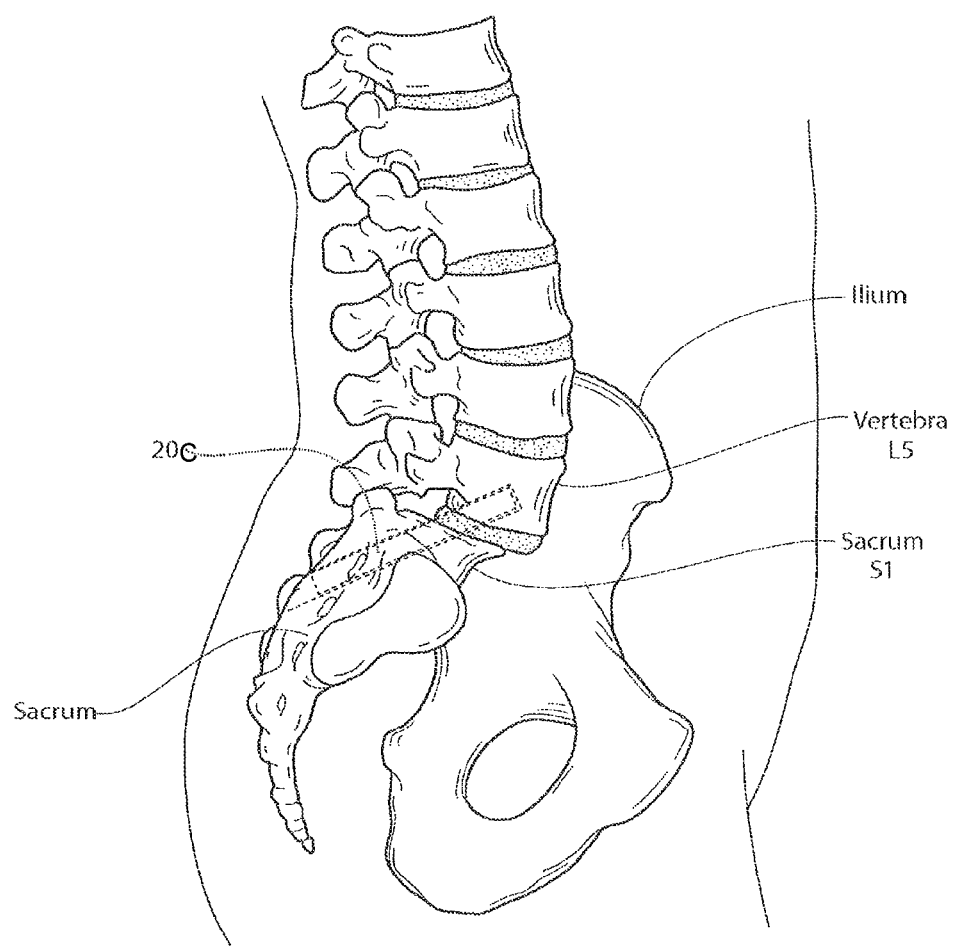
FIG. 78C is an anatomic lateral view showing the assembly shown in FIG. 78B.

FIG. 78A shows, in an exploded view prior to implantation, a representative configuration of an assembly of one or more implant structures 20C sized and configured to stabilize the spondylolisthesis at the L5/S1 articulation. FIGS. 78B and 78C show the assembly after implantation.

As shown, the implant structure 20C extends from a posterolateral region of the sacral vertebra S1, across the intervertebral disc into an opposite anterolateral region of the lumbar vertebra L5. The implant structure 20C extends in an angled path (e.g., about 20.degree. to about 40.degree. off horizontal) through the sacral vertebra S1 in a superior direction, through the adjoining intervertebral disc, and terminates in the lumbar vertebra L5.

A physician can employ a posterior approach for implanting the implant structure 20C shown in FIGS. 78A, 78B, and 78C, which includes forming a pilot bore over a guide pin inserted in the angled path from the posterior of the sacral vertebra S1 through the intervertebral disc and into an opposite anterolateral region of the lumbar vertebra L5, forming a broached bore, inserting the implant structure 20C, and withdrawing the guide pin. The incision site is then closed. As previously described, more than one implant structure 20C can be placed in the same manner to stabilize a spondylolisthesis. Furthermore, a physician can fixate the implant structure(s) 20C using the anterior trans-iliac lumbar path, as shown in FIG. 75A/B or 76A/B/C.

The physician can, if desired, combine stabilization of the spondylolisthesis, as shown in FIG. 78A/B/C, with a reduction, realigning L5 and S-1. The physician can also, if desired, combine stabilization of the spondylolisthesis, as shown in FIG. 78A/B/C (with or without reduction of the spondylolisthesis), with a lumbar facet fusion, as shown in FIGS. 72 to 74. The physician can also, if desired, combine stabilization of the spondylolisthesis, as shown in FIG. 78A/B/C, with a decompression, e.g., by the posterior removal of the spinous process and laminae bilaterally.

Removal of Implant

In some situations, it may be desirable to remove the implant structure 20C from the patient after implantation. However, bone ingrowth over time into the bony in-growth region 24C of the implant 20C can make removal difficult and require the separation of the implant structure 20C from the bone. In some embodiments, osteotomes can be used to chisel and cut out the implant structure 20C from the bone.

Figure 79A:
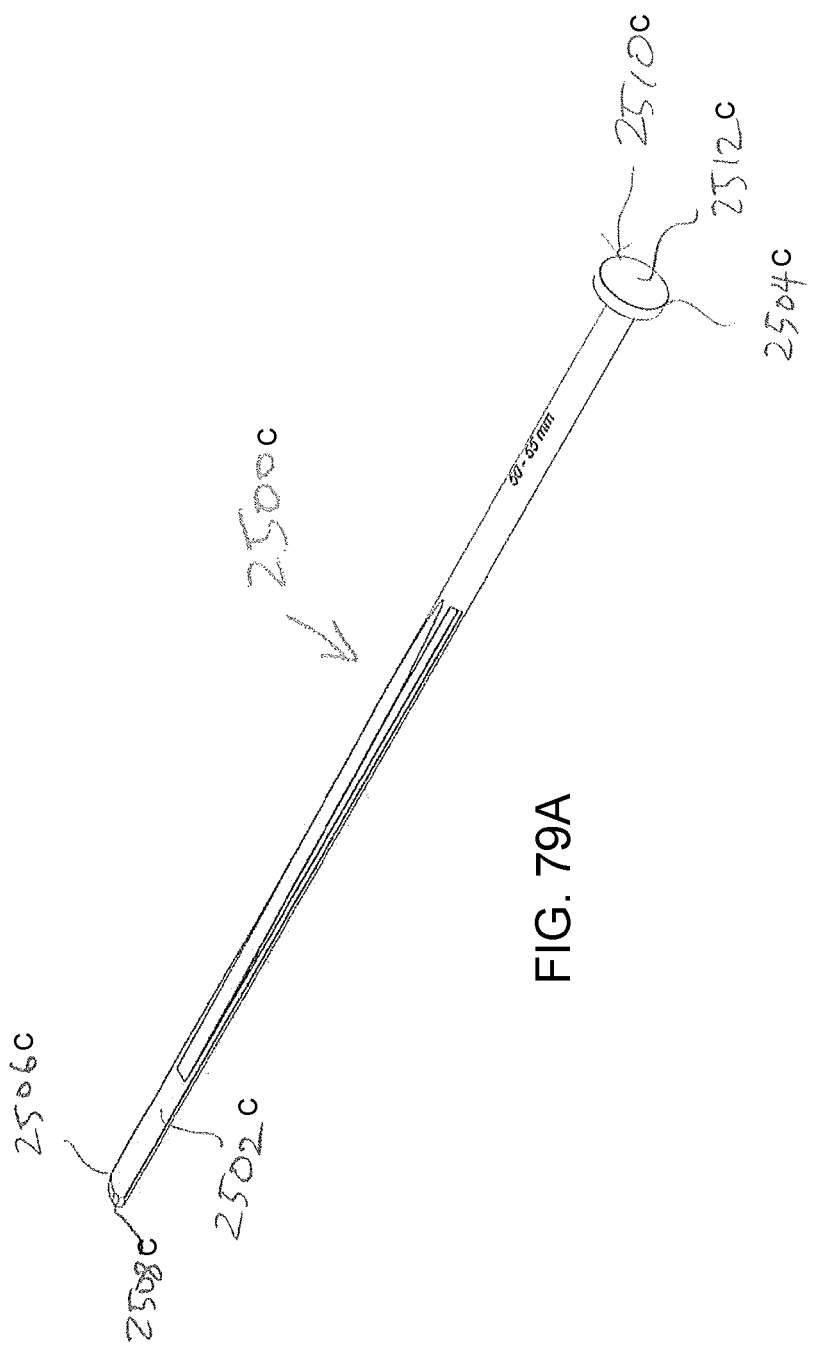
FIGS. 79A-79N illustrate an embodiment of a single bladed removal system.
Figure 79B:
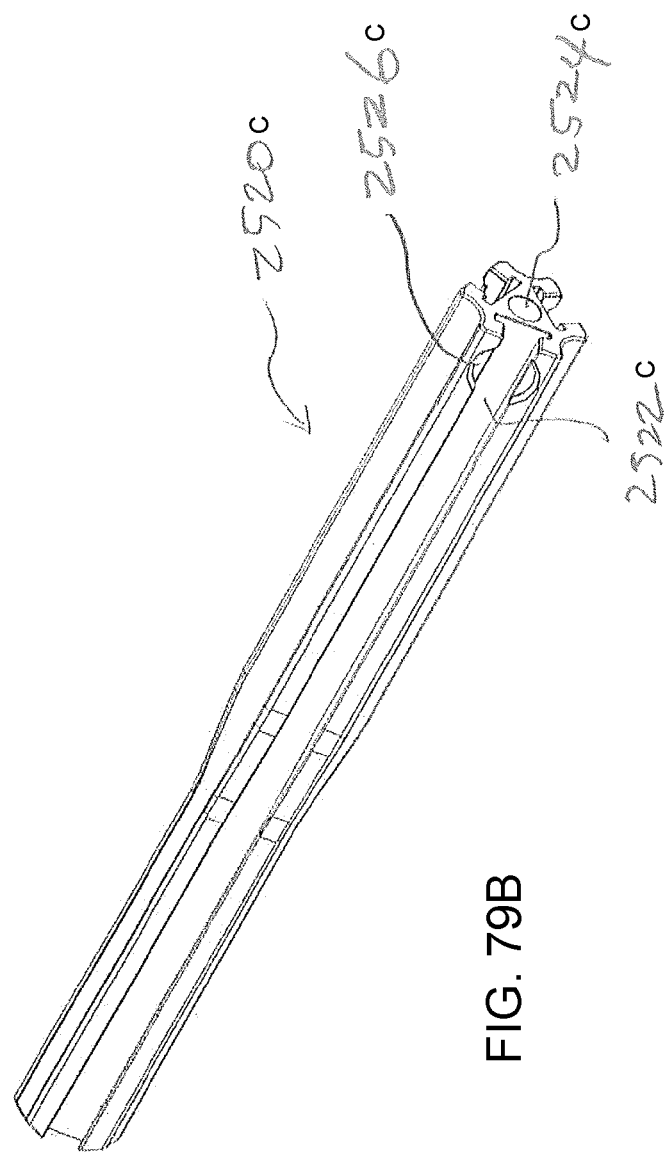
Figure 79C:
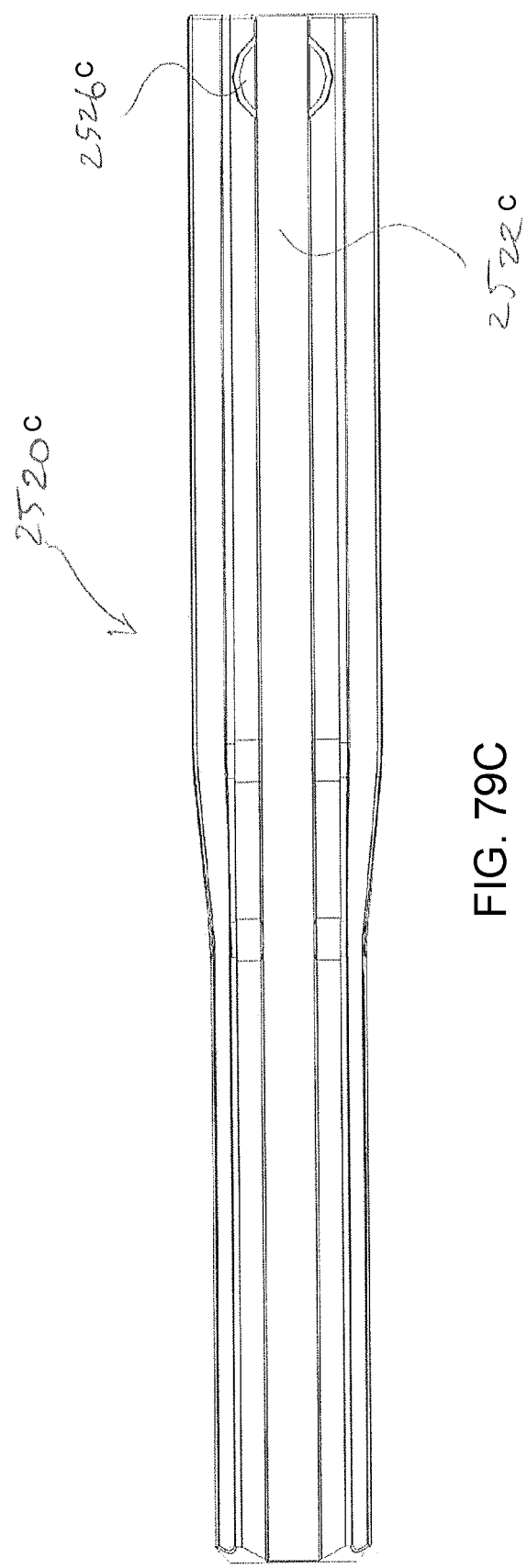

FIGS. 79A-79C illustrate an embodiment of an implant removal system that is based on a single bladed osteotome 2500C for removing an implant structure 20C from bone. As illustrated in FIG. 79A, the single bladed osteotome 2500C can have a flat, elongate body 2502C with a proximal end 2504C and a distal end 2506C. The distal end 2506C can terminate in a blade portion 2508C having a sharp edge, like a chisel, for cutting bone. In some embodiments, the blade portion 2508C can be oriented at an angle that is substantially perpendicular to the longitudinal axis of the elongate body 2502C. In other embodiments, the blade portion 2508C can be oriented at an oblique angle with respect to the longitudinal axis of the elongate body 2502C. In some embodiments, the blade portion 2508C has a straight edge or a curved edge. In some embodiments, the blade portion 2508C U-shaped. In some embodiments, the blade portion 2508C has a width equal to that of one of the faces or sides of the rectilinear implant structure 20C. In other embodiments, the width of the blade portion 2508C can be slightly less than or slightly greater than the width of one of the faces or sides of the implant structure 20C. Slightly less can mean up to 5, 10, 15, or 20% less, and slightly more can mean up to 5, 10, 15 or 20% more. The proximal end 2504C can terminate in a head 2510C with a flat surface 2512C for striking.

Figure 79D:
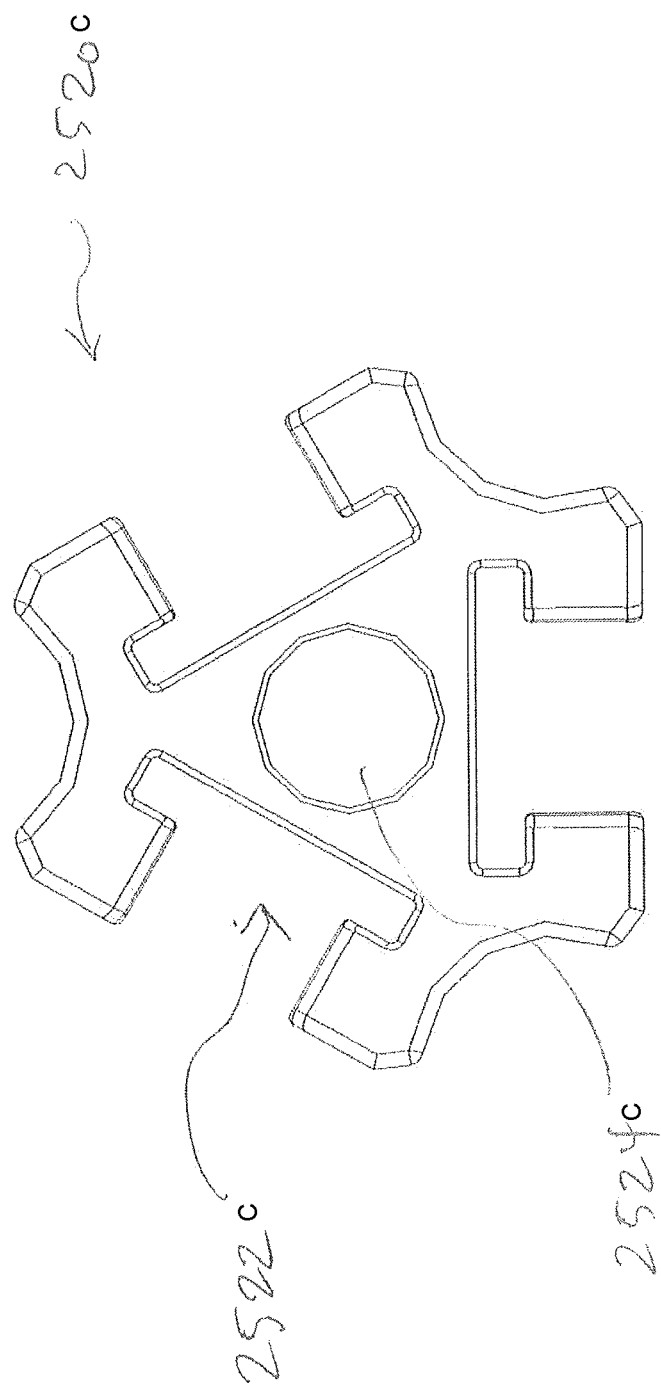

As shown in FIGS. 79B-79D, the single bladed osteotome 2500C can be used with an osteotome guide 2520C having a plurality of channels 2522C for receiving the single bladed osteotome 2500C. In some embodiments, the number of channels 2522C matches the number of sides of the rectilinear implant structure 20C. The osteotome guide 252C0 can have a cross-sectional shape and size that generally matches the cross-sectional shape and size of the implant structure 20C, with the channels 2522C located along each face of the osteotome guide 2520C such that the single bladed osteotome 2500C can be aligned with the faces or sides of the implant structure 20C. In some embodiments, the corners of the osteotome guide 2520C between adjacent faces can be hollowed or scooped out to reduce the amount of materials used to fabricate the osteotome guide, thereby reducing the costs and weight of the device. The osteotome guide 2520C can be cannulated and have a lumen 2524C for receiving a guide pin 2540C that can be inserted into the lumen of the implant structure 20C. In some embodiments, one or more faces of the osteotome guide 2520C can have a receptacle 2526C for receiving a stop 2509C that can be used to fix in place a blade 2501C disposed within the channel 2522C.

Figure 79E:
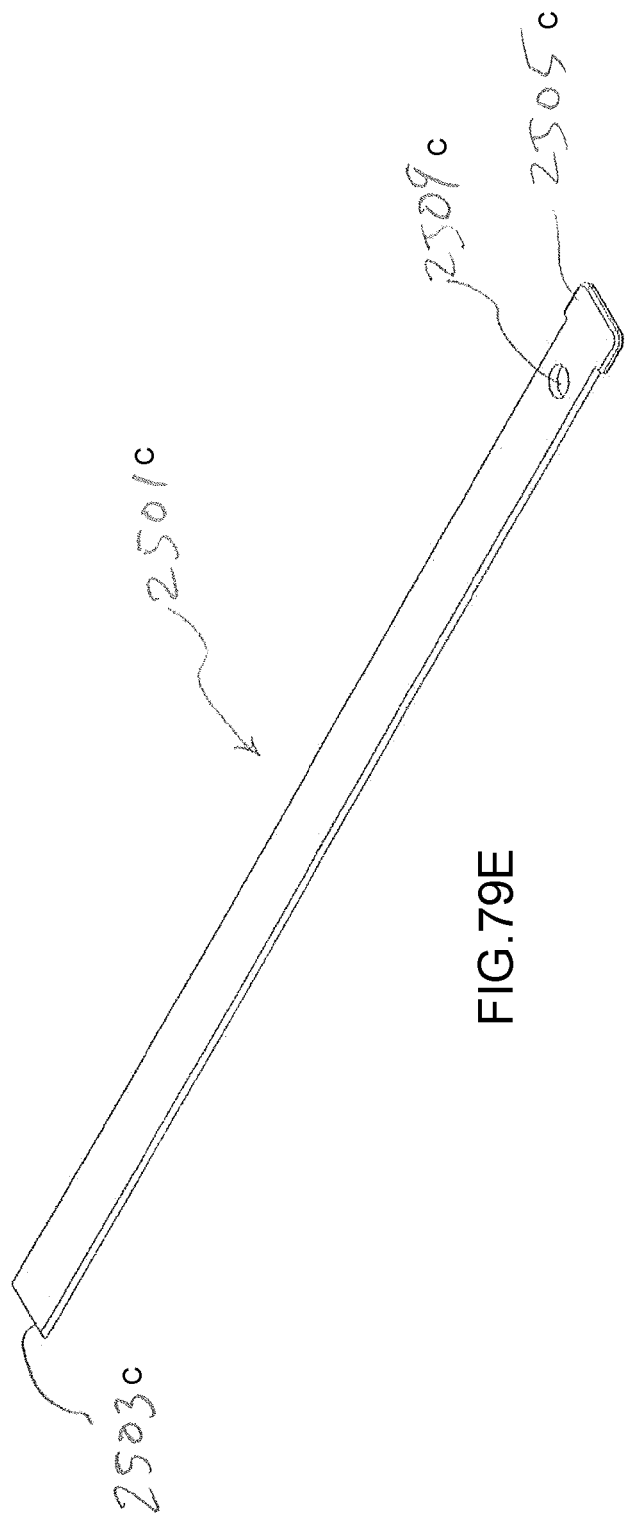
Figure 79F:
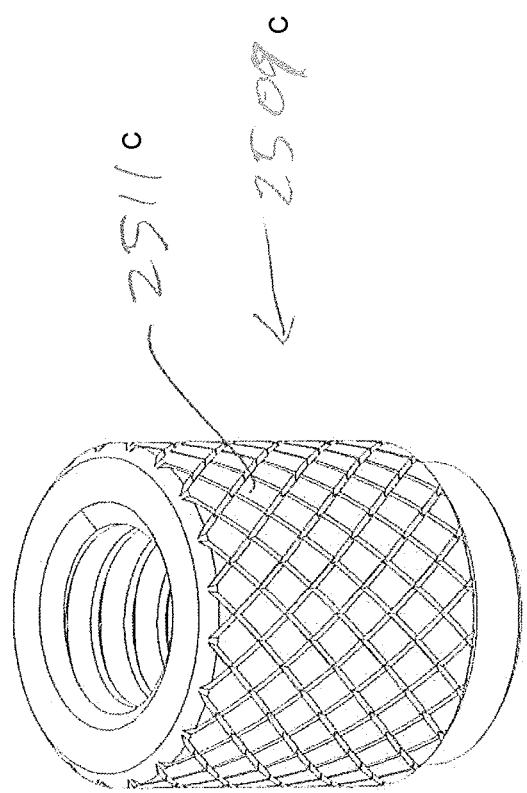
Figure 79G:
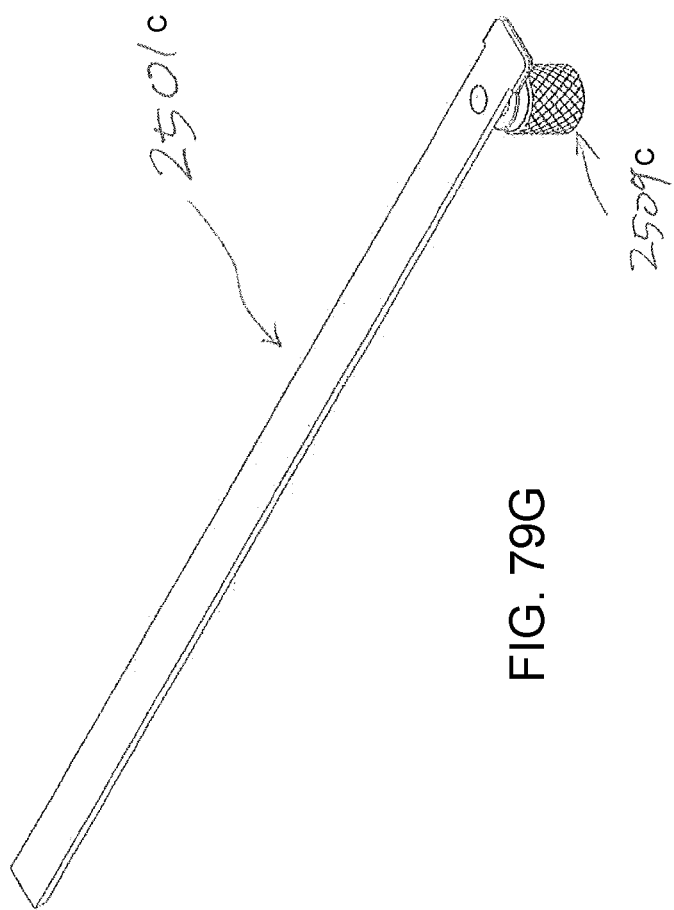

As illustrated in FIGS. 79E-79G, the blade 2501C can be a blank that fits within the channel 2522C with a length that is slightly longer than the length of the osteotome guide 2520C, allowing the blade 2501C to be inserted into the channel and tapped into the bone to secure the alignment of the osteotome guide 2520C over the implant to be removed. The blade 2501C can have a chiseled end 2503C for biting into the bone and a proximal end 2505C that is wider than the channel 2522C to limit the penetration of the blade 2501C into the bone to a predetermined depth. The blade 2501C can also have a receptacle 2507C for receiving the stop 2509C. The stop 2509C can be a nut with a knurled or textured gripping portion 2511C and can be attached to the receptacle of the blade 2501C or the osteotome guide by any means, such as complementary threads and grooves, for example.

Figure 79H:
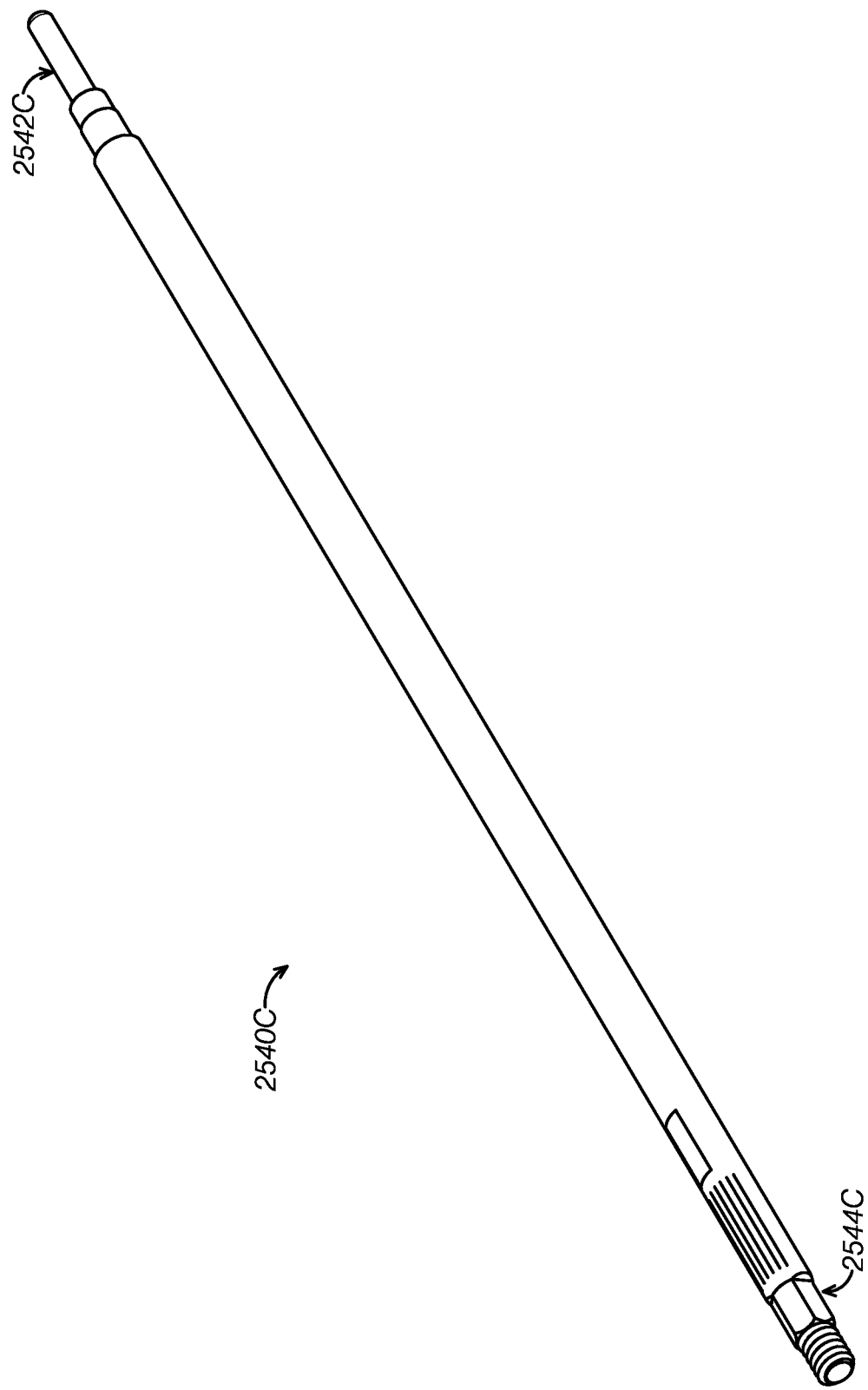
Figure 79I:
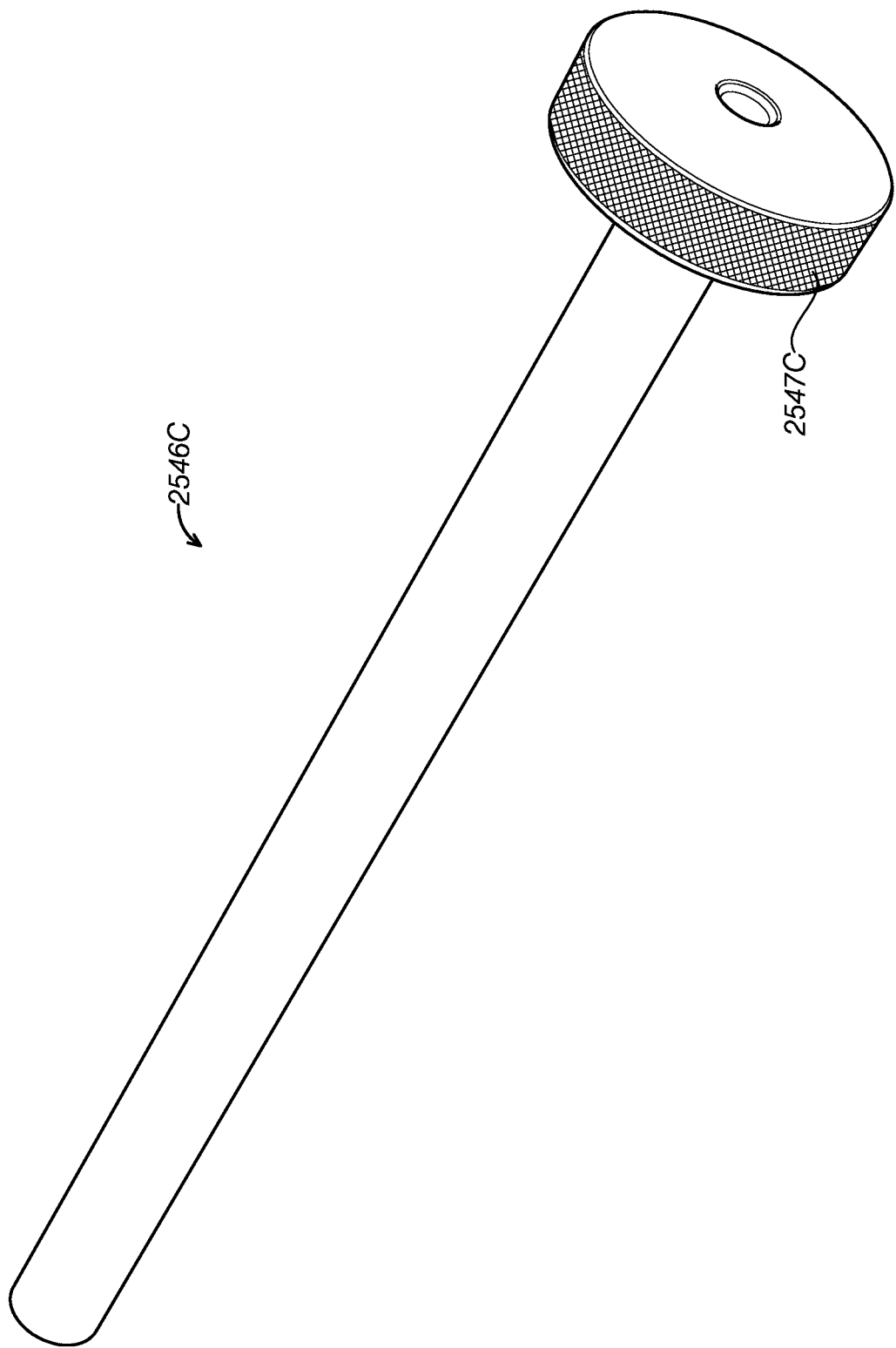

In some embodiments as illustrated in FIG. 79H, the guide pin 2540C can have a distal portion 2542C that can be inserted into the lumen of the implant 20C. In some embodiments, the distal portion 2542C can be threaded and can be fastened and secured to the implant structure 20C by screwing the threaded end into complementary threads in the lumen of the implant structure 20C. In some embodiments, the proximal portion 2544C of the guide pin 2540C can be threaded so that a pull shaft 2546C for pulling out the implant 20C, illustrated in FIG. 79I, can be attached to the proximal portion 2544C of the guide pin 2540C. The pull shaft 2546C can have a knurled or textured handle portion 2547C for gripping. After the guide pin 2540C is inserted into the implant structure 20C, the osteotome guide 2520C can be disposed over the guide pin 2540C until the osteotome guide 2520C abuts against the bone. Alternatively, in some embodiments, the osteotome guide 2520C can be held about 3 to 5 mm, or 1 to 10 mm proud of the bone surface, such as the ileum or vertebra, by using a stop and/or collar, described below.

Figure 79J:
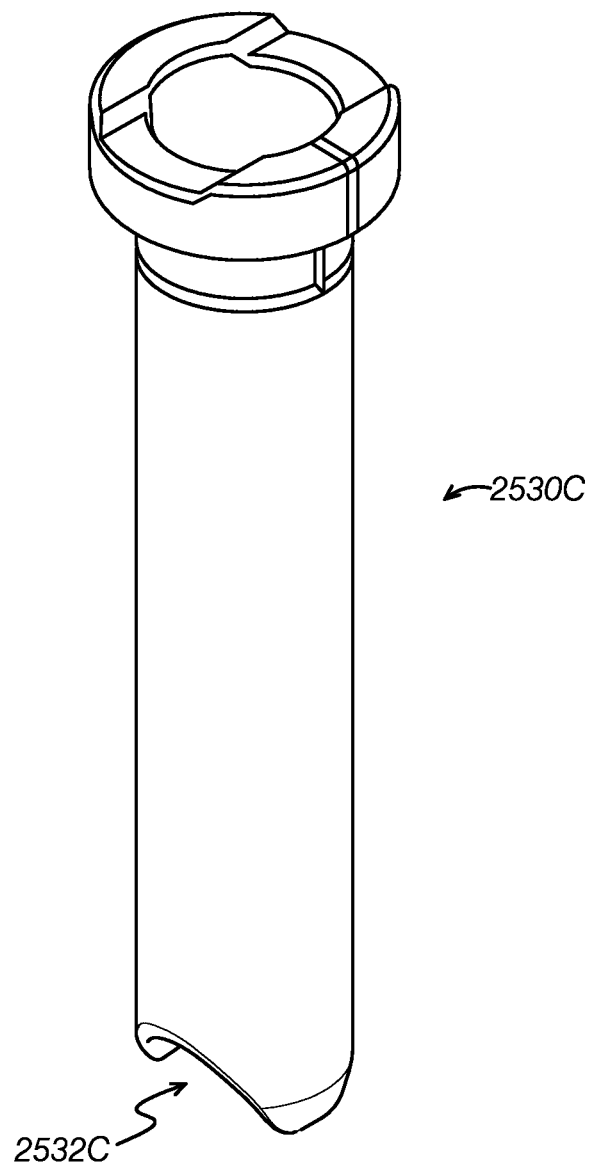
Figure 79K:
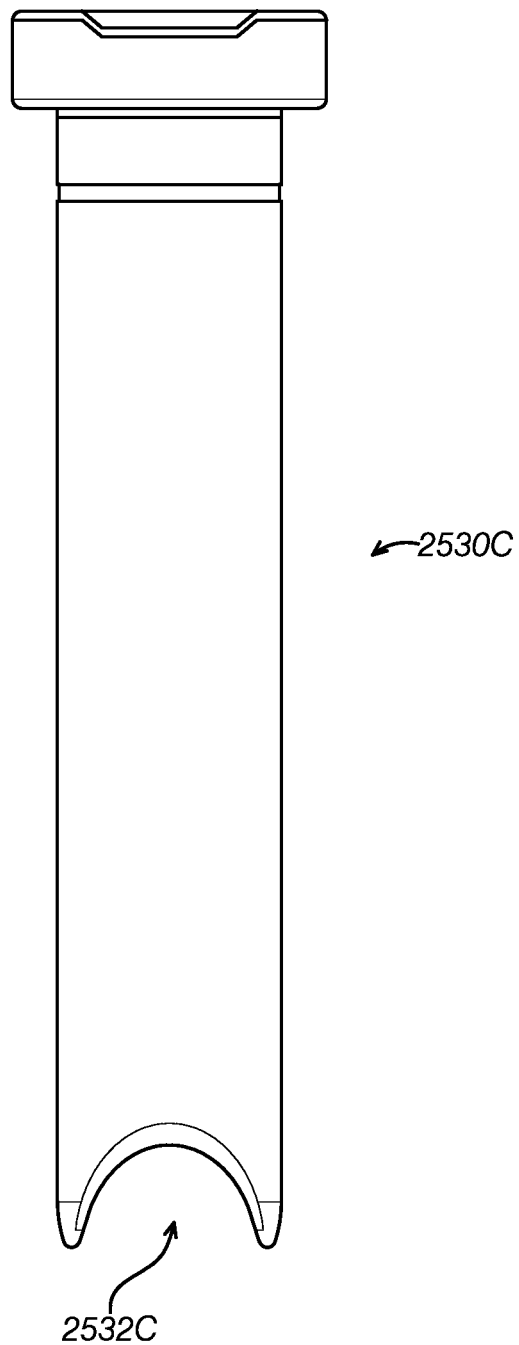

In some embodiments as illustrated in FIGS. 79J and 79K, the osteotome guide 2520C can be used in conjunction with a dilator 2530C having a lumen sized to receive the osteotome guide 2520C. In some embodiments, the distal end of the dilator 2530C can have one or more cutouts 2532C that allow the dilator 2530C to be centered over one implant structure while allowing the distal rim of the dilator 2530C to be placed over other implant structures 20 or other structures that extend out of the bone surface. The cutouts 2532C are particularly useful when there is a cluster of implant structures 20C embedded in the bone in one area and in relatively close proximity. The dilator 2530C can be rotated to line up the cutouts 2532C with any implant structures 20C surrounding the centered implant structure 20C. In some embodiments, the cutouts 2532C can be curved or arched such as semicircular, while in other embodiments, the cutouts can be rectilinear, such as rectangular or square.

Figure 79L:
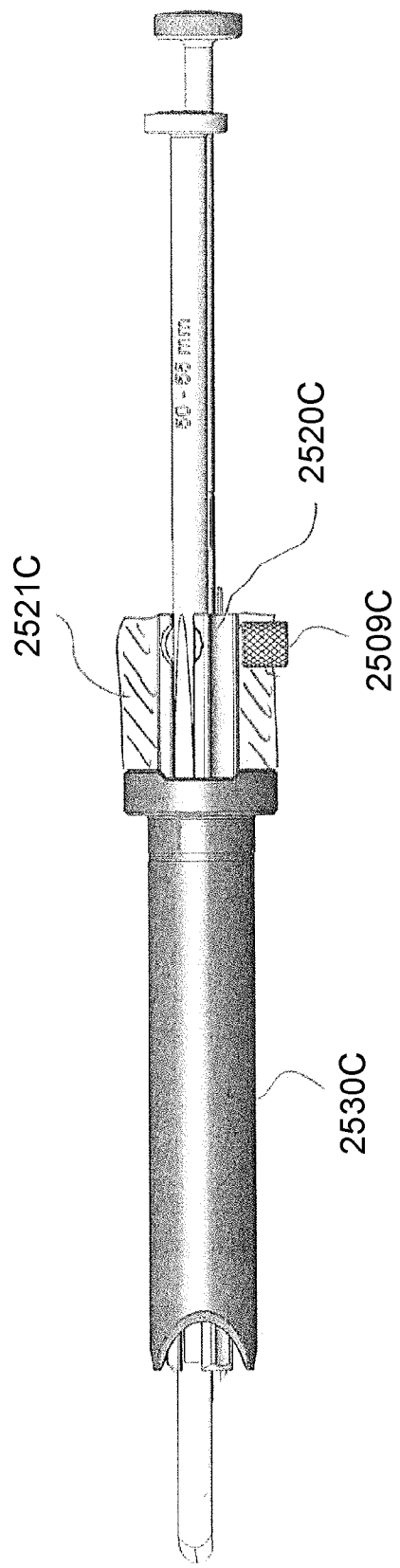

In some embodiments as illustrated in FIG. 79L, the osteotome guide 2520C can have an adjustable collar 2521C that can be fastened along a plurality of positions along the osteotome guide 2520C. In some embodiments, the collar 2521C can be fastened and secured to the osteotome guide 2520C using the stop 2509C and receptacle 2526C. The dilator 2530C can be disposed over the guide pin 2540C until it abuts against the bone. Then the osteotome guide 2520C can be disposed over the guide pin 2540C and into the lumen of the dilator 2530C until the collar 2521C on the osteotome guide 2520C abuts against the proximal end of the dilator 2530C. The collar 2521C can be adjusted and positioned such that the distal end of the osteotome guide 2520C is left proud, i.e. above, the surface of the bone as set forth above. In some embodiments, the osteotome guide 2520C is left proud of the bone surface because the proximal end of the implant structure 20C itself is proud of the bone surface, and therefore, the collar 2521C prevents the distal end of the osteotome guide 2520C from striking or pushing into the proximal end of the implant structure 20C.

Figure 79M:
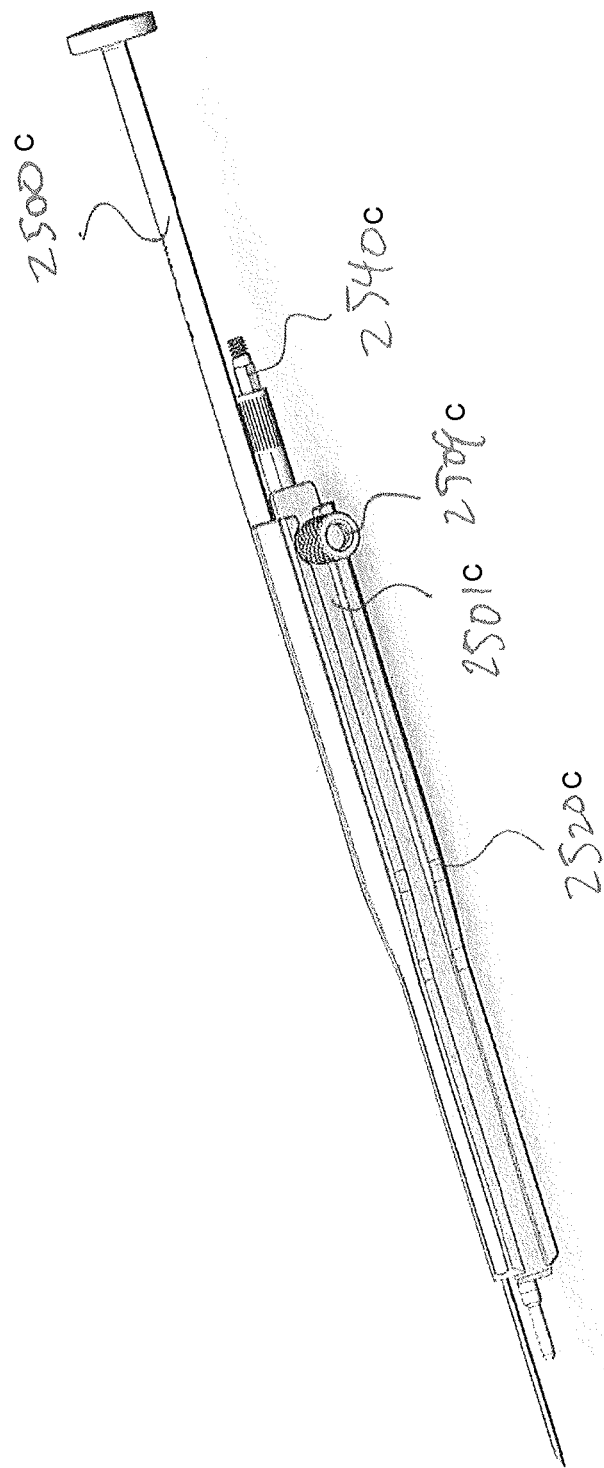
Figure 79N:
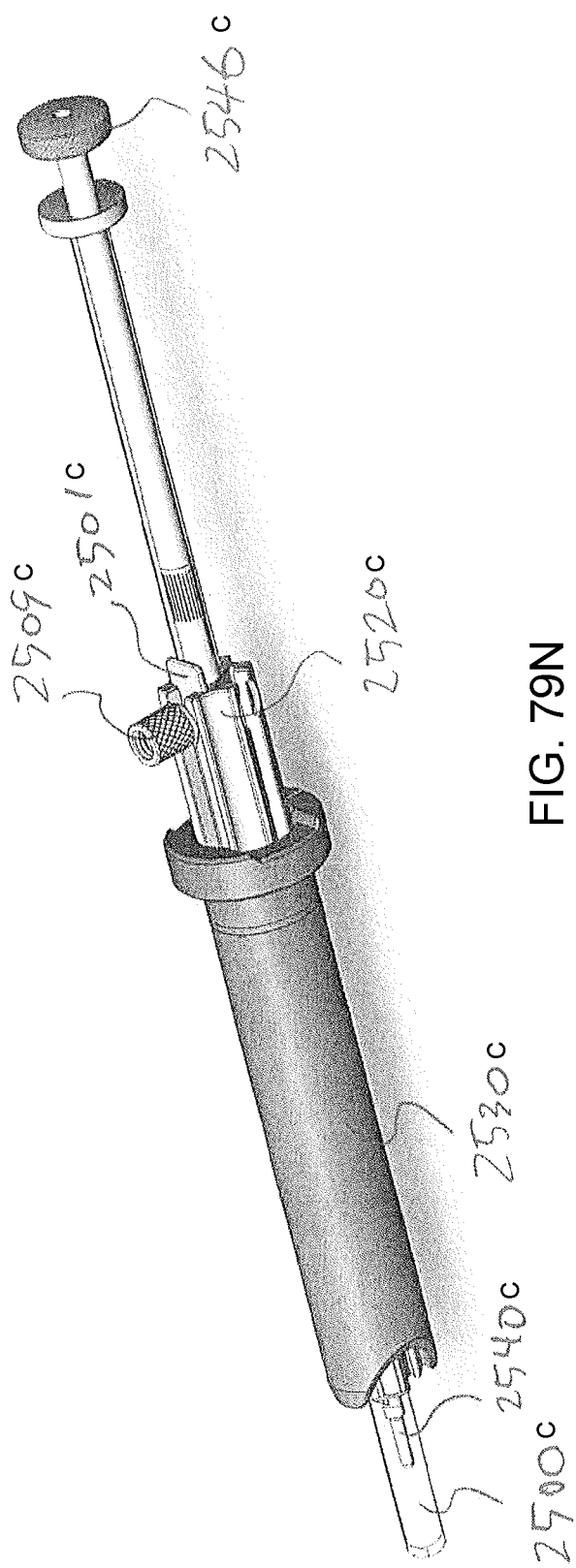

FIGS. 79M and 79N illustrate the removal system as assembled. Once the guide pin 2540C, dilator 2530C, and osteotome guide 2520C are in place and aligned over the implant structure 20C to be removed, the single bladed osteotome 2500C can be inserted into the channel 2522C in the osteotome guide 2520C and pushed into contact with the bone surrounding the implant structure 20C. When the osteotome guide 2520C is properly aligned, the blade portion 2508C of the single bladed osteotome 2500C will be aligned with one face or side of the implant structure 20C. In some embodiments, a blade 2501C that can be inserted into the channels 2522C can be used to help align the osteotome guide 2520C with the implant structure 20C. In some embodiments, the channels 2522C are positioned such that the spacing between the blade portion 2510C of the osteotome and face of the implant is about 0.1, 0.2, 0.3, 0.4, 0.5, 0.6, 0.7, 0.8, 0.9 or 1.0 mm or less. After the osteotome guide 2520C has been aligned and the one or more faces of the implant have been cut free, the blade 2501C can be removed and the single bladed osteotome 2500C can be inserted into the channel 2522C to cut the remaining face. The single bladed osteotome 2500C can be advanced into the bone by striking the head 2510C of the osteotome 2500C with a hammer or some other striking device. The osteotome 2500C can include markings to indicate the depth of penetration of the osteotome 2500C into the bone. In addition, the osteotome 2500C can include an adjustable stop to limit the depth of penetration of the osteotome 2500C to a predetermined depth. For example, the stop on the osteotome 2500C can be set to limit the depth of penetration to the depth of the implant structure 20C in the bone, thereby reducing or eliminating the chance of excess penetration which can lead to damage of nerve tissue and other sensitive tissues. Once the proper depth has been reached, the osteotome 2500C can be removed from the first channel 2522C and inserted into the second channel 2522C to cut the bone along the second face or side of the implant structure 20C. This process can be repeated until all sides of the implant structure 20C have been cut away from the bone. For example, for removing an implant structure 20C with a triangular cross-section, the osteotome would be used three times in an osteotome guide 2520C with three channels to cut the bone away from each face or side of the implant structure 20C. The guide pin 2540C which can be screwed into and attached to the implant structure 20C can be used to pull the cutout implant structure 20C out of the bone. This method of implant structure removal does not require torque to be applied to the implant structure, in contrast to removal of screw type implants.

FIGS. 80A-80D illustrate an embodiment of double bladed removal system based on a double bladed osteotome 2600C having elongate body 2602C with a first flat and elongate section 2604C and a second flat and elongate section 2606C that are joined together at an angle that corresponds to the angle between two adjacent faces of the rectilinear implant structure 20C. For example, for an implant structure 20C with a triangular cross-sectional profile, the angle between the faces of the implant structure 20C can be 60 degrees, and therefore, the angle between the first flat and elongate section 2604C and second flat and elongate section 2606C can also be 60 degrees. Triangles having different angles are also contemplated as well as the angles found in other rectilinear geometries, such as 90 degree angles for rectangular and square cross-sections. In some embodiments, the width of first flat and elongate section 2604C and the second flat and elongate section 2606C can be substantially equivalent to the width of two adjacent faces of the implant structure 20C. In some embodiments, the width of first flat and elongate section 2604C and the second flat and elongate section 2606C can be slightly larger than the width of two adjacent faces of the implant structure 20C in order to accommodate the gap between the double bladed osteotome 2600C and the implant structure 20C during the cutting process and to ensure that the entire face of each face of the implant is cut away from the ingrown bone. The distal ends of the first flat and elongate section 2604C and the second flat and elongate section 2606C can terminate in a first bladed portion 2608C and a second bladed portion 2610C, respectively, that together form a V shaped bladed portion 2609C. The proximal portion of the double bladed osteotome 2600C can terminate in a head 2612C with a surface 2614C for striking.

In some embodiments, the double bladed osteotome 2600C can have a proximal portion 2616C that is cannulated with a lumen 2618C for receiving a guide pin 2540C that can be attached to the implant structure 20C as described above. The V shaped bladed portion 2609C can be offset from the axis of the lumen 2618C such that when the double bladed osteotome 2600C is disposed over the guide pin 38C the V shaped bladed portion 2609C can be rotated until it is aligned with two faces of the implant structure 20C. The V shaped bladed portion 2609C is itself a self-aligning feature that facilitates the alignment of the V shaped bladed portion 2609C with the faces of the implant structure 20C. For example, the apex of the V shaped bladed portion 2609C can be aligned with a corner of implant structure 20C that joins two faces. In addition, the osteotome 2600C can be used with a dilator 2530C as described above. Once the V shaped bladed portion 2609C is aligned with the implant structure 20C, the double bladed osteotome 2600C can be advanced to cut the bone through impacts to the head 2612C of the osteotome 2600C. The spacing between the blade portion 2609C and the face of the implant can be the same as described above for the single bladed osteotome. Stop features to prevent excess advancement into bone and depth indicators can also be included or attached to the guide pin 2540C and/or the osteotome 2600C. The osteotome 2600C can be retracted, rotated and aligned to cut the remaining faces of implant structure 20C from the bone. For an implant structure 20C having three or four faces, two cuts are needed to cut every face of the implant structure 20C from the bone. As described above, after the faces of the implant structure 20C have been cut from the bone, the guide pin 2540C, which can be screwed into the implant structure 20C, can be pulled in order to remove the implant structure 20C from the bone.

In some embodiments, the width of first flat and elongate section 2604C and the second flat and elongate section 2606C can each be about half the width of the faces of the implant structure 20C, or slightly more than half the width of the faces of the implant structure 20C. In this embodiment, the number of cuts needed to cut each face of the implant structure 20C from the bone is equal to the number of faces of the implant structure 20C.

Figure 80A:
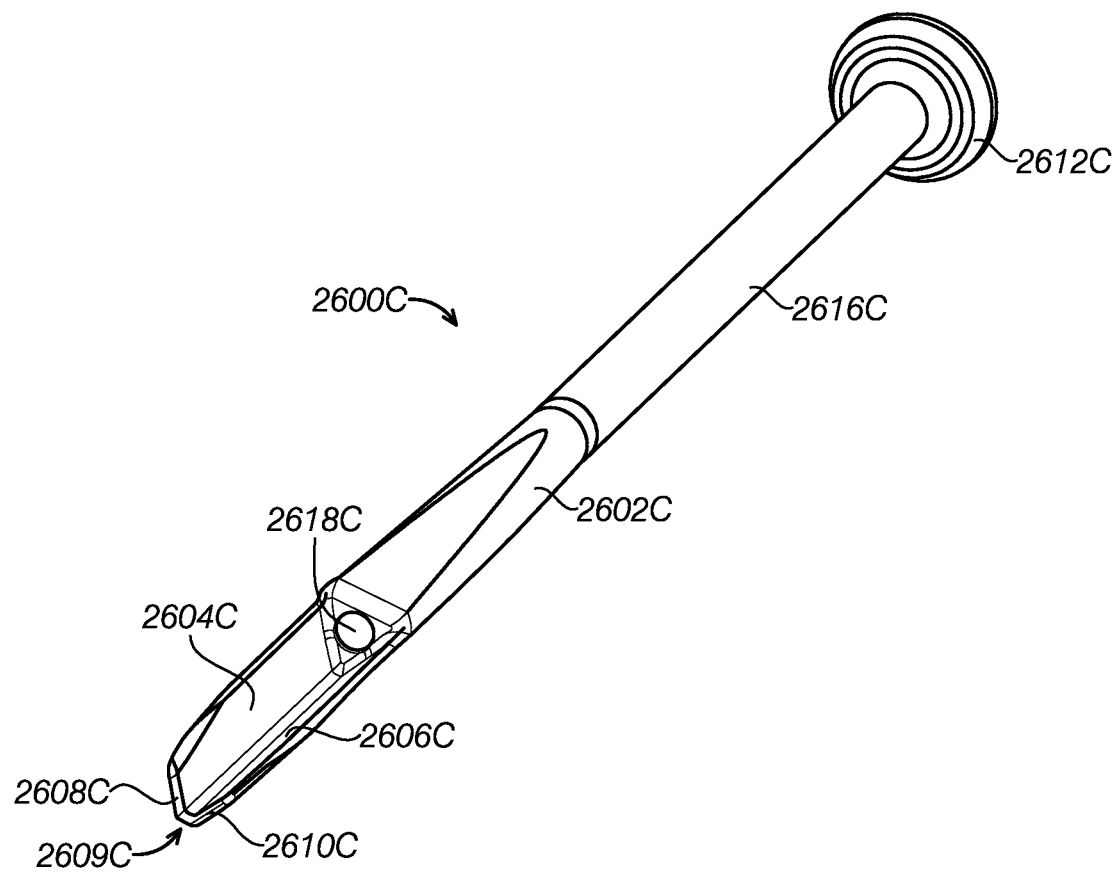
FIGS. 80A-80D illustrate an embodiment of a double bladed removal system.
Figure 80B:
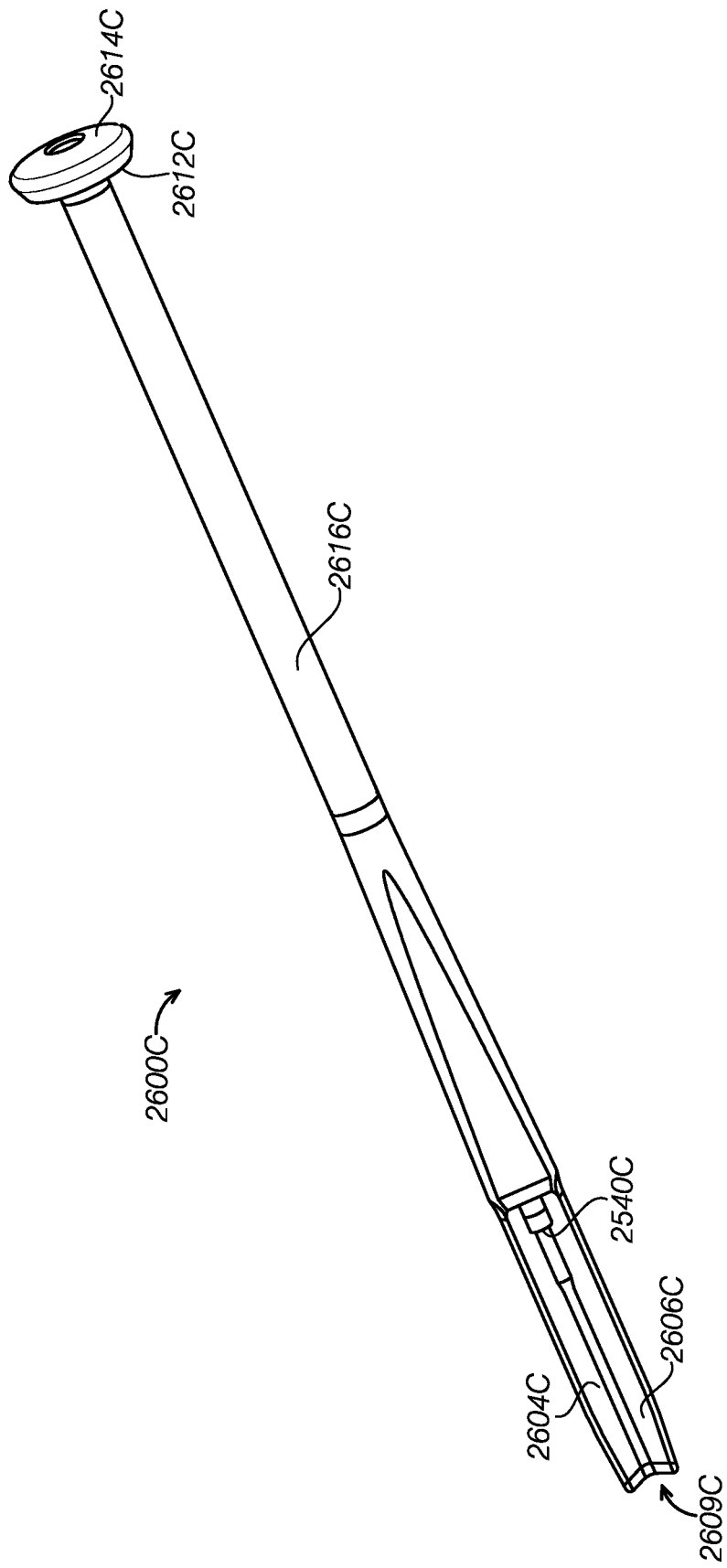
Figure 80C:
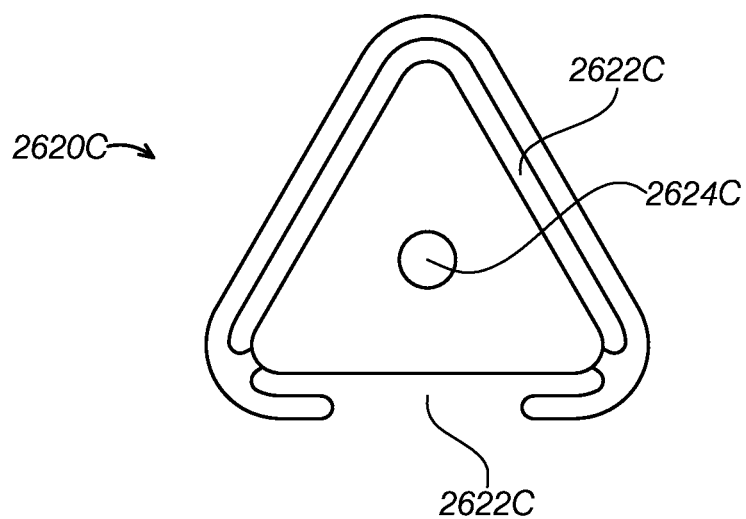
Figure 80D:
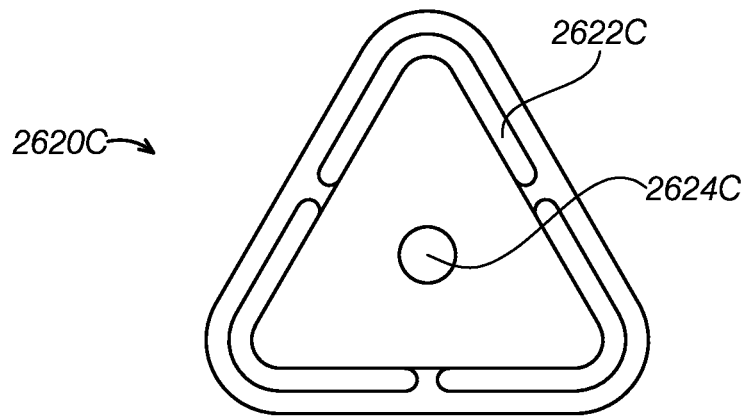

In some embodiments as illustrated in FIGS. 80C and 80D, the double bladed osteotome 2600C can be used with an osteotome guide 2620C having channels 2622C for receiving the double bladed osteotome 2600C, similar to the osteotome guide describe above expect that the channels are sized and shaped to receive the double bladed osteotome 2600C. As described above, the osteotome guide 2620C can be used with a dilator 2530C. In some embodiments, the osteotome guide 2620C can have one channel to receive a double bladed osteotome and another channel to receive a single bladed osteotome. The osteotome guide 2620C can have a lumen 2624C for receiving the guide pin.

In some embodiments, as the width of the bladed portion of the osteotome is increased, the greater the friction and/or resistance that occurs when the osteotome is advanced through the bone. Therefore, if the surgeon encounters too much resistance when trying to advance the a double bladed osteotome, the surgeon can switch to a smaller double bladed osteotome or a single bladed osteotome. In some embodiments, the thickness of the blade portion of the osteotome can be less than about 2.5, 2.25, 2.0, 1.75, 1.5, 1.25, or 1.0 mm, or between about 1.0 to 2.5 mm or 1.25 to 2.25 mm or 1.5 to 2.0 mm Increasing the thickness of the blade portion increases the durability and the capability of the osteotome to tolerate the high forces generated during impact into the bone, but at the cost of increasing friction and/or resistance.

The implant structure 20C may be removed for a variety of reasons. In some situations, it can be desirable to replace an old implant with a new implant, for example in an implant rescue procedure. The procedures described above can be used to remove the old implant structure, leaving a cavity that is slightly larger than the original implant structure. To provide a tight fit within the cavity, the new implant structure can be larger than the old implant structure. In some embodiments, the new implant structure can be between about 0.25 to 2.0 mm, or 0.5 to 1.0 mm larger for each face of the new implant. This sizing can be particularly appropriate when replacement of the old implant occurs relatively soon after the original implantation procedure, such as less than 1, 2, 3, or 4 weeks after the original implantation procedure, because the bone ingrowth into the old implant structure is less than an implant structure than has been implanted for a long time, such as over 1, 2, 3, 4, 6, or 12 months. Removal of old implants residing in the bone for a long time may be more difficult due to increased bone ingrowth, and consequently, the cavity after removal may be larger. In this situation, a larger new implant can be used, having each face being about 2 mm larger than the old implant structure. In some embodiments, the surgeon can measure the size of the cavity and select the appropriately sized new implant.

II. Conclusion

The various representative embodiments of the assemblies of the implant structures 20, as described, make possible the achievement of diverse interventions involving the fusion and/or stabilization of lumbar and sacral vertebra in a non-invasive manner, with minimal incision, and without the necessitating the removing the intervertebral disc. The representative lumbar spine interventions described can be performed on adults or children and include, but are not limited to, lumbar interbody fusion; translaminar lumbar fusion; lumbar facet fusion; trans-iliac lumbar fusion; and the stabilization of a spondylolisthesis. It should be appreciated that such interventions can be used in combination with each other and in combination with conventional fusion/fixation techniques to achieve the desired therapeutic objectives.

Significantly, the various assemblies of the implant structures 20C as described make possible lumbar interbody fusion without the necessity of removing the intervertebral disc. For example, in conventional anterior lumbar interbody fusion procedures, the removal of the intervertebral disc is a prerequisite of the procedure. However, when using the assemblies as described to achieve anterior lumbar interbody fusion, whether or not the intervertebral disc is removed depends upon the condition of the disc, and is not a prerequisite of the procedure itself. If the disc is healthy and has not appreciably degenerated, one or more implant structures 20C can be individually inserted in a minimally invasive fashion, across the intervertebral disc in the lumbar spine area, leaving the disc intact.

In all the representative interventions described, the removal of a disc, or the scraping of a disc, is at the physician's discretion, based upon the condition of the disc itself, and is not dictated by the procedure. The bony in-growth or through-growth regions 24C of the implant structures 20C described provide both extra-articular and intra osseous fixation, when bone grows in and around the bony in-growth or through-growth regions 24C.

Conventional tissue access tools, obturators, cannulas, and/or drills can be used during their implantation. No disc preparation, removal of bone or cartilage, or scraping are required before and during formation of the insertion path or insertion of the implant structures 20C, so a minimally invasive insertion path sized approximately at or about the maximum outer diameter of the implant structures 20C need be formed. Still, the implant structures 20C, which include the elongated bony in-growth or through-growth regions 24C, significantly increase the size of the fusion area, from the relatively small surface area of a given joint between adjacent bones, to the surface area provided by an elongated bony in-growth or through-growth regions 24C. The implant structures 20C can thereby increase the surface area involved in the fusion and/or stabilization by 3-fold to 4-fold, depending upon the joint involved.

The implant structures 20C can obviate the need for autologous grafts, bone graft material, additional pedicle screws and/or rods, hollow modular anchorage screws, cannulated compression screws, cages, or fixation screws. Still, in the physician's discretion, bone graft material and other fixation instrumentation can be used in combination with the implant structures 20C.

The implant structures 20C make possible surgical techniques that are less invasive than traditional open surgery with no extensive soft tissue stripping and no disc removal. The assemblies make possible straightforward surgical approaches that complement the minimally invasive surgical techniques. The profile and design of the implant structures 20C minimize rotation and micro-motion. Rigid implant structures 20C made from titanium provide immediate post-op fusion stability. A bony in-growth region 24C comprising a porous plasma spray coating with irregular surface supports stable bone fixation/fusion. The implant structures 20C and surgical approaches make possible the placement of larger fusion surface areas designed to maximize post-surgical weight bearing capacity and provide a biomechanically rigorous implant designed specifically to stabilize the heavily loaded lumbar spine.

Long Implant for Sacroiliac Joint Fusion

Figure 81:
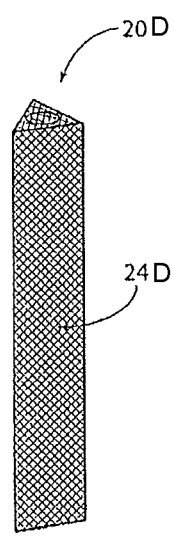
FIG. 81 illustrates an embodiment of an implant structure.
Figure 83:
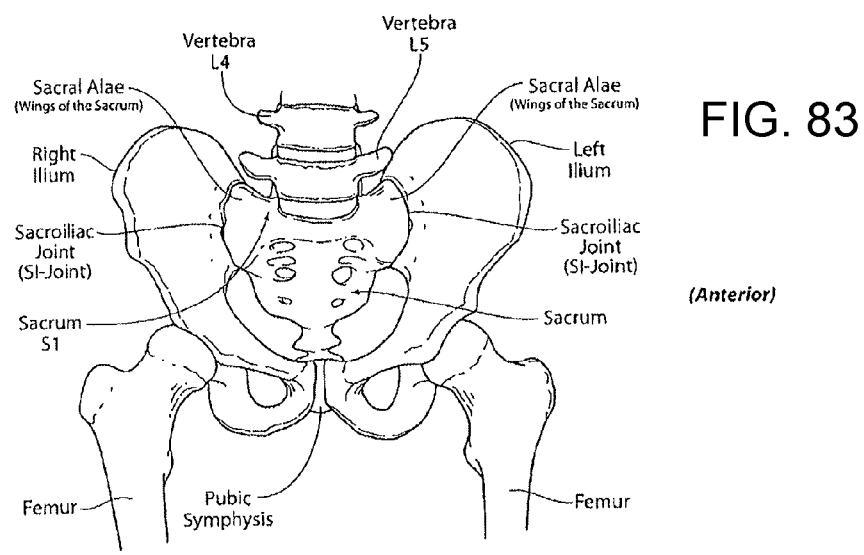
FIGS. 83 and 84 are, respectively, anterior and posterior anatomic views of the human hip girdle comprising the sacrum and the hip bones (the right ilium, and the left ilium), the sacrum being connected with both hip bones at the sacroiliac joint (in shorthand, the SI-Joint).
Figure 84:
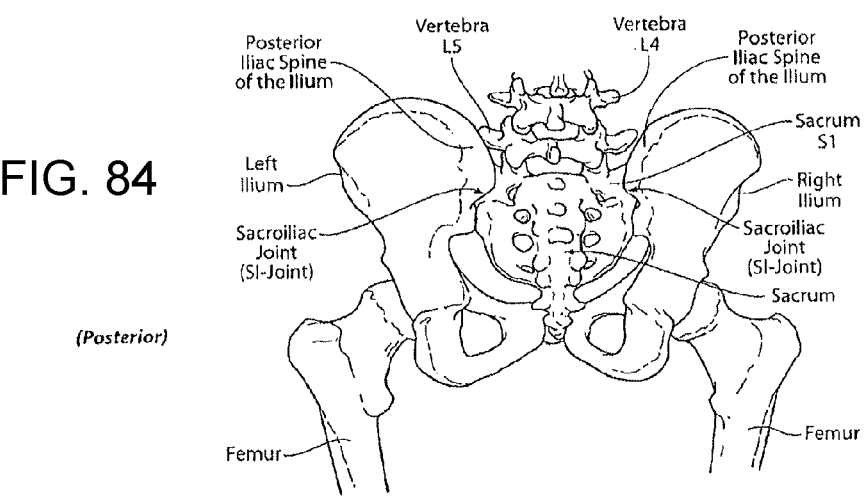

Elongated, stem-like implant structures 20D like that shown in FIG. 81 make possible the fixation of the SI-Joint (shown in anterior and posterior views, respectively, in FIGS. 83 and 84) in a minimally invasive manner. These implant structures 20D can be effectively implanted through the use a lateral surgical approach. The procedure is desirably aided by conventional lateral, inlet, and outlet visualization techniques, e.g., using X-ray image intensifiers such as a C-arms or fluoroscopes to produce a live image feed, which is displayed on a TV screen.

In one embodiment of a lateral approach (see FIGS. 85, 86, and 87A/B), one or more implant structures 20D are introduced laterally through the ilium, the SI-Joint, and into the sacrum. This path and resulting placement of the implant structures 20D are best shown in FIGS. 86 and 87A/B. In the illustrated embodiment, three implant structures 20D are placed in this manner. Also in the illustrated embodiment, the implant structures 20D are rectilinear in cross section and triangular in this case, but it should be appreciated that implant structures 20D of other rectilinear cross sections can be used.

Before undertaking a lateral implantation procedure, the physician identifies the SI-Joint segments that are to be fixated or fused (arthrodesed) using, e.g., the Fortin finger test, thigh thrust, FABER, Gaenslen's, compression, distraction, and diagnostic SI joint injection.

Figure 82A:
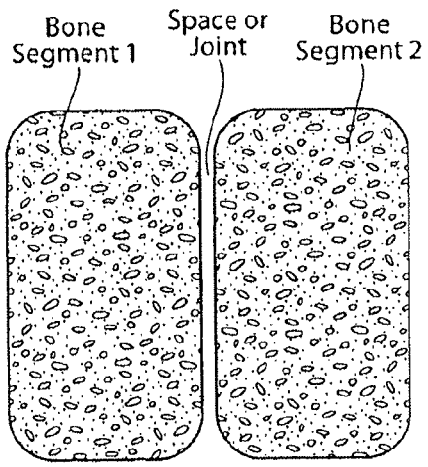
FIGS. 82A-82D are side section views of the formation of a broached bore in bone according to one embodiment of the invention.
Figure 82B:
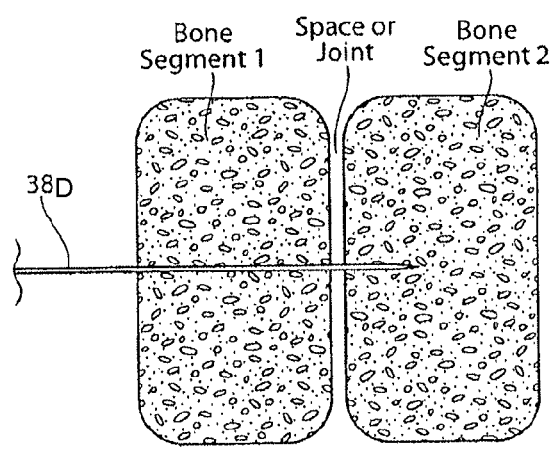

Aided by lateral, inlet, and outlet C-arm views, and with the patient lying in a prone position, the physician aligns the greater sciatic notches and then the alae (using lateral visualization) to provide a true lateral position. A 3 cm incision is made starting aligned with the posterior cortex of the sacral canal, followed by blunt tissue separation to the ilium. From the lateral view, the guide pin 38D (with sleeve (not shown)) (e.g., a Steinmann Pin) is started resting on the ilium at a position inferior to the sacrum end plate and just anterior to the sacral canal. In the outlet view, the guide pin 38D should be parallel to the sacrum end plate at a shallow angle anterior (e.g., 15 degree to 20 degree off the floor, as FIG. 87A shows). In a lateral view, the guide pin 38D should be posterior to the sacrum anterior wall. In the outlet view, the guide pin 38D should be superior to the first sacral foramen and lateral of mid-line. This corresponds generally to the sequence shown diagrammatically in FIGS. 82A and 82B. A soft tissue protector (not shown) is desirably slipped over the guide pin 38D and firmly against the ilium before removing the guide pin sleeve (not shown).

Figure 82C:
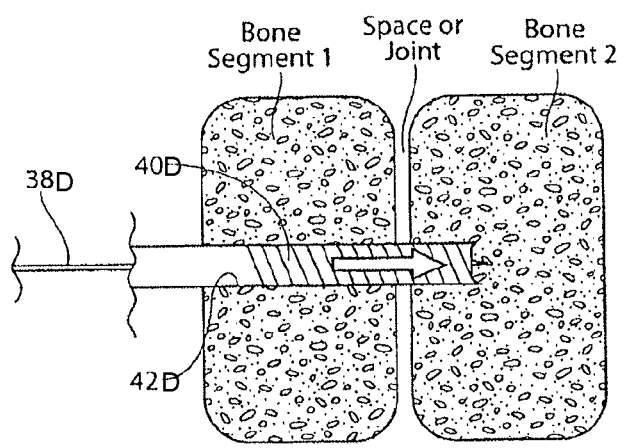

Over the guide pin 38D (and through the soft tissue protector), the pilot bore 42D is drilled in the manner previously described, as is diagrammatically shown in FIG. 82C. The pilot bore 42D extends through the ilium, through the SI-Joint, and into the sacrum. The drill bit 40D is removed.

Figure 82D:
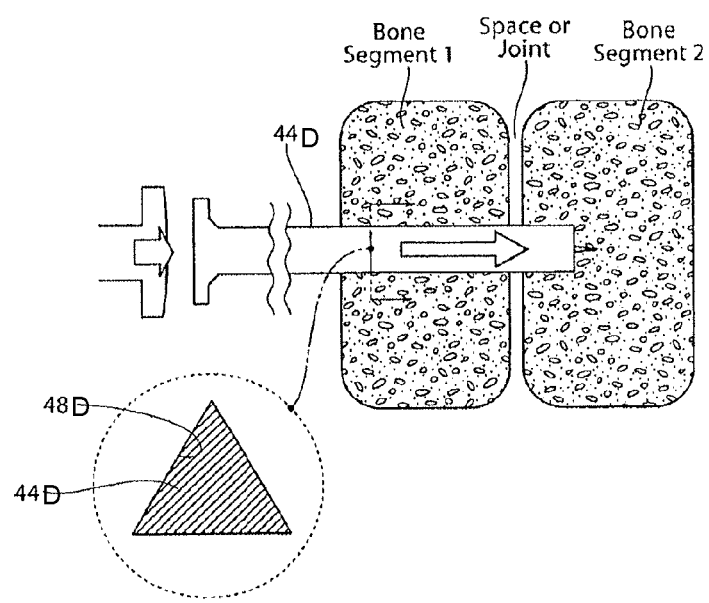

The shaped broach 44D is tapped into the pilot bore 42D over the guide pin 38D (and through the soft tissue protector) to create a broached bore 48D with the desired profile for the implant structure 20D, which, in the illustrated embodiment, is triangular. This generally corresponds to the sequence shown diagrammatically in FIG. 82D. The triangular profile of the broached bore 48D is also shown in FIG. 85.

Figure 82E:
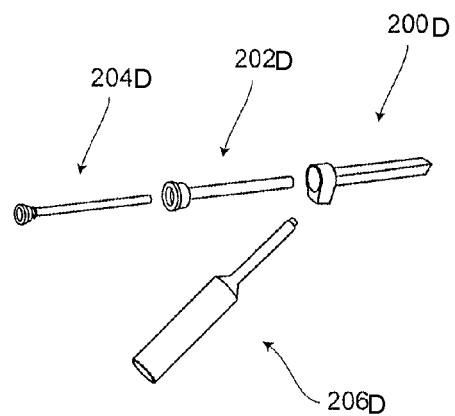
FIGS. 82E and 82F illustrate the assembly of a soft tissue protector system for placement over a guide wire.
Figure 82F:
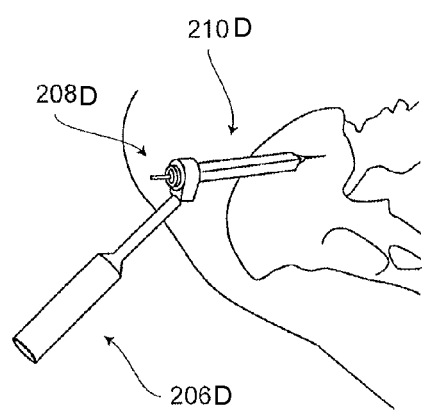

FIGS. 82E and 82F illustrate an embodiment of the assembly of a soft tissue protector or dilator or delivery sleeve 200D with a drill sleeve 202D, a guide pin sleeve 204D and a handle 206D. In some embodiments, the drill sleeve 202D and guide pin sleeve 204D can be inserted within the soft tissue protector 200D to form a soft tissue protector assembly 210D that can slide over the guide pin 208D until bony contact is achieved. The soft tissue protector 200D can be any one of the soft tissue protectors or dilators or delivery sleeves disclosed herein. In some embodiments, an expandable dilator or delivery sleeve 200D as disclosed herein can be used in place of a conventional soft tissue dilator. In the case of the expandable dilator, in some embodiments, the expandable dilator can be slid over the guide pin and then expanded before the drill sleeve 202D and/or guide pin sleeve 204D are inserted within the expandable dilator. In other embodiments, insertion of the drill sleeve 202D and/or guide pin sleeve 204D within the expandable dilator can be used to expand the expandable dilator.

In some embodiments, a dilator can be used to open a channel though the tissue prior to sliding the soft tissue protector assembly 210D over the guide pin. The dilator(s) can be placed over the guide pin, using for example a plurality of sequentially larger dilators or using an expandable dilator. After the channel has been formed through the tissue, the dilator(s) can be removed and the soft tissue protector assembly can be slid over the guide pin. In some embodiments, the expandable dilator can serve as a soft tissue protector after being expanded. For example, after expansion the drill sleeve and guide pin sleeve can be inserted into the expandable dilator.

Figure 85:
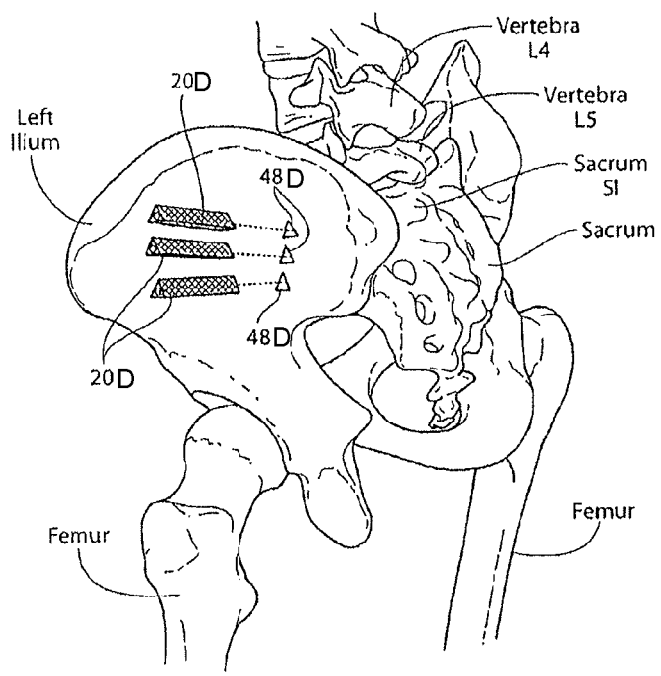
FIGS. 85, 86, 87A and 87B are anatomic views showing, respectively, a pre-implanted perspective, implanted perspective, implanted anterior view, and implanted craniocaudal section view, the implantation of three implant structures for the fixation of the SI-Joint using a lateral approach through the ilium, the SI-Joint, and into the sacrum.
Figure 86:
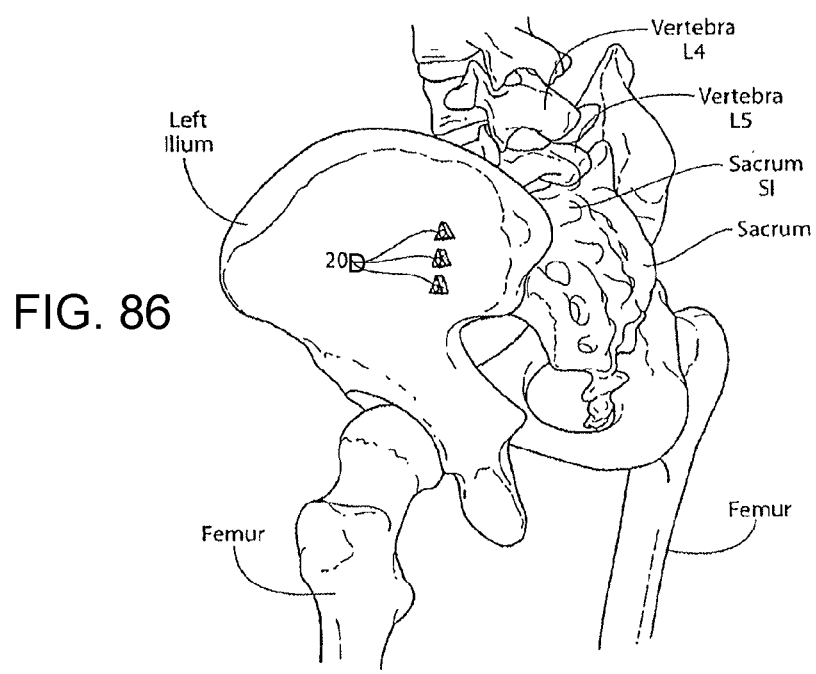
Figure 87A:
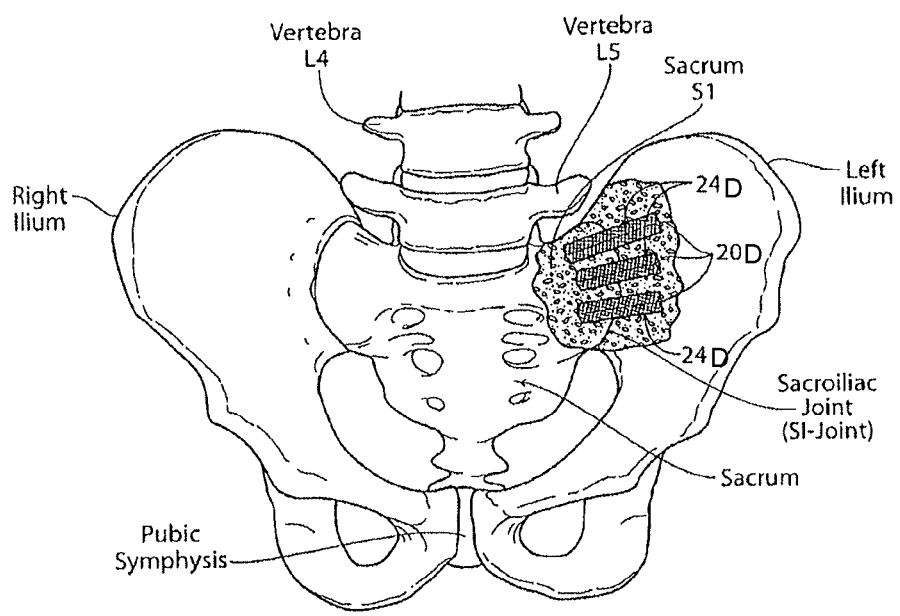
Figure 87B:
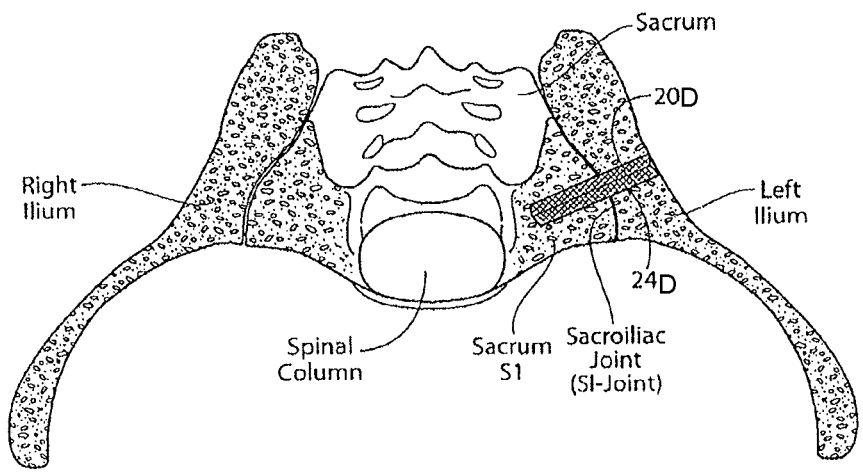

As shown in FIGS. 85 and 86, a triangular implant structure 20D can be now tapped through the soft tissue protector over the guide pin 38D through the ilium, across the SI-Joint, and into the sacrum, until the proximal end of the implant structure 20D is flush against the lateral wall of the ilium (see also FIGS. 87A and 87B). The guide pin 38D and soft tissue protector are withdrawn, leaving the implant structure 20D residing in the broached passageway, flush with the lateral wall of the ilium (see FIGS. 87A and 87B). In the illustrated embodiment, two additional implant structures 20D are implanted in this manner, as FIG. 86 best shows. In other embodiments, the proximal ends of the implant structures 20D are left proud of the lateral wall of the ilium, such that they extend 1, 2, 3 or 4 mm outside of the ilium. This ensures that the implants 20D engage the hard cortical portion of the ilium rather than just the softer cancellous portion, through which they might migrate if there was no structural support from hard cortical bone. The hard cortical bone can also bear the loads or forces typically exerted on the bone by the implant 20D.

The implant structures 20D are sized according to the local anatomy. For the SI-Joint, representative implant structures 20D can range in size, depending upon the local anatomy, from about 35 mm to about 60 mm in length, and about a 7 mm inscribed diameter (i.e. a triangle having a height of about 10.5 mm and a base of about 12 mm). The morphology of the local structures can be generally understood by medical professionals using textbooks of human skeletal anatomy along with their knowledge of the site and its disease or injury. The physician is also able to ascertain the dimensions of the implant structure 20D based upon prior analysis of the morphology of the targeted bone using, for example, plain film x-ray, fluoroscopic x-ray, or MRI or CT scanning.

Using a lateral approach, one or more implant structures 20D can be individually inserted in a minimally invasive fashion across the SI-Joint, as has been described. Conventional tissue access tools, obturators, cannulas, and/or drills can be used for this purpose. Alternatively, the novel tissue access tools described above and in U.S. Provisional Patent Application No. 61/609,043, titled "TISSUE DILATOR AND PROTECTER" and filed Mar. 9, 2012, which is hereby incorporated by reference in its entirety, can also be used. No joint preparation, removal of cartilage, or scraping are required before formation of the insertion path or insertion of the implant structures 20D, so a minimally invasive insertion path sized approximately at or about the maximum outer diameter of the implant structures 20D can be formed.

The implant structures 20D can obviate the need for autologous bone graft material, additional pedicle screws and/or rods, hollow modular anchorage screws, cannulated compression screws, threaded cages within the joint, or fracture fixation screws. Still, in the physician's discretion, bone graft material and other fixation instrumentation can be used in combination with the implant structures 20D.

In a representative procedure, one to six, or perhaps up to eight, implant structures 20D can be used, depending on the size of the patient and the size of the implant structures 20D. After installation, the patient would be advised to prevent or reduce loading of the SI-Joint while fusion occurs. This could be about a six to twelve week period or more, depending on the health of the patient and his or her adherence to post-op protocol.

The implant structures 20D make possible surgical techniques that are less invasive than traditional open surgery with no extensive soft tissue stripping. The lateral approach to the SI-Joint provides a straightforward surgical approach that complements the minimally invasive surgical techniques. The profile and design of the implant structures 20D minimize or reduce rotation and micromotion. Rigid implant structures 20D made from titanium provide immediate post-op SI Joint stability. A bony in-growth region 24D comprising a porous plasma spray coating with irregular surface supports stable bone fixation/fusion. The implant structures 20D and surgical approaches make possible the placement of larger fusion surface areas designed to maximize post-surgical weight bearing capacity and provide a biomechanically rigorous implant designed specifically to stabilize the heavily loaded SI-Joint.

To improve the stability and weight bearing capacity of the implant, the implant can be inserted across three or more cortical walls. For example, after insertion the implant can traverse two cortical walls of the ilium and at least one cortical wall of the sacrum. The cortical bone is much denser and stronger than cancellous bone and can better withstand the large stresses found in the SI-Joint. By crossing three or more cortical walls, the implant can spread the load across more load bearing structures, thereby reducing the amount of load borne by each structure. In addition, movement of the implant within the bone after implantation is reduced by providing structural support in three locations around the implant versus two locations.

Long Implant

Figure 88A:
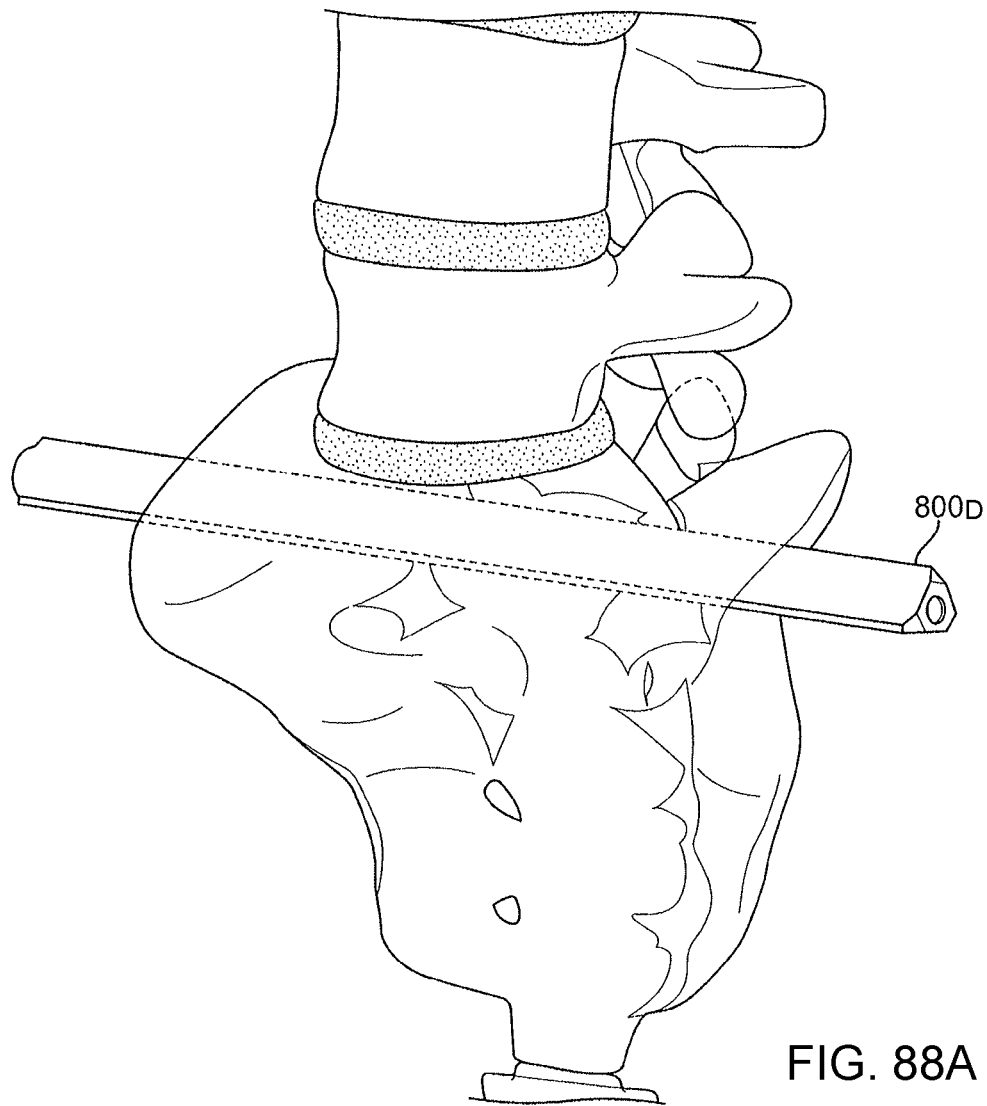
FIGS. 88A-88C illustrate an embodiment of a long implant that has been implanted across the sacrum. The two ilia are not shown . . . .
Figure 88B:
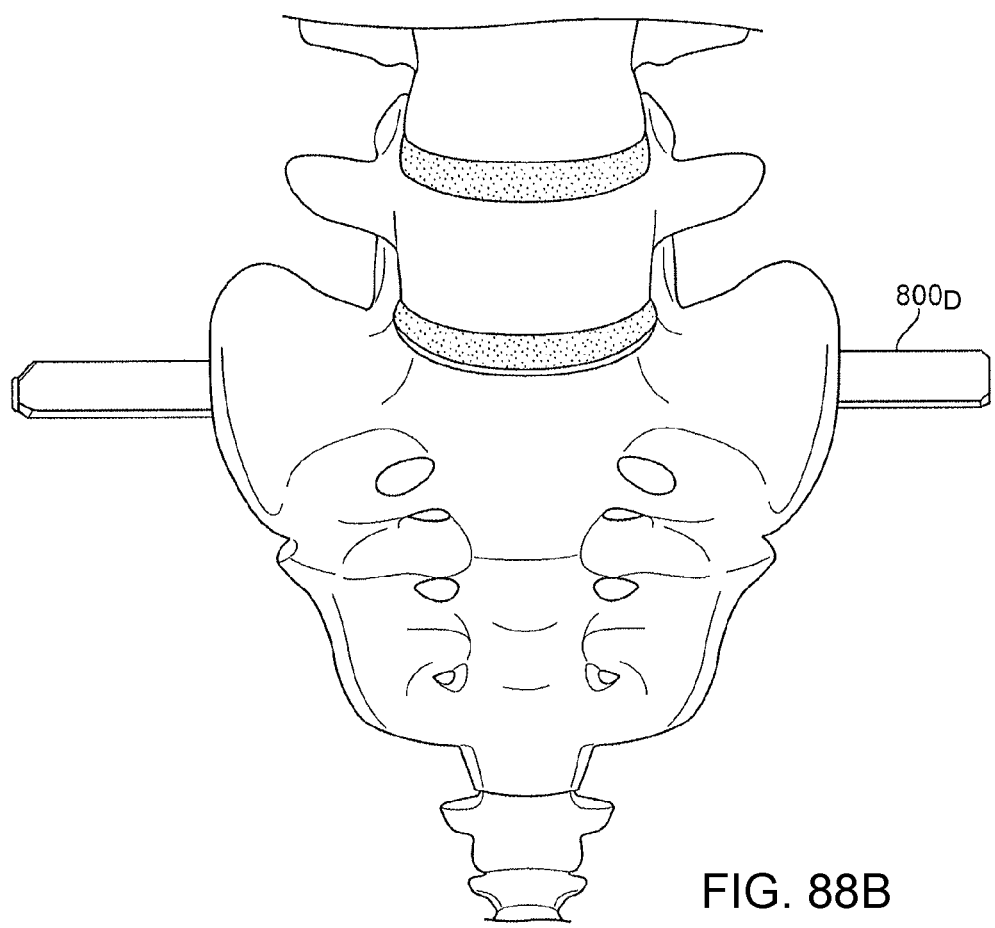
Figure 88C:
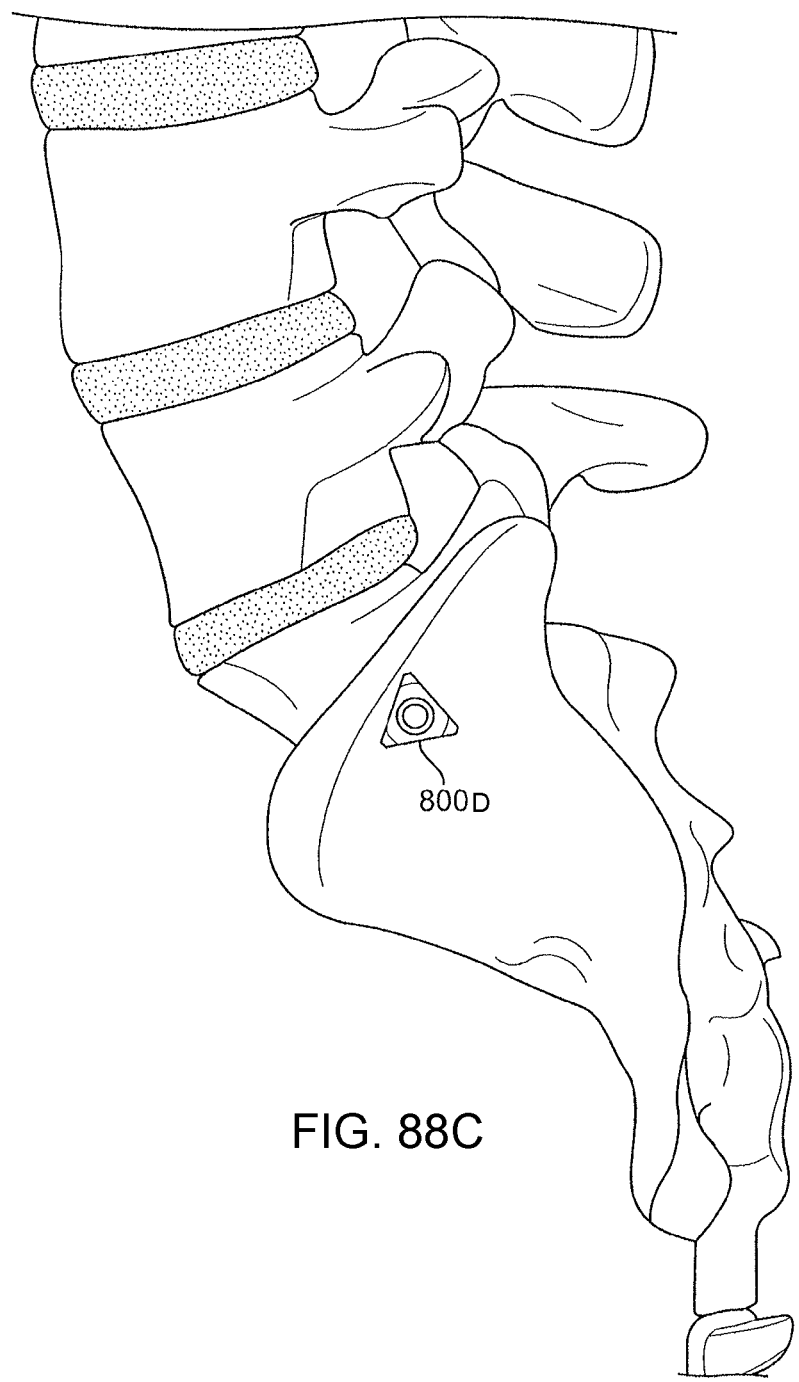

FIGS. 88A-88C illustrate an embodiment of a long implant 800D for SI-Joint fusion or fixation that has been implanted through both SI-Joints of the patient. The length of the long implant 800D can be selected to enter one side of the first ilium, cross the first SI-Joint, traverse the sacrum, cross the second SI-Joint, and exit the second ilium. In some embodiments, the length of the long implant 800D can additionally include extra length to leave a predetermined length of implant proud of both surfaces of the ilium. For example, the long implant 800D can have a length such that the implant is proud of each surface of the ilium by between about 1 to 10 mm, or between about 2 to 8 mm, or about 1, 2, 3, 4, 5, 6, 7, 8, 9 or 10 mm, or less than about 1, 2, 3, 4, 5, 6, 7, 8, 9 or 10 mm. In some embodiments, the long implant 800D can be generally between about 100 mm to about 300 mm, or about 150 mm to about 250 mm.

Besides the length, the long implant 800D can share many of the same features as described above for the regular sized implant. For example, the transverse cross-sectional profile of the long implant 800D can be rectilinear, such as triangular or rectangular. The long implant 800D can be made of a metal or metal alloy, such as titanium. In some embodiments, the surface of the long implant 800D can be roughened and/or provided with a texture that promotes bone tissue ingrowth and integration. For example, a porous and/or irregular surface texture can be provided by titanium plasma spray coating the surface of the long implant. The long implant 800D can also have a lumen for receiving a guidewire, and one or both ends of the lumen can have internal screw threads. In some embodiments, the distal end of the long implant can be slightly tapered to facilitate insertion into a bone cavity and to provide a visual identification of the distal end of the implant.

In some embodiments, as illustrated in FIGS. 88A-88C, the long implant 800D can be implanted through the first ilium (not shown) and across first SI-Joint, through the sacrum and above the S1 foramen, across the second SI-Joint, and through the second ilium (not shown). In some embodiments, the long implant 800D can be implanted between the S1 and S2 vertebrae.

Figure 89A:
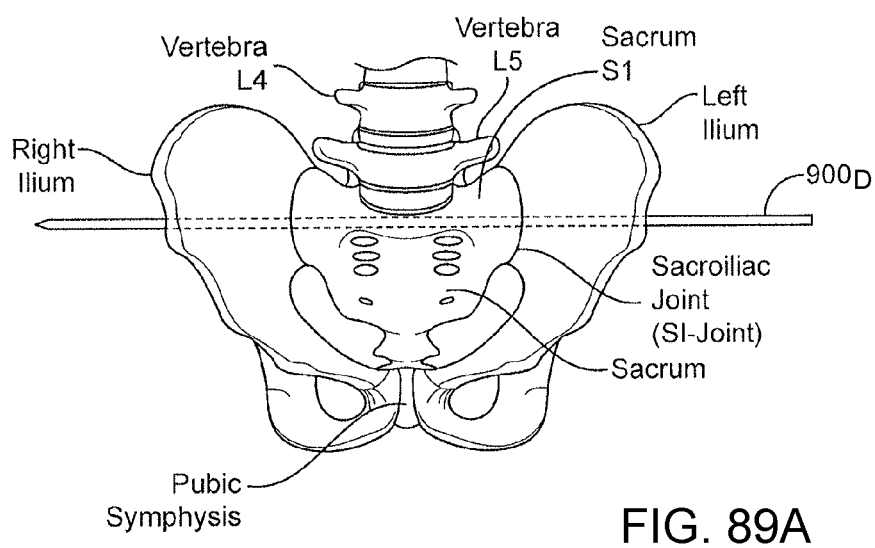
FIGS. 89A-89C illustrate an embodiment of the insertion of a guide pin through the SI-Joints and the formation of aligned cavities in the bone.
Figure 89B:
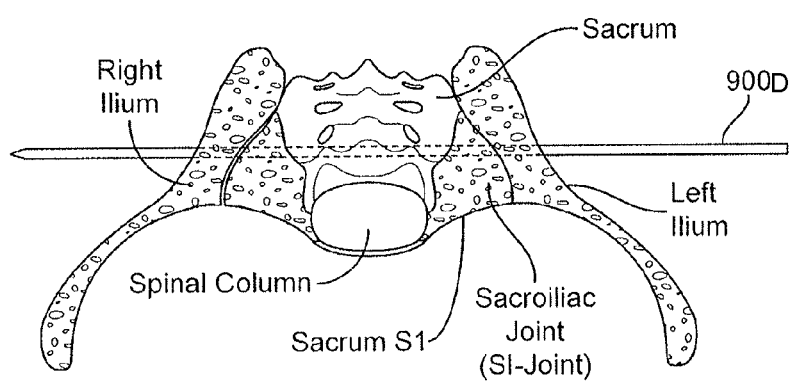

As shown in FIGS. 89A and 89B, to implant the long implant 800D, a guide pin 900D can be inserted, by for example drilling, through the first ilium and across first SI-Joint, through the sacrum and above the S1 foramen and/or between the S1 and S2 vertebrae, across the second SI-Joint, and through the second ilium. An incision can be made through the skin and tissue to the ilium to facilitate passage of the guide pin 900D. Since the length of the guide pin 900D is known, the operator can measure the lengths of the guide pin 900D extending from both sides of the ilium and determine the length of guide pin 900D residing within bone by subtracting the length outside the body from the total length of the guide pin 900D. Once the length of guide pin 900D within the bone is known, the size of the long implant 900D that should be used can be selected by taking that length and adding the length of implant that is desired to be left proud from each surface of the bone. In some embodiments, the length of the implant 800D to be used can be estimated before surgery by imaging the pelvis region of the patient including the sacrum and the ilium. For example, an X-ray or CAT scan can be taken of the pelvis region, allowing the distance between the illium surfaces to be determined.

Figure 89C:
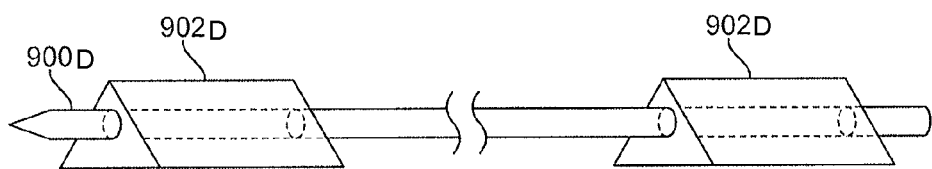
Figure 90A:
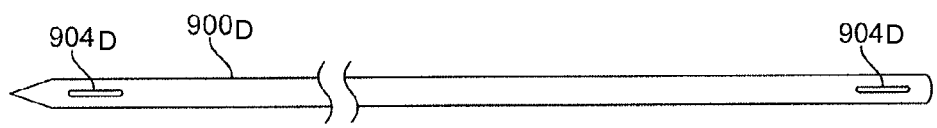
FIGS. 90A and 90B illustrate an embodiment of a guide pin and broach with alignment features.
Figure 90B:
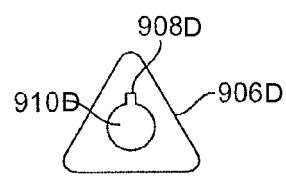

After the guide pin 900D is inserted, a cavity 902D can be formed through the ilium and SI-Joint and into the sacrum on both sides to receive the implant. The cavity can be formed as described above by drilling a bore and then shaping the bore using a broach. In some embodiments, the cavity can have a rectilinear transverse cross-section. As shown in FIG. 89C, the two cavities 902D should be aligned together so that the long implant 900D can be inserted through both cavities 902D. In one embodiment, the guide pin 900D can have alignment features at both the distal end and the proximal end to facilitate alignment of the instrumentation such as the dilators and/or broach used to form the cavity. For example, as illustrated in FIGS. 90A and 90B, the alignment feature 904D can be a line, ridge, or slot that runs across the length of the guide pin 900D or at least runs across both ends of the guide pin. Alternatively, the alignment feature 904D can be a pin, such as a triangular pin or flat edge pin, that is located at each end of the guide pin. The broach 906D can have a complementary alignment feature 908D along its guide pin lumen 910D, such as a slot or ridge, that registers the broach with the guide pin in the proper alignment. In some embodiments, once a first cavity has been formed, the second cavity can be aligned with the first cavity using fluoroscopy. The first cavity is readily visible under fluoroscopy and allows the operator to determine or confirm the proper orientation of the broach used to form the second cavity.

After the cavities are formed, the long implant 900D can be inserted into the first cavity and impacted through the sacrum and out the second cavity. Some advantages of using a long implant 900D over separate shorter implants is that the long implant may provide enhanced stability, particularly in the sacrum. Use of the long implant may allow a more medial implant location relative to the implant location of separate implants, and generally the bone quality is better as the implant location moves medially.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiment whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A broach for shaping a bore in bone to receive an implant, the broach comprising:
    a distal end that comprises a plurality of cutting surfaces formed as teeth, each of which is disposed at an apex of the distal end and having a tip pointed distally to cut into bone; and
    an elongate body portion extending proximally from the distal end, the elongate body portion comprising a longitudinal axis, exactly three faces, and exactly three apices each formed at the junction between adjacent faces,
    the broach sized, configured and arranged to be withdrawn from the bone after shaping the bore.

2. The broach of claim 1, wherein the distal end is a pyramid-shaped distal end that comprises exactly three distal end faces that taper towards the pointed tip, wherein each of the three distal end faces is an extension of one of the three faces of the elongate body portion.

3. The broach of claim 2, wherein the pyramid-shaped distal end further comprises exactly three distal end apices, each of which is formed at a junction between adjacent distal end faces, wherein the plurality of cutting surfaces formed as teeth are each disposed at one of the three distal end apices.

4. The broach of claim 1, wherein the distal end comprises a plurality of beveled faces that are each tapered in a distal direction.

5. The broach of claim 1, further comprising a central lumen that extends to the plurality of cutting surfaces formed as teeth.

6. The broach of claim 1, wherein the elongate body portion further comprises a plurality of side channels that extend along the longitudinal axis of the elongate body portion.

7. The broach of claim 6, wherein each of the plurality of side channels is circumferentially in between first and second cutting surfaces of the plurality of cutting surfaces.

8. A broach for shaping a bore in bone to receive an implant, the broach comprising:
    a pyramid-shaped distal end; and
    an elongate body portion extending proximally from the pyramid-shaped distal end, the elongate body portion comprising a longitudinal axis, exactly three faces and exactly three apices formed at the junctions between adjacent faces, the three apices of the elongate body portion having a constant radial dimension along the elongate body portion,
    the pyramid-shaped distal end comprising exactly three distal end faces that taper in a distal direction, wherein each of the three distal end faces is an extension of one of the three faces of the elongate body portion,
    the pyramid-shaped distal end further comprising exactly three distal end apices, each of which is formed at a junction between adjacent distal end faces,
    the pyramid-shaped distal end comprising a plurality of cutting surfaces formed as teeth, each of which is disposed at one of the three distal end apices and having a tip pointed distally to cut into bone,
    the broach sized, configured and arranged to be withdrawn from the bone after shaping the bore.

9. The broach of claim 8, further comprising a central lumen that extends to the plurality of cutting surfaces.

10. The broach of claim 8, wherein the elongate body portion further comprises a plurality of side channels that extend along the longitudinal axis of the elongate body portion.

11. The broach of claim 10, wherein each of the plurality of side channels is circumferentially in between first and second cutting surfaces of the plurality of cutting surfaces.

* * * * *